(12) United States Patent
Groth et al.

(10) Patent No.: US 10,875,915 B2
(45) Date of Patent: Dec. 29, 2020

(54) ANTI-CXCR5 ANTIBODIES AND COMPOSITIONS AND USES THEREOF

(71) Applicants: PFIZER INC., New York, NY (US); THE REGENTS OF THE UNIVERSITY OF CALIFORNIA, Oakland, CA (US)

(72) Inventors: Rachel Groth, Walnut Creek, CA (US); William Brian Snyder, Escondido, CA (US); Xianjun Cao, San Diego, CA (US); Robert Joseph Dunn, San Diego, CA (US); Joseph Dal Porto, Los Gatos, CA (US); Michael Karin, La Jolla, CA (US)

(73) Assignees: PFIZER INC., New York, NY (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/202,749

(22) Filed: Nov. 28, 2018

(65) Prior Publication Data
US 2019/0169283 A1 Jun. 6, 2019

Related U.S. Application Data

(60) Provisional application No. 62/732,985, filed on Sep. 18, 2018, provisional application No. 62/593,830, filed on Dec. 1, 2017.

(51) Int. Cl.
| | | |
|---|---|---|
| *C07K 16/24* | (2006.01) | |
| *C07K 16/28* | (2006.01) | |
| *A61P 37/06* | (2006.01) | |
| *A61P 19/02* | (2006.01) | |
| *C12N 15/62* | (2006.01) | |
| *A61K 39/00* | (2006.01) | |
| *C07K 16/40* | (2006.01) | |

(52) U.S. Cl.
CPC .............. *C07K 16/24* (2013.01); *A61P 19/02* (2018.01); *A61P 37/06* (2018.01); *C07K 16/2866* (2013.01); *C07K 16/40* (2013.01); *C12N 15/62* (2013.01); *A61K 2039/54* (2013.01); *A61K 2039/545* (2013.01); *C07K 2317/24* (2013.01); *C07K 2317/30* (2013.01); *C07K 2317/33* (2013.01); *C07K 2317/41* (2013.01); *C07K 2317/565* (2013.01); *C07K 2317/732* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| WO | 2004056312 A2 | 7/2004 |
|---|---|---|
| WO | 2009032661 A1 | 3/2009 |
| WO | 2012010582 A1 | 1/2012 |
| WO | 2016028573 A1 | 2/2016 |
| WO | 2019108639 A1 | 6/2019 |

OTHER PUBLICATIONS

Lloyd et al. Protein Engineering, Design & Selection, 22, 159-168, 2009. (Year: 2009).*
Dübel, Stephan Ed., Handbook of Therapeutic Antibodies, Chapter 6, Saldanha "Molecular Engineering I; Humanization," Wiley-VCH (2007) pp. 119-144.
Hall et al. "Chapter 10: Tissue Cross-Reactivity Studies for Monoclonal Antibodies: Predictive Valie and Use for Selection of Relevant Animal Species for Toxicity Testing" Preclinical Safety Evaluation of Biopharmaceuticals (2008) pp. 207-240.
International Search Report issued in PCT/US2018/062829, dated Apr. 18, 2019, 9 pages.
Written Opinion issued in PCT/US2018/062829, dated Apr. 18, 2019, 11 pages.
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering (2004) vol. 87, No. 5, pp. 614-622.
Ansel et al. "A chemokine-driven positive feedback loop organizes lymphoid follicles" Nature (2000) vol. 406, pp. 309-314.
Ansel et al. "In Vivo-activated CD4 T Cells Upregulate CXC Chemokine Receptor 5 and Reprogram Their Response to Lymphoid Chemokines" J Exp Med (1999) vol. 190, No. 8, pp. 1123-1134.
Belouski et al "Sample Stability and Variablility of B-Cell Subsets in Blood from Healthy Subjects and Patients with Systemic Lupus Erythematosus" Cytometry Part B (2010) vol. 78B, pp. 49-58.
Breitfeld et al. "Follicular B Helper T Cells Express CXC Chemokine Receptor 5, Localize to B Cell Follicles, and Support Immunoglobulin Production" J Exp Med (2000) vol. 192, No. 11, pp. 1545-1551.
Carlsen et al "B cell attracting chemokine 1 (CXCL13) and its receptor CXCR5 are expressed in normal and aberrant gut associated lymphoid tissue" Gut (2002( vol. 51, pp. 364-371.
Cohen et al "Safety, Tolerability, Pharmacokinetic and Pharmacodynamic Properties of SBI-087, a CD20-Directed B-cell Depleting Agent: Phase 1 Dose Escalating Studies in Patients With Either Mild Rheumatoid Arthritis or Systemic Lupus" Clinical Therapeutics (2016) vol. 38, pp. 1417-1434.e2.
Crotty et al. "Follicular Helper CD4 T Cells (TFH)" Annu. Rev. Immunol. (2011) vol. 29, pp. 621-663.
Crotty et al. "T follicular helper cell differentiation, function, and roles in disease" Immunity (2014) vol. 41, No. 4, pp. 529-542.

(Continued)

*Primary Examiner* — Elly-Gerald Stoica
(74) *Attorney, Agent, or Firm* — Scully Scott Murphy and Presser

(57) ABSTRACT

The invention provides antibodies, and antigen-binding fragments thereof, that specifically bind to CXCR5. The antibodies can be afucosylated and exhibit increased ADCC compared with the otherwise identical fucosylated antibodies. The invention includes uses, and associated methods of using the antibodies.

15 Claims, 11 Drawing Sheets

Specification includes a Sequence Listing.

(56) References Cited

OTHER PUBLICATIONS

Cyster et al. "Chemokines and B-cell Homing Follicles" Mechanisms of B Cell Neoplasia (1998) pp. 87-93.
Deane et al. "Developability of Biotheraputics: Computational Approaches. Edited by Sandeep Kumar and Satish K. Singh" mAbs (2017) vol. 9, No. 1, pp. 12-14.
Evers et al. "Critical Review of Preclinical Approaches to Investigate Cytochrome P450-Mediated Therapeutic Protein Drug-Drug Interactions and Recommendations for Best Practices: A White Paper" Drug Metab Dispos (2013) vol. 41, pp. 1598-1609.
Flynn et al. "Regulation of chemokine receptor expression in human microglia and astrocytes" Journal of Neuroimmunology (2003) vol. 136, pp. 84-93.
Hardtke et al. "Balanced expression of CXCR5 and CCR7 on follicular T helper cells determines their transient positioning to lymph node follicles and is essential for efficient B-cell help" Blood (2005) vol. 106, No. 6, pp. 1924-1931.
Haynes et al. "Role of CXCR5 and CCR7 in Follicular Th Cell Positioning and Appearance of a Programmed Cell Death Gene-1High Germinal Center-Assocaited Subpopulation" The Journal of Immunology (2007) vol. 179, pp. 5099-5108.
Huang et al. "Therapeutic Protein-Drug Interactions and Implications for Drug Development" Clinical Pharmacology & Therapeutics (2010) vol. 87, No. 4, pp. 497-503.
Krzyzanski et al "A cell-level model of pharmacodynamics-mediated drug disposition" J Pharmaconet Pharmacodyn (2016) vol. 43, pp. 513-527.
Leach et al "Use of Tissue Cross-reactivity Studies in the Development of Antibody-based Biopharmaceuticals: History, Experience, Methodology, and Future Directions" Toxicologic Pathology (2010) vol. 38, pp. 1138-1166.
Lee et al. "CYP-Mediated Therapeutic Protein-Drug Interactions" Clin Pharmacokinet (2016) vol. 49, No. 5, pp. 295-310.
Lin et al. "Preclinical Pharmacokinetics, Interspecies Scaling, and Tissue Distribution of a Humanized Monoclonal Antibody against Vascular Endothelial Growth Factor" The Journal of Pharacology and Experimental Therapeutics (1999) vol. 288, pp. 371-378.
Lobo et al. "Antibody Pharmacokinetics and Pharmacodynamics" The Journal of Pharmaceutical Sciences (2004) vol. 93, No. 11, pp. 2645-2668.
Mahmoud et al. "Drug Interaction Studies of Therapeutic Proteins or Monoclonal Antibodies" Journal of Clinical Pharmacology (2007) vol. 47, pp. 1540-1554.
Mascelli et al. "Molecular, Biologic, and Pharacokinetic Properties of Monoclonal Antibodies: Impact of These Parameters on Early Clinical Development" J Clin Pharmacol (2007) vol. 47, pp. 553-565.
Mcheyzer-Williams et al. "Molecular programming of B cell memory" Nat Rev Immunol (2012) vol. 12, No. 1, pp. 24-34.
Schaerli et al. "CXC Chemokine Receptor 5 Expression Defines Follicular Homing T Cells with B Cell Helper Function" J Exp Med (2000) vol. 192, No. 11, pp. 1553-1562.
Schmutz et al. "Chemokine receptors in the rheumatoid synovium: upregulation of CXCR5" Arthritis Res Ther (2005) vol. 7, pp. R217-R229.
Tangye et al. "The good, the bad and the ugly—TFH cells in human health and disease" Nature Reviews Immunology (2013) vol. 13, pp. 412-426.
Vinuesa et al. "Dysregulation of germinal centers in autoimmune disease" Nature Reviews Immunology (2009) vol. 9, pp. 845-857.
Vinuesa et al. "How T Cells Earn the Follicular Rite of Passage" Immunity (2011) vol. 35, pp. 671-680.
Vugmeyster et al. "Pharmacokinetics and toxicology of therapeutic proteins: Advances and challenges" World J Chem (2002) vol. 3, No. 4, pp. 73-92.
Wang et al. "Pharmacodynamics-Mediated Drug Disposition (PDMDD) and Precursor Pool Lifespan Model for Single Dose of Romiplostim in Healthy Subjects" The AAPS Journal (2010) vol. 12, No. 4, pp. 729-740.
Warren "Target-induced natural killer cell loss as a measure of NK cell responses" Journal of Immunological Methods (2011) vol. 370, pp. 86-92.

* cited by examiner

FIG 6 h  MNYPLTLEMD---LENLEDLFWELDRLDNYNDTSLVENHLCPATEGPLMASFKAVFVPVAY
m  MNYPLTLDMGSITYNMDDLYKELAFYSNSTEIPLQDSNFCSTVEGPLLTSFKAVFMPVAY
                            N

SLIFLLGVIGNVLVLVILERHRQTRSSTETFLFHLAVADLLLVFILPFAVAEGSVGWVLG
SLIFLLGMMGNILVLVILERHHTRSSTETFLFHLAVADLLLVFILPFAVAEGSVGWVLG
                                                      L1

TFLCKTVIALHKVNFYCSSLLLACIAVDRYLAIVHAVHAYRHRRLLSIHITCGTIWLVGF
TFLCKTVIALHKINFYCSSLLLACIAVDRYLAIVHAVHAYRRRRLLSIHITCTAIWLAGF
  L1

LLALPEILFAKVSQGHHNNSLPRCTFSQENQAETHAWFTSRFLYHVAGFLLPMLVMGWCY
LFAIPELLFAKVGQPHNNDSLPQCTFSQENEAETRAWFTSRFLYHIGGFLLPMLVMGWCY
       L2

VGVVHRLRQAQRRPQRQKAVRVAILVTSIFFLCWSPYHIVIFLDTLARLKAVDNTCKLNG
VGVVHRLLQAQRRPQRQKAVRVAILVTSIFFLCWSPYHIVIFLDTLERLKAVNSSCELSG
                                                     L3

SLPVAITMCEFLGLAHCCLNPMLYTFAGVKFRSDLSRLLTKLGCTGPASLCQLFPSWRRS
YLSVAITICEFLGLAHCCLNPMLYTFAGVKFRSDLSRLLTKLGCAGPASLCQLFPNWRKS

SLSESENATSLTTF
SLSESENATSLTTF

SEQUENCE LISTING

```
<160> NUMBER OF SEQ ID NOS: 100

<210> SEQ ID NO 1
<211> LENGTH: 111
<212> TYPE: PRT
<213> ORGANISM: Artificial Sequence
<220> FEATURE:
<223> OTHER INFORMATION: Synthetic Construct

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr His
                20                  25                  30

Gly Thr Ser Leu Met His Trp Tyr Gln Gln Lys Pro Gly Lys Ala Pro
            35                  40                  45

Lys Leu Leu Ile Tyr Ala Ala Ser Asn Val Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Arg
                85                  90                  95

Lys Val Pro Trp Thr Phe Gly Gln Gly Thr Lys Val Glu Ile Lys
            100                 105                 110

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Glu Ser Val Glu Tyr His Gly Thr Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Ala Ala Ser Asn Val Glu Ser Gly
1               5

<210> SEQ ID NO 4
<211> LENGTH: 9
<212> TYPE: PRT
```

<213> ORGANISM: Artificial Sequence
<220> FEATURE:
<223> OTHER INFORMATION: Synthetic Construct

<400> SEQUENCE: 4

```
Gln Gln Ser Arg Lys Val Pro Trp Thr
1               5
```

<210> SEQ ID NO 5
<211> LENGTH: 111
<212> TYPE: PRT
<213> ORGANISM: Artificial Sequence
<220> FEATURE:
<223> OTHER INFORMATION: Synthetic Construct

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr His
                20                  25                  30

Gly Thr Ser Leu Met His Trp Tyr Gln Gln Lys Pro Gly Lys Ala Pro
            35                  40                  45

Lys Leu Leu Ile Tyr Ala Ala Ser Asn Val Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Arg
                85                  90                  95

Lys Val Pro Trp Thr Phe Gly Gln Gly Thr Lys Val Glu Ile Lys
            100                 105                 110
```

<210> SEQ ID NO 6
<211> LENGTH: 119
<212> TYPE: PRT
<213> ORGANISM: Artificial Sequence
<220> FEATURE:
<223> OTHER INFORMATION: Synthetic Construct

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
                20                  25                  30

Tyr Met Ser Trp Val Arg Gln Ala Pro Gly Lys Gly Leu Glu Trp Val
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Val Tyr Gly Ser Thr Leu His Tyr Trp Gly Gln Gly
            100                 105                 110

Thr Leu Val Thr Val Ser Ser
        115
```

<210> SEQ ID NO 7
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 7

Gly Phe Thr Phe Thr Asp Phe Tyr
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Ile Arg Asn Lys Ala Asn Gly Tyr Thr
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Ala Arg Val Tyr Gly Ser Thr Leu His Tyr
1               5                   10

<210> SEQ ID NO 10
<211> LENGTH: 119
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg Val Tyr Gly Ser Thr Leu His Tyr Trp Gly Gln Gly
            100                 105                 110

Thr Leu Val Thr Val Ser Ser
        115

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Val Arg Val Tyr Gly Ser Thr Leu His Tyr
```

-continued

```
1               5                   10
```

<210> SEQ ID NO 12
<211> LENGTH: 119
<212> TYPE: PRT
<213> ORGANISM: Artificial Sequence
<220> FEATURE:
<223> OTHER INFORMATION: Synthetic Construct

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Ser Ser
65                  70                  75                  80

Leu Tyr Leu Gln Met Asn Ser Leu Arg Ala Glu Asp Thr Ala Val Tyr
                85                  90                  95

Tyr Cys Val Arg Val Tyr Gly Ser Thr Leu His Tyr Trp Gly Gln Gly
            100                 105                 110

Thr Leu Val Thr Val Ser Ser
        115
```

<210> SEQ ID NO 13
<211> LENGTH: 106
<212> TYPE: PRT
<213> ORGANISM: Artificial Sequence
<220> FEATURE:
<223> OTHER INFORMATION: Synthetic Construct

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Asn Tyr Ile
            20                  25                  30

His Trp Tyr Gln Gln Lys Pro Gly Lys Ala Pro Lys Arg Leu Ile Tyr
        35                  40                  45

Glu Thr Ser Arg Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
            100                 105
```

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

```
Ser Ser Val Asn Tyr
1               5
```

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Glu Thr Ser Arg Leu Ala Ser Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Gln Gln Trp Ser Ser Asn Pro Leu Thr
1               5

<210> SEQ ID NO 17
<211> LENGTH: 121
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Thr Tyr Thr Phe Tyr Pro Asp Ile Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Glu Asp Tyr Arg Gly Ala Leu Glu His Trp Gly Gln
            100                 105                 110

Gly Thr Leu Val Thr Val Ser Ser Ala
        115                 120

<210> SEQ ID NO 18
<211> LENGTH: 121
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Ser Trp Val Arg Gln Ala Pro Gly Lys Gly Leu Glu Trp Val
        35                  40                  45

```
Ala Thr Ile Ser Ser Gly Gly Thr Tyr Thr Phe Tyr Pro Asp Ile Leu
        50                  55                  60

Lys Gly Arg Ile Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Glu Asp Tyr Arg Gly Ala Leu Glu His Trp Gly Gln
            100                 105                 110

Gly Thr Leu Val Thr Val Ser Ser Ala
            115                 120
```

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

```
Gly Phe Thr Phe Arg Ser Tyr Gly
 1               5
```

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

```
Ile Ser Ser Gly Gly Thr Tyr
 1               5
```

<210> SEQ ID NO 21
<211> LENGTH: 13
<212> TYPE: PRT
<213> ORGANISM: Artificial Sequence
<220> FEATURE:
<223> OTHER INFORMATION: Synthetic Construct

<400> SEQUENCE: 21

```
Ala Arg Arg Gly Glu Asp Tyr Arg Gly Ala Leu Glu His
 1               5                  10
```

<210> SEQ ID NO 22
<211> LENGTH: 218
<212> TYPE: PRT
<213> ORGANISM: Artificial Sequence
<220> FEATURE:
<223> OTHER INFORMATION: Synthetic Construct

<400> SEQUENCE: 22

```
Asp Val Val Thr Gln Ser Pro Asp Ser Leu Ala Val Ser Leu Gly
 1               5                  10                  15

Gln Arg Ala Thr Ile Ser Cys Arg Ala Ser Glu Ser Val Glu Tyr His
                 20                  25                  30

Gly Thr Ser Leu Met His Trp Tyr Gln Gln Lys Pro Gly Gln Pro Pro
             35                  40                  45

Lys Leu Leu Ile Tyr Ala Ala Ser Asn Val Glu Ser Gly Val Pro Ala
         50                  55                  60

Arg Phe Ser Gly Ser Gly Ser Gly Thr Asp Phe Ser Leu Asn Ile His
 65                  70                  75                  80
```

```
Pro Val Glu Glu Gly Asp Ile Ala Met Tyr Phe Cys Gln Gln Ser Arg
                85                  90                  95

Lys Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 23
<211> LENGTH: 448
<212> TYPE: PRT
<213> ORGANISM: Artificial Sequence
<220> FEATURE:
<223> OTHER INFORMATION: Synthetic Construct

<400> SEQUENCE: 23

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Phe
            20                  25                  30

Tyr Met Ser Trp Val Arg Gln Pro Pro Gly Arg Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Gly Asp Ser Ala Thr Tyr
                85                  90                  95

Tyr Cys Val Arg Val Tyr Gly Ser Thr Leu His Tyr Trp Gly Gln Gly
            100                 105                 110

Thr Ile Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

<210> SEQ ID NO 24
<211> LENGTH: 213
<212> TYPE: PRT
<213> ORGANISM: Artificial Sequence
<220> FEATURE:
<223> OTHER INFORMATION: Synthetic Construct

<400> SEQUENCE: 24

Gln Ile Val Leu Thr Gln Ser Pro Ala Val Met Ser Ala Ser Pro Gly
1               5                   10                  15

Glu Lys Val Thr Met Thr Cys Ser Ala Ser Ser Ser Val Asn Tyr Ile
            20                  25                  30

His Trp Tyr Gln Gln Lys Ser Gly Thr Ser Pro Lys Arg Trp Ile Tyr
        35                  40                  45

Glu Thr Ser Arg Leu Ala Ser Gly Val Pro Val Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ser Ser Asn Pro Leu Thr
            85                  90                  95

Phe Gly Ala Gly Thr Lys Leu Glu Leu Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 25
<211> LENGTH: 449
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Arg Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Phe Tyr Pro Asp Ile Leu
    50                  55                  60

Lys Gly Arg Ile Thr Ile Ser Arg Asp Asn Ala Lys Asn Thr Leu Tyr
65                  70                  75                  80

Leu Gln Met Ser Asn Leu Lys Ser Glu Asp Thr Ala Met Tyr Tyr Cys
                85                  90                  95

Ala Arg Arg Gly Glu Asp Tyr Arg Gly Ala Leu Glu His Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 26
<211> LENGTH: 218
<212> TYPE: PRT
<213> ORGANISM: Artificial Sequence
<220> FEATURE:
<223> OTHER INFORMATION: Synthetic Construct

<400> SEQUENCE: 26

Asp Val Val Val Thr Gln Ser Pro Asp Ser Leu Ala Val Ser Leu Gly
1               5                   10                  15

Gln Arg Ala Thr Ile Ser Cys Arg Ala Ser Glu Ser Val Glu Tyr His
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Gly Asp Val Ser Met Phe Phe Cys Gln Gln Ser Arg
                85                  90                  95

Lys Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 27
<211> LENGTH: 448
<212> TYPE: PRT
<213> ORGANISM: Artificial Sequence
<220> FEATURE:
<223> OTHER INFORMATION: Synthetic Construct

<400> SEQUENCE: 27

Glu Val Lys Leu Val Glu Ser Gly Gly Gly Leu Val Gln Pro Gly Asp
1               5                   10                  15

Ser Leu Arg Leu Ser Cys Ala Thr Ser Gly Phe Thr Phe Thr Asp Phe
            20                  25                  30

Tyr Met Ser Trp Val Arg Gln Pro Pro Gly Arg Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Gly Asp Ser Ala Thr Tyr
                85                  90                  95

Tyr Cys Val Arg Val Tyr Gly Ser Thr Leu His Tyr Trp Gly Gln Gly
            100                 105                 110

Thr Ile Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

<210> SEQ ID NO 28
<211> LENGTH: 218
<212> TYPE: PRT
<213> ORGANISM: Artificial Sequence
<220> FEATURE:
<223> OTHER INFORMATION: Synthetic Construct

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr His
            20                  25                  30

Gly Thr Ser Leu Met His Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Arg
                85                  90                  95

Lys Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 29
<211> LENGTH: 448
<212> TYPE: PRT
<213> ORGANISM: Artificial Sequence
<220> FEATURE:
```

<223> OTHER INFORMATION: Synthetic Construct

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Val Tyr Gly Ser Thr Leu His Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445

<210> SEQ ID NO 30
<211> LENGTH: 107
<212> TYPE: PRT
<213> ORGANISM: Artificial Sequence
<220> FEATURE:
<223> OTHER INFORMATION: Synthetic Construct

<400> SEQUENCE: 30

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 31
<211> LENGTH: 329
<212> TYPE: PRT
<213> ORGANISM: Artificial Sequence
<220> FEATURE:
<223> OTHER INFORMATION: Synthetic Construct

<400> SEQUENCE: 31

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
```

Tyr Val Asp Gly Val Glu Val His Asn Ala Lys Thr Lys Pro Arg Glu
165                     170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 32
<211> LENGTH: 372
<212> TYPE: PRT
<213> ORGANISM: Artificial Sequence
<220> FEATURE:
<223> OTHER INFORMATION: Synthetic Construct

<400> SEQUENCE: 32

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

-continued

```
Gly His His Asn Asn Ser Leu Pro Arg Cys Thr Phe Ser Gln Glu Asn
            195                 200                 205

Gln Ala Glu Thr His Ala Trp Phe Thr Ser Arg Phe Leu Tyr His Val
210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
            245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
            275                 280                 285

Ala Val Asp Asn Thr Cys Lys Leu Asn Gly Ser Leu Pro Val Ala Ile
290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
            325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
            355                 360                 365

Leu Thr Thr Phe
            370

<210> SEQ ID NO 33
<211> LENGTH: 372
<212> TYPE: PRT
<213> ORGANISM: Artificial Sequence
<220> FEATURE:
<223> OTHER INFORMATION: Synthetic Construct

<400> SEQUENCE: 33

Met Asn Tyr Pro Leu Met Leu Glu Met Asp Leu Glu Asn Leu Glu Asp
1               5                   10                  15

Leu Phe Leu Glu Phe Asp Lys Phe Asp Asn Tyr Asn Asp Thr Ser Leu
                20                  25                  30

Val Glu Asn His Leu Cys Pro Ala Thr Glu Gly Pro Leu Met Ala Ser
            35                  40                  45

Phe Lys Ala Val Phe Val Pro Val Ala Tyr Ser Leu Ile Phe Leu Leu
        50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175
```

```
Gly Phe Leu Phe Ala Leu Pro Glu Ile Leu Phe Ala Lys Val Ser Gln
            180                 185                 190

Ala His Pro Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Pro Gln Arg Gln Lys
            245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Val Arg Leu Lys
            275                 280                 285

Ala Val Asp Asn Thr Cys Glu Leu Asn Gly Ser Leu Pro Val Ala Ile
            290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
            325                 330                 335

Leu Thr Lys Leu Gly Cys Thr Gly Pro Ala Ser Leu Cys Gln Leu Phe
            340                 345                 350

Pro Ser Trp Arg Lys Ser Ser Leu Ser Glu Ser Glu Asn Ala Thr Ser
            355                 360                 365

Leu Thr Thr Phe
            370

<210> SEQ ID NO 34
<211> LENGTH: 374
<212> TYPE: PRT
<213> ORGANISM: Artificial Sequence
<220> FEATURE:
<223> OTHER INFORMATION: Synthetic Construct

<400> SEQUENCE: 34

Met Asn Tyr Pro Leu Thr Leu Asp Met Gly Ser Ile Thr Tyr Asn Met
1               5                   10                  15

Asp Asp Leu Tyr Lys Glu Leu Ala Phe Tyr Ser Asn Ser Thr Glu Ile
            20                  25                  30

Pro Leu Gln Asp Ser Asn Phe Cys Ser Thr Val Glu Gly Pro Leu Leu
        35                  40                  45

Thr Ser Phe Lys Ala Val Phe Met Pro Val Ala Tyr Ser Leu Ile Phe
50                  55                  60

Leu Leu Gly Met Met Gly Asn Ile Leu Val Leu Val Ile Leu Glu Arg
65                  70                  75                  80

His Arg His Thr Arg Ser Ser Thr Glu Thr Phe Leu Phe His Leu Ala
                85                  90                  95

Val Ala Asp Leu Leu Leu Val Phe Ile Leu Pro Phe Ala Val Ala Glu
            100                 105                 110

Gly Ser Val Gly Trp Val Leu Gly Thr Phe Leu Cys Lys Thr Val Ile
        115                 120                 125

Ala Leu His Lys Ile Asn Phe Tyr Cys Ser Ser Leu Leu Leu Ala Cys
    130                 135                 140

Ile Ala Val Asp Arg Tyr Leu Ala Ile Val His Ala Val His Ala Tyr
145                 150                 155                 160
```

```
Arg Arg Arg Arg Leu Leu Ser Ile His Ile Thr Cys Thr Ala Ile Trp
                165                 170                 175

Leu Ala Gly Phe Leu Phe Ala Leu Pro Glu Leu Leu Phe Ala Lys Val
            180                 185                 190

Gly Gln Pro His Asn Asn Asp Ser Leu Pro Gln Cys Thr Phe Ser Gln
        195                 200                 205

Glu Asn Glu Ala Glu Thr Arg Ala Trp Phe Thr Ser Arg Phe Leu Tyr
    210                 215                 220

His Ile Gly Gly Phe Leu Leu Pro Met Leu Val Met Gly Trp Cys Tyr
225                 230                 235                 240

Val Gly Val Val His Arg Leu Leu Gln Ala Gln Arg Arg Pro Gln Arg
                245                 250                 255

Gln Lys Ala Val Arg Val Ala Ile Leu Val Thr Ser Ile Phe Phe Leu
            260                 265                 270

Cys Trp Ser Pro Tyr His Ile Val Ile Phe Leu Asp Thr Leu Glu Arg
        275                 280                 285

Leu Lys Ala Val Asn Ser Ser Cys Glu Leu Ser Gly Tyr Leu Ser Val
    290                 295                 300

Ala Ile Thr Leu Cys Glu Phe Leu Gly Leu Ala His Cys Cys Leu Asn
305                 310                 315                 320

Pro Met Leu Tyr Thr Phe Ala Gly Val Lys Phe Arg Ser Asp Leu Ser
                325                 330                 335

Arg Leu Leu Thr Lys Leu Gly Cys Ala Gly Pro Ala Ser Leu Cys Gln
            340                 345                 350

Leu Phe Pro Asn Trp Arg Lys Ser Ser Leu Ser Glu Ser Glu Asn Ala
        355                 360                 365

Thr Ser Leu Thr Thr Phe
    370

<210> SEQ ID NO 35
<211> LENGTH: 111
<212> TYPE: PRT
<213> ORGANISM: Artificial Sequence
<220> FEATURE:
<223> OTHER INFORMATION: Synthetic Construct

<400> SEQUENCE: 35

Asp Val Val Thr Gln Ser Pro Asp Ser Leu Ala Val Ser Leu Gly
1               5                   10                  15

Gln Arg Ala Thr Ile Ser Cys Arg Ala Ser Glu Ser Val Glu Tyr His
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Gly Asp Ile Ala Met Tyr Phe Cys Gln Gln Ser Arg
                85                  90                  95

Lys Val Pro Trp Thr Phe Gly Gly Gly Thr Lys Leu Glu Ile Lys
            100                 105                 110

<210> SEQ ID NO 36
<211> LENGTH: 120
<212> TYPE: PRT
<213> ORGANISM: Artificial Sequence
```

```
<220> FEATURE:
<223> OTHER INFORMATION: Synthetic Construct

<400> SEQUENCE: 36

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Phe
            20                  25                  30

Tyr Met Ser Trp Val Arg Gln Pro Pro Gly Arg Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Gly Asp Ser Ala Thr Tyr
                85                  90                  95

Tyr Cys Val Arg Val Tyr Gly Ser Thr Leu His Tyr Trp Gly Gln Gly
            100                 105                 110

Thr Ile Leu Thr Val Ser Ser Ala
        115                 120

<210> SEQ ID NO 37
<211> LENGTH: 106
<212> TYPE: PRT
<213> ORGANISM: Artificial Sequence
<220> FEATURE:
<223> OTHER INFORMATION: Synthetic Construct

<400> SEQUENCE: 37

Gln Ile Val Leu Thr Gln Ser Pro Ala Val Met Ser Ala Ser Pro Gly
1               5                   10                  15

Glu Lys Val Thr Met Thr Cys Ser Ala Ser Ser Ser Val Asn Tyr Ile
            20                  25                  30

His Trp Tyr Gln Gln Lys Ser Gly Thr Ser Pro Lys Arg Trp Ile Tyr
        35                  40                  45

Glu Thr Ser Arg Leu Ala Ser Gly Val Pro Val Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 38
<211> LENGTH: 121
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Arg Ser Tyr
            20                  25                  30

Gly Met Ser Trp Val Arg Gln Thr Pro Asp Lys Arg Leu Glu Trp Val
        35                  40                  45
```

```
Ala Thr Ile Ser Ser Gly Gly Thr Tyr Thr Phe Tyr Pro Asp Ile Leu
 50                  55                  60

Lys Gly Arg Ile Thr Ile Ser Arg Asp Asn Ala Lys Asn Thr Leu Tyr
 65                  70                  75                  80

Leu Gln Met Ser Asn Leu Lys Ser Glu Asp Thr Ala Met Tyr Tyr Cys
                 85                  90                  95

Ala Arg Arg Gly Glu Asp Tyr Arg Gly Ala Leu Glu His Trp Gly Gln
            100                 105                 110

Gly Thr Ser Val Thr Val Ser Ser Ala
            115                 120
```

<210> SEQ ID NO 39
<211> LENGTH: 111
<212> TYPE: PRT
<213> ORGANISM: Artificial Sequence
<220> FEATURE:
<223> OTHER INFORMATION: Synthetic Construct

<400> SEQUENCE: 39

```
Asp Val Val Val Thr Gln Ser Pro Asp Ser Leu Ala Val Ser Leu Gly
 1               5                  10                  15

Gln Arg Ala Thr Ile Ser Cys Arg Ala Ser Glu Ser Val Glu Tyr His
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Val Glu Ser Gly Val Pro Ala
 50                  55                  60

Arg Phe Ser Gly Ser Gly Ser Gly Thr Asp Phe Ser Leu Asn Ile His
 65                  70                  75                  80

Pro Val Glu Glu Gly Asp Val Ser Met Phe Phe Cys Gln Gln Ser Arg
                 85                  90                  95

Lys Val Pro Trp Thr Phe Gly Gly Gly Thr Lys Leu Glu Ile Lys
            100                 105                 110
```

<210> SEQ ID NO 40
<211> LENGTH: 120
<212> TYPE: PRT
<213> ORGANISM: Artificial Sequence
<220> FEATURE:
<223> OTHER INFORMATION: Synthetic Construct

<400> SEQUENCE: 40

```
Glu Val Lys Leu Val Glu Ser Gly Gly Gly Leu Val Gln Pro Gly Asp
 1               5                  10                  15

Ser Leu Arg Leu Ser Cys Ala Thr Ser Gly Phe Thr Phe Thr Asp Phe
            20                  25                  30

Tyr Met Ser Trp Val Arg Gln Pro Pro Gly Arg Ala Leu Glu Trp Leu
        35                  40                  45

Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Ala Gly Asp Ser Ala Thr Tyr
                 85                  90                  95

Tyr Cys Val Arg Val Tyr Gly Ser Thr Leu His Tyr Trp Gly Gln Gly
            100                 105                 110

Thr Ile Leu Thr Val Ser Ser Ala
            115                 120
```

```
<210> SEQ ID NO 41
<211> LENGTH: 219
<212> TYPE: PRT
<213> ORGANISM: Artificial Sequence
<220> FEATURE:
<223> OTHER INFORMATION: Synthetic Construct

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Ser Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 42
<211> LENGTH: 446
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Asn
            20                  25                  30

Ala Met Asn Trp Val Arg Gln Ala Pro Gly Lys Gly Leu Glu Arg Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
```

85                  90                  95
Tyr Cys Val Thr Met Ile Pro Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 43
<211> LENGTH: 219
<212> TYPE: PRT
<213> ORGANISM: Artificial Sequence
<220> FEATURE:
<223> OTHER INFORMATION: Synthetic Construct

<400> SEQUENCE: 43

Asp Ile Val Met Thr Gln Ala Ala Pro Ser Val Ala Val Thr Pro Gly

```
  1               5                  10                 15
Ala Ser Val Ser Ile Ser Cys Arg Ser Ser Lys Ser Leu Leu His Ser
                20                 25                 30

Ser Gly Lys Thr Tyr Leu Tyr Trp Phe Leu Gln Arg Pro Gly Gln Ser
                35                 40                 45

Pro Gln Leu Leu Ile Tyr Arg Leu Ser Ser Leu Ala Ser Gly Val Pro
 50                 55                 60

Asp Arg Phe Ser Gly Ser Gly Ser Gly Thr Ala Phe Thr Leu Arg Ile
 65                 70                 75                 80

Ser Arg Val Glu Ala Glu Asp Val Gly Val Tyr Tyr Cys Met Gln His
                85                 90                 95

Leu Glu Tyr Pro Tyr Thr Phe Gly Gly Gly Thr Lys Leu Glu Ile Lys
                100                105                110

Arg Thr Val Ala Ala Pro Ser Val Phe Ile Phe Pro Pro Ser Asp Glu
                115                120                125

Gln Leu Lys Ser Gly Thr Ala Ser Val Val Cys Leu Leu Asn Asn Phe
130                135                140

Tyr Pro Arg Glu Ala Lys Val Gln Trp Lys Val Asp Asn Ala Leu Gln
145                150                155                160

Ser Gly Asn Ser Gln Glu Ser Val Thr Glu Gln Asp Ser Lys Asp Ser
                165                170                175

Thr Tyr Ser Leu Ser Ser Thr Leu Thr Leu Ser Lys Ala Asp Tyr Glu
                180                185                190

Lys His Lys Val Tyr Ala Cys Glu Val Thr His Gln Gly Leu Ser Ser
                195                200                205

Pro Val Thr Lys Ser Phe Asn Arg Gly Glu Cys
210                215

<210> SEQ ID NO 44
<211> LENGTH: 440
<212> TYPE: PRT
<213> ORGANISM: Artificial Sequence
<220> FEATURE:
<223> OTHER INFORMATION: Synthetic Construct

<400> SEQUENCE: 44

Gln Val Gln Leu Lys Glu Ser Gly Pro Gly Leu Val Ala Pro Ser Glu
 1               5                  10                 15

Ser Leu Ser Ile Thr Cys Thr Val Ser Gly Phe Ser Leu Ile Asp Tyr
                20                 25                 30

Gly Val Asn Trp Ile Arg Gln Pro Pro Gly Lys Gly Leu Glu Trp Leu
                35                 40                 45

Gly Val Ile Trp Gly Asp Gly Thr Thr Tyr Tyr Asn Pro Ser Leu Lys
 50                 55                 60

Ser Arg Leu Ser Ile Ser Lys Asp Asn Ser Lys Ser Gln Val Phe Leu
 65                 70                 75                 80

Lys Val Thr Ser Leu Thr Thr Asp Asp Thr Ala Met Tyr Tyr Cys Ala
                85                 90                 95

Arg Ile Val Tyr Trp Gly Gln Gly Thr Leu Val Thr Val Ser Ala Ala
                100                105                110

Ser Thr Lys Gly Pro Ser Val Phe Pro Leu Ala Pro Ser Ser Lys Ser
                115                120                125

Thr Ser Gly Gly Thr Ala Ala Leu Gly Cys Leu Val Lys Asp Tyr Phe
130                135                140

Pro Glu Pro Val Thr Val Ser Trp Asn Ser Gly Ala Leu Thr Ser Gly
```

```
                145                 150                 155                 160
Val His Thr Phe Pro Ala Val Leu Gln Ser Ser Gly Leu Tyr Ser Leu
                    165                 170                 175

Ser Ser Val Val Thr Val Pro Ser Ser Leu Gly Thr Gln Thr Tyr
                180                 185                 190

Ile Cys Asn Val Asn His Lys Pro Ser Asn Thr Lys Val Asp Lys Lys
                195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                    245                 250                 255

Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
            275                 280                 285

Gln Tyr Asn Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                    325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                    405                 410                 415

Phe Ser Cys Ser Val Met His Glu Ala Leu His Asn His Tyr Thr Gln
                420                 425                 430

Lys Ser Leu Ser Leu Ser Pro Gly
            435                 440

<210> SEQ ID NO 45
<211> LENGTH: 216
<212> TYPE: PRT
<213> ORGANISM: Artificial Sequence
<220> FEATURE:
<223> OTHER INFORMATION: Synthetic Construct

<400> SEQUENCE: 45

Gln Pro Val Leu Thr Gln Pro Pro Ser Val Ser Lys Asp Leu Arg Gln
1               5                   10                  15

Thr Ala Thr Leu Thr Cys Thr Gly Asn Ser Asn Asn Val Gly Asn Gln
                20                  25                  30

Gly Ala Thr Trp Leu Gln Gln His Gln Gly His Pro Pro Lys Leu Leu
            35                  40                  45

Ser Tyr Lys Asn Asn Asn Arg Pro Ser Gly Ile Ser Glu Arg Phe Ser
        50                  55                  60

Ala Ser Arg Ser Gly Asn Thr Ala Ser Leu Thr Ile Thr Gly Leu Gln
```

```
                65                  70                  75                  80
Pro Glu Asp Glu Ala Asp Tyr Tyr Cys Ser Ala Trp Asp Ser Ser Leu
                    85                  90                  95

Ser Ala Trp Val Phe Gly Gly Thr Gln Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
            210                 215

<210> SEQ ID NO 46
<211> LENGTH: 441
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Val Val Trp Gly Gln Gly Thr Leu Val Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
                180                 185                 190

Tyr Ile Cys Asn Val Asn His Lys Pro Ser Asn Thr Lys Val Asp Lys
                195                 200                 205

Lys Val Glu Pro Lys Ser Cys Asp Lys Thr His Thr Cys Pro Pro Cys
```

```
                210                 215                 220
Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 47
<211> LENGTH: 111
<212> TYPE: PRT
<213> ORGANISM: Artificial Sequence
<220> FEATURE:
<223> OTHER INFORMATION: Synthetic Construct

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr His
            20                  25                  30

Gly Thr Ser Leu Met His Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Arg
                85                  90                  95

Lys Val Pro Trp Thr Phe Gly Gln Gly Thr Lys Val Glu Ile Lys
            100                 105                 110

<210> SEQ ID NO 48
<211> LENGTH: 111
<212> TYPE: PRT
```

<213> ORGANISM: Artificial Sequence
<220> FEATURE:
<223> OTHER INFORMATION: Synthetic Construct

<400> SEQUENCE: 48

```
Asp Val Gln Met Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr His
            20                  25                  30

Gly Thr Ser Leu Met His Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Arg
                85                  90                  95

Lys Val Pro Trp Thr Phe Gly Gln Gly Thr Lys Val Glu Ile Lys
            100                 105                 110
```

<210> SEQ ID NO 49
<211> LENGTH: 111
<212> TYPE: PRT
<213> ORGANISM: Artificial Sequence
<220> FEATURE:
<223> OTHER INFORMATION: Synthetic Construct

<400> SEQUENCE: 49

```
Asp Val Gln Val Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr His
            20                  25                  30

Gly Thr Ser Leu Met His Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Arg
                85                  90                  95

Lys Val Pro Trp Thr Phe Gly Gln Gly Thr Lys Val Glu Ile Lys
            100                 105                 110
```

<210> SEQ ID NO 50
<211> LENGTH: 111
<212> TYPE: PRT
<213> ORGANISM: Artificial Sequence
<220> FEATURE:
<223> OTHER INFORMATION: Synthetic Construct

<400> SEQUENCE: 50

```
Asp Val Gln Val Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr His
            20                  25                  30

Gly Thr Ser Leu Met His Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60
```

```
Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Phe Cys Gln Gln Ser Arg
                 85                  90                  95

Lys Val Pro Trp Thr Phe Gly Gln Gly Thr Lys Val Glu Ile Lys
            100                 105                 110

<210> SEQ ID NO 51
<211> LENGTH: 111
<212> TYPE: PRT
<213> ORGANISM: Artificial Sequence
<220> FEATURE:
<223> OTHER INFORMATION: Synthetic Construct

<400> SEQUENCE: 51

Asp Ile Gln Val Thr Gln Ser Pro Ser Ser Leu Ser Ala Ser Val Gly
  1               5                  10                  15

Asp Arg Val Thr Ile Thr Cys Arg Ala Ser Glu Ser Val Glu Tyr His
                 20                  25                  30

Gly Thr Ser Leu Met His Trp Tyr Gln Gln Lys Pro Gly Lys Ala Pro
             35                  40                  45

Lys Leu Leu Ile Tyr Ala Ala Ser Asn Val Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Arg
                 85                  90                  95

Lys Val Pro Trp Thr Phe Gly Gln Gly Thr Lys Val Glu Ile Lys
            100                 105                 110

<210> SEQ ID NO 52
<211> LENGTH: 121
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Thr Asp Phe
                 20                  25                  30

Tyr Met Ser Trp Val Arg Gln Ala Pro Gly Lys Gly Leu Glu Trp Leu
             35                  40                  45

Gly Phe Ile Arg Asn Lys Ala Asn Gly Tyr Thr Thr Glu Tyr Ser Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Val Arg Val Tyr Gly Ser Thr Leu His Tyr Trp Gly Gln Gly
            100                 105                 110

Thr Leu Val Thr Val Ser Ser Ala Ser
            115                 120

<210> SEQ ID NO 53
<211> LENGTH: 119
<212> TYPE: PRT
```

<213> ORGANISM: Artificial Sequence
<220> FEATURE:
<223> OTHER INFORMATION: Synthetic Construct

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ala Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Val Tyr Gly Ser Thr Leu His Tyr Trp Gly Gln Gly
            100                 105                 110

Thr Leu Val Thr Val Ser Ser
        115
```

<210> SEQ ID NO 54
<211> LENGTH: 119
<212> TYPE: PRT
<213> ORGANISM: Artificial Sequence
<220> FEATURE:
<223> OTHER INFORMATION: Synthetic Construct

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Phe
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg Val Tyr Gly Ser Thr Leu His Tyr Trp Gly Gln Gly
            100                 105                 110

Thr Leu Val Thr Val Ser Ser
        115
```

<210> SEQ ID NO 55
<211> LENGTH: 119
<212> TYPE: PRT
<213> ORGANISM: Artificial Sequence
<220> FEATURE:
<223> OTHER INFORMATION: Synthetic Construct

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Phe
            20                  25                  30
```

```
Tyr Met Ser Trp Val Arg Gln Ala Pro Gly Lys Gly Leu Glu Trp Val
        35                  40                  45

Ala Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Val Tyr Gly Ser Thr Leu His Tyr Trp Gly Gln Gly
            100                 105                 110

Thr Leu Val Thr Val Ser Ser
        115

<210> SEQ ID NO 56
<211> LENGTH: 119
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ala Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg Val Tyr Gly Ser Thr Leu His Tyr Trp Gly Gln Gly
            100                 105                 110

Thr Leu Val Thr Val Ser Ser
        115

<210> SEQ ID NO 57
<211> LENGTH: 119
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
```

```
                    85                  90                  95

Tyr Cys Ala Arg Val Tyr Gly Ser Thr Leu His Tyr Trp Gly Gln Gly
                100                 105                 110

Thr Leu Val Thr Val Ser Ser
            115

<210> SEQ ID NO 58
<211> LENGTH: 106
<212> TYPE: PRT
<213> ORGANISM: Artificial Sequence
<220> FEATURE:
<223> OTHER INFORMATION: Synthetic Construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Asn Tyr Ile
                20                  25                  30

His Trp Tyr Gln Gln Lys Pro Gly Lys Ala Pro Lys Arg Trp Ile Tyr
            35                  40                  45

Glu Thr Ser Arg Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
                100                 105

<210> SEQ ID NO 59
<211> LENGTH: 106
<212> TYPE: PRT
<213> ORGANISM: Artificial Sequence
<220> FEATURE:
<223> OTHER INFORMATION: Synthetic Construct

<400> SEQUENCE: 59

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Asn Tyr Ile
                20                  25                  30

His Trp Tyr Gln Gln Lys Pro Gly Lys Ala Pro Lys Arg Leu Ile Tyr
            35                  40                  45

Glu Thr Ser Arg Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
                100                 105

<210> SEQ ID NO 60
<211> LENGTH: 106
<212> TYPE: PRT
<213> ORGANISM: Artificial Sequence
<220> FEATURE:
<223> OTHER INFORMATION: Synthetic Construct

<400> SEQUENCE: 60
```

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Asn Tyr Ile
            20                  25                  30

His Trp Tyr Gln Gln Lys Pro Gly Lys Ala Pro Lys Arg Trp Ile Tyr
                35                  40                  45

Glu Thr Ser Arg Leu Ala Ser Gly Val Pro Ser Arg Phe Ser Gly Ser
            50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
                100                 105

<210> SEQ ID NO 61
<211> LENGTH: 106
<212> TYPE: PRT
<213> ORGANISM: Artificial Sequence
<220> FEATURE:
<223> OTHER INFORMATION: Synthetic Construct

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Asn Tyr Ile
            20                  25                  30

His Trp Tyr Gln Gln Lys Pro Gly Lys Ala Pro Lys Arg Leu Ile Tyr
                35                  40                  45

Glu Thr Ser Arg Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
                100                 105

<210> SEQ ID NO 62
<211> LENGTH: 106
<212> TYPE: PRT
<213> ORGANISM: Artificial Sequence
<220> FEATURE:
<223> OTHER INFORMATION: Synthetic Construct

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Asn Tyr Ile
            20                  25                  30

His Trp Tyr Gln Gln Lys Pro Gly Lys Ala Pro Lys Leu Leu Ile Tyr
                35                  40                  45

Glu Thr Ser Arg Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr

```
                         85                  90                  95

Phe Gly Gln Gly Thr Lys Val Glu Ile Lys
            100                 105

<210> SEQ ID NO 63
<211> LENGTH: 122
<212> TYPE: PRT
<213> ORGANISM: Artificial Sequence
<220> FEATURE:
<223> OTHER INFORMATION: Synthetic Construct

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Thr Tyr Thr Phe Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Glu Asp Tyr Arg Gly Ala Leu Glu His Trp Gly Gln
            100                 105                 110

Gly Thr Leu Val Thr Val Ser Ser Ala Ser
        115                 120

<210> SEQ ID NO 64
<211> LENGTH: 49
<212> TYPE: DNA
<213> ORGANISM: Artificial Sequence
<220> FEATURE:
<223> OTHER INFORMATION: Synthetic Construct

<400> SEQUENCE: 64
atcacgcggc cgcctcacca tgaagttgcc tgttaggctg ttggtgctg              49

<210> SEQ ID NO 65
<211> LENGTH: 48
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (26)..(26)
<223> OTHER INFORMATION: n can be a or t
<220> FEATURE:
<221> NAME/KEY: misc_feature
<222> LOCATION: (41)..(41)
<223> OTHER INFORMATION: n can be c or t

<400> SEQUENCE: 65
atcacgcggc cgcctcacca tggagncaga cacactcctg ntatgggt               48

<210> SEQ ID NO 66
<211> LENGTH: 49
<212> TYPE: DNA
<213> ORGANISM: Artificial Sequence
<220> FEATURE:
<223> OTHER INFORMATION: Synthetic Construct
<220> FEATURE:
```

<221> NAME/KEY: misc_feature
<222> LOCATION: (45)..(45)
<223> OTHER INFORMATION: n can be c or g

<400> SEQUENCE: 66
atcacgcggc cgcctcacca tgagtgtgct cactcaggtc ctggngttg         49

<210> SEQ ID NO 67
<211> LENGTH: 52
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (26)..(26)
<223> OTHER INFORMATION: n can be a or g
<220> FEATURE:
<221> NAME/KEY: misc_feature
<222> LOCATION: (38)..(38)
<223> OTHER INFORMATION: n can be a or t
<220> FEATURE:
<221> NAME/KEY: misc_feature
<222> LOCATION: (41)..(41)
<223> OTHER INFORMATION: n can be c or t
<220> FEATURE:
<221> NAME/KEY: misc_feature
<222> LOCATION: (46)..(46)
<223> OTHER INFORMATION: n can be a or c
<220> FEATURE:
<221> NAME/KEY: misc_feature
<222> LOCATION: (47)..(47)
<223> OTHER INFORMATION: n can be a or t

<400> SEQUENCE: 67
atcacgcggc cgcctcacca tgaggncccc tgctcagntt nttggnntct tg         52

<210> SEQ ID NO 68
<211> LENGTH: 49
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (28)..(28)
<223> OTHER INFORMATION: n can be a or t
<220> FEATURE:
<221> NAME/KEY: misc_feature
<222> LOCATION: (41)..(41)
<223> OTHER INFORMATION: n can be a or t

<400> SEQUENCE: 68
atcacgcggc cgcctcacca tggatttnca ggtgcagatt ntcagcttc         49

<210> SEQ ID NO 69
<211> LENGTH: 46
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (27)..(27)
<223> OTHER INFORMATION: n can be g or t
<220> FEATURE:
<221> NAME/KEY: misc_feature
<222> LOCATION: (29)..(29)
<223> OTHER INFORMATION: n can be c or t
<220> FEATURE:
<221> NAME/KEY: misc_feature
<222> LOCATION: (30)..(30)
<223> OTHER INFORMATION: n can be c or t

```
<220> FEATURE:
<221> NAME/KEY: misc_feature
<222> LOCATION: (33)..(33)
<223> OTHER INFORMATION: n can be c or t
<220> FEATURE:
<221> NAME/KEY: misc_feature
<222> LOCATION: (35)..(35)
<223> OTHER INFORMATION: n can be g or c
<220> FEATURE:
<221> NAME/KEY: misc_feature
<222> LOCATION: (38)..(38)
<223> OTHER INFORMATION: n can be c or t
<220> FEATURE:
<221> NAME/KEY: misc_feature
<222> LOCATION: (40)..(40)
<223> OTHER INFORMATION: n can be c or t
<220> FEATURE:
<221> NAME/KEY: misc_feature
<222> LOCATION: (44)..(44)
<223> OTHER INFORMATION: n can be g or a

<400> SEQUENCE: 69
atcacgcggc cgcctcacca tgaggtncnn tgntnagntn ctgngg            46

<210> SEQ ID NO 70
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (26)..(26)
<223> OTHER INFORMATION: n can be a or t
<220> FEATURE:
<221> NAME/KEY: misc_feature
<222> LOCATION: (43)..(43)
<223> OTHER INFORMATION: n can be g or t
<220> FEATURE:
<221> NAME/KEY: misc_feature
<222> LOCATION: (44)..(44)
<223> OTHER INFORMATION: n can be a or t
<220> FEATURE:
<221> NAME/KEY: misc_feature
<222> LOCATION: (45)..(45)
<223> OTHER INFORMATION: n can be c or t
<220> FEATURE:
<221> NAME/KEY: misc_feature
<222> LOCATION: (46)..(46)
<223> OTHER INFORMATION: n can be c or t
<220> FEATURE:
<221> NAME/KEY: misc_feature
<222> LOCATION: (48)..(48)
<223> OTHER INFORMATION: n can be a or t

<400> SEQUENCE: 70
atcacgcggc cgcctcacca tgggcntcaa gatggagtca cannnncngg        50

<210> SEQ ID NO 71
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (29)..(29)
<223> OTHER INFORMATION: n can be c or t
<220> FEATURE:
<221> NAME/KEY: misc_feature
<222> LOCATION: (32)..(32)
<223> OTHER INFORMATION: n can be g or t
<220> FEATURE:
<221> NAME/KEY: misc_feature
<222> LOCATION: (36)..(36)
```

<223> OTHER INFORMATION: n can be c or t
<220> FEATURE:
<221> NAME/KEY: misc_feature
<222> LOCATION: (38)..(38)
<223> OTHER INFORMATION: n can be a or c
<220> FEATURE:
<221> NAME/KEY: misc_feature
<222> LOCATION: (39)..(39)
<223> OTHER INFORMATION: n can be a or c

<400> SEQUENCE: 71
atcacgcggc cgcctcacca tgtgggganc tntttncnnt ttttcaattg          50

<210> SEQ ID NO 72
<211> LENGTH: 44
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (25)..(25)
<223> OTHER INFORMATION: n can be a or g
<220> FEATURE:
<221> NAME/KEY: misc_feature
<222> LOCATION: (29)..(29)
<223> OTHER INFORMATION: n can be a or t
<220> FEATURE:
<221> NAME/KEY: misc_feature
<222> LOCATION: (32)..(32)
<223> OTHER INFORMATION: n can be c or g

<400> SEQUENCE: 72
atcacgcggc cgcctcacca tggtntccnc anctcagttc cttg               44

<210> SEQ ID NO 73
<211> LENGTH: 47
<212> TYPE: DNA
<213> ORGANISM: Artificial Sequence
<220> FEATURE:
<223> OTHER INFORMATION: Synthetic Construct

<400> SEQUENCE: 73
atccacgcgg ccgcctcacc atgtatatat gtttgttgtc tatttct            47

<210> SEQ ID NO 74
<211> LENGTH: 47
<212> TYPE: DNA
<213> ORGANISM: Artificial Sequence
<220> FEATURE:
<223> OTHER INFORMATION: Synthetic Construct

<400> SEQUENCE: 74
atcacgcggc cgcctcacca tggaagcccc agctcagctt ctcttcc            47

<210> SEQ ID NO 75
<211> LENGTH: 34
<212> TYPE: DNA
<213> ORGANISM: Artificial Sequence
<220> FEATURE:
<223> OTHER INFORMATION: Synthetic Construct

<400> SEQUENCE: 75
cagttggtgc agcatccgta cgtttgattt ccag                          34

<210> SEQ ID NO 76
<211> LENGTH: 39
<212> TYPE: DNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (33)..(33)
<223> OTHER INFORMATION: n can be c or g

<400> SEQUENCE: 76
actagcggcc gcatgaaatg cagctgggtc atnttcttc                                    39

<210> SEQ ID NO 77
<211> LENGTH: 37
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (26)..(26)
<223> OTHER INFORMATION: n can be a or g
<220> FEATURE:
<221> NAME/KEY: misc_feature
<222> LOCATION: (33)..(33)
<223> OTHER INFORMATION: n can be c or g
<220> FEATURE:
<221> NAME/KEY: misc_feature
<222> LOCATION: (34)..(34)
<223> OTHER INFORMATION: n can be c or t

<400> SEQUENCE: 77
actagcggcc gcatgggatg gagctntatc atnntct                                      37

<210> SEQ ID NO 78
<211> LENGTH: 40
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(19)
<223> OTHER INFORMATION: n can be a or t

<400> SEQUENCE: 78
actagcggcc gcatgaagnt gtggttaaac tgggtttttt                                   40

<210> SEQ ID NO 79
<211> LENGTH: 37
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: n can be a or g
<220> FEATURE:
<221> NAME/KEY: misc_feature
<222> LOCATION: (25)..(25)
<223> OTHER INFORMATION: n can be c or t
<220> FEATURE:
<221> NAME/KEY: misc_feature
<222> LOCATION: (34)..(34)
<223> OTHER INFORMATION: n can be a or g

<400> SEQUENCE: 79
actagcggcc gcatgnactt tgggntcagc ttgnttt                                      37

<210> SEQ ID NO 80
<211> LENGTH: 42
<212> TYPE: DNA
```

```
<213> ORGANISM: Artificial Sequence
<220> FEATURE:
<223> OTHER INFORMATION: Synthetic Construct

<400> SEQUENCE: 80
actagcggcc gcatggactc caggctcaat ttagttttcc tt                            42

<210> SEQ ID NO 81
<211> LENGTH: 39
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (22)..(22)
<223> OTHER INFORMATION: n can be c or t
<220> FEATURE:
<221> NAME/KEY: misc_feature
<222> LOCATION: (24)..(24)
<223> OTHER INFORMATION: n can be g or a
<220> FEATURE:
<221> NAME/KEY: misc_feature
<222> LOCATION: (26)..(26)
<223> OTHER INFORMATION: n can be c or g
<220> FEATURE:
<221> NAME/KEY: misc_feature
<222> LOCATION: (30)..(30)
<223> OTHER INFORMATION: n can be g or a

<400> SEQUENCE: 81
actagcggcc gcatggctgt cntngngctn ctcttctgc                                39

<210> SEQ ID NO 82
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: n can be a or g
<220> FEATURE:
<221> NAME/KEY: misc_feature
<222> LOCATION: (25)..(25)
<223> OTHER INFORMATION: n can be g or t
<220> FEATURE:
<221> NAME/KEY: misc_feature
<222> LOCATION: (28)..(28)
<223> OTHER INFORMATION: n can be a or g
<220> FEATURE:
<221> NAME/KEY: misc_feature
<222> LOCATION: (34)..(34)
<223> OTHER INFORMATION: n can be c or a

<400> SEQUENCE: 82
actagcggcc gcatggnatg gagcnggntc tttntctt                                 38

<210> SEQ ID NO 83
<211> LENGTH: 35
<212> TYPE: DNA
<213> ORGANISM: Artificial Sequence
<220> FEATURE:
<223> OTHER INFORMATION: Synthetic Construct

<400> SEQUENCE: 83
actagcggcc gcatgagagt gctgattctt ttgtg                                    35

<210> SEQ ID NO 84
<211> LENGTH: 42
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: n can be a or c
<220> FEATURE:
<221> NAME/KEY: misc_feature
<222> LOCATION: (29)..(29)
<223> OTHER INFORMATION: n can be a or c

<400> SEQUENCE: 84
actagcggcc gcatggnttg ggtgtgganc ttgctattcc tg          42

<210> SEQ ID NO 85
<211> LENGTH: 39
<212> TYPE: DNA
<213> ORGANISM: Artificial Sequence
<220> FEATURE:
<223> OTHER INFORMATION: Synthetic Construct

<400> SEQUENCE: 85
actagcggcc gcatggattt tgggctgatt tttttattg             39

<210> SEQ ID NO 86
<211> LENGTH: 39
<212> TYPE: DNA
<213> ORGANISM: Artificial Sequence
<220> FEATURE:
<223> OTHER INFORMATION: Synthetic Construct

<400> SEQUENCE: 86
actagcggcc gcatgggcag acttacattc tcattcctg             39

<210> SEQ ID NO 87
<211> LENGTH: 39
<212> TYPE: DNA
<213> ORGANISM: Artificial Sequence
<220> FEATURE:
<223> OTHER INFORMATION: Synthetic Construct

<400> SEQUENCE: 87
actagcggcc gcatgatggt gttaagtctt ctgtacctg             39

<210> SEQ ID NO 88
<211> LENGTH: 31
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(20)
<223> OTHER INFORMATION: n can be a or c
<220> FEATURE:
<221> NAME/KEY: misc_feature
<222> LOCATION: (21)..(21)
<223> OTHER INFORMATION: n can be g or a
<220> FEATURE:
<221> NAME/KEY: misc_feature
<222> LOCATION: (27)..(27)
<223> OTHER INFORMATION: n can be g or a

<400> SEQUENCE: 88
gggggtgtcg tcgacgctgn ngagacngtg a                    31

<210> SEQ ID NO 89
```

<211> LENGTH: 330
<212> TYPE: PRT
<213> ORGANISM: Artificial Sequence
<220> FEATURE:
<223> OTHER INFORMATION: Synthetic Construct

<400> SEQUENCE: 89

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | | 115 | | | | | 120 | | | | | 125 | | |
| Lys | Pro | Lys | Asp | Thr | Leu | Met | Ile | Ser | Arg | Thr | Pro | Glu | Val | Thr | Cys |
| 130 | | | | | 135 | | | | | 140 | | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | | 180 | | | | | 185 | | | | | 190 | |
| His | Gln | Asp | Trp | Leu | Asn | Gly | Lys | Glu | Tyr | Lys | Cys | Lys | Val | Ser | Asn |
| | | | | 195 | | | | | 200 | | | | | 205 | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | | 260 | | | | | 265 | | | | | 270 | |
| Asn | Tyr | Lys | Thr | Thr | Pro | Pro | Val | Leu | Asp | Ser | Asp | Gly | Ser | Phe | Phe |
| | | | 275 | | | | | 280 | | | | | 285 | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

<210> SEQ ID NO 90
<211> LENGTH: 107
<212> TYPE: PRT
<213> ORGANISM: Artificial Sequence
<220> FEATURE:
<223> OTHER INFORMATION: Synthetic Construct -continued

<400> SEQUENCE: 90

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 91
<211> LENGTH: 113
<212> TYPE: PRT
<213> ORGANISM: Artificial Sequence
<220> FEATURE:
<223> OTHER INFORMATION: Synthetic Construct

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 92
<211> LENGTH: 11
<212> TYPE: PRT
<213> ORGANISM: Artificial Sequence
<220> FEATURE:
<223> OTHER INFORMATION: Synthetic Construct

<400> SEQUENCE: 92

Trp Gly Gln Gly Thr Leu Val Thr Val Ser Ser
1               5                   10

<210> SEQ ID NO 93
<211> LENGTH: 107
<212> TYPE: PRT
<213> ORGANISM: Artificial Sequence
<220> FEATURE:
<223> OTHER INFORMATION: Synthetic Construct

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 94
<211> LENGTH: 10
<212> TYPE: PRT
<213> ORGANISM: Artificial Sequence
<220> FEATURE:
<223> OTHER INFORMATION: Synthetic Construct

<400> SEQUENCE: 94

```
Phe Gly Gly Gly Thr Lys Val Glu Ile Lys
1               5                   10
```

<210> SEQ ID NO 95
<211> LENGTH: 333
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 95

| | | | | | |
|---|---|---|---|---|---|
| gacatccaga | tgacccagag | cccttccagc | ctgagcgctt | ccgtgggaga | tagggtgacc | 60 |
| atcacctgca | gggccagcga | gtccgtggag | taccacggca | ccagcctgat | gcactggtac | 120 |
| cagcagaagc | ccggcaaggc | ccccaagctg | ctgatctacg | ccgccagcaa | cgtggagagc | 180 |
| ggcgtgccta | gcagattcag | cggcagcgga | agcggcaccg | acttcaccct | gaccattagc | 240 |
| agcctgcagc | ccgaggactt | cgccacctac | tactgtcagc | agagcaggaa | ggtgccctgg | 300 |
| accttcggcc | agggcaccaa | ggtcgagatc | aag |  |  | 333 |

<210> SEQ ID NO 96
<211> LENGTH: 357
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 96

| | | | | | |
|---|---|---|---|---|---|
| gaggtgcagc | tggtggagag | cggaggagga | ctggtgcagc | ctggcggaag | cctgagactg | 60 |
| agctgcgccg | ccagcggctt | cacctttacc | gacttctaca | tgagctgggt | gaggcaggct | 120 |
| cccggcaaag | gactggagtg | ggtgggtttc | atcaggaaca | aggccaacgg | ctacaccacc | 180 |
| gagtatagcg | cctccgtgaa | gggcaggttc | accatcagca | gggacaacgc | caagaacagc | 240 |
| ctgtacctgc | agatgaacag | cctgagggcc | gaggacaccg | ccgtgtacta | ctgcgccaga | 300 |
| gtgtacggca | gcacactgca | ctactggggc | cagggcaccc | tggtgaccgt | gagcagc | 357 |

<210> SEQ ID NO 97
<211> LENGTH: 657
<212> TYPE: DNA
<213> ORGANISM: Artificial Sequence
<220> FEATURE:
<223> OTHER INFORMATION: Synthetic Construct

<400> SEQUENCE: 97

```
gacatccaga tgacccagag cccttccagc ctgagcgctt ccgtgggaga tagggtgacc    60
atcacctgca gggccagcga gtccgtggag taccacggca ccagcctgat gcactggtac   120
cagcagaagc ccggcaaggc ccccaagctg ctgatctacg ccgccagcaa cgtggagagc   180
ggcgtgccta gcagattcag cggcagcgga agcggcaccg acttcaccct gaccattagc   240
agcctgcagc ccgaggactt cgccacctac tactgtcagc agagcaggaa ggtgccctgg   300
accttcggcc agggcaccaa ggtcgagatc aagcgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca aagtctacgc ctgcgaagtc   600
acccatcagg cctgagctc gcccgtcaca aagagcttca caggggaga gtgttag      657
```

<210> SEQ ID NO 98
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 98

```
gaggtgcagc tggtggagag cggaggagga ctggtgcagc ctggcggaag cctgagactg    60
agctgcgccg ccagcggctt caccttttacc gacttctaca tgagctgggt gaggcaggct   120
cccggcaaag gactggagtg ggtgggtttc atcaggaaca aggccaacgg ctacaccacc   180
gagtatagcg cctccgtgaa gggcaggttc accatcagca gggacaacgc caagaacagc   240
ctgtacctgc agatgaacag cctgagggcc gaggacaccg ccgtgtacta ctgcgccaga   300
gtgtacggca gcacactgca ctactggggc cagggcaccc tggtgaccgt gagcagcgcg   360
tcgaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagaaagt tgagcccaaa   660
tcttgtgaca aaactcacac atgcccaccg tgcccagcac ctgaactcct ggggggaccg   720
tcagtcttcc tcttccccc aaaacccaag gacaccctca tgatctcccg gacccctgag   780
gtcacatgcg tggtggtgga cgtgagccac gaagaccctg aggtcaagtt caactggtac   840
gtggacggcg tggaggtgca taatgccaag acaaagccgc gggaggagca gtacaacagc   900
acgtaccgtg tggtcagcgt cctcaccgtc ctgcaccagg actggctgaa tggcaaggag   960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
```

```
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtcccc gggttga                                       1347
```

```
<210> SEQ ID NO 99
<211> LENGTH: 990
<212> TYPE: DNA
<213> ORGANISM: Artificial Sequence
<220> FEATURE:
<223> OTHER INFORMATION: Synthetic Construct

<400> SEQUENCE: 99
```

```
gcgtcgacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctggggggga  360 ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag gcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc cccgggttga                                    990
```

```
<210> SEQ ID NO 100
<211> LENGTH: 324
<212> TYPE: DNA
<213> ORGANISM: Artificial Sequence
<220> FEATURE:
<223> OTHER INFORMATION: Synthetic Construct

<400> SEQUENCE: 100
```

```
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca gggg gagagtg ttag                                        324
```

ANTI-CXCR5 ANTIBODIES AND COMPOSITIONS AND USES THEREOF

RELATED APPLICATIONS

This application claims priority to U.S. Ser. No. 62/593,830 filed Dec. 1, 2017, and U.S. Ser. No. 62/732,985 filed Sep. 18, 2018, the contents of each of which are incorporated herein by reference in their entirety.

SEQUENCE LISTING

The specification further incorporates by reference the Sequence Listing submitted herewith on Mar. 10, 2020. Pursuant to 37 C.F.R. § 1.52(e)(5), the Sequence Listing text file, identified as W2023-706510_SL.txt, is 112,039 bytes and was created on Mar. 10, 2020. The Sequence Listing, electronically filed herewith, does not extend beyond the scope of the specification and thus does not contain new matter.

PARTIES TO A JOINT RESEARCH STATEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are THE REGENTS OF THE UNIVERSITY OF CALIFORNIA on behalf of its SAN DIEGO CAMPUS and PFIZER INC.

FIELD

The present invention relates to antibodies, and antigen-binding fragments thereof, that specifically bind C—X—C chemokine receptor type 5 (CXCR5), and compositions, methods and uses thereof. The antibodies are fucosylated and/or afucosylated and can exhibit altered effector function.

BACKGROUND

C—X—C chemokine receptor type 5 (CXCR5), also known as CD185 or Burkitt lymphoma receptor 1 (BLR1), is a naturally occurring, G-protein-coupled receptor expressed by B cells, bona fide follicular T helper (Tfh) cells, and circulating Tfh-like cells (referred to interchangeably herein as "cTfh" and "Tfh-like" cells). CXCR5 plays an important role in the immune response and is a potential target for treating autoimmune diseases, such as systemic lupus erythematosus (SLE).

Germinal centers (GCs), a critical component of the humoral immune response, are sites where antigen-activated B cells proliferate, differentiate, and undergo somatic hypermutation and immunoglobulin (Ig) class switching of the antibodies they produce. Bona fide Tfh cells provide instructive signals to aid this process, which culminates in the production of affinity-matured antibodies. Humoral "memory" of the GC reaction is maintained by long-lived plasma cells, which sustain antibody levels, and by memory B cells which, upon re-challenge with antigen, trigger secondary GC reactions with cognate help from memory Tfh cells that lead to the production of more high-affinity plasma cells (McHeyzer-Williams et al., 2011, Nature Rev. Immunol. 12(1):24-34). Circulating Tfh-like cells (hereinafter referred to as "Tfh-like" or "cTfh") are thought to differentiate into bona fide Tfh cells upon re-encountering antigen to support these memory responses as well (Crotty et al., 2011, Annu. Rev. Immmunol. 29:621-663).

Importantly, the generation of autoreactive B cells can also arise from GC reactions, with undesired consequences. Indeed, numerous chronic, systemic autoimmune diseases, such as SLE, RA, myositis, Sjogren's syndrome, ANCA-associated vasculitis, and scleroderma, show evidence of autoreactive humoral responses. For example, many of the autoantibodies that are hallmarks of these diseases are high-affinity, somatically mutated, and Ig-switched, suggesting that they arose from autoreactive GC reactions (Vinuesa et al., 2009, Nature Rev. Immunol. 9(12):845-857). In addition, increased frequencies of circulating Tfh-like cells have been detected in the peripheral blood of patients with many of these autoimmune diseases, the levels of which often correlate with autoantibody titers and/or disease severity (Tangye et al., 2013, Nature Rev. Immunol. 13(6):412-426). Taken together, these data highlight B cells, bona fide Tfh cells, and circulating Tfh-like cells as potential therapeutic targets for many systemic autoimmune diseases.

CXCR5 is expressed by B cells, bona fide Tfh cells, and circulating Tfh-like cells and mediates their trafficking to and participation in GC reactions along a gradient of the CXCR5 ligand, CXCL13 (Vinuesa and Oyster, 2011, Immunity 35(5):671-680; Ansel et al., 1999, J. Exp. Med. 190(8): 1123-1134; Ansel et al., 2000, Nature 406(6793):309-314; Oyster et al., 1999, Curr. Top. Microbiol. Immunol. 246:87-92; Hardtke et al., 2005, Blood 106(6):1924-1931; Haynes et al., 2007, J. Immunol. 179(8):5099-5108). As such, targeting CXCR5 may have therapeutic benefit for treatment of autoimmune diseases.

In addition, targeting CXCR5 may also have therapeutic benefit in cancers characterized by the proliferation of cells expressing CXCR5, such as cancers of the pancreas, colon, bladder, T-cell leukemia, and B-cell leukemia.

SUMMARY OF THE INVENTION

This application discloses isolated antibodies, and antigen-binding fragments thereof, which specifically bind CXCR5 (C—X—C chemokine receptor type 5). In certain aspects, the antibodies, and antigen-binding fragments thereof, bind CXCR5 and decrease CXCR5 binding to CXCL13. In other aspects, the antibodies can be fucosylated, but more preferably, they are afucosylated. In certain aspects, the antibodies, and antigen-binding fragments thereof, exhibit altered effector function. In certain aspects, the antibodies, and antigen-binding fragments thereof, are afucosylated and exhibit increased antibody-dependent cellular cytotoxicity (ADCC) compared to otherwise identical but fucosylated antibodies, and antigen-binding fragments thereof.

In certain aspects, the present disclosure provides isolated antibodies, and antigen-binding fragments thereof, that specifically bind CXCR5, wherein the antibody, and antigen-binding fragment thereof, binds to an epitope comprising leucine (Leu; L) at amino acid residue number 11 (L11) according to the numbering of SEQ ID NO:32.

In another aspect, the disclosure provides isolated antibodies or antigen-binding fragments thereof, that specifically bind CXCR5, wherein the antibody, and antigen-binding fragment thereof, binds to an epitope comprising an aspartate (Asp; D) at amino acid residue number 22 according to the numbering of SEQ ID NO:32.

Those skilled in the art will recognize, or be able to ascertain using no more than routine experimentation, many equivalents to the specific embodiments of the invention described herein. Such equivalents are intended to be encompassed by the following embodiments (E).

E1. An isolated antibody or antigen-binding fragment thereof, that specifically binds C—X—C-chemokine receptor 5 (CXCR5), wherein the antibody, or antigen-binding fragment thereof, binds an epitope within the N domain of human CXCR5 (hCXCR5) or cynomolgus monkey CXCR5 (cynoCXCR5).

E2. The antibody, or antigen-binding fragment thereof, of E1, wherein the antibody, or antigen-binding fragment thereof, binds an epitope within amino acid residues 1-50 of hCXCR5 according to the numbering of the amino acid sequence of SEQ ID NO:32, or binds to an epitope within amino acid residues 1-50 of cynoCXCR5 according to the numbering of SEQ ID NO:33.

E3. The antibody, or antigen-binding fragment thereof, of any one of E1-E2, wherein the antibody, or antigen-binding fragment thereof, binds an epitope comprising leucine at amino acid residue number 11 according to the numbering of the amino acid sequence of SEQ ID NO:32.

E4. The antibody, or antigen-binding fragment thereof, of any one of E1-E3, wherein the antibody or antigen-binding fragment thereof, binds an epitope comprising aspartate at amino acid residue number 22 according to the numbering of the amino acid sequence of SEQ ID NO:32.

E5. The antibody, or antigen-binding fragment thereof, of any one of E1-E4, wherein the antibody or antigen-binding fragment thereof, binds an epitope comprising leucine at amino acid residue number 11 and aspartate at amino acid residue number 22 according to the numbering of the amino acid sequence of SEQ ID NO:32.

E6. The antibody, or antigen-binding fragment thereof, of any one of E1-E5, wherein the antibody, or antigen-binding fragment thereof, binds an epitope comprising leucine at amino acid residue number 11 according to the numbering of the amino acid sequence of SEQ ID NO:32, but does not bind hCXCR5 when said residue is not leucine.

E7. The antibody, or antigen-binding fragment thereof, of any one of E1-E6, wherein the antibody, or antigen-binding fragment thereof, binds an epitope comprising leucine at amino acid residue number 11 according to the numbering of the amino acid sequence of SEQ ID NO:32, but does not bind hCXCR5 when said residue is threonine.

E8. The antibody, or antigen-binding fragment thereof, of any one of E1-E7, wherein the antibody, or antigen-binding fragment thereof, binds an epitope comprising aspartate at amino acid residue number 22 according to the numbering of the amino acid sequence of SEQ ID NO:32, but does not bind hCXCR5 when said residue is not aspartate.

E9. The antibody, or antigen-binding fragment thereof, of any one of E1-E8, wherein the antibody, or antigen-binding fragment thereof, binds an epitope comprising aspartate at amino acid residue number 22, according to the numbering of the amino acid sequence of SEQ ID NO:32, but does not bind hCXCR5 when said residue is alanine.

E10. The antibody, or antigen-binding fragment thereof, of any one of E1-E9, wherein the antibody, or antigen-binding fragment thereof, binds an epitope comprising leucine at amino acid residue number 11 and aspartate at amino acid residue number 22, according to the numbering of the amino acid sequence of SEQ ID NO:32, but does not bind said epitope where the leucine is substituted by threonine and/or the aspartate is substituted by alanine.

E11. The antibody, or antigen-binding fragment thereof, of any one of E1-E10, wherein the antibody, or an antigen-binding fragment thereof, binds hCXCR5 expressed on human B cells with an apparent affinity of an EC50 of about 6.60 pM with a standard deviation of about plus or minus 2.33 pM.

E12. The antibody, or antigen-binding fragment thereof, of any one of E1-E11, wherein the antibody, or an antigen-binding fragment thereof, binds hCXCR5 expressed on human circulating follicular T helper-like (Tfh-like) cells with an apparent affinity of an EC50 of about 5.89 pM with a standard deviation of about plus or minus 1.40 pM.

E13. The antibody, or antigen-binding fragment thereof, of any one of E1-E12, wherein the antibody, or an antigen-binding fragment thereof, binds hCXCR5 expressed on human follicular T helper (Tfh) cells with an apparent affinity of an EC50 of about 10.6 pM.

E14. The antibody, or antigen-binding fragment thereof, of any one of E1-E13, wherein the antibody, or an antigen-binding fragment thereof, binds cynoCXCR5 expressed on cynomolgus monkey B cells with an apparent affinity of an EC50 of about 1.32 pM.

E15. The antibody, or antigen-binding fragment thereof, of any one of E1-E14, wherein the antibody, or an antigen-binding fragment thereof, binds cynoCXCR5 expressed on cynomolgus monkey Tfh-like cells with an apparent affinity of an EC50 of about 10.5 pM.

E16. The antibody, or antigen-binding fragment thereof, of any one of E1-E15, wherein the antibody, or antigen-binding fragment thereof, antagonizes CXCR5-CXCL13 signaling in a cAMP reporter assay with an EC50 of about 961 pM.

E17. The antibody, or antigen-binding fragment thereof, of any one of E1-E16, wherein the antibody, or an antigen-binding fragment thereof, exhibits ADCC activity against human B cells expressing hCXCR5 with an EC50 of about 2.01 pM with a standard deviation of about plus or minus 2.28 pM.

E18. The antibody, or antigen-binding fragment thereof, of any one of E1-E17, wherein the antibody, or an antigen-binding fragment thereof, exhibits ADCC activity against human Tfh-like cells expressing hCXCR5 with an EC50 of about 4.28 pM with a standard deviation of about plus or minus 2.88 pM.

E19. The antibody, or antigen-binding fragment thereof, of any one of E1-E18, wherein the antibody, or an antigen-binding fragment thereof, exhibits ADCC activity against human Tfh cells expressing hCXCR5 with an EC50 of about 0.11 pM.

E20. The antibody, or antigen-binding fragment thereof, of any one of E1-E19, wherein the antibody, or an antigen-binding fragment thereof, exhibits ADCC activity against cynomolgus monkey B cells expressing cynoCXCR5 with an EC50 of about 15.3 pM with a standard deviation of about plus or minus 11.7 pM.

E21. The antibody, or antigen-binding fragment thereof, of any one of E1-E20, wherein the antibody, or an antigen-binding fragment thereof, binds hCXCR5 but does not detectably bind human chemokine receptors CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR6, CXCR7, and XCR1.

E22. The antibody, or antigen-binding fragment thereof, of any one of E1-E21, wherein the antibody, or an antigen-binding fragment thereof, depletes B cells in the peripheral blood.

E23. The antibody, or antigen-binding fragment thereof, of E22, wherein the depletion of B cells in the peripheral blood is reversible.

E24. The antibody, or antigen-binding fragment thereof, of any one of E1-E23, wherein the antibody, or an antigen-binding fragment thereof, depletes Tfh-like cells in the peripheral blood.

E25. The antibody, or antigen-binding fragment thereof, of any one of E1-E24, wherein the antibody, or an antigen-binding fragment thereof, depletes Tfh cells in the spleen.

E26. The antibody, or antigen-binding fragment thereof, of any one of E1-E24, wherein the antibody, or an antigen-binding fragment thereof, impairs a humoral immune memory response.

E27. The antibody, or antigen-binding fragment thereof, of E26, wherein the impaired humoral immune memory response is to tetatus toxoid in cynomolgus monkeys.

E28. The antibody, or antigen-binding fragment thereof, of any one of E1-E27, wherein the antibody, or an antigen-binding fragment thereof, inhibits binding of CXCR5 to CXCL13.

E29. The antibody, or antigen-binding fragment thereof, of any one of E1-E28, wherein the antibody, or an antigen-binding fragment thereof, inhibits CXCL13 inhibition of cAMP production in a cell otherwise triggered by forskolin leading to an increase in cAMP level compared to the level of cAMP in the absence of the antibody, or antigen-binding fragment thereof.

E30. The antibody, or antigen-binding fragment thereof, of any one of E1-E29, wherein the antibody, or an antigen-binding fragment thereof, inhibits CXCL13 inhibition of cAMP production with an EC50 of about 961 pM.

E31. The antibody, or antigen-binding fragment thereof, of E30, wherein the maximal inhibition of CXCL13 inhibition is at least about 60%, 70%, or 80%.

E32. The antibody, or antigen-binding fragment thereof, of any one of E1-E31, wherein the antibody, or an antigen-binding fragment thereof, binds CXCR5-expressing human B cells (e.g., CXCR5+ human B cells) with an apparent affinity of an EC50 of less than about 26 pM, but does not bind cells expressing CXCR5 mouse, rat, or rabbit orthologs.

E33. The antibody, or antigen-binding fragment thereof, of any one of E1-E32, wherein the antibody, or an antigen-binding fragment thereof, triggers ADCC of CXCR5-expressing cells in human donor and cynomolgus peripheral blood mononuclear cells (PBMCs) and human donor tonsillar mononuclear cells (TMC).

E34. An isolated antibody that specifically binds hCXCR5 and competes with the antibody, or antigen-binding fragment thereof, of any one of E1-E33.

E35. The antibody, or antigen-binding fragment thereof, of any one of E1-E34, wherein the antibody, or an antigen-binding fragment thereof, binds CXCR5+ human B cells with an apparent affinity of an EC50 of less than about 26 pM, but does not substantially bind cells expressing CXCR5 orthologs. In some embodiments, the antibody, or an antigen-binding fragment thereof, shows undetectable binding to cells expressing CXCR5 orthologs, e.g., based on any of the assays described herein; or binds to cells expressing CXCR5 orthologs with an apparent affinity of an EC50 of at least 10,000-fold greater than binding to hCXCR5.

E36. The antibody, or antigen-binding fragment thereof, of any one of E1-E35, wherein the antibody, or an antigen-binding fragment thereof, comprises a CDR-L1 comprising the amino acid sequence of SEQ ID NO:2; a CDR-L2 comprising the amino acid sequence of SEQ ID NO:3; a CDR-L3 comprising the amino acid sequence of SEQ ID NO:4; a CDR-H1 comprising the amino acid sequence of SEQ ID NO:7; a CDR-H2 comprising the amino acid sequence of SEQ ID NO:8; and a CDR-H3 comprising the amino acid sequence of SEQ ID NO:9.

E37. The antibody, or antigen-binding fragment thereof, of any one of E1-E36, wherein the antibody, or an antigen-binding fragment thereof, comprises a CDR-L1 comprising the amino acid sequence of SEQ ID NO:2; a CDR-L2 comprising the amino acid sequence of SEQ ID NO:3; a CDR-L3 comprising the amino acid sequence of SEQ ID NO:4; a CDR-H1 comprising the amino acid sequence of SEQ ID NO:7; a CDR-H2 comprising the amino acid sequence of SEQ ID NO:8; and a CDR-H3 comprising the amino acid sequence of SEQ ID NO:11.

E38. The antibody, or antigen-binding fragment thereof, of any one of E1-E37, wherein the antibody, or an antigen-binding fragment thereof, comprises a CDR-L1 the amino acid sequence of SEQ ID NO:14; a CDR-L2 comprising the amino acid sequence of SEQ ID NO:15; a CDR-L3 comprising the amino acid sequence of SEQ ID NO:16; a CDR-H1 comprising the amino acid sequence of SEQ ID NO:19; a CDR-H2 comprising the amino acid sequence of SEQ ID NO:20; and a CDR-H3 comprising the amino acid sequence of SEQ ID NO:21.

E39. The antibody, or antigen-binding fragment thereof, of any one of E1-E38, wherein the antibody, or an antigen-binding fragment thereof, comprises a VL comprising an amino acid sequence selected from the group consisting of the amino acid sequence of SEQ ID NOs:1, 5, 13, 35, 37, 48-51, 39 and 58-62, and a VH comprising an amino acid sequence selected from the group consisting of the amino acid sequence of SEQ ID NOs:6, 10, 12, 17, 18, 36, 40, 53-57 and 63.

E40. The antibody, or antigen-binding fragment thereof, of any one of E1-E39, wherein the antibody, or an antigen-binding fragment thereof, comprises a VL comprising an amino acid sequence selected from the group consisting of the amino acid sequence of SEQ ID NOs:1, 5, 13, 35, 37, 48-51, 39 and 58-62, and a VH comprising an amino acid sequence selected from the group consisting of the amino acid sequence of SEQ ID NOs:6, 10, 12, 17, 18, 36, 40, 53-57 and 63.

E41. The antibody, or antigen-binding fragment thereof, of any one of E1-E40, wherein the antibody, or an antigen-binding fragment thereof, comprises a VL comprising an amino acid sequence encoded by the insert of the plasmid deposited with the ATCC and having Accession Number PTA-124324 and a VH comprising an amino acid sequence encoded by the insert of the plasmid deposited with the ATCC having Accession Number PTA-124323.

E42. The antibody, or antigen-binding fragment thereof, of any one of E1-E35 and E39-E40, wherein the antibody, or an antigen-binding fragment thereof, comprises a VL comprising the amino acid sequence of SEQ ID NO:13, and a VH comprising the amino acid sequence of SEQ ID NO:17.

E43. The antibody, or antigen-binding fragment thereof, of any one of E1-E35 and E38-E40, wherein the antibody, or an antigen-binding fragment thereof, comprises a VL comprising the amino acid sequence of SEQ ID NO:13, and a VH comprising the amino acid sequence of SEQ ID NO:18.

E44. The antibody, or antigen-binding fragment thereof, of any one of E1-E35 and E38-E40, wherein the antibody, or an antigen-binding fragment thereof, comprises a VL comprising the amino acid sequence of SEQ ID NO:37, and a VH comprising the amino acid sequence of SEQ ID NO:38.

E45. The antibody, or antigen-binding fragment thereof, of any one of E1-E36 and E39-E41, wherein the antibody, or an antigen-binding fragment thereof, comprises a VL comprising the amino acid sequence of SEQ ID NO:35, and a VH comprising the amino acid sequence of SEQ ID NO:36.

E46. The antibody, or antigen-binding fragment thereof, of any one of E1-E36 and E39-E41, wherein the antibody, or an antigen-binding fragment thereof, comprises a VL comprising the amino acid sequence of SEQ ID NO:47, and a VH comprising the amino acid sequence of SEQ ID NO:52.

E47. The antibody, or antigen-binding fragment thereof, of any one of E1-E36 and E39-E41, wherein the antibody, or an antigen-binding fragment thereof, comprises a VL comprising the amino acid sequence of SEQ ID NO:5, and a VH comprising the amino acid sequence of SEQ ID NO:6.

E48. The antibody, or antigen-binding fragment thereof, of any one of E1-E36 and E39-E41, wherein the antibody, or an antigen-binding fragment thereof, comprises a VL comprising the amino acid sequence of SEQ ID NO:5, and a VH comprising the amino acid sequence of SEQ ID NO:10.

E49. The antibody, or antigen-binding fragment thereof, of any one of E1-E36 and E39-E41, wherein the antibody, or an antigen-binding fragment thereof, comprises a VL comprising the amino acid sequence of SEQ ID NO:1, and a VH comprising the amino acid sequence of SEQ ID NO:6.

E50. The antibody, or antigen-binding fragment thereof, of any one of E1-E35, E37, and E39-E41, wherein the antibody, or an antigen-binding fragment thereof, comprises a VL comprising the amino acid sequence of SEQ ID NO:1, and a VH comprising the amino acid sequence of SEQ ID NO:12.

E51. The antibody, or antigen-binding fragment thereof, of any one of E1-E35, E37, and E39-E41, wherein the antibody, or an antigen-binding fragment thereof, comprises a VL comprising the amino acid sequence of SEQ ID NO:39, and a VH comprising the amino acid sequence of SEQ ID NO:40.

E52. The antibody, or antigen-binding fragment thereof, of any one of E1-E35, E37, and E39-E41, wherein the antibody, or an antigen-binding fragment thereof, comprises a LC comprising the amino acid sequence of SEQ ID NO:22, and a HC comprising the amino acid sequence of SEQ ID NO:23.

E53. The antibody, or antigen-binding fragment thereof, of any one of E1-E35 and E38-E40, wherein the antibody, or an antigen-binding fragment thereof, comprises a LC comprising the amino acid sequence of SEQ ID NO:24, and a HC comprising the amino acid sequence of SEQ ID NO:25.

E54. The antibody, or antigen-binding fragment thereof, of any one of E1-E35, E37, and E39-E41, wherein the antibody, or an antigen-binding fragment thereof, comprises a LC comprising the amino acid sequence of SEQ ID NO:26, and a HC comprising the amino acid sequence of SEQ ID NO:27.

E55. The antibody, or antigen-binding fragment thereof, of any one of E1-E35, E37, and E39-E41, wherein the antibody, or an antigen-binding fragment thereof, comprises a LC comprising the amino acid sequence of SEQ ID NO:28, and a HC comprising the amino acid sequence of SEQ ID NO:29.

E56. The antibody, or antigen-binding fragment thereof, of any one of E1-E35, E37, and E39-E41, wherein the antibody, or an antigen-binding fragment thereof, comprises a VL encoded by the nucleic acid sequence of SEQ ID NO:95, and a VH encoded by the nucleic acid sequence of SEQ ID NO:96.

E57. The antibody, or antigen-binding fragment thereof, of any one of E1-E35, E37, and E39-E41, wherein the antibody, or an antigen-binding fragment thereof, comprises a LC encoded by the nucleic acid sequence of SEQ ID NO:97, and a HC encoded by the nucleic acid sequence of SEQ ID NO:98.

E58. The antibody, or antigen-binding fragment thereof, of any one of E1-E57, wherein the antibody, or an antigen-binding fragment thereof, comprises a VL framework sequence and a VH framework sequence, and wherein one or both of the VL framework sequence or VH framework sequence is at least 90%, 91%, 92%, 93%, 94%, 95%, 96%, 97%, 98% or 99% identical to the human germline sequence form which it was derived and wherein the human germline VL sequence from which the VL framework sequence is derived is selected from the group consisting of DPK9, DPK12, DPK18, DPK24, HK102_V1, DPK1, DPK8, DPK3, DPK21, Vg_38K, DPK22, DPK15, DPL16, DPL8, V1-22, Vλ consensus, Vλ1 consensus, Vλ3 consensus, Vκ consensus, Vκ1 consensus, Vκ2 consensus and Vκ3, and wherein the human germline VH sequence from which the VH framework sequence is derived is selected from the group consisting of DP54, DP47, DP50, DP31, DP46, DP71, DP75, DP10, DP7, DP49, DP51, DP38, DP79, DP78, DP73, VH3, VH5, VH1 and VH4.

E59. The antibody, or antigen-binding fragment thereof, of any one of E1-E58, wherein the antibody, or an antigen-binding fragment thereof, is afucosylated.

E60. The antibody, or antigen-binding fragment thereof, of E59, wherein the antibody, or an antigen-binding fragment thereof, exhibits enhanced ADCC.

E61. An isolated antibody, or antigen-binding fragment thereof, comprising the CDR-H1, CDR-H2, and CDR-H3 sequence of a VH comprising an amino acid sequence selected from the group consisting of the amino acid sequence of SEQ ID NOs:6, 7, 8, 25, 17, 18, 23, 27, 52, 53, 54, 55, 56, 57 and 63.

E62. An isolated antibody, or antigen-binding fragment thereof, comprising the CDR-L1, CDR-L2, and CDR-L3 sequence of a VL comprising an amino acid sequence selected from the group consisting of the amino acid sequence of SEQ ID NOs:1, 2, 13, 22, 24, 26, 47, 48, 49, 50, 51, 58, 59, 60, 61 and 62.

E63. The antibody, or antigen-binding fragment thereof, of any one of E1-E62, comprising the CDR-H1, CDR-H2, and CDR-H3 sequences as set forth in the amino acid sequence of SEQ ID NO:6.

E64. The antibody, or antigen-binding fragment thereof, of any one of E1-E62, comprising the CDR-L1, CDR-L2, and CDR-L3 sequences of the amino acid sequence of SEQ ID NO:1.

E65. The antibody, or antigen-binding fragment thereof, of any one of E1-E64, comprising one or more of the following amino acid substitutions:
  1, 2, 3, 4, 5, or 6 substitutions in CDR-L1 to the corresponding residue of a human germline VL sequence,
  1, 2, 3, 4, or 5 substitutions in CDR-L2 to the corresponding residue of a human VL germline sequence,
  1, 2, 3, 4, 5, or 6 substitutions in CDR L3 to the corresponding residue of a human germline VL sequence,
  1, 2, 3, 4, 5, or 6 substitutions substitution in CDR-H1 to the corresponding residue of a human germline VH sequence,
  1, 2, 3, 4, 5, 6, 7, or 8 substitutions in CDR H2 to the corresponding residue of a human germline VH sequence,
  wherein the human germline VL sequence is selected from the group consisting of DPK9, DPK12, DPK18, DPK24, HK102_V1, DPK1, DPK8, DPK3, DPK21, Vg_38K, DPK22, DPK15, DPL16, DPL8, V1-22, Vκ1 consensus, Vκ2 consensus and Vκ3 consensus, and the human germline VH is selected from the group consisting of DP54, DP47, DP50, DP31, DP46, DP71, DP75, DP10, DP7, DP49, DP51, DP38, DP79, DP78, DP73, VH3, VH5, VH1, and VH4.

E66. The antibody, or antigen-binding fragment thereof, of any one of E61-E65, comprising a VH framework sequence derived from a human germline VH sequence selected from the group consisting of DP54, DP47, DP50, DP31, DP46, DP71, DP75, DP10, DP7, DP49, DP51, DP38, DP79, DP78, DP73, VH3, VH5, VH1, and VH4.

E67. The antibody, or antigen-binding fragment thereof, of any one of E61-E66, comprising a framework VH sequence derived from a human VH3 germline sequence.

E68. The antibody, or antigen-binding fragment thereof, of any one of E61-E67, comprising a framework VH sequence derived from a human germline VH sequence selected from the group consisting of DP54, DP47, DP50, DP31, DP46, DP49, and DP51.

E69. The antibody, or antigen-binding fragment thereof, of any one of E61-E68, comprising a framework VH sequence derived from a human germline VH sequence selected from the group consisting of DP54, DP47, DP50, and DP31.

E70. The antibody, or antigen-binding fragment thereof, of any one of E61-E69, comprising a VH framework sequence derived from a human germline DP54 sequence.

E71. The antibody, or antigen-binding fragment thereof, of any one of E61-E70, comprising a VL framework sequence derived from a human germline VL sequence selected from the group consisting of DPK9, DPK12, DPK18, DPK24, HK102_V1, DPK1, DPK8, DPK3, DPK21, Vg_38K, DPK22, DPK15, DPL16, DPL8, V1-22, Vκ consensus, Vκ1 consensus, Vκ2 consensus, and Vκ3 consensus.

E72. The antibody, or antigen-binding fragment thereof, of any one of E61-E71, comprising a VL framework sequence derived from a human germline VL sequence selected from the group consisting of DPK9, DPK12, DPK18, DPK24, HK102_V1, DPK1, DPK8, DPK3, DPK21, Vg_38K, DPK22, DPK15, Vκ consensus, Vκ1 consensus, Vκ2 consensus, and Vκ3.

E73. The antibody, or antigen-binding fragment thereof, of any one of E61-E72, comprising a VL framework sequence derived from a human germline Vκ1 sequence.

E74. The antibody, or antigen-binding fragment thereof, of any one of E61-E73, comprising a VL framework sequence derived from a human germline VL sequence selected from the group consisting of DPK9, HK102_V1, DPK1, and DPK8.

E75. The antibody, or antigen-binding fragment thereof, of any one of E61-E74, comprising a VL framework sequence derived from a human germline DPK9 sequence.

E76. The antibody, or antigen-binding fragment thereof, of any one of E61-E75, comprising a VL framework sequence and a VH framework sequence, and wherein one or both of the VL framework sequence or VH framework sequence is at least 90% identical to the human germline sequence from which it was derived.

E77. The antibody, or antigen-binding fragment thereof, of any one of E61-E76, comprising a VL framework sequence and a VH framework sequence, and wherein one or both of the VL framework sequence or VH framework sequence is at least 66%, 76%, 80%, 90%, 91%, 92%, 93%, 94%, 95%, 96%, 97%, 98%, or 99% identical to the human germline sequence from which it was derived.

E78. The antibody, or antigen-binding fragment thereof, of any one of E61-E77, comprising a VL framework sequence and a VH framework sequence, and wherein one or both of the VL framework sequence or VH framework sequence is identical to the human germline sequence from which it was derived.

E79. The antibody, or antigen-binding fragment thereof, of any one of E61-E78, comprising a VH comprising an amino acid sequence at least 90% identical to SEQ ID NO:6.

E80. The antibody, or antigen-binding fragment thereof, of any one of E61-E79, comprising a VH comprising an amino acid sequence at least 92% identical to SEQ ID NO:6.

E81. The antibody, or antigen-binding fragment thereof, of any one of E61-E80, comprising a VH comprising the amino acid sequence of SEQ ID NO:6.

E82. The antibody, or antigen-binding fragment thereof, of any one of E61-E81, comprising a VL comprising an amino acid sequence at least 66% identical to SEQ ID NO:1.

E83. The antibody, or antigen-binding fragment thereof, of any one of E61-E82, comprising a VL comprising an amino acid sequence at least 66%, 76%, 80%, 91%, 92%, 93%, 94%, 95%, 96%, 97%, 98%, or 99%, identical to SEQ ID NO:1.

E84. The antibody, or antigen-binding fragment thereof, of any one of E61-E83, comprising a VL comprising the amino acid sequence of SEQ ID NO:1.

E85. The antibody, or antigen-binding fragment thereof, of any one of E1-E84, comprising an Fc domain.

E86. The antibody, or antigen-binding fragment thereof, of E85, wherein the Fc domain is the Fc domain of an IgA (for example IgA1 or IgA2), IgD, IgE, IgM, or IgG (for example IgG1, IgG2, IgG3, or IgG4).

E87. The antibody, or antigen-binding fragment thereof, of E86 wherein the Fc domain is the Fc domain of an IgG.

E88. The antibody, or antigen-binding fragment thereof, of E87, wherein the IgG is selected from the group consisting of IgG1, IgG2, IgG3, or IgG4.

E89. The antibody, or antigen-binding fragment thereof, of E88, wherein the IgG is IgG1.

E90. The antibody, or antigen-binding fragment thereof, of any one of E1-E89, comprising a heavy chain comprising an amino acid sequence at least 90% identical to SEQ ID NO:29.

E91. The antibody, or antigen-binding fragment thereof, of any one of E1-E89, comprising a heavy chain comprising an amino acid sequence at least 91%, 92%, 93%, 94%, 95%, 96%, 97%, 98%, or 99%, identical to SEQ ID NO:29.

E92. The antibody, or antigen-binding fragment thereof, of any one of E1-E89, comprising a heavy chain comprising the amino acid sequence of SEQ ID NO:29.

E93. The antibody, or antigen-binding fragment thereof, of any one of E1-E93, comprising a LC comprising an amino acid sequence at least 90% identical to SEQ ID NO:28.

E94. The antibody, or antigen-binding fragment thereof, of any one of E1-E93, comprising a LC comprising an amino acid sequence at least 91%, 92%, 93%, 94%, 95%, 96%, 97%, 98%, or 99%, identical to SEQ ID NO:28.

E95. The antibody, or antigen-binding fragment thereof, of any one of E1-E94, comprising a LC comprising the amino acid sequence of SEQ ID NO:28.

E96. An isolated antibody, or antigen-binding fragment thereof, comprising the VH sequence encoded by the insert of plasmid deposited at the ATCC and having ATCC Accession No. PTA-124323.

E97. An isolated antibody, or antigen-binding fragment thereof, comprising the VL sequence encoded by the insert of the plasmid deposited at the ATCC and having ATCC Accession No. PTA-124324.

E98. An antibody, or antigen-binding fragment thereof, that competes for binding to human CXCR5 with one or more of mouse 11G2, chimeric 11G2, h11G2 VH (XC152)/VL (XC151), h11G2 VH (XC152)NL (XC153), h11G2 VH (XC152)NL (XC154), h11G2 VH (XC152)NL (XC346), h11G2 VH (XC152)/VL (XC347), h11G2 VH (XC152)/VL (XC348), h11G2 VH (XC152)/VL (XC349), h11G2 VH (XC155)/VL (XC151), h11G2 VH (XC155)NL (XC153), h11G2 VH (XC155)/VL (XC154), h11G2 VH (XC155)NL (XC346), h11G2 VH (XC155)NL (XC347), h11G2 VH (XC155)NL (XC3484), h11G2 VH (XC155) NL (XC349), h11G2 VH (XC156)/VL (XC151), h11G2 VH (XC156)/VL (XC153), h11G2 VH (XC156)/VL (XC154), h11G2 VH (XC156)/VL (XC346), h11G2 VH (XC156)/VL (XC347), h11G2 VH (XC156)NL (XC348), h11G2 VH (XC156)/VL (XC349), h11G2 VH (XC157) NL (XC151), h11G2 VH (XC157)NL (XC153), h11G2 VH (XC157)NL (XC154), h11G2 VH (XC157)NL (XC346), h11G2 VH (XC157)/VL (XC347), h11G2 VH (XC157)/VL (XC348), h11G2 VH (XC157)/VL (XC349), h11G2 VH (XC350)/VL (XC151), h11G2 VH (XC350)/VL (XC153), h11G2 VH (XC350)/VL (XC154), h11G2 VH (XC350)/VL (XC346), h11G2 VH (XC350)/VL (XC347), h11G2 VH (XC350)/VL (XC348), h11G2 VH (XC350)/VL (XC349), h11G2 VH (XC351)/VL (XC151), h11G2 VH (XC351)/VL (XC153), h11G2 VH (XC351)/VL (XC154), h11G2 VH (XC351)/VL (XC346), h11G2 VH (XC351)/VL (XC347), h11G2 VH (XC351)/VL (XC348), and h11G2 VH (XC351)/VL (XC349), h11G2 VH (XC352)/VL (XC151), h11G2 VH (XC352)/VL (XC153), h11G2 VH (XC352)/VL (XC154), h11G2 VH (XC352)/VL (XC346), h11G2 VH (XC352)/VL (XC347), h11G2 VH (XC352)/VL (XC348), h11G2 VH (XC352)/VL (XC349), h11G2 VH (XC353)/VL (XC151), h11G2 VH (XC353)/VL (XC153), h11G2 VH (XC353)/VL (XC154), h11G2 VH (XC353)/VL (XC346), h11G2 VH (XC353)/VL (XC347), h11G2 VH (XC353)/VL (XC348), h11G2 VH (XC353)/VL (XC349), h11G2 VH (XC354)/ VL (XC151), h11G2 VH (XC354)/VL (XC153), h11G2 VH (XC354)/VL (XC154), h11G2 VH (XC354)/VL (XC346), h11G2 VH (XC354)/VL (XC347), h11G2 VH (XC354)/VL (XC348), h11G2 VH (XC354)/VL (XC349), mouse 41A10, chimeric 41A10, h41A10 VH (XC147)/ VL (XC142), h41A10 VH (XC147)/VL (XC143), h41A10 VH (XC147)/VL (XC144), h41A10 VH (XC147)/VL (XC145), h41A10 VH (XC147)/VL (XC146), h41A10 VH (XC147)/VL (XC149), h41A10 VH (XC148)/VL (XC142), h41A10 VH (XC148)/VL (XC143), h41A10 VH (XC148)/VL (XC144), h41A10 VH (XC148)/VL (XC145), h41A10 VH (XC148)/VL (XC146), h41A10 VH (XC148)/VL (XC149), h41A10 VH (XC150)/VL (XC142), h41A10 VH (XC150)/VL (XC143), h41A10 VH (XC150)/VL (XC144), h41A10 VH (XC150)/VL (XC145), h41A10 VH (XC150)/VL (XC146), h41A10 VH (XC150)/VL (XC149), mouse 5H7, and chimeric 5H7.

E99. An antibody, or antigen-binding fragment thereof, that competes for binding to human CXCR5 with CXCL13 with the antibody of any one of E1-E98.

E100. The antibody, or antigen-binding fragment thereof, of any one of E1-E99, wherein the antibody or antigen-binding fragment is an Fc fusion protein, a monobody, a maxibody, a bifunctional antibody, an scFab, an scFv, a peptibody.

E101. The antibody, or antigen-binding fragment thereof, of E1-E100, wherein the antibody, or antigen-binding fragment thereof, binds human CXCR5 with a $K_D$ about or less than a value selected from the group consisting of about 10 nM, SnM, 2 nM, 1 nM, 900 pM, 800 pM, 700 pM, 600 pM, 500 pM, 400 pM, 300 pM, 250 pM, 200 pM, 150 pM, 100 pM, 50 pM, 40 pM, 30 pM, 25 pM, 20 pM, 15 pM, 10 pM, 5 pM, and 1 pM.

E102. The antibody, or antigen-binding fragment thereof, of E1-E101, wherein the antibody, or antigen-binding fragment thereof, binds cynomolgus monkey CXCR5 with a $K_D$ about or less than a value selected from the group consisting of about 10 nM, 5 nM, 2 nM, 1 nM, 900 pM, 800 pM, 700 pM, 600 pM, 500 pM, 400 pM, 300 pM, 250 pM, 200 pM, 150 pM, 100 pM, 50 pM, 40 pM, 30 pM, 25 pM, 20 pM, 15 pM, 13 pM, 10 pM, 5 pM, and 1 pM.

E103. The antibody, or antigen-binding fragment thereof, of E1-E102, wherein the binding KD of the antibody or antigen-binding fragment to cynomolgus CXCR5 is within 1 order of magnitude of the binding $K_D$ of the antibody, or antigen-binding fragment thereof, to human CXCR5.

E104. The antibody, or antigen-binding fragment thereof, of E1-E103, wherein the ratio of binding $K_D$ of the antibody or antigen binding fragment to human CXCR5 compared with the binding to cynomolgus CXCR5 is between 5:1 and 1:5.

E105. The antibody, or antigen-binding fragment thereof, of E1-E104, wherein the ratio of binding $K_D$ of the antibody or antigen binding fragment to human CXCR5 compared with the binding to cynomolgus CXCR5 is between 2:1 and 1:2.

E106. The antibody, or antigen-binding fragment thereof, of E1-E105, wherein the ratio of binding $K_D$ of the antibody or antigen binding fragment to cynomologous CXCR5 compared with the binding to human CXCR5 is within a range whose lower value is selected from the group consisting of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, and 6.2, and whose upper value is selected from the group consisting of 1.4, 1.5, 1.6, 1.7, 1.8, 1.9, 2.0, 2.1, 2.2, 2.3, 2.4, 2.5, 2.6, 2.7, 2.8, 2.9, 3.0 3.1, 3.2, 3.3, 3.4, 3.5, 3.6, 3.7, 3.8, 3.9, 4.0, 4.1, 4.2, 4.3, 4.4, 4.5, 6.2, 9, 9.2, and 10.

E107. The antibody, or antigen-binding fragment thereof, of E1-E106, wherein the ratio of binding $K_D$ of the antibody or antigen binding fragment to cynomologous CXCR5 of SEQ ID NO:33 compared with the binding to human CXCR5 of SEQ ID NO:32 is between about 1.0 and about 10.0.

E108. The antibody, or antigen-binding fragment thereof, of any one of E1-107, wherein the predicted half life in human ranges from about one (1) day, to twenty-one (21) days.

E109. The antibody, or antigen-binding fragment thereof, of any one of E1-108, wherein the predicted half life in human is about seventeen (17) days.

E110. An antibody, or antigen-binding fragment thereof, comprising the CDRs of an antibody, or antigen-binding fragment thereof, selected from the group consisting of mouse 11G2 VH, mouse 11G2 VL, chimeric 11G2 VH, chimeric 11G2 VL, humanized 11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), h11G2 VH (XC354), h11G2 VL (XC151), h11G2 VL (XC153), h11G2 VL (XC154), h11G2 VL (XC346), h11G2 VL (XC347), h11G2 VL (XC348), h11G2 VL (XC349), mouse 41A10 VH, mouse 41A10 VL, chimeric 41A10 VH, chimeric 41A10 VL, humanized 41A10 VH (XC147), h41A10 VH (XC148), h41A10 VH (XC150), h41A10 VL (XC142), h41A10 VL (XC143), h41A10 VL (XC144), h41A10 VL (XC145), h41A10 VL (XC146), h41A10 VL (XC149), mouse 5H7 VH, mouse 5H7 VL, chimeric 5H7 VH, and chimeric 5H7 VL.

E111. An antibody, or antigen-binding fragment thereof, comprising a VL and a VH of an antibody, or antigen-binding fragment thereof, selected from the group consisting of mouse 11G2 VH, mouse 11G2 VL, chimeric 11G2 VH, chimeric 11G2 VL, h11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), h11G2 VH (XC354), h11G2 VL (XC151), h11G2 VL (XC153), h11G2 VL (XC154), h11G2 VL (XC346), h11G2 VL (XC347), h11G2 VL (XC348), h11G2 VL (XC349), mouse 41A10 VH, mouse 41A10 VL, chimeric 41A10 VH, chimeric 41A10 VL, humanized 41A10 VH (XC147), h41A10 VH (XC148), h41A10 VH (XC150), h41A10 VL (XC142), h41A10 VL (XC143), h41A10 VL (XC144), h41A10 VL (XC145), h41A10 VL (XC146), h41A10 VL (XC149), mouse 5H7 VH, mouse 5H7 VL, chimeric 5H7 VH, and chimeric 5H7 VL.

E112. An antibody, or antigen-binding fragment thereof, selected from the group consisting of
  a. an antibody comprising a mouse 11G2 VH and mouse 11G2 VL;
  b. an antibody comprising a chimeric 11G2 VH and chimeric 11G2 VL;
  c. an antibody comprising a humanized 11G2 VH (XC152) and a VL selected from the group consisting of mouse 11G2 VL, chimeric 11G2 VL, h11G2 VL (XC151), h11G2 VL (XC153), h11G2 VL (XC154), h11G2 VL (XC346), h11G2 VL (XC347), h11G2 VL (XC348), and h11G2 VL (XC349);
  d. an antibody comprising a humanized 11G2 VH (XC155), and a VL selected from the group consisting of mouse 11G2 VL, chimeric 11G2 VL, h11G2 VL (XC151), h11G2 VL (XC153), h11G2 VL (XC154), h11G2 VL (XC346), h11G2 VL (XC347), h11G2 VL (XC348), and h11G2 VL (XC349);
  e. an antibody comprising a humanized 11G2 VH (XC156), and a VL selected from the group consisting of mouse 11G2 VL, chimeric 11G2 VL, h11G2 VL (XC151), h11G2 VL (XC153), h11G2 VL (XC154), h11G2 VL (XC346), h11G2 VL (XC347), h11G2 VL (XC348), and h11G2 VL (XC349);
  f. an antibody comprising a humanized 11G2 VH (XC157), and a VL selected from the group consisting of mouse 11G2 VL, chimeric 11G2 VL, h11G2 VL (XC151), h11G2 VL (XC153), h11G2 VL (XC154), h11G2 VL (XC346), h11G2 VL (XC347), h11G2 VL (XC348), and h11G2 VL (XC349);
  g. an antibody comprising a humanized 11G2 VH (XC350), and a VL selected from the group consisting of mouse 11G2 VL, chimeric 11G2 VL, h11G2 VL (XC151), h11G2 VL (XC153), h11G2 VL (XC154), h11G2 VL (XC346), h11G2 VL (XC347), h11G2 VL (XC348), and h11G2 VL (XC349);
  h. an antibody comprising a h11G2 VH (XC351), and a VL selected from the group consisting of mouse 11G2 VL, chimeric 11G2 VL, h11G2 VL (XC151), h11G2 VL (XC153), h11G2 VL (XC154), h11G2 VL (XC346), h11G2 VL (XC347), h11G2 VL (XC348), and h11G2 VL (XC349);
  i. an antibody comprising a h11G2 VH (XC352), and a VL selected from the group consisting of mouse 11G2 VL, chimeric 11G2 VL, h11G2 VL (XC151), h11G2 VL (XC153), h11G2 VL (XC154), h11G2 VL (XC346), h11G2 VL (XC347), h11G2 VL (XC348), and h11G2 VL (XC349);
  j. an antibody comprising a h11G2 VH (XC353), and a VL selected from the group consisting of mouse 11G2 VL, chimeric 11G2 VL, h11G2 VL (XC151), h11G2 VL (XC153), h11G2 VL (XC154), h11G2 VL (XC346), h11G2 VL (XC347), h11G2 VL (XC348), and h11G2 VL (XC349);
  k. an antibody comprising a h11G2 VH (XC354), and a VL selected from the group consisting of mouse 11G2 VL, chimeric 11G2 VL, h11G2 VL (XC151), h11G2 VL (XC153), h11G2 VL (XC154), h11G2 VL (XC346), h11G2 VL (XC347), h11G2 VL (XC348), and h11G2 VL (XC349);
  l. an antibody comprising a h11G2 VL (XC151), and a VH selected from the group consisting of mouse 11G2 VH, chimeric 11G2 VH, h11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), and h11G2 VH (XC354);
  m. an antibody comprising a h11G2 VL (XC153), and a VH selected from the group consisting of mouse 11G2 VH, chimeric 11G2 VH, h11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), and h11G2 VH (XC354);
  n. an antibody comprising a h11G2 VL (XC154), and a VH selected from the group consisting of mouse 11G2 VH, chimeric 11G2 VH, h11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), and h11G2 VH (XC354);

o. an antibody comprising a h11G2 VL (XC346), and a VH selected from the group consisting of mouse 11G2 VH, chimeric 11G2 VH, h11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), and h11G2 VH (XC354);
p. an antibody comprising a h11G2 VL (XC347), and a VH selected from the group consisting of mouse 11G2 VH, chimeric 11G2 VH, h11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), and h11G2 VH (XC354);
q. an antibody comprising a h11G2 VL (XC348), and a VH selected from the group consisting of mouse 11G2 VH, chimeric 11G2 VH, h11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), and h11G2 VH (XC354);
r. an antibody comprising a h11G2 VL (XC349), and a VH selected from the group consisting of mouse 11G2 VH, chimeric 11G2 VH, h11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), and h11G2 VH (XC354);
s. an antibody comprising a mouse 41A10 VH, and a VL selected from the group consisting of mouse 41A10 VL, chimeric 41A10 VL, h41A10 VL (XC142), h41A10 VL (XC143), h41A10 VL (XC144), h41A10 VL (XC145), h41A10 VL (XC146), and h41A10 VL (XC149);
t. an antibody comprising a chimeric 41A10 VH, and a VL selected from the group consisting of mouse 41A10 VL, chimeric 41A10 VL, h41A10 VL (XC142), h41A10 VL (XC143), h41A10 VL (XC144), h41A10 VL (XC145), h41A10 VL (XC146), and h41A10 VL (XC149);
u. an antibody comprising a humanized 41A10 VH (XC147), and a VL selected from the group consisting of mouse 41A10 VL, chimeric 41A10 VL, h41A10 VL (XC142), h41A10 VL (XC143), h41A10 VL (XC144), h41A10 VL (XC145), h41A10 VL (XC146), and h41A10 VL (XC149);
v. an antibody comprising a h41A10 VH (XC148), and a VL selected from the group consisting of mouse 41A10 VL, chimeric 41A10 VL, h41A10 VL (XC142), h41A10 VL (XC143), h41A10 VL (XC144), h41A10 VL (XC145), h41A10 VL (XC146), and h41A10 VL (XC149);
w. h41A10 VH (XC150), and a VL selected from the group consisting of mouse 41A10 VL, chimeric 41A10 VL, h41A10 VL (XC142), h41A10 VL (XC143), h41A10 VL (XC144), h41A10 VL (XC145), h41A10 VL (XC146), h41A10 VL (XC149), and h41A10 VL (XC142);
x. an antibody comprising a mouse 41A10 VL, and a VH selected from the group consisting of mouse 41A10 VH, chimeric 41A10 VH, h41A10 VH (XC147), h41A10 VL (XC148), and h41A10 VH (XC150);
y. an antibody comprising a chimeric 41A10 VL, and a VH selected from the group consisting of mouse 41A10 VH, chimeric 41A10 VH, h41A10 VH (XC147), h41A10 VL (XC148), and h41A10 VH (XC150);
z. an antibody comprising a h41A10 VL (XC143), and a VH selected from the group consisting of mouse 41A10 VH, chimeric 41A10 VH, h41A10 VH (XC147), h41A10 VL (XC148), and h41A10 VH (XC150);
aa. an antibody comprising a h41A10 VL (XC144), and a VH selected from the group consisting of mouse 41A10 VH, chimeric 41A10 VH, h41A10 VH (XC147), h41A10 VL (XC148), and h41A10 VH (XC150);
bb. an antibody comprising a h41A10 VL (XC145), and a VH selected from the group consisting of mouse 41A10 VH, chimeric 41A10 VH, h41A10 VH (XC147), h41A10 VL (XC148), and h41A10 VH (XC150);
cc. an antibody comprising a h41A10 VL (XC146), and a VH selected from the group consisting of mouse 41A10 VH, chimeric 41A10 VH, h41A10 VH (XC147), h41A10 VL (XC148), and h41A10 VH (XC150);
dd. an antibody comprising a h41A10 VL (XC149), and a VH selected from the group consisting of mouse 41A10 VH, chimeric 41A10 VH, h41A10 VH (XC147), h41A10 VL (XC148), and h41A10 VH (XC150);
ee. an antibody comprising a mouse 5H7 VH, and a VL selected from the group consisting of mouse 5H7 and chimeric 5H7 VL;
ff. mouse 5H7 VL, and a VH selected from the group consisting of mouse 5H7 VH and chimeric 5H7 VH;
gg. an antibody comprising a h11G2 VH (XC152) and h11G2 VL (XC151);
hh. an antibody comprising a h11G2 VH (XC155) and h11G2 VL (XC153);
ii. an antibody comprising a h11G2 VH (XC155) and h11G2 VL (XC154);
jj. an antibody comprising a h11G2 VH (XC156) and h11G2 VL (XC153);
kk. an antibody comprising a h11G2 VH (XC157) and h11G2 (XC154);
ll. an antibody comprising a mouse 11G2 VH and a mouse 11G2 VL;
mm. an antibody comprising a chimeric 11G2 HC and a chimeric 11G2 LC;
nn. an antibody comprising a h11G2 VH (XC152) and a h11G2 VL (XC151);
oo. an antibody comprising a h11G2 VH (XC155) and a h11G2 VL (XC154);
pp. an antibody comprising a h11G2 VH (XC156) and a h11G2 VL (XC153);
qq. an antibody comprising a h11G2 VH (XC157) and a h11G2 VL (XC154);
rr. an antibody comprising a mouse 41A10 VH and a mouse 41A10 VL;
ss. an antibody comprising a chimeric 41A10 HC and chimeric 41A10 LC;
tt. an antibody comprising a h41A10 VH (XC147) and a h41A10 VL(XC142);
uu. an antibody comprising a h41A10 VH(XC147) and a h41A10 VL(XC143);
vv. an antibody comprising a h41A10 VH(XC147) and a h41A10 VL(XC144);
ww. an antibody comprising a h41A10 VH(XC147) and a h41A10 VL(XC145);
xx. an antibody comprising a h41A10 VH(XC148) and a h41A10 VL(XC142);
yy. an antibody comprising a h41A10 VH(XC148) and a h41A10 VL(XC143);
zz. an antibody comprising a h41A10 VH(XC148) and a h41A10VL(XC144);

aaa. an antibody comprising a mouse 5H7 VH and a mouse 5H7 VL; and bbb. an antibody comprising a chimeric 5H7 HC and a chimeric 5H7 LC.

E113. An antibody, or antigen-binding fragment thereof, selected from the group consisting of:

(a) an antibody comprising a VH comprising the amino acid sequence of SEQ ID NO:36 and a VL comprising the amino acid sequence of SEQ ID NO:35;

(b) an antibody comprising a CDR-H1 comprising the sequence of SEQ ID:7, a CDR-H2 comprising the amino acid sequence of SEQ ID NO:8, a CDR-H3 comprising the amino acid sequence of SEQ ID NO:9, a CDR-L1 comprising the amino acid sequence of SEQ ID NO:2, a CDR-L2 comprising the amino acid sequence of SEQ ID NO:3, and a CDR-L3 comprising the sequence of SEQ ID NO:4;

(c) an antibody comprising a CDR-H1 comprising the sequence of SEQ ID:7, a CDR-H2 comprising the amino acid sequence of SEQ ID NO:8, a CDR-H3 comprising the amino acid sequence of SEQ ID NO:11, a CDR-L1 comprising the amino acid sequence of SEQ ID NO:2, a CDR-L2 comprising the amino acid sequence of SEQ ID NO:3, and a CDR-L3 comprising the sequence of SEQ ID NO:4;

(d) an antibody comprising a CDR-H1 comprising the sequence of SEQ ID:19, a CDR-H2 comprising the amino acid sequence of SEQ ID NO:20, a CDR-H3 comprising the amino acid sequence of SEQ ID NO:21, a CDR-L1 comprising the amino acid sequence of SEQ ID NO:14, a CDR-L2 comprising the amino acid sequence of SEQ ID NO:15, and a CDR-L3 comprising the sequence of SEQ ID NO:16;

(e) an antibody comprising a CDR-H1, a CDR-H2, a CDR-H3, as set forth in the amino acid sequence of SEQ ID NO:6, and a CDR-L1, a CDR-L2, and a CDR-L3 as set forth in the amino acid sequence of SEQ ID NO: 1;

(f) an antibody comprising a CDR-H1, a CDR-H2, a CDR-H3, encoded by the insert of the plasmid deposited at the ATCC having Accession NO. PTA-124323, and a CDR-L1, a CDR-L2, and a CDR-L3 encoded by the insert of the plasmid deposited at the ATCC having Accession number PTA-124324;

(g) an antibody comprising a VH comprising the amino acid sequence of SEQ ID NO:52 (XC152) and a VL comprising an amino acid sequence selected from the group consisting of SEQ ID NOs:1, 5, 35, 47, 48, 49, 50, and 51;

(h) an antibody comprising a VH comprising the amino acid sequence of SEQ ID NO:6 (XC155) and a VL comprising an amino acid sequence selected from the group consisting of SEQ ID NOs:1, 5, 35, 47, 48, 49, 50, and 51;

(i) an antibody comprising a VH comprising the amino acid sequence of SEQ ID NO:10 (XC156) and a VL comprising an amino acid sequence selected from the group consisting of SEQ ID NOs:1, 5, 35, 47, 48, 49, 50, and 51;

(j) an antibody comprising a VH comprising the amino acid sequence of SEQ ID NO:12 (XC157) and a VL comprising an amino acid sequence selected from the group consisting of SEQ ID NOs:1, 5, 35, 47, 48, 49, 50, and 51;

(k) an antibody comprising a VH comprising the amino acid sequence of SEQ ID NO:53 (XC350) and a VL comprising an amino acid sequence selected from the group consisting of SEQ ID NOs:1, 5, 35, 47, 48, 49, 50, and 51;

(l) an antibody comprising a VH comprising the amino acid sequence of SEQ ID NO:54 (XC351) and a VL comprising an amino acid sequence selected from the group consisting of SEQ ID NOs:1, 5, 35, 47, 48, 49, 50, and 51;

(m) an antibody comprising a VH comprising the amino acid sequence of SEQ ID NO:55 (XC352) and a VL comprising an amino acid sequence selected from the group consisting of SEQ ID NOs:1, 5, 35, 47, 48, 49, 50, and 51;

(n) an antibody comprising a VH comprising the amino acid sequence of SEQ ID NO:56 (XC353) and a VL comprising an amino acid sequence selected from the group consisting of SEQ ID NOs:1, 5, 35, 47, 48, 49, 50, and 51;

(o) an antibody comprising a VH comprising the amino acid sequence of SEQ ID NO:55 (XC354) and a VL comprising an amino acid sequence selected from the group consisting of SEQ ID NOs:1, 5, 35, 47, 48, 49, 50, and 51;

(p) an antibody comprising a VL comprising the amino acid sequence of SEQ ID NO:47 (XC151) and a VH comprising an amino acid sequence selected from the group consisting of SEQ ID NOs:6, 10, 12, 36, 52, 53, 54, 55, 56, and 57;

(q) an antibody comprising a VL comprising the amino acid sequence of SEQ ID NO:5 (XC153) and a VH comprising an amino acid sequence selected from the group consisting of SEQ ID NOs:6, 10, 12, 36, 52, 53, 54, 55, 56, and 57;

(r) an antibody comprising a VL comprising the amino acid sequence of SEQ ID NO:1 (XC154) and a VH comprising an amino acid sequence selected from the group consisting of SEQ ID NOs:6, 10, 12, 36, 52, 53, 54, 55, 56, and 57;

(s) an antibody comprising a VL comprising the amino acid sequence of SEQ ID NO:48 (XC346) and a VH comprising an amino acid sequence selected from the group consisting of SEQ ID NOs:6, 10, 12, 36, 52, 53, 54, 55, 56, and 57;

(t) an antibody comprising a VL comprising the amino acid sequence of SEQ ID NO:49 (XC347) and a VH comprising an amino acid sequence selected from the group consisting of SEQ ID NOs:6, 10, 12, 36, 52, 53, 54, 55, 56, and 57;

(u) an antibody comprising a VL comprising the amino acid sequence of SEQ ID NO:50 (XC348) and a VH comprising an amino acid sequence selected from the group consisting of SEQ ID NOs:6, 10, 12, 36, 52, 53, 54, 55, 56, and 57;

(v) an antibody comprising a VL comprising the amino acid sequence of SEQ ID NO:51 (XC349) and a VH comprising an amino acid sequence selected from the group consisting of SEQ ID NOs:6, 10, 12, 36, 52, 53, 54, 55, 56, and 57;

(w) an antibody comprising a VH comprising the amino acid sequence of SEQ ID NO:38 (m 41A10 VH), and a VL comprising an amino acid sequence selected from the group consisting of SEQ ID NOs:13, 37, 58, 59, 60, 61 and 62;

(x) an antibody comprising a VH comprising the amino acid sequence of SEQ ID NO:17 (XC148), and a VL comprising an amino acid sequence selected from the group consisting of SEQ ID NOs:13, 37, 58, 59, 60, 61 and 62;

(y) an antibody comprising a VH comprising the amino acid sequence of SEQ ID NO:18 (XC147), and a VL comprising an amino acid sequence selected from the group consisting of SEQ ID NOs:13, 37, 58, 59, 60, 61 and 62;

(z) an antibody comprising a VH comprising the amino acid sequence of SEQ ID NO:63 (XC150), and a VL comprising an amino acid sequence selected from the group consisting of SEQ ID NOs:13, 37, 58, 59, 60, 61 and 62;

(aa) an antibody comprising a VL comprising amino acid sequence of SEQ ID NO:37 (mouse h41A10 VL), and a VH comprising an amino acid sequence selected from the group consisting of SEQ ID NOs:17, 18, 38 and 63;

(bb) an antibody comprising a VL comprising amino acid sequence of SEQ ID NO:13 (h41A10 XC142 VL), and a VH comprising an amino acid sequence selected from the group consisting of SEQ ID NOs:17, 18, 38 and 63;

(cc) an antibody comprising a VL comprising amino acid sequence of SEQ ID NO:58 (h41A10 XC143 VL), and a VH comprising an amino acid sequence selected from the group consisting of SEQ ID NOs:17, 18, 38 and 63;

(dd) an antibody comprising a VL comprising amino acid sequence of SEQ ID NO:59 (h41A10 XC144 VL), and a VH comprising an amino acid sequence selected from the group consisting of SEQ ID NOs:17, 18, 38 and 63;

(ee) an antibody comprising a VL comprising amino acid sequence of SEQ ID NO:60 (h41A10 XC145 VL), and a VH comprising an amino acid sequence selected from the group consisting of SEQ ID NOs:17, 18, 38 and 63;

(ff) an antibody comprising a VL comprising amino acid sequence of SEQ ID NO:61 (h41A10 XC1446 VL), and a VH comprising an amino acid sequence selected from the group consisting of SEQ ID NOs:17, 18, 38 and 63;

(gg) an antibody comprising a VL comprising amino acid sequence of SEQ ID NO:62 (h41A10 XC149 VL), and a VH comprising an amino acid sequence selected from the group consisting of SEQ ID NOs:17, 18, 38 and 63;

(hh) an antibody comprising a VH comprising the amino acid sequence of SEQ ID NO:40 (mouse 5H7 VH), and a VL comprising the amino acid sequence of SEQ ID NO:39;

(ii) an antibody comprising a VH comprising the amino acid sequence of SEQ ID NO:52 and a VL comprising the amino acid sequence of SEQ ID NO:47;

(jj) an antibody comprising a VH comprising the amino acid sequence of SEQ ID NO:6 and a VL comprising the amino acid sequence of SEQ ID NO:5;

(kk) an antibody comprising a VH comprising the amino acid sequence of SEQ ID NO:6 and a VL comprising the amino acid sequence of SEQ ID NO:1;

(ll) (ii) an antibody comprising a VH comprising the amino acid sequence of SEQ ID NO:10 and a VL comprising the amino acid sequence of SEQ ID NO:5;

(mm) an antibody comprising a VH comprising the amino acid sequence of SEQ ID NO:10 and a VL comprising the amino acid sequence of SEQ ID NO:5; and (nn) an antibody comprising a VH comprising the amino acid sequence of SEQ ID NO:12 and a VL comprising the amino acid sequence of SEQ ID NO:1.

E114. An antibody, or antigen-binding fragment thereof, that competes for binding to human CXCR5 with an antibody or antigen-binding fragment thereof of any one of E1-E113.

E115. An isolated nucleic acid encoding the antibody, or antigen-binding fragment thereof, of any one of E1-E114.

E116. An isolated nucleic acid molecule, comprising at least one nucleic acid sequence encoding the antibody, or antigen-binding fragment thereof, of any one of E1-E109.

E117. An isolated nucleic acid molecule comprising a nucleic acid sequence selected from the group consisting the sequence set forth as SEQ ID NOs: 95, 96, 97 and 98.

E118. An isolated nucleic acid molecule comprising the nucleic acid sequence as set forth as SEQ ID NO:95.

E119. An isolated nucleic acid molecule comprising the nucleic acid sequence as set forth as SEQ ID NO: 96.

E120. An isolated nucleic acid molecule comprising the nucleic acid sequence as set forth as SEQ ID NO:95, and the nucleic acid sequence as set forth as SEQ ID NO:96.

E121. An isolated nucleic acid molecule comprising the nucleic acid sequence as set forth as SEQ ID NO:97.

E122. An isolated nucleic acid molecule comprising the nucleic acid sequence as set forth as SEQ ID NO:98.

E123. An isolated nucleic acid molecule comprising the nucleic acid sequence as set forth as SEQ ID NO:97, and the nucleic acid sequence as set forth as SEQ ID NO:98.

E124. An isolated nucleic acid molecule comprising the nucleic acid sequence of the insert of the plasmid deposited with the ATCC and having Accession No. PTA-124323.

E125. An isolated nucleic acid molecule comprising the nucleic acid sequence of the insert of the plasmid deposited with the ATCC and having Accession No. PTA-124324.

E126. An isolated nucleic acid encoding the VH, VL, or both, of an antibody or an antigen-binding fragment thereof that specifically binds CXCR5, wherein said nucleic acid comprises the nucleic acid sequence of SEQ ID NO:95, the nucleic acid sequence of SEQ ID NO:107, or both.

E127. An isolated nucleic acid encoding the heavy chain, light chain, or both, of an antibody or an antigen-binding fragment thereof that specifically binds CXCR5, wherein said nucleic acid comprises the nucleic acid sequence of SEQ ID NO:97, the nucleic acid sequence of SEQ ID NO:98, or both.

E128. An isolated nucleic acid encoding the VH of an antibody or an antigen-binding fragment thereof that specifically binds CXCR5, wherein said nucleic acid comprises the nucleic acid sequence of the insert of the plasmid deposited with the ATCC and having the Accession Number PTA-124323.

E129. An isolated nucleic acid encoding the VL of an antibody or an antigen-binding fragment thereof that specifically binds CXCR5, wherein said nucleic acid comprises the nucleic acid sequence of the insert of the plasmid deposited with the ATCC and having the Accession Number PTA-124324.

E130. An isolated nucleic acid encoding the VL and VH of an antibody, or an antigen-binding fragment thereof, that specifically binds CXCR5, wherein said nucleic acid comprises the nucleic acid sequence of the insert of the plasmid deposited with the ATCC and having the Accession Number PTA-124324 and the nucleic acid sequence of the insert of the plasmid deposited with the ATCC and having the Accession Number PTA-124323.

E131. A vector comprising the nucleic acid molecule of any one of E115-E130.

E132. A host cell comprising the nucleic acid molecule of any one of E115-E130, or the vector of E131.

E133. The host cell of E132, wherein said cell is a mammalian cell.

E134. The host cell of E133, wherein said host cell is a CHO cell, a COS cell, a HEK-293 cell, an NSO cell, a PER.C6® cell, or an Sp2.0 cell.

E135. The host cell of any one of E132-134, wherein said host cell lacks a functional alpha-1,6-fucosyltransferase (FUT8).

E136. The host cell of any one of E132-135, wherein said cell does not express a functional alpha-1,6-fucosyltransferase enzyme.

E137. The host cell of any one of E132-136, wherein said cell lacks a FUT8 gene encoding a functional enzyme.

E138. The host cell of any one of E132-137, wherein said cell lacks a gene encoding a functional FUT8 gene.

E139. The host cell of any one of E132-139, wherein said cell is a Potelligent® CHOK1SV cell, or a Lec13 CHO cell.

E140. The host cell of E139, wherein said cell is a Potelligent® CHOK1SV cell.

E141. A method of making an antibody or antigen-binding fragment thereof, comprising culturing the host cell of any one of E1-E114, under a condition wherein said antibody or antigen-binding fragment is expressed by said host cell.

E142. The method of E141, further comprising isolating said antibody or antigen-binding fragment thereof.

E143. A method of making an afucosylated anti-CXCR5 antibody, or an antigen-binding fragment thereof, said method comprising culturing a host cell comprising the nucleic acid molecule of any one of E115-E130, or the vector of E131, wherein said host cell lacks a functional FUT8.

E144. The method of E143, wherein the host cell is a Potelligent® CHOK1SV cell.

E145. An isolated antibody, or antigen-binding fragment thereof, produced using the method of any one of E141-E114.

E146. The isolated antibody, or antigen-binding fragment thereof, of any one of E1-E114, wherein said antibody, or antigen-binding fragment thereof, is afucosylated.

E147. The afucosylated antibody, or antigen-binding fragment thereof, of E146, wherein said afucosylated antibody, or antigen-binding fragment thereof, exhibits enhanced antibody-dependent cellular cytotoxicity (ADCC) compared with an otherwise identical antibody, or antigen-binding fragment thereof, which is fucosylated.

E148. The afucosylated antibody, or antigen-binding fragment thereof, of E146, wherein said afucosylated antibody, or antigen-binding fragment thereof, exhibits about 2-fold, about 5-fold, about 7-fold, about 10-fold, about 20-fold, about 30-fold, about 40-fold, about 50-fold, about 60-fold, about 70-fold, about 80-fold, about 90-fold, about 100-fold, about 110-fold, about 120-fold, about 130-fold, about 140-fold, and about 143-fold greater ADCC compared with an otherwise identical antibody, or antigen-binding fragment thereof, which is fucosylated.

E149. A pharmaceutical composition comprising an antibody or antigen-binding fragment thereof of any one of E1-E114 and E145-E148, and a pharmaceutically acceptable carrier or excipient.

E150. The pharmaceutical composition of E149, wherein said antibody, or antigen-binding fragment thereof, is afucosylated.

E151. A method of reducing the activity of CXCR5, comprising administering to a subject in need thereof a therapeutically effective amount of the antibody, or antigen-binding fragment thereof, of any one of E1-E114 and E145-E148, or the pharmaceutical composition of any one of E149 and E150.

E152. A method of treating an inflammatory disease, comprising administering to a subject in need thereof a therapeutically effective amount of the antibody, or antigen-binding fragment thereof, of any one of E1-E114 and E145-E148, or the pharmaceutical composition of any one of E149-E150.

E153. A method of treating a subject in need of immunosuppression comprising administering to a subject in need thereof a therapeutically effective amount of the antibody, or antigen-binding fragment thereof, of any one of E1-E114 and E145-E148, or the pharmaceutical composition of any one of E149 and E150.

E154. A method of treating an autoimmune disease, disorder or condition, comprising administering to a subject in need thereof a therapeutically effective amount of the antibody, or antigen-binding fragment thereof, of any one of E1-E114 and E145-E148, or the pharmaceutical composition of any one of E149 and E150.

E155. A method of decreasing the number of cells expressing CXCR5 in a subject in need thereof, said method comprising administering to the subject a therapeutically effective amount of the antibody, or antigen-binding fragment thereof, of any one of E1-E114 and E145-E148, or the pharmaceutical composition of any one of E149 and E150.

E156. The method of E155, wherein the cells express CXCR5 on their surface.

E157. The method of E156, wherein the cells are B cells and Tfh-like cells.

E158. The method of any one of E151-E157, wherein said subject is a human.

E159. The method of any one of E151-E158, comprising administering said antibody or antigen-binding fragment thereof, or pharmaceutical composition, intravenously.

E160. The method of any one of E151-E158, comprising administering said antibody or antigen-binding fragment thereof, or pharmaceutical composition, subcutaneously.

E161. The method of any one of E151-E160, wherein said antibody or antigen-binding fragment thereof, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, once every four months, once every five months, once every six months, once every seven months, once every eight months, once every nine months, once every ten months, once every eleven months or once every twelve months.

E162. A method of decreasing the number of CXCR5+ cells in a sample, said method comprising contacting said cell with the antibody, or antigen-binding fragment thereof, of any one of E1-E114 and E145-E148, or the pharmaceutical composition of any one of E149 and E150.

E163. The antibody, or antigen-binding fragment thereof, of any one of E1-E114 and E145-E148, or the pharmaceutical composition of any one of E149 and E150, for use as a medicament.

E164. The antibody, or antigen-binding fragment thereof, of any one of E1-E114 and E145-E148, or the pharmaceutical composition of any one of E149 and E150, for use in reducing the activity of CXCR5 in a subject.

E165. The antibody, or antigen-binding fragment thereof, of any one of E1-E114 and E145-E148, or the pharmaceutical composition of any one of E149 and E150, for use in treating a subject in need of immunosuppression.

E166. The antibody, or antigen-binding fragment thereof, of any one of E1-E114 and E145-E148, or the pharmaceutical composition of any one of E149 and E150, for use in treating an autoimmune disease, disorder or condition in a subject.

E167. Use of an antibody, or antigen-binding fragment thereof, of any one of E1-E114 and E145-E148 in the manufacture of a medicament for treating an immune disease, disorder or condition.

E168. Use of a pharmaceutical composition of any one of E149 and E150 in the manufacture of a medicament for treating an immune disease, disorder or condition.

E169. A method of treating a medical condition, comprising administering to a subject in need thereof a therapeutically effective amount of the antibody, or antigen-binding fragment thereof, of any one of E1-E114 and E145-E148, or the pharmaceutical composition of any one of E149 and E150.

E170. The method of E169, wherein the condition is selected from the group consisting of inflammatory responses such as inflammatory skin diseases including psoriasis and dermatitis (e. g. atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; gastritis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e. g. Type I diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-person syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; idiopathic myxedema; graft versus host disease; muscular dystrophy (Duchenne, Becker, Myotonic, Limb-girdle, Facioscapulohumeral, Congenital, Oculopharyngeal, Distal, Emery-Dreifuss) and controlling the proliferation of cancer cells expressing CXCR5 such as cancers of the pancreas, colon, bladder, T-cell leukemia, and B-cell leukemia.

E171. A method of detecting CXCR5 in a sample, tissue, or cell using the antibody, or antigen-binding fragment thereof, of any one of E1-E114 and E145-E148, or the pharmaceutical composition of any one of E149 and E150, comprising contacting the sample, tissue or cell with the antibody and detecting the antibody.

E172. An isolated antibody, or antigen-binding fragment thereof, that specifically binds CXCR5,
  wherein the antibody is at least one antibody selected from the group consisting of:
  (a) an antibody comprising a CDR-L1 comprising the amino acid sequence of SEQ ID NO:2; a CDR-L2 comprising the amino acid sequence of SEQ ID NO:3; a CDR-L3 comprising the amino acid sequence of SEQ ID NO:4; a CDR-H1 comprising the amino acid sequence of SEQ ID NO:7; a CDR-H2 comprising the amino acid sequence of SEQ ID NO:8; and a CDR-H3 comprising the amino acid sequence of SEQ ID NO:9;
  (b) an antibody comprising a CDR-L1 comprising the amino acid sequence of SEQ ID NO:2; a CDR-L2 comprising the amino acid sequence of SEQ ID NO:3; a CDR-L3 comprising the amino acid sequence of SEQ ID NO:4; a CDR-H1 comprising the amino acid sequence of SEQ ID NO:7; a CDR-H2 comprising the amino acid sequence of SEQ ID NO:8; and a CDR-H3 comprising the amino acid sequence of SEQ ID NO:11;
  (c) an antibody comprising a CDR-L1 comprising the amino acid sequence of SEQ ID NO:14; a CDR-L2 comprising the amino acid sequence of SEQ ID NO:15; a CDR-L3 comprising the amino acid sequence of SEQ ID NO:16; a CDR-H1 comprising the amino acid sequence of SEQ ID NO:19; a CDR-H2 comprising the amino acid sequence of SEQ ID NO:20; and a CDR-H3 comprising the amino acid sequence of SEQ ID NO:21;
  (d) an antibody comprising a VL comprising an amino acid sequence encoded by the insert of the plasmid deposited with the ATCC and having Accession Number PTA-124324 and a VH comprising an amino acid sequence encoded by the insert of the plasmid deposited with the ATCC having Accession Number PTA-124323;
  (e) an antibody comprising a VL comprising the amino acid sequence of SEQ ID NO:1, and a VH comprising the amino acid sequence of SEQ ID NO:6;
  (f) an antibody comprising a VL comprising the amino acid sequence of SEQ ID NO:13, and a VH comprising the amino acid sequence of SEQ ID NO:18;
  (g) an antibody comprising a VL comprising the amino acid sequence of SEQ ID NO:47, and a VH comprising the amino acid sequence of SEQ ID NO:52;
  (h) an antibody comprising a VL comprising the amino acid sequence of SEQ ID NO:5, and a VH comprising the amino acid sequence of SEQ ID NO:6;
  (i) an antibody comprising a VL comprising the amino acid sequence of SEQ ID NO:5, and a VH comprising the amino acid sequence of SEQ ID NO:10;

(j) an antibody comprising a VL comprising the amino acid sequence of SEQ ID NO:13, and a VH comprising the amino acid sequence of SEQ ID NO:17;
(k) an antibody comprising a VL comprising the amino acid sequence of SEQ ID NO:1, and a VH comprising the amino acid sequence of SEQ ID NO:12;
(l) an antibody comprising a LC comprising the amino acid sequence of SEQ ID NO:22, and a HC comprising the amino acid sequence of SEQ ID NO:23;
(m) an antibody comprising a LC comprising the amino acid sequence of SEQ ID NO:24, and a HC comprising the amino acid sequence of SEQ ID NO:25;
(n) an antibody comprising a LC comprising the amino acid sequence of SEQ ID NO:26, and a HC comprising the amino acid sequence of SEQ ID NO:27;
(o) an antibody comprising a LC comprising the amino acid sequence of SEQ ID NO:28, and a HC comprising the amino acid sequence of SEQ ID NO:29;
(p) an antibody comprising a VL encoded by the nucleic acid sequence of SEQ ID NO:95, and a VH encoded by the nucleic acid sequence of SEQ ID NO:96; and
(q) an antibody comprising a LC encoded by the nucleic acid sequence of SEQ ID NO:97, and a HC encoded by the nucleic acid sequence of SEQ ID NO:98.

E173. An isolated antibody or antigen-binding fragment thereof, that specifically binds C—X—C-chemokine receptor 5 (CXCR5), wherein the antibody, or antigen-binding fragment thereof, is at least one antibody selected from the group consisting of:
(a) an antibody or antigen-binding fragment thereof that binds a hCXCR5 epitope comprising leucine at amino acid residue number 11 according to the numbering of the amino acid sequence of SEQ ID NO:32, but does not bind said epitope wherein said residue is not leucine;
(b) an antibody or antigen-binding fragment thereof that binds a hCXCR5 epitope comprising leucine at amino acid residue number 11 according to the numbering of the amino acid sequence of SEQ ID NO:32, but does not bind said epitope wherein said residue is threonine;
(c) an antibody or antigen-binding fragment thereof that binds a hCXCR5 epitope comprising aspartate at amino acid residue number 22 according to the numbering of the amino acid sequence of SEQ ID NO:32, but does not bind said epitope wherein said residue is not aspartate;
(d) an antibody or antigen-binding fragment thereof that binds a hCXCR5 epitope comprising aspartate at amino acid residue number 22 according to the numbering of the amino acid sequence of SEQ ID NO:32, but does not bind said epitope wherein said residue is alanine;
(e) an antibody or antigen-binding fragment thereof, that binds a hCXCR5 epitope comprising leucine at amino acid residue number 11 and aspartate at amino acid residue number 22, according to the numbering of the amino acid sequence of SEQ ID NO:32, but does not bind said epitope wherein said leucine is substituted by threonine and/or said aspartate is substituted with alanine;
(f) an antibody or antigen-binding fragment thereof that binds hCXCR5, or a fragment thereof, comprising leucine at amino acid residue number 11 according to the numbering of the amino acid sequence of SEQ ID NO:32, but does not bind hCXCR5, or a fragment thereof, wherein said residue is not leucine;
(g) an antibody or antigen-binding fragment thereof that binds hCXCR5, or a fragment thereof, comprising leucine at amino acid residue number 11 according to the numbering of the amino acid sequence of SEQ ID NO:32, but does not bind hCXCR5, or a fragment thereof, wherein said residue is threonine;
(h) an antibody or antigen-binding fragment thereof that binds hCXCR5, or a fragment thereof, comprising aspartate at amino acid residue number 22 according to the numbering of the amino acid sequence of SEQ ID NO:32, but does not bind hCXCR5, or a fragment thereof, wherein said residue is not aspartate;
(i) an antibody or antigen-binding fragment thereof that binds hCXCR5, or a fragment thereof, comprising aspartate at amino acid residue number 22 according to the numbering of the amino acid sequence of SEQ ID NO:32, but does not bind hCXCR5, or a fragment thereof, wherein said residue is alanine; and
(j) an antibody or antigen-binding fragment thereof, that binds hCXCR5, or a fragment thereof, comprising leucine at amino acid residue number 11 and aspartate at amino acid residue number 22, according to the numbering of the amino acid sequence of SEQ ID NO:32, but does not bind hCXCR5, or a fragment thereof, wherein said leucine is substituted by threonine and/or said aspartate is substituted with alanine.

E174. An isolated antibody or antigen-binding fragment thereof, that specifically binds C—X—C-chemokine receptor 5 (CXCR5), wherein the antibody, or antigen-binding fragment thereof, is at least one antibody selected from the group consisting of:
(a) an antibody, or an antigen-binding fragment thereof, that binds hCXCR5 expressed on human B cells with an apparent affinity of an EC50 of about 6.60 pM with a standard deviation of about plus or minus 2.33 pM;
(b) an antibody, or an antigen-binding fragment thereof, that binds hCXCR5 expressed on human circulating follicular T helper-like cells with an apparent affinity of an EC50 of about 5.89 pM with a standard deviation of about plus or minus 1.40 pM;
(c) an antibody, or an antigen-binding fragment thereof, that binds hCXCR5 expressed on human follicular T helper (Tfh) cells with an apparent affinity of an EC50 of about 10.6 pM;
(d) an antibody, or an antigen-binding fragment thereof, that binds cynoCXCR5 expressed on cynomolgus monkey B cells with an apparent affinity of an EC50 of about 1.32 pM;
(e) an antibody, or an antigen-binding fragment thereof, that binds cynoCXCR5 expressed on cynomolgus monkey Tfh-like cells with an apparent affinity of an EC50 of about 10.5 pM;
(f) an antibody, or antigen-binding fragment thereof, that antagonizes CXCR5-CXCL13 signaling in a cAMP reporter assay with an EC50 of about 961 pM;
(g) an antibody, or an antigen-binding fragment thereof, that exhibits ADCC activity against human B cells expressing hCXCR5 with an EC50 of about 2.01 pM with a standard deviation of about plus or minus 2.28 pM;
(h) an antibody, or an antigen-binding fragment thereof, that exhibits ADCC activity against human Tfh-like cells expressing hCXCR5 with an EC50 of about 4.28 pM with a standard deviation of about plus or minus 2.88 pM;
(i) an antibody, or an antigen-binding fragment thereof, that exhibits ADCC activity against human Tfh cells expressing hCXCR5 with an EC50 of about 0.11 pM;

(j) an antibody, or an antigen-binding fragment thereof, that exhibits ADCC activity against cynomolgus monkey B cells expressing cynoCXCR5 with an EC50 of about 15.3 pM with a standard deviation of about plus or minus 11.7 pM;

(k) an antibody, or an antigen-binding fragment thereof, that binds hCXCR5 but does not detectably bind human chemokine receptors CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR6, CXCR7, and XCR1;

(l) an antibody, or antigen-binding fragment thereof, that inhibits binding of CXCR5 to CXCL13.

(m) an antibody, or antigen-binding fragment thereof, that binds CXCR5+ human B cells with an apparent affinity of an EC50 of less than about 26 pM, but does not bind cells expressing CXCR5 mouse, rat or rabbit orthologs;

(n) an antibody, or antigen-binding fragment thereof, that antagonizes CXCL13 inhibition of cAMP release triggered by forskolin;

(o) an antibody, or antigen-binding fragment thereof, that triggers ADCC of CXCR5-expressing cells in human donor and cynomolgus PBMCs and human donor TMCs;

(p) an antibody, or antigen-binding fragment thereof, that binds human CXCR5 but does not bind human chemokine receptors CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR6, CXCR7, or XCR1;

(q) an antibody, or an antigen-binding fragment thereof, that depletes B cells in the peripheral blood;

(r) an antibody, or an antigen-binding fragment thereof, that depletes Tfh-like cells in the peripheral blood;

(s) an antibody, or an antigen-binding fragment thereof, that depletes bona fide Tfh cells in the spleen; and (t) an antibody, or an antigen-binding fragment thereof, that impairs humoral immune memory response.

E175. The antibody of any one of E172-E174, wherein said antibody, or antigen-binding fragment thereof, exhibits at least one of the following biological activities:

(a) binds CXCR5+ human B cells with an apparent affinity of an EC50 of less than about 26 pM, but does not bind cells expressing CXCR5 mouse, rat or rabbit orthologs;

(b) antagonizes CXCL13 inhibition of cAMP release triggered by forskolin;

(c) triggers ADCC of CXCR5-expressing cells in human donor and cynomolgus PBMCs and human donor TMCs;

(d) binds human CXCR5 but does not bind human chemokine receptors CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR6, CXCR7, or XCR1;

(e) depletes B cells in the peripheral blood;

(f) depletes Tfh-like cells in the peripheral blood;

(g) depletes bona fide Tfh cells in the spleen; or (h) impairs a humoral immune memory response.

E176. The antibody of any one of E172-E175, wherein said antibody, or antigen-binding fragment thereof, is afucosylated.

E177. An isolated nucleic acid encoding the antibody, or antigen-binding fragment thereof, of any one of E172-E176.

E178. An isolated nucleic acid encoding the VH, VL, or both, of an antibody or an antigen-binding fragment thereof that specifically binds CXCR5, wherein said nucleic acid comprises: the nucleic acid sequence of SEQ ID NO:95, the nucleic acid sequence of SEQ ID NO:96, or both.

E179. An isolated nucleic acid encoding the heavy chain, light chain, or both, of an antibody or an antigen-binding fragment thereof that specifically binds CXCR5, wherein said nucleic acid comprises: the nucleic acid sequence of SEQ ID NO:97, the nucleic acid sequence of SEQ ID NO:98, or both.

E180. An isolated nucleic acid encoding the VH, VL, or both, of an antibody or an antigen-binding fragment thereof that specifically binds CXCR5, wherein said nucleic acid comprises the nucleic acid sequence of the insert of the plasmid deposited with the ATCC and having the Accession Number PTA-124323, the nucleic acid sequence of the insert of the plasmid deposited with the ATCC and having the Accession Number PTA-124324, or both.

E181. A vector comprising the nucleic acid of any one of E177-E180.

E182. A host cell comprising the vector of E181.

E183. The host cell of E182, wherein said host cell is a mammalian cell selected from the group consisting of a CHO cell, a COS cell, a HEK-293 cell, an NSO cell, a PER.C6® cell, or an Sp2.0 cell.

E184. The host cell of E183, wherein said cell lacks a functional alpha-1,6-fucosyltransferase (FUT8).

E185. The host cell of E184, wherein said cell is a Potelligent® CHOK1SV cell or a Lec13 CHO cell.

E186. A method of making an antibody, or antigen-binding fragment thereof, comprising the Potelligent® CHOK1SV cell of E185, under a condition wherein said antibody, or antigen-binding fragment thereof is expressed by said host cell and is afucosylated.

E187. The method of E186, further comprising isolating said antibody, or antigen-binding fragment thereof.

E188. The afucosylated antibody, or antigen-binding fragment thereof, of E186, wherein said antibody exhibits enhanced ADCC activity when compared to an otherwise identical antibody, or antigen-binding fragment thereof, that is fucosylated.

E189. A pharmaceutical composition comprising an antibody, or antigen-binding fragment thereof, of any one of E172-E176 and E188, and a pharmaceutically acceptable carrier or excipient.

E190. The antibody, or antigen-binding fragment thereof, of any one of E172-E176, E188, and the pharmaceutical composition of E189, for use in treating an immune disease, disorder or condition.

E191. Use of an antibody, or antigen-binding fragment thereof, of any one of E172-E176, E188, or the pharmaceutical composition of E189, for treating an immune disease, disorder or condition.

E192. A method for treating or preventing an immune disease, disorder or condition mediated by CXCR5 in a human subject in need thereof, said method comprising administering to the subject an effective amount of the pharmaceutical composition of E189, wherein said disease, disorder or condition is selected from the group consisting of inflammatory responses such as inflammatory skin diseases including psoriasis and dermatitis (e. g. atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; ARDS); dermatitis;

meningitis; encephalitis; uveitis; colitis; gastritis; glomerulonephritis; allergic conditions such as eczema and asthma and other conditions involving infiltration of T cells and chronic inflammatory responses; atherosclerosis; leukocyte adhesion deficiency; rheumatoid arthritis (RA); systemic lupus erythematosus (SLE); diabetes mellitus (e.g., Type I diabetes mellitus or insulin dependent diabetes mellitis); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; idiopathic myxedema; graft versus host disease; muscular dystrophy (Duchenne, Becker, Myotonic, Limb-girdle, Facioscapulohumeral, Congenital, Oculopharyngeal, Distal, Emery-Dreifuss) and controlling the proliferation of cancer cells expressing CXCR5 such as cancers of the pancreas, colon, bladder, T-cell leukemia, and B-cell leukemia.

E193. The method of E192, wherein said disease is SLE or rheumatoid arthritis.

E194. Use of an antibody, or antigen-binding fragment thereof, of any one of E172-E176, or E188 in the manufacture of a medicament for treating an immune disease, disorder or condition.

E195. A method of detecting CXCR5 in a sample, tissue, or cell using the antibody, or antigen-binding fragment thereof, according to any one of E172-E176, comprising contacting the sample, tissue or cell with the antibody and detecting the antibody.

E196. A method of reducing a biological activity of CXCR5 in a subject in need thereof, said method comprising administering a therapeutically effective amount of the antibody, or antigen binding fragment thereof, of any one of E172-E176 or E188, or the pharmaceutical composition of E189.

E197. The method of E196, wherein the antibody mediates depletion of at least one cell expressing CXCR5 selected from the group consisting of a Tfh cell in the spleen, a B cell in peripheral blood, and a Tfh-like cell in peripheral blood.

E198. A method of inhibiting a humoral immune response in a subject in need thereof, the method comprising administering a therapeutically effective amount of the antibody, or antigen-binding fragment thereof, of any one of E172-E176, or E188, or the pharmaceutical composition of E189.

E199. The method of E198, wherein the antibody mediates depletion of at least one cell expressing CXCR5 selected from the group consisting of a Tfh cell in the spleen, a B cell in peripheral blood, and a Tfh-like cell in peripheral blood.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiment(s). It should be understood, however, that the invention is not limited to the precise arrangements and instrumentalities shown.

FIG. 2A shows G2S2, FIG. 2B shows G2S1, FIG. 2C shows G2, FIG. 2D shows G1, FIG. 2E shows G0, FIG. 2F shows G-1, and FIG. 2G shows G-2.

FIG. 6 shows the alignment of human and mouse CXCR5 amino acid sequences. The figure also shows various extracellular domains of CXCR5, labeled as "N," "L1", "L2," and "L3" which are underlined.

DETAILED DESCRIPTION

Figure 1:
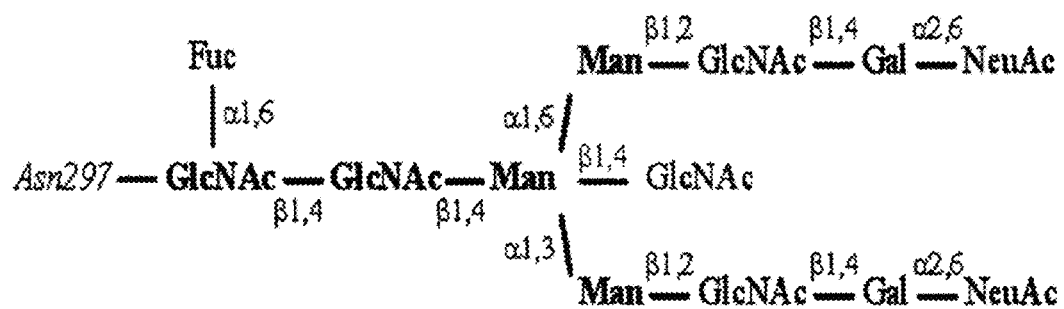
FIG. 1 is a diagram illustrating a canonical biantennary glycoform that is typically present in immunoglobulin heavy chain constant regions. The diagram shows an asparagine-linked (N-linked) glycoform on an IgG constant domain at amino acid residue number 297 (Asparagine 297; Asn297) according to the Eu numbering of Edelman et al., 1969, Proc. Natl. Acad. Sci. USA 63(1):78-85 as described in Kabat et al., 1991.
Figure 2A:
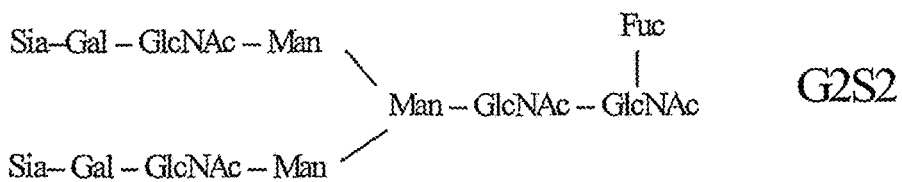
FIGS. 2A-2G are a diagram depicting exemplary biantennary glycoforms typically present in immunoglobulin heavy chain constant regions. "G0" refers to a biantennary structure wherein no terminal sialic acids (NeuAcs) or Gals are present, "G1" refers to a biantennary structure having one Gal and no NeuAcs and "G2" refers to a biantennary structure with two terminal Gals and no NeuAcs. In each glycoform, a fucose is typically present in antibodies produced in mammalian cells, e.g., CHO cells.
Figure 2B:
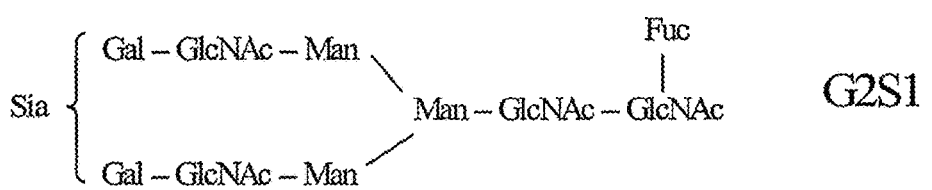
Figure 2C:
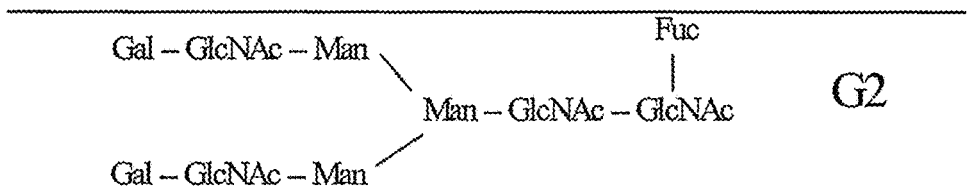
Figure 2D:
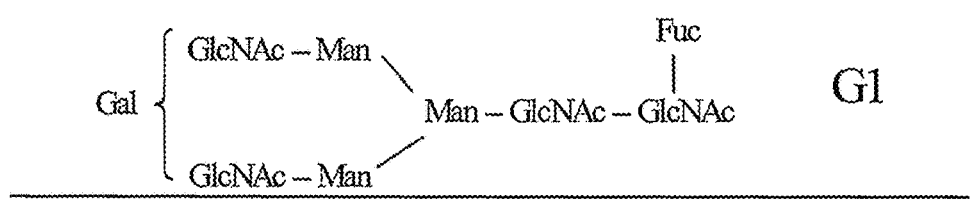
Figure 2E:
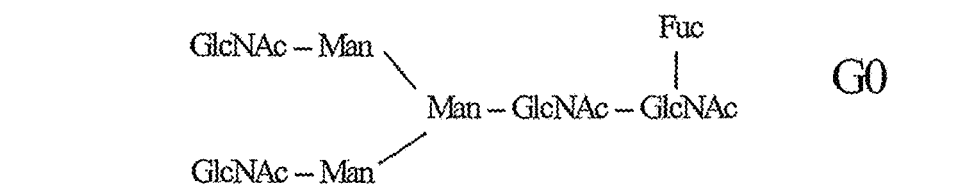
Figure 2F:
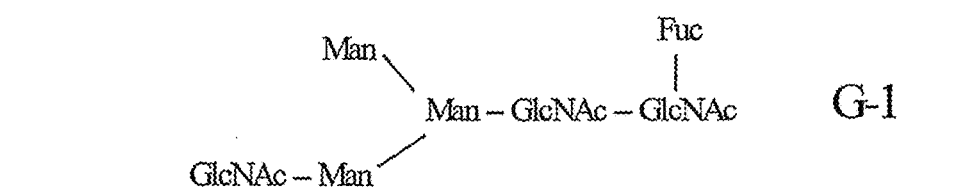
Figure 2G:
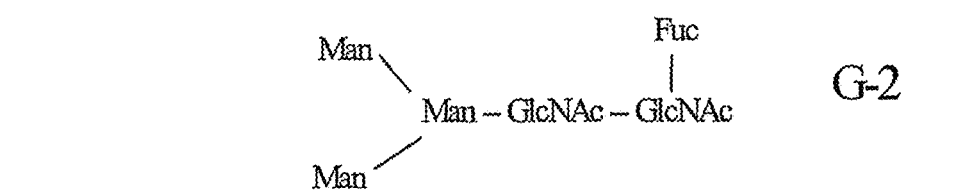

Disclosed herein are antibodies that specifically bind to CXCR5 and further, antibodies that antagonize CXCR5 activity or its interaction with CXCL13. Methods of making CXCR5 antibodies, compositions comprising these antibodies, and methods of using these antibodies are provided.

Fucosylated and afucosylated antibodies that bind CXCR5 are provided. In some embodiments, afucosylated antibody heavy chains and light chains that are capable of forming antibodies that bind CXCR5 are also provided. In some embodiments, afucosylated antibodies, heavy chains, and light chains comprising one or more particular complementarity determining regions (CDRs) are provided. In some embodiments, afucosylated anti-CXCR5 antibodies have altered effector function. In some embodiments, the antibodies of the invention have enhanced ADCC activity relative to otherwise identical fucosylated anti-CXCR5 antibodies of the invention.

Polynucleotides encoding antibodies that bind CXCR5, or antigen-binding fragments thereof, are provided. Polynucleotides encoding antibody heavy chains or light chains are also provided. Host cells that express fucosylated and/or afucosylated anti-CXCR5 antibodies are provided. Methods of treatment using afucosylated and fucosylated antibodies to CXCR5 are provided. Such methods include, but are not limited to, methods of treating diseases associated with or mediated by CXCR5 expression and/or binding to CXCL13, including, but not limited to, inflammatory and immune diseases.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al, Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANI- MAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds); Gene Transfer Vectors for Mammalian Cells (J. M. Miller and M. P. Calos, eds., 1987); PCR: The Polymerase Chain Reaction, (Mullis et al, eds., 1994); Current Protocols in Immunology (J. E. Coligan et al, eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999)); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

CXCR5 antibodies, whether fucosylated or afucosylated, can be used in the prevention, treatment, and/or amelioration of diseases, disorders or conditions caused by and/or associated with CXCR5 activity. Such diseases, disorders or conditions include, but are not limited to, inflammatory responses such as systemic lupus erythematosus (SLE); chronic inflammatory responses; atherosclerosis; leukocyte adhesion deficiency; rheumatoid arthritis; diabetes mellitus (e. g. Type I diabetes mellitus or insulin dependent diabetes mellitis); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-person syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; idiopathic myxedema; graft versus host disease; muscular dystrophy (Duchenne, Becker, Myotonic, Limb-girdle, Facioscapulohumeral, Congenital, Oculopharyngeal, Distal, Emery-Dreifuss), and controlling the proliferation of cancer cells expressing CXCR5 such as cancers of the pancreas, colon, bladder, T-cell leukemia, and B-cell leukemia as would be appreciated by one skilled in the art provided with the teachings disclosed herein.

I. Definitions

The present invention may be understood more readily by reference to the following detailed description of exemplary embodiments of the invention and the examples included therein.

Unless otherwise defined, all technical and scientific terms used herein have the same meaning as commonly understood by one of ordinary skill in the art to which this invention belongs. In case of conflict, the present specification, including definitions, will control.

Further, unless otherwise required by context or expressly indicated, singular terms shall include pluralities and plural terms shall include the singular.

It is understood that aspect and embodiments of the invention described herein include "consisting" and/or "consisting essentially of" aspects and embodiments. As used herein, the singular form "a", "an", and "the" includes plural references unless indicated otherwise.

In this application, the use of "or" means "and/or" unless expressly stated or understood by one skilled in the art. In the context of a multiple dependent claim, the use of "or" refers back to more than one preceding independent or dependent claim.

"About" or "approximately," when used in connection with a measurable numerical variable, refers to the indicated value of the variable and to all values of the variable that are within the experimental error of the indicated value (e.g. within the 95% confidence interval for the mean) or within 10 percent of the indicated value, whichever is greater. Numeric ranges are inclusive of the numbers defining the range.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

It is to be understood that the terminology used herein is for the purpose of describing particular embodiments only and is not intended to be limiting. In this specification and in the claims that follow, reference will be made to a number of terms that shall be defined to have the following meanings.

the term "isolated molecule" (where the molecule is, for example, a polypeptide, a polynucleotide, or an antibody or fragment thereof) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, "substantially pure" means an object species is the predominant species present (i.e., on a molar basis it is more abundant than any other individual species in the composition), and preferably a substantially purified fraction is a composition wherein the object species (e.g., a glycoprotein, including an antibody or receptor) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species. In certain embodiments a substantially pure material is at least 50% pure (i.e., free from contaminants), more preferably, at least 90% pure, more preferably, at least 95% pure, yet more preferably, at least 98% pure, and most preferably, at least 99% pure.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i. e. "algorithms").

The term "similarity" is a related concept, but in contrast to "identity", refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all nonconservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

Polypeptide or antibody "fragments" or "portions" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments or portions may also be generated by one or more internal deletions.

A variant antibody may comprise 1, 2, 3, 4, 5, up to 10, up to 20, up to 30 or more amino acid substitutions and/or deletions and/or insertions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" shown below, or as further described below in reference to amino acid classes, may be introduced and the products screened.

TABLE 1

Amino Acids and Substitutions

| Original Residue | Conservative Substitutions | Exemplary Substitutions |
| --- | --- | --- |
| alanine Ala (A) | Val | Val; Leu; Ile |
| arginine Arg (R) | Lys | Lys; Gln; Asn |
| asparagine Asn (N) | Gln | Gln; His; Asp, Lys; Arg |
| aspartatic Asp (D) | Glu | Glu; Asn |
| cysteine Cys (C) | Ser | Ser; Ala |
| glutamine Gln (Q) | Asn | Asn; Glu |

TABLE 1-continued

Amino Acids and Substitutions

| Original Residue | Conservative Substitutions | Exemplary Substitutions |
|---|---|---|
| glutamic Glu (E) | Asp | Asp; Gln |
| glycine Gly (G) | Ala | Ala |
| histidine His (H) | Arg | Asn; Gln; Lys; Arg |
| isoleucine Ile (I) | Leu | Leu; Val; Met; Ala; Phe; Norleucine |
| leucine Leu (L) | Ile | Norleucine; Ile; Val; Met; Ala; Phe |
| lysine Lys (K) | Arg | Arg; Gln; Asn |
| methionine Met (M) | Leu | Leu; Phe; Ile |
| phenylalanine Phe (F) | Tyr | Leu; Val; Ile; Ala; Tyr |
| proline Pro (P) | Ala | Ala |
| serine Ser (S) | Thr | Thr |
| threonine Thr (T) | Ser | Ser |
| tryptophan Trp (W) | Tyr | Tyr; Phe |
| tyrosine Tyr (Y) | Phe | Trp; Phe; Thr; Ser |
| valine Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a beta-sheet or helical conformation, (b) the charge or hydrophobicity of the molecule at the target site, or (c) the bulk of the side chain. Naturally occurring residues are divided into groups based on common side-chain properties:
  i. Non-polar: Norleucine, Met, Ala, Val, Leu, Ile;
  ii. Polar without charge: Cys, Ser, Thr, Asn, Gln;
  iii. Acidic (negatively charged): Asp, Glu;
  iv. Basic (positively charged): Lys, Arg;
  v. Residues that influence chain orientation: Gly, Pro; and
  vi. Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen-binding fragment thereof that competes with the intact antibody for specific binding, fusion proteins comprising an antigen-binding fragment, and any other modified configuration of the immunoglobulin molecule that comprises an antigen recognition site. Antigen-binding fragments include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a fragment of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_{34}$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

The terms "antigen-binding portion" or "antigen-binding fragment" of an antibody (or simply "antibody portion"), as used interchangeably herein, refers to one or more fragments of an antibody that retain the ability to specifically bind to an antigen (e.g., CXCR5). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al. Proc. Natl. Acad. Sci. USA 85:5879-5883 (1988)). Such single chain antibodies are also intended to be encompassed within the term "antigen-binding fragment" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. Proc. Natl. Acad. Sci. USA 90:6444-6448 (1993); Poljak et al., 1994, Structure 2:1121-1123).

Antibodies may be derived from any mammal, including, but not limited to, humans, monkeys, pigs, horses, rabbits, dogs, cats, mice, etc., or other animals such as birds (e.g. chickens), fish (e.g., sharks) and camelids (e.g., llamas).

A "variable region" of an antibody refers to the variable region of the antibody light chain (VL) or the variable region of the antibody heavy chain (VH), either alone or in combination. As known in the art, the variable regions of the heavy and light chains each consist of four framework regions (FRs) connected by three "complementarity determining regions (CDRs)" also known as hypervariable regions (HVR), and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J. Mol. Biol. 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198.

The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

"Contact residue" as used herein with respect to an antibody or the antigen specifically bound thereby, refers to an amino acid residue present on an antibody/antigen comprising at least one heavy atom (i.e., not hydrogen) that is within 4 A or less of a heavy atom of an amino acid residue present on the cognate antibody/antigen.

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4.

As stated previously herein, residues in a variable domain are typically numbered according Kabat, which is a numbering system used for heavy chain variable domains or light chain variable domains of the compilation of antibodies. See, Kabat et al., 1991, Sequences of Proteins of Immunological Interest, 5th Ed. Public Health Service, National Institutes of Health, Bethesda, Md. Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. The algorithm implemented in the version 2.3.3 release of Abysis (www.abysis.org) can be used to assign Kabat numbering to variable regions CDR-L1, CDR-L2, CDR-L3, CDR-H2, and CDR-H3, and the AbM definition can then be used for CDR-H1.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

The antibody, or antigen-binding fragment thereof, of the invention may be affinity matured. For example, an affinity matured antibody can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and WO2004/058184).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody or vice versa. The term also encompasses an antibody comprising a V region from one individual from one species (e.g., a first mouse) and a constant region from another individual from the same species (e.g., a second mouse).

The term "antigen (Ag)" refers to the molecular entity used for immunization of an immunocompetent vertebrate to produce the antibody (Ab) that recognizes the Ag or to screen an expression library (e.g., phage, yeast or ribosome display library, among others). Herein, Ag is termed more broadly and is generally intended to include target molecules that are specifically recognized by the Ab, thus including fragments or mimics of the molecule used in an immunization process for raising the Ab or in library screening for selecting the Ab. Thus, for antibodies of the invention binding to CXCR5, full-length CXCR5 from mammalian species (e.g., human, monkey, mouse and rat CXCR5), including monomers and multimers, such as dimers, trimers, etc. thereof, as well as truncated and other variants of CXCR5, are referred to as an antigen.

Generally, the term "epitope" refers to the area or region of an antigen (e.g., a protein, nucleic acid, carbohydrate, or lipid, etc.) to which an antibody specifically binds, i.e., an area or region in physical contact with the antibody. Thus, the term "epitope" refers to that portion of a molecule capable of being recognized by and bound by an antibody at one or more of the antibody's antigen-binding regions. Typically, an epitope is defined in the context of a molecular interaction between an "antibody, or antigen-binding fragment thereof" (Ab), and its corresponding antigen. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to CXCR5, e.g., the antibodies compete for binding to the antigen.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. Also, an antibody "specifically binds" or "preferentially binds" to a target if it binds with greater affinity, avidity, more readily, and/or with greater duration to that target in a sample than it binds to other substances present in the sample. For example, an antibody that specifically or preferentially binds to an CXCR5 epitope is an antibody that binds this epitope with greater affinity, avidity, more readily, and/or with greater duration than it binds to other CXCR5 epitopes or non-CXCR5 epitopes. It is also understood by reading this definition, for example, that an antibody (or moiety or epitope) which specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, an antibody, and the like, which recognizes and binds to a specific molecule, but does not substantially recognize or bind other molecules in a sample. For instance, an antibody or a peptide receptor which recognizes and binds to a cognate ligand or binding partner (e.g., an anti-CXCR5 antibody that binds CXCR5) in a sample, but does not substantially recognize or bind other molecules in the sample, specifically binds to that cognate ligand or binding partner. Thus, under designated assay conditions, the specified binding moiety (e.g., an antibody or an antigen-binding fragment thereof or a receptor or a ligand binding fragment thereof) binds preferentially to a particular target molecule and does not bind in a significant amount to other components present in a test sample.

A variety of assay formats may be used to select an antibody or peptide that specifically binds a molecule of interest. For example, solid-phase ELISA immunoassay, immunoprecipitation, Biacore™ (GE Healthcare, Piscataway, N.J.), KinExA, fluorescence-activated cell sorting (FACS), Octet™ (FortéBio, Inc., Menlo Park, Calif.) and Western blot analysis are among many assays that may be used to identify an antibody that specifically reacts with an antigen or a receptor, or ligand binding fragment thereof, that specifically binds with a cognate ligand or binding partner. Typically, a specific or selective reaction will be at least twice the background signal or noise, more typically more than 10 times background, even more typically, more than 50 times background, more typically, more than 100 times background, yet more typically, more than 500 times background, even more typically, more than 1000 times background, and even more typically, more than 10,000 times background. Additionally, an antibody is said to "specifically bind" an antigen when the equilibrium dissociation constant ($K_D$) is ≤1 μM, preferably ≤100 nM, more preferably ≤10 nM, even more preferably, ≤100 pM, yet more preferably, ≤10 pM, and even more preferably, ≤1 pM. In some embodiments, an antibody is said to "specifically bind" an antigen when the equilibrium dissociation constant ($K_D$) is ≤7 nM.

The term "binding affinity" is herein used as a measure of the strength of a non-covalent interaction between two molecules, e.g., and antibody, or fragment thereof, and an antigen. The term "binding affinity" is used to describe monovalent interactions (intrinsic activity).

Additionally, to determine the binding affinity of CXCR5 antibodies to CXCR5-expressing cells, cell binding experiments can be performed to determine the apparent affinity. The apparent affinity of antibody binding to cells expressing the target can be calculated as the $EC_{50}$ of equilibrium binding titration curves in which the geometric mean fluorescence intensity (gMFI) of the antigen binding population is quantified by flow cytometry.

Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation using, e.g., the surface plasmon resonance (SPR) method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D=k_d/k_a$. The value of the dissociation constant can be determined directly by well-known methods, and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art, such as Surface Plasmon Resonance (SPR), e.g. by using a Biacore™ system, or KinExA.

A competitive binding assay can be conducted in which the binding of the antibody to the antigen is compared to the binding of the target by another ligand of that target, such as another antibody or a soluble receptor that otherwise binds the target. The concentration at which 50% inhibition occurs is known as the $K_i$. Under ideal conditions, the $K_i$ is equivalent to $K_D$. The $k_i$ value will never be less than the $K_D$, so measurement of $K_i$ can conveniently be substituted to provide an upper limit for $K_D$.

Following the above definition, binding affinities associated with different molecular interactions, e.g., comparison of the binding affinity of different antibodies for a given antigen, may be compared by comparison of the $K_D$ values for the individual antibody/antigen complexes. $K_D$ values for antibodies or other binding partners can be determined using methods well established in the art. One method for determining the $K_D$ is by using surface plasmon resonance, typically using a biosensor system such as a Biacore® system.

Similarly, the specificity of an interaction may be assessed by determination and comparison of the $K_D$ value for the interaction of interest, e.g., a specific interaction between an antibody and an antigen, with the $K_D$ value of an interaction not of interest, e.g., a control antibody known not to bind CXCR5.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1\times10^{-6}$M or more, more preferably $1\times10^{-5}$ M or more, more preferably $1\times10^{-4}$ M or more, more preferably $1\times10^{-3}$ M or more, even more preferably $1\times10^{-2}$ M or more. An antibody of the invention is preferably capable of binding to its target with an affinity that is at least two-fold, 10-fold, 50-fold, 100-fold 200-fold, 500-fold, 1,000-fold or 10,000-fold or greater than its affinity for binding to another non-CXCR5 molecule.

The term "compete", as used herein with regard to an antibody, means that a first antibody, or an antigen-binding fragment thereof, binds to an epitope in a manner sufficiently similar to the binding of a second antibody, or an antigen-binding fragment thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Standard competition assays may be used to determine whether two antibodies compete with each other. One suitable assay for antibody competition involves the use of the Biacore technology, which can measure the extent of interactions using surface plasmon resonance (SPR) technology, typically using a biosensor system (such as a BIACORE® system). For example, SPR can be used in an in vitro competitive binding inhibition assay to determine the ability of one antibody to inhibit the binding of a second antibody. Another assay for measuring antibody competition uses an ELISA-based approach.

Furthermore, a high throughput process for "binning" antibodies based upon their competition is described in International Patent Application No. WO2003/48731. Competition is present if one antibody (or fragment) reduces the binding of another antibody (or fragment) to CXCR5. For example, a sequential binding competition assay may be used, with different antibodies being added sequentially. The first antibody may be added to reach binding that is close to saturation. Then, the second antibody is added. If the binding of second antibody to CXCR5 is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other.

In addition, an exemplary antibody epitope binning assay using domain swapping between human and mouse CXCR5 proteins to assess potential epitopes among several antibodies is provided in Example 8. The skilled artisan would appreciate, armed with the teachings provided herein, that there are a wide variety of assays known in the art that can be used to determine the binding to a target of at least two antibodies relative to each other, and such assays are included herein.

CXCR5 antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which a CXCR5 antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with CXCR5 antibody.

In addition, the epitope to which the CXCR5 antibody binds can be determined in a systematic screening by using overlapping peptides derived from the CXCR5 sequence and determining binding by the antibody. According to the gene fragment expression assays, the open reading frame encoding CXCR5 can be fragmented either randomly or by specific genetic constructions and the reactivity of the expressed fragments of CXCR5 with the antibody to be tested is determined. The gene fragments may, for example, be produced by PCR and then transcribed and translated into protein in vitro, in the presence of radioactive amino acids. The binding of the antibody to the radioactively labeled CXCR5 fragments is then determined by immunoprecipitation and gel electrophoresis.

Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant CXCR5 in which various residues of the CXCR5 polypeptide have been replaced with alanine. By assessing binding of the antibody to the mutant CXCR5, the importance of the particular CXCR5 residues to antibody binding can be assessed.

Yet another method which can be used to characterize a CXCR5 antibody is to use competition assays with other antibodies known to bind to the same antigen, i.e., various fragments on CXCR5, to determine if the CXCR5 antibody binds to the same epitope as other antibodies. Competition assays are well known to those of skill in the art.

Further, the epitope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, hydrogen/deuterium exchange Mass Spectrometry (H/D-MS) and various competition binding methods well-known in the art. As each method relies on a unique principle, the description of an epitope is intimately linked to the method by which it has been determined. Thus, the epitope for a given antibody/antigen pair will be defined differently depending on the epitope mapping method employed.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterion, e.g., by distance between atoms (e.g., heavy, i.e., non-hydrogen atoms) in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag (e.g. using alanine scanning).

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described at the amino acid level, e.g., determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

Epitopes characterized by competition binding are said to be overlapping if the binding of the corresponding antibodies are mutually exclusive, i.e., binding of one antibody excludes simultaneous or consecutive binding of the other antibody. The epitopes are said to be separate (unique) if the antigen is able to accommodate binding of both corresponding antibodies simultaneously.

The definition of the term "paratope" is derived from the above definition of "epitope" by reversing the perspective. Thus, the term "paratope" refers to the area or region on the antibody which specifically binds an antigen, i.e., the amino acid residues on the antibody which make contact with the antigen (CXCR5) as "contact" is defined elsewhere herein.

The epitope and paratope for a given antibody/antigen pair may be identified by routine methods. For example, the general location of an epitope may be determined by assessing the ability of an antibody to bind to different fragments or variant CXCR5 polypeptides. The specific amino acids within CXCR5 that make contact with an antibody (epitope) and the specific amino acids in an antibody that make contact with CXCR5 (paratope) may also be determined using routine methods, such as those described in the examples. For example, the antibody and target molecule may be combined and the antibody/antigen complex may be crystallized. The crystal structure of the complex may be determined and used to identify specific sites of interaction between the antibody and its target.

An antibody according to the current invention may bind to the same epitope or domain of CXCR5 as the antibodies of the invention that are specifically disclosed herein. Analyses and assays that may be used for the purpose of such identification include assays assessing the competition for binding of CXCR5 between the antibody of interest and CXCR5 receptor, in biological activity assays as described in Examples 1-10, and in analysis of the crystal structure of the antibody.

An antibody of the invention may have the ability to compete or cross-compete with another antibody of the invention for binding to CXCR5 as described herein. For example, an antibody of the invention may compete or cross-compete with antibodies described herein for binding to CXCR5, or to a suitable fragment or variant of CXCR5 that is bound by the antibodies disclosed herein.

That is, if a first antibody competes with a second antibody for binding to CXCR5, but it does not compete where the second antibody is first bound to CXCR5, it is deemed to "compete" with the second antibody (also referred to as unidirectional competition). Where an antibody competes with another antibody regardless of which antibody is first bound to CXCR5, then the antibody "cross-competes" for binding to CXCR5 with the other antibody. Such competing or cross-competing antibodies can be identified based on their ability to compete/cross-compete with a known antibody of the invention in standard binding assays. For example, SPR e.g. by using a Biacore™ system, ELISA assays or flow cytometry may be used to demonstrate competition/cross-competition. Such competition/cross-competition may suggest that the two antibodies bind to identical, overlapping or similar epitopes.

An antibody of the invention may therefore be identified by a method that comprises a binding assay which assesses whether or not a test antibody is able to compete/cross-compete with a reference antibody for a binding site on the target molecule. Methods for carrying out competitive binding assays are disclosed herein and/or are well known in the art. For example they may involve binding a reference antibody of the invention to a target molecule using conditions under which the antibody can bind to the target molecule. The antibody/target complex may then be exposed to a test/second antibody and the extent to which the test antibody is able to displace the reference antibody of the invention from antibody/target complexes may be assessed.

An alternative method may involve contacting a test antibody with a target molecule under conditions that allow for antibody binding, then adding a reference antibody of the invention that is capable of binding that target molecule and assessing the extent to which the reference antibody of the invention is able to displace the test antibody from antibody/target complexes or to simultaneously bind to the target (i.e., non-competing antibody).

The ability of a test antibody to inhibit the binding of a reference antibody of the invention to the target demonstrates that the test antibody can compete with a reference antibody of the invention for binding to the target and thus that the test antibody binds to the same, or substantially the same, epitope or region on the CXCR5 protein as the reference antibody of the invention. A test antibody that is identified as competing with a reference antibody of the invention in such a method is also an antibody of the present invention. The fact that the test antibody can bind CXCR5 in the same region as a reference antibody of the invention and can compete with the reference antibody of the invention suggests that the test antibody may act as a ligand at the same binding site as the antibody of the invention and that the test antibody may therefore mimic the action of the reference antibody and is, thus, an antibody of the invention. This can be confirmed by comparing the activity of CXCR5 in the presence of the test antibody with the activity of CXCR5 in the presence of the reference antibody under otherwise identical conditions, using an assay as more fully described elsewhere herein.

The reference antibody of the invention may be an antibody as described herein, such as 11G2, 41A10, 5H7, and any variant, or portion thereof, as described herein that retains the ability to bind to CXCR5. An antibody of the invention may bind to the same epitope as the reference antibodies described herein or any variant or portion thereof as described herein that retains the ability to bind to CXCR5.

As stated previously elsewhere herein, specific binding may be assessed with reference to binding of the antibody to a molecule that is not the target. This comparison may be made by comparing the ability of an antibody to bind to the target and to another molecule. This comparison may be made as described above in an assessment of $K_D$ or $K_i$. The other molecule used in such a comparison may be any molecule that is not the target molecule. Preferably, the other molecule is not identical to the target molecule. Preferably the target molecule is not a fragment of the target molecule.

The other molecule used to determine specific binding may be unrelated in structure or function to the target. For example, the other molecule may be an unrelated material or accompanying material in the environment.

The other molecule used to determine specific binding may be another molecule involved in the same in vivo pathway as the target molecule, i.e., CXCR5. By ensuring that the antibody of the invention has specificity for CXCR5 over another such molecule, unwanted in vivo cross-reactivity may be avoided.

The antibody of the invention may retain the ability to bind to some molecules that are related to the target molecule.

Alternatively, the antibody of the invention may have specificity for a particular target molecule. For example, it may bind to one target molecule as described herein, but may not bind, or may bind with significantly reduced affinity to a different target molecule as described herein. For example, a full length mature human CXCR5 may be used as the target, but the antibody that binds to that target may be unable to bind to or may bind with lesser affinity to, e.g.

other CXCR5 proteins from other species, such as other mammalian CXCR5. In some embodiments, the antibody binds to both human and mouse CXCR5.

An "Fc fusion" protein is a protein wherein one or more polypeptides are operably linked to an Fc polypeptide. An Fc fusion combines the Fc region of an immunoglobulin with a fusion partner.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As known in the art, a "constant region" of an antibody refers to the constant region of the antibody light chain or the constant region of the antibody heavy chain, either alone or in combination.

The terms "IgG Fc region", "Fc region", "Fc domain" and "Fc", as interchangeably used herein refer to the portion of an IgG molecule that correlates to a crystallizable fragment obtained by papain digestion of an IgG molecule. As used herein, the terms relate to the constant region of an antibody excluding the first constant region immunoglobulin domain and further relates to portions of that region. Thus, Fc refers to the last two constant region immunoglobulin domains of IgA, IgD, and IgG, and the last three constant region immunoglobulin domains of IgE and IgM, and the flexible hinge N-terminal to these domains, or portions thereof. For IgA and IgM, Fc may include the J chain. For IgG, Fc comprises immunoglobulin domains Cγ2 and Cγ3 (C gamma 2 and C gamma 3) and the hinge between Cγ1 (C gamma 1) and Cγ2 (C gamma 2). Although the boundaries of the Fc region may vary, the human IgG heavy chain Fc region is usually defined to comprise residues C226 or P230 to its carboxyl-terminus, wherein the numbering is according to the EU index of Edelman et al., 1969, Proc. Natl. Acad. Sci. USA 63(1):78-85 as described in Kabat et al., 1991. Typically, the Fc domain comprises from about amino acid residue 236 to about 447 of the human IgG1 constant domain. An exemplary human wild type IgG1 Fc domain amino acid sequence is set forth in SEQ ID NO:31. Fc polypeptide may refer to this region in isolation, or this region in the context of an antibody, or an antigen-binding fragment thereof, or Fc fusion protein.

The heavy chain constant domain comprises the Fc region and further comprises the CH1 domain and hinge as well as the CH2 and CH3 (and, optionally, CH4 of IgA and IgE) domains of the IgG heavy chain.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain or antigen-binding fragment thereof) and can be assessed using various assays known in the art for evaluating such antibody effector functions.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRI receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (IT AM) in its cytoplasmic domain Inhibiting receptor FcγRIIB contains an immunoreceptor tyrosine-based inhibition motif (ITIM) in its cytoplasmic domain, (see, e.g., Daeron, Annu. Rev. Immunol. 15:203-234 (1997)). FcRs are reviewed, for example, in Ravetch and Kinet, Annu. Rev. Immunol 9:457-92 (1991); Capel et ah, Immunomethods 4:25-34 (1994); and de Haas et ah, J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et ah, J. Immunol. 117:587 (1976) and Kim et ah, J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et ah, Nature Biotechnology, 15(7):637-640 (1997); Hinton et ah, J. Biol. Chem. 279(8):6213-6216 (2004); WO 2004/92219 (Hinton et al).

"Effector functions" refer to biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, macrophages, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. Proc. Natl. Acad. Sci. (USA) 95:652-656 (1998). Additional antibodies with altered Fc region amino acid sequences and increased or decreased ADCC activity are described, e.g., in U.S. Pat. Nos. 7,923,538, and 7,994,290.

An antibody having an "enhanced ADCC activity" refers to an antibody that is more effective at mediating ADCC in vitro or in vivo compared to the parent antibody, wherein the antibody and the parent antibody differ in at least one structural aspect, and when the amounts of such antibody and parent antibody used in the assay are essentially the same. In some embodiments, the antibody and the parent antibody have the same amino acid sequence, but the antibody is afucosylated while the parent antibody is fucosylated. In some embodiments, ADCC activity will be determined using the in vitro ADCC assay as herein disclosed, but other assays or methods for determining ADCC activity, e.g. in an animal model etc., are contemplated. In some embodiments, an antibody with enhanced ADCC activity has enhanced affinity for Fc gamma RIIIA. In some embodiments, an antibody with enhanced ADCC activity has enhanced affinity for Fc gamma RIIIA (V158). In some embodiments, an antibody with enhanced ADCC activity has enhanced affinity for Fc gamma RIIIA (F158).

An antibody with "altered" FcR binding affinity or ADCC activity is one which has either enhanced or diminished FcR binding activity and/or ADCC activity compared to a parent antibody, wherein the antibody and the parent antibody differ in at least one structural aspect. An antibody that "displays increased binding" to an FcR binds at least one FcR with better affinity than the parent antibody. An antibody that "displays decreased binding" to an FcR, binds at least one FcR with lower affinity than a parent antibody. Such antibodies that display decreased binding to an FcR may possess little or no appreciable binding to an FcR, e.g., 0-20 percent binding to the FcR compared to a native sequence IgG Fc region.

"Enhanced affinity for Fc gamma RIIIA" refers to an antibody that has greater affinity for Fc gamma RIIIA (also referred to, in some instances, as CD 16a) than a parent antibody, wherein the antibody and the parent antibody differ in at least one structural aspect. In some embodiments, the antibody and the parent antibody have the same amino acid sequence, but the antibody is afucosylated while the parent antibody is fucosylated. Any suitable method for determining affinity for Fc gamma RIIIA may be used. In some embodiments, affinity for Fc gamma RIIIA is determined by a method described herein. In some embodiments, an antibody with enhanced affinity for Fc gamma RIIIA has enhanced ADCC activity. In some embodiments, an antibody with enhanced affinity for Fc gamma RIIIA has enhanced affinity for Fc gamma RIIIA(V158). In some embodiments, an antibody with enhanced affinity for Fc gamma RIIIA has enhanced affinity for Fc gamma RIIIA (F158).

L-fucose, also referred to as 6-deoxy-L-galactose, is a monosaccharide that is a component of some N- and O-linked glycans and glycolipids in animals. See Becker and Lowe, Glycobiology 13:41R-51R (2003). Fucose is typically added as a terminal modification to glycans, including glycans attached to blood group antigens, selectins and antibodies. Fucose can be attached to glycans via α(1,2)-, α(1,3)-, α(1,4)- and α(1,6)-linkages by specific fucosyltransferases. α(1,2)-fucose linkages are typically associated with the H-blood group antigens. α(1,3)- and α(1,4)-fucose linkages are associated with modification of LewisX antigens. α(1,6)-fucose linkages are associated with N-linked GlcNAc molecules, such as those on antibodies.

The carbohydrate moieties of the present invention will be described with reference to commonly used nomenclature for the description of oligosaccharides. A review of carbohydrate chemistry which uses this nomenclature is found in Hubbard and Ivan (1981) Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic acid (IUB-IUPAC Joint Commission on Biochemical Nomenclature, 1982, J. Biol. Chem. 257: 3347-3351; (1982) J. Biol. Chem. 257: 3352).

The carbohydrate structures of the present invention occur on the protein expressed as N-linked oligosaccharides. "N-linked glycosylation" refers to the attachment of the carbohydrate moiety via GlcNAc to an asparagine residue in a polypeptide chain. The N-linked carbohydrates all contain a common Man 1-6(Man1-3)Manβ1-4GlcNAcβ1-4GlcNAcβ-R core structure. Therefore, in the core structure described, R represents an asparagine residue of the produced glycoprotein. The sequence of the protein produced will contain an asparagine-X-serine, asparagine-X-threonine, and asparagine-X-cysteine, wherein X is any amino acid except proline (Asn-Xaa-Ser/Thr). "O-linked" carbohydrates, by contrast are characterized by a common core structure, which is the GalNAc attached to the hydroxyl group of a threonine or serine but no consensus sequence is required. Of the N-linked carbohydrates the most important are the "complex" N-linked carbohydrates such as the "bi-antennary" structures described herein.

The skilled artisan will recognize that the glycoprotein immunoglobulin G (IgG) is associated with three types of complex biantennary structures containing zero, one or two galactose residues (Wormland et al., 1997, Biochemistry 36:1370-1380) commonly known as G0, G1 and G2, respectively. With respect to human antibody molecules of the IgG class each has an N-linked oligosaccharide attached at the amide side chain of Asn 297 of the β-4 bend of the inner face of the CH2 domain of the Fc region (Beale and Feinstein, 1976, Q. Rev. Biophys. 9:253-259; Jefferis et al., 1995, Immunol. Letts. 44:111-117). The oligosaccharide moiety attached at Asn 297 of the IgG CH2 domain is of the complex biantennary type having the identified hexasaccharide core structure and variable outer sugar residues (see Jefferis et al., 1997, supra; Wyss and Wagner, 1996, Current Opinions in Biotech. 7:409-416). The core structure (GlcNAc2Man3GlcNAc) is typical of biantennary oligosaccharides and is represented schematically in FIG. 1.

Since each core structure may have a bisecting N-acetylglucoseamine, core fucose and either galactose or sialic acid outer saccharides, there are a total of 36 structurally unique oligosaccharides which may occupy the Asn 297 site (Jefferis and Lund, supra). It will also be recognized that within a particular CH2 domain, glycosylation at Asn 297 may be asymmetric owing to different oligosaccharide chains attached at either Asn 297 residue within the two chain Fc domain. For example, while the heavy chain synthesized within a single antibody-secreting cell may be homogeneous in its amino acid sequence, it is generally differentially glycosylated resulting in a large number of structurally unique Ig glycoforms.

The major types of complex oligosaccharide structures, also referred to as "glycoforms," found in the CH2 domain of the IgG are depicted in International Patent Publication No. WO 99/22764 at page 7.

According to the present invention G0 refers to a biantennary structure wherein no terminal sialic acids (NeuAcs) or Gals are present, G1 refers to a biantennary structure having one Gal and no NeuAcs and G2 refers to a biantennary structure with two terminal Gals and no NeuAcs. See, e.g., FIGS. 2A-2G, depicting exemplary structures of G0, G1, G-1 and G2.

"Afucosylated" antibody or an antibody "lacking fucose" refers to an IgG1 or IgG3 isotype antibody that lacks fucose in its constant region glycosylation. Glycosylation of human IgG1 or IgG3 occurs at Asn297 as core fucosylated biantennary complex oligosaccharide glycosylation terminated with up to 2 Gal residues. In some embodiments, an afucosylated antibody lacks fucose at Asn297. These structures are designated as G0, G1 (a 1,6 or a 1,3) or G2 glycan residues, depending on the amount of terminal Gal residues. See, e.g., Raju, T. S., BioProcess Int. 1: 44-53 (2003). CHO type glycosylation of antibody Fc is described, e.g., in Routier, F. FL, Glycoconjugate J. 14: 201-207 (1997). Various antibody glycoforms are shown in FIGS. 2A-2G.

In some embodiments, the "fucosyl" or "afucosylated", as used interchangeably herein, antibody refers to an antibody that has been glycoengineered to lack core fucose. Antibodies with reduced fucose content in glycan moietites have increased affinity to FcγRIIIa (CD16), and as a result, possess enhanced activity-dependent cellular cytotoxicity (ADCC) activity. Afucosyl antibodies can be produced using the Potelligent® CHOK1SV cell line (Lonza Biologics), which lacks both alleles of the gene responsible for fucose addition (α1,6-fucosyltransferase). Afucosyl or reduced fusose antibodies can also be generated by modifying the oligosaccharide biosynthesis activities in various ways. For example, overexpression of N-acetylglucosamine-transferase III (GnTIII) in the Golgi apparatus of the production cell line generates bisected oligosaccharide structures associated with the Fc constant region of the antibody and suppresses fucosylation. In such expression systems, the level of GnTIII expression correlates with the generation of afucosylated IgG1 glycoforms and resulting enhanced ADCC activity. Fucosylation can also be decreased in cell culture by use of sugar analogs, such as, but not limited to, fucose analogs as described in WO 2012/019165. Thus, afucosylated, or reduced fucose, antibodies can be produced using a wide variety of methods well-known in the art.

In some embodiments, an afucosylated antibody has enhanced affinity for Fc gamma RIIIA. In some embodiments, an afucosylated antibody has enhanced affinity for Fc gamma RIIIA(V158). In some embodiments, an afucosylated antibody has enhanced affinity for Fc gamma RIIIA (F158).

"Glycoform" refers to a complex oligosaccharide structure comprising linkages of various carbohydrate units. Such structures are described in, e.g., Essentials of Glycobiology Varki et al., eds., Cold Spring Harbor Laboratory Press, Cold Spring Harbor, N.Y. (1999), which also provides a review of standard glycobiology nomenclature. Such glycoforms include, but are not limited to, G2, G1, G0, G-1, and G-2 (see, e.g., International Patent Publication No. WO 99/22764).

"Glycosylation pattern" is defined as the pattern of carbohydrate units that are covalently attached to a protein (e.g., the glycoform) as well as to the site(s) to which the glycoform(s) are covalently attached to the peptide backbone of a protein, more specifically to an immunoglobulin protein.

In some embodiments, at least 85 percent of a batch of antibodies recombinantly expressed in non glycomodified CHO host cells are fucosylated at Asn297. When referring to a composition comprising a plurality of antibodies, the antibodies are considered to be afucosylated if less than about 5 percent of the antibodies in the composition comprise fucose at at least one Asn297. Even more preferably, the level of afucosylation is about 100%, that is, no fucose is detected on either heavy chain Asn297 glycoform using standard methods for measuring fucosylation of an antibody. Methods of measuring fucose include any methods known in the art, including the methods described herein. In some embodiments, fucose is undetectable in a composition comprising a plurality of afucosylated antibodies. In some embodiments, an afucosylated antibody has enhanced ADCC activity.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, e.g., as described in Gazzano-Santoro et al., J. Immunol. Methods 202: 163 (1996), may be performed. Antibodies with altered Fc region amino acid sequences and increased or decreased Clq binding capability are described, e.g., in U.S. Pat. No. 6,194,551 B1, U.S. Pat. Nos. 7,923,538, 7,994,290 and WO 1999/51642. See also, e.g., Idusogie et al, J.

As used herein, the terms "wild-type amino acid," "wild-type IgG," "wild-type antibody," or "wild-type mAb," refer to a sequence of amino or nucleic acids that occurs naturally within a certain population (e.g., human, mouse, rats, cell, etc.).

"C—X—C chemokine receptor type 5" or "CXCR5," used interchangeably herein, also referred to in the art as "CD185" and "Burkitt lymphoma receptor 1 (BLR1)," is a G-protein-coupled receptor expressed on certain cells. The term CXCR5 includes CXCR5 homologs and orthologs, including human, cynomolgus monkey, rat, rabbit, and mouse, among others. As used herein, "CXCR5" refers to a mammalian CXCR5, such as human, rat or mouse, as well as non-human primate, bovine, ovine, or porcine CXCR5. Nonlimiting exemplary examples of CXCR5 include human (see, e.g., Genbank Accession Number P60568, SEQ ID NO:32), cynomolgus monkey (see, e.g., Genbank Accession Number Q29615, SEQ ID NO:33), and mouse (SEQ ID NO:34) CXCR5. The term "CXCR5" also encompasses fragments, variants, isoforms, and other homologs of such CXCR5 molecules. Variant CXCR5 molecules will generally be characterized by having the same type of activity as naturally occurring CXCRT5, such as the ability to bind CXCR5 receptor, the ability to induce receptor-mediated activity, and the ability to bind, or not, the antibody, or antigen-binding fragment thereof, of the invention.

The CXCR5 may comprise one or more, two or more, three or more, four or more, five or more, six or more, seven or more, eight or more, nine or more, ten or more, twelve or more or fifteen or more surface accessible residues of CXCR5. FIG. 6 shows the amino acid sequence of wild type mouse and human CXCR5 where exemplary surface accessible residues are underline. Where the CXCR5 comprises a homomultimeric form of CXCR5, the target may comprise one or more, two or more, three or more, four or more, five or more, six or more, seven or more, eight or more, nine or more, ten or more, twelve or more, or fifteen or more surface accessible residues of a first subunit of CXCR5, and one or more, two or more, three or more, four or more, five or more, six or more, seven or more, eight or more, nine or more, ten or more, twelve or more, or fifteen or more surface accessible residues of a second subunit of CXCR5. The target molecule may comprise a known epitope from CXCR5.

Figure 5:
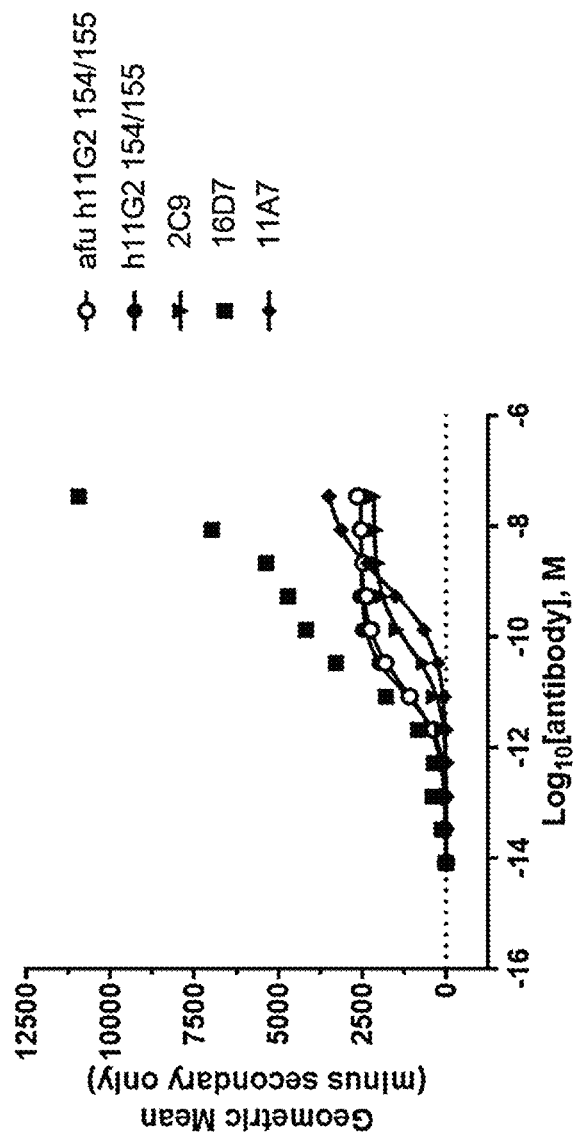
FIG. 5 depicts a graph showing the binding affinity to CXCR5 expressing cells of antibodies: afucosylated h11G2 XC154/XC155 (open circles), fucosylated h11G2 XC154/XC155 (closed circles), 2C9 (closed triangles), 16D7 (closed squares), and 11A7 (closed ovals).

As stated previously, the aligned amino acid sequences of wild type human CXCR5 (hCXCR5) and mouse CXCR5 (mCXCR5) indicating (by underlining) various exemplary extracellular regions (labelled "N," "L1," "L2," and "3") of the proteins is shown in FIG. 5.

As outlined elsewhere herein, certain positions of the antibody molecule can be altered. By "position" as used herein is meant a location in the sequence of a protein. Positions may be numbered sequentially, or according to an established format, for example the EU index and Kabat index can be used to number amino acid residues of an antibody. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1.

The term "Tfh cell" or "Tfh" or "bona fide Tfh" or "germinal center Tfh cell" or "GC Tfh cell," as used interchangeably herein, refers to follicular helper T cells found within the germinal center (GC), which is a structure consisting of GC Tfh cells, GC B cells, follicular dendritic cells (FDCs), macrophages, and stroma. See Crotty, 2014, Immunity 41(4):529-542. Tfh cells are identified by constitutive expression of the B cell follicle homing receptor CXCR5. Functionally, Tfh cells provide instructive signals to B cells to guide isotype switching, somatic hypermutations, and rapid cellular division to seed germinal centers.

The terms "Tfh-like cells," "circulating Tfh cells" and "cTfh", used interchangeably herein, refer to Tfh cells that have exited the germinal center. Upon exiting the GC, the cells acquire a less activated, less polarized phenotype and are referred to as "circulating follicular helper T cells" (cTfh) or "Tfh-like cells". See Crotty, 2014, Immunity 41(4):529-542. These cells express CXCR5. In comparison to germinal center Tfh cells (i.e., "bona fide Tfh cells" or "GC Tfh cells" or "Tfh"), cTfh cells (i.e., Tfh-like cells) express reduced levels of ICOS, Bcl-6, and cellular activation markers such as CD69 and HLA-DR, but maintain the ability to stimulate Ab production and Ig class switching in B cells in vitro upon reactivation with cognate antigens.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR2 ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a polynucleotide of this invention.

Host cells may be prokaryotic cells or eukaryotic cells. Exemplary eukaryotic cells include mammalian cells, such as primate or non-primate animal cells; fungal cells, such as yeast; plant cells; and insect cells.

Any host cell susceptible to cell culture, and to expression of protein or polypeptides, may be utilized in accordance with the present invention. In certain embodiments, the host cell is mammalian. Mammalian cell lines available as hosts for expression are well known in the art and include many immortalized cell lines available from the American Type Culture Collection (ATCC). Nonlimiting exemplary mammalian cells include, but are not limited to, NS0 cells, HEK 293 and Chinese hamster ovary (CHO) cells, and their derivatives, such as 293-6E and CHO DG44 cells, CHO DX611, and Potelligent® CHOK1SV cells (BioWa/Lonza, Allendale, N.J.). Mammalian host cells also include, but are not limited to, human cervical carcinoma cells (HeLa, ATCC CCL 2), baby hamster kidney (BHK, ATCC CCL 10) cells, monkey kidney cells (COS), and human hepatocellular carcinoma cells (e.g., Hep G2). Other non-limiting examples of mammalian cells that may be used in accordance with the present invention include human retinoblasts (PER.C6®; CruCell, Leiden, The Netherlands); monkey kidney CV1 line transformed by SV40 (COS-7, ATCC CRL 1651); human embryonic kidney line 293 (HEK 293) or 293 cells subcloned for growth in suspension culture (Graham et al., 1977, J. Gen Virol. 36:59); mouse sertoli cells (TM4, Mather, 1980, Biol. Reprod. 23:243-251); monkey kidney cells (CV1 ATCC CCL 70); African green monkey kidney cells (VERO-76, ATCC CRL-1 587); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., 1982, Annals N.Y. Acad. Sci. 383:44-68); MRC 5 cells; FS4 cells; a human hepatoma line (Hep G2); and numerous myeloma cell lines, including, but not limited to, BALB/c mouse myeloma line (NS0/1, ECACC No: 85110503), NS0 cells and Sp2/0 cells.

Additionally, any number of commercially and non-commercially available cell lines that express polypeptides or proteins may be utilized in accordance with the present invention. One skilled in the art will appreciate that different cell lines might have different nutrition requirements and/or might require different culture conditions for optimal growth and polypeptide or protein expression, and will be able to modify conditions as needed.

The invention includes any eukaryotic expression system known in the art or disclosed herein for production of proteins of interest, such as expression in an insect cell system, a yeast expression system, or a mammalian cell system, such as, but not limited to, CHO cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "treatment" is an approach for obtaining beneficial or desired clinical results. For purposes of this invention, beneficial or desired clinical results include, but are not limited to, one or more of the following: improved survival rate (reduced mortality), reduction in inflammatory response to the disease, reduction in the amount of tissue fibrosis, improvement in the appearance of the disease lesions, limitation of the pathological lesions to focal sites, decreased extent of damage from the disease, decreased duration of the disease, and/or reduction in the number, extent, or duration of symptoms related to the disease. The term includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

"Ameliorating" means a lessening or improvement of one or more symptoms as compared to not administering a CXCR5 antibody. "Ameliorating" also includes shortening or reduction in duration of a symptom.

As used herein, an "effective dosage" or "effective amount" of drug, compound, or pharmaceutical composition is an amount sufficient to affect any one or more beneficial or desired results. In more specific aspects, an effective amount prevents, alleviates or ameliorates symptoms of disease or infection, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a CXCR5-mediated disease, disorder or condition, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats. In some embodiments, the individual is considered to be at risk for a disease, disorder or condition mediated by or associated with CXCR5 binding to its receptor and signaling mediated thereby. In certain embodiments, the subject has an autoimmune disease, disorder or condition, such as type 1 diabetes. In certain embodiments, the subject is in need of immunosuppression therapy.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Exemplary methods and materials are described herein, although methods and materials similar or equivalent to those described herein can also be used in the practice or testing of the present invention. The materials, methods, and examples are illustrative only and not intended to be limiting.

II. Anti-CXCR5 Antibodies

The present invention relates to antibodies that bind to CXCR5. Preferably, the antibodies specifically bind to CXCR5, i.e., they bind to CXCR5 but they do not detectably bind, or bind at a lower affinity, to other molecules. The invention further relates to anti-CXCR5 antibodies that exhibit an altered effector function. In some embodiments, the altered effector function is increased ADCC. In some embodiments, the antibodies lack, or contain detectably decreased levels of, fucose (i.e., they are afucosylated). The invention also relates to compositions comprising such antibodies as well as uses for such antibodies, including therapeutic and pharmaceutical uses.

In one embodiment, the disclosure provides any of the following, or compositions (including pharmaceutical compositions) comprising, an antibody having a light chain sequence, or a fragment thereof, and a heavy chain, or a fragment thereof, derived from any of the following antibodies: 11G2, 41A10, and 5H7.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody fragment (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the CXCR5 antibody is a monoclonal antibody. In some embodiments, the antibody is a human or humanized antibody.

The CXCR5 antibodies of the invention may be made by any method known in the art. General techniques for production of human and mouse antibodies are known in the art and/or are described herein.

Following initial identification, the activity of a candidate CXCR5 antibody can be further confirmed and refined by bioassays, known to test the targeted biological activities. In some embodiments, an in vitro cell assay is used to further characterize a candidate CXCR5 antibody. For example, bioassays can be used to screen candidates directly. Some of the methods for identifying and characterizing CXCR5 antibody are described in detail in the Examples.

In some aspects, the antibody, or antigen-binding fragment thereof, comprises at least one amino acid sequence selected from the group consisting of the sequence of mouse 11G2 VH, mouse 11G2 VL, h11G2 VH (XC155), h11G2 VH (XC156), h11G2 VH (XC157), h11G2 VH (XC350), h11G2 VH (XC351), h11G2 VH (XC352), h11G2 VH (XC353), h11G2 VH (XC354), h11G2 VL (XC151), h11G2 VL (XC153), h11G2 VL (XC154), h11G2 VL (XC346), h11G2 VL (XC347), h11G2 VL (XC348), h11G2 VL (XC349), mouse 41A10 VH, mouse 41A10 VL, h41A10 VH (XC147), h41A10 VH (XC148), h41A10 VH (XC150), h41A10 VL (XC142), h41A10 VL (XC143), h41A10 VL (XC144), h41A10 VL (XC145), h41A10 VL (XC146), h41A10 VL (XC149), mouse 5H7 VH, and mouse 5H7 VL.

In some aspects, the antibody, or antigen-binding fragment thereof, competes with any of the antibodies above for binding to CXCR5.

In some aspects, the antibody, or antigen-binding fragment thereof, comprises a VH amino acid sequence and a VL amino acid sequence comprising the following combinations: An antibody, or antigen-binding fragment thereof, that competes for binding to human CXCR5 with one or more of mouse 11G2, chimeric 11G2, h11G2 VH (XC152)/VL (XC151), h11G2 VH (XC152)/VL (XC153), h11G2 VH (XC152)/VL (XC154), h11G2 VH (XC152)/VL (XC346), h11G2 VH (XC152)/VL (XC347), h11G2 VH (XC152)/VL (XC348), h11G2 VH (XC152)/VL (XC349), h11G2 VH (XC155)/VL (XC151), h11G2 VH (XC155)/VL (XC153), h11G2 VH (XC155)/VL (XC154), h11G2 VH (XC155)/VL (XC346), h11G2 VH (XC155)/VL (XC347), h11G2 VH (XC155)/VL (XC3484), h11G2 VH (XC155)/VL (XC349), h11G2 VH (XC156)/VL (XC151), h11G2 VH (XC156)/VL (XC153), h11G2 VH (XC156)/VL (XC154), h11G2 VH (XC156)/VL (XC346), h11G2 VH (XC156)/VL (XC347), h11G2 VH (XC156)/VL (XC348), h11G2 VH (XC156)/VL (XC349), h11G2 VH (XC157)/VL (XC151), h11G2 VH (XC157)/VL (XC153), h11G2 VH (XC157)/VL (XC154), h11G2 VH (XC157)/VL (XC346), h11G2 VH (XC157)/VL (XC347), h11G2 VH (XC157)/VL (XC348), h11G2 VH (XC157)/VL (XC349), h11G2 VH (XC350)/VL (XC151), h11G2 VH (XC350)/VL (XC153), h11G2 VH (XC350)/VL (XC154), h11G2 VH (XC350)/VL (XC346), h11G2 VH (XC350)/VL (XC347), h11G2 VH (XC350)/VL (XC348), h11G2 VH (XC350)/VL (XC349), h11G2 VH (XC351)/VL (XC151), h11G2 VH (XC351)/VL (XC153), h11G2 VH (XC351)/VL (XC154), h11G2 VH (XC351)/VL (XC346), h11G2 VH (XC351)/VL (XC347), h11G2 VH (XC351)/VL (XC348), and h11G2 VH (XC351)/VL (XC349), h11G2 VH (XC352)/VL (XC151), h11G2 VH (XC352)/VL (XC153), h11G2 VH (XC352)/VL (XC154), h11G2 VH (XC352)/VL (XC346), h11G2 VH (XC352)/VL (XC347), h11G2 VH (XC352)/VL (XC348), h11G2 VH (XC352)/VL (XC349), h11G2 VH (XC353)/VL (XC151), h11G2 VH (XC353)/VL (XC153), h11G2 VH (XC353)/VL (XC154), h11G2 VH (XC353)/VL (XC346), h11G2 VH (XC353)/VL (XC347), h11G2 VH (XC353)/VL (XC348), h11G2 VH (XC353)/VL (XC349), h11G2 VH (XC354)/VL (XC151), h11G2 VH (XC354)/VL (XC153), h11G2 VH (XC354)/VL (XC154), h11G2 VH (XC354)/VL (XC346), h11G2 VH (XC354)/VL (XC347), h11G2 VH (XC354)/VL (XC348), h11G2 VH (XC354)/VL (XC349), mouse 41A10, chimeric 41A10, h41A10 VH (XC147)/VL (XC142), h41A10 VH (XC147)/VL (XC143), h41A10 VH (XC147)/VL (XC144), h41A10 VH (XC147)/VL (XC145), h41A10 VH (XC147)/VL (XC146), h41A10 VH (XC147)/VL (XC149), h41A10 VH (XC148)/VL (XC142), h41A10 VH (XC148)/VL (XC143), h41A10 VH (XC148)/VL (XC144), h41A10 VH (XC148)/VL (XC145), h41A10 VH (XC148)/VL (XC146), h41A10 VH (XC148)/VL (XC149), h41A10 VH (XC150)/VL (XC142), h41A10 VH (XC150)/VL (XC143), h41A10 VH (XC150)/VL (XC144), h41A10 VH (XC150)/VL (XC145), h41A10 VH (XC150)/VL (XC146), h41A10 VH (XC150)/VL (XC149), mouse 5H7, and chimeric 5H7.

In some aspects, the antibody, or antigen-binding fragment thereof, competes with any of the antibodies above for binding to CXCR5.

In some aspects, the antibody, or antigen-binding fragment thereof, comprises a CDR-L1, a CDR-L2, and a CDR-L3 as set forth in the amino acid sequence of at least one of SEQ ID NOs:1, 5, 35, 47, 48, 49, 50, and 51.

In some aspects, the antibody, or antigen-binding fragment thereof, further comprises a CDR-H1, a CDR-H2, and a CDR-H3 as set forth in the amino acid sequence of at least one of SEQ ID NOs:6, 10, 12, 36, 52, 53, 54, 55, 56, 57.

In some aspects, the antibody, or antigen-binding fragment thereof, comprises a CDR-L1, a CDR-L2, a CDR-L3 as set forth in the amino acid sequence of SEQ ID NO:1, and a CDR-H1, a CDR-H2, and a CDR-H3 as set forth in the amino acid sequence of SEQ ID NO:6.

In some aspects, the antibody, or antigen-binding fragment thereof, comprises a CDR-L1, a CDR-L2, a CDR-L3 as set forth in the amino acid sequence of SEQ ID NO:1, and a CDR-H1, a CDR-H2, and a CDR-H3 as set forth in the amino acid sequence of SEQ ID NO:10.

In some aspects, the antibody, or antigen-binding fragment thereof, comprises a CDR-L1, a CDR-L2, a CDR-L3 as set forth in the amino acid sequence of SEQ ID NO:1, and a CDR-H1, a CDR-H2, and a CDR-H3 as set forth in the amino acid sequence of SEQ ID NO:12.

In some aspects, the antibody, or antigen-binding fragment thereof, comprises a CDR-L1, a CDR-L2, a CDR-L3 as set forth in the amino acid sequence of SEQ ID NO:1, and a CDR-H1, a CDR-H2, and a CDR-H3 as set forth in the amino acid sequence of SEQ ID NO:52.

In some aspects, the antibody, or antigen-binding fragment thereof, further comprises a CDR-H1, a CDR-H2, and a CDR-H3 as set forth in the amino acid sequence of SEQ ID NO:6, and a CDR-L1, a CDR-L2, and a CDR-L3 as set forth in the amino acid sequence of at least one of SEQ ID NOs:1, 5, 35, 47, 48, 49, 50, and 51.

In some aspects, the antibody, or antigen-binding fragment thereof, further comprises a CDR-H1, a CDR-H2, and a CDR-H3 as set forth in the amino acid sequence of SEQ ID NO:10, and a CDR-L1, a CDR-L2, and a CDR-L3 as set forth in the amino acid sequence of at least one of SEQ ID NOs:1, 5, 35, 47, 48, 49, 50, and 51.

In some aspects, the antibody, or antigen-binding fragment thereof, further comprises a CDR-H1, a CDR-H2, and a CDR-H3 as set forth in the amino acid sequence of SEQ ID NO:12, and a CDR-L1, a CDR-L2, and a CDR-L3 as set forth in the amino acid sequence of at least one of SEQ ID NOs:1, 5, 35, 47, 48, 49, 50, and 51.

In some aspects, the antibody, or antigen-binding fragment thereof, further comprises a CDR-H1, a CDR-H2, and a CDR-H3 as set forth in the amino acid sequence of SEQ ID NO:52, and a CDR-L1, a CDR-L2, and a CDR-L3 as set forth in the amino acid sequence of at least one of SEQ ID NOs:1, 5, 35, 47, 48, 49, 50, and 51.

In some aspects, the antibody, or antigen-binding fragment thereof, further comprises a CDR-H1, a CDR-H2, and a CDR-H3 as set forth in the amino acid sequence of SEQ ID NO:27, and a CDR-L1, a CDR-L2, and a CDR-L3 as set forth in the amino acid sequence of SEQ ID NO:26.

In some aspects, the antibody, or antigen-binding fragment thereof, comprises a CDR-L1, a CDR-L2, and a CDR-L3 as set forth in the amino acid sequence encoded by the insert of the plasmid deposited with the ATCC having the Accession number PTA-124324.

In some aspects, the antibody, or antigen-binding fragment thereof, comprises a CDR-H1, a CDR-H2, and a CDR-H3 as set forth in the amino acid sequence encoded by the insert of the plasmid deposited with the ATCC having Accession number PTA-124323.

In some aspects, the antibody, or antigen-binding fragment thereof, comprises a CDR-L1, a CDR-L2, and a CDR-L3 amino acid sequence encoded by the insert of the plasmid deposited with the ATCC having the Accession number PTA-124324, and a CDR-H1, a CDR-H2, and a CDR-H3 amino acid sequence encoded by the insert of the plasmid deposited with the ATCC having Accession number PTA-124323.

In some aspects, the antibody, or antigen-binding fragment thereof, competes with any of the antibodies above for binding to CXCR5.

In some aspects, the antibody, or antigen-binding fragment thereof, comprises a CDR-L1 comprising the amino acid sequence of SEQ ID NO:2, a CDR-L2 comprising the amino acid sequence of SEQ ID NO:3, a CDR-L3 comprising the amino acid sequence of SEQ ID NO:4, a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:9.

In some aspects, the antibody, or antigen-binding fragment thereof, comprises a CDR-L1 comprising the amino acid sequence of SEQ ID NO:2, a CDR-L2 comprising the amino acid sequence of SEQ ID NO:3, a CDR-L3 comprising the amino acid sequence of SEQ ID NO:4, a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:11.

In some aspects, the antibody, or antigen-binding fragment thereof, comprises a CDR-L1 comprising the amino acid sequence of SEQ ID NO:2, a CDR-L2 comprising the amino acid sequence of SEQ ID NO:3, a CDR-L3 comprising the amino acid sequence of SEQ ID NO:4, a CDR-H1 comprising the amino acid sequence of SEQ ID NO:19, a CDR-H2 comprising the amino acid sequence of SEQ ID NO:20, and a CDR-H3 comprising the amino acid sequence of SEQ ID NO:21.

In some aspects, the antibody, or antigen-binding fragment thereof, comprises a CDR-L1 comprising the amino acid sequence of SEQ ID NO:14, a CDR-L2 comprising the amino acid sequence of SEQ ID NO:15, a CDR-L3 comprising the amino acid sequence of SEQ ID NO:16, a CDR-H1 comprising the amino acid sequence of SEQ ID NO:19, a CDR-H2 comprising the amino acid sequence of SEQ ID NO:20, and a CDR-H3 comprising the amino acid sequence of SEQ ID NO:21.

In some aspects, the antibody, or antigen-binding fragment thereof, comprises a CDR-L1 comprising the amino acid sequence of SEQ ID NO:14, a CDR-L2 comprising the amino acid sequence of SEQ ID NO:15, a CDR-L3 comprising the amino acid sequence of SEQ ID NO:16, a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:9.

In some aspects, the antibody, or antigen-binding fragment thereof, comprises a CDR-L1 comprising the amino acid sequence of SEQ ID NO:14, a CDR-L2 comprising the amino acid sequence of SEQ ID NO:15, a CDR-L3 comprising the amino acid sequence of SEQ ID NO:16, a CDR-H1 comprising the amino acid sequence of SEQ ID NO:8, a CDR-H2 comprising the amino acid sequence of SEQ ID NO:9, and a CDR-H3 comprising the amino acid sequence of SEQ ID NO:10.

In some aspects, the antibody, or antigen-binding fragment thereof, comprises the CDR-H1, CDR-H2, and CDR-H3 amino acid sequences as set forth in at least one of the sequences of SEQ ID NOs:6, 10, 12, 36, 52, 53, 54, 55, 56, and 57.

In some aspects, the antibody, or antigen-binding fragment thereof, comprises the CDR-L1, CDR-L2, and CDR-L3 amino acid sequences as set forth in at least one of the sequences of SEQ ID NOs:1, 5, 35, 47, 48, 49, 50 and 51.

In some aspects, the antibody, or antigen-binding fragment thereof, comprises the CDR-L1, CDR-L2, and CDR-L3 amino acid sequences as set forth in SEQ ID NO:5.

The antibody, or antigen-binding fragment thereof, may comprise a VH comprising an amino acid sequence at least 90% identical to the amino acid sequence of SEQ ID NO:6. The VH may comprise an amino acid sequence at least 91%, 92%, 93%, 94%, 95%, 96%, 97%, 98%, or 99%, identical to the amino acid sequence of SEQ ID NO:6. The VH may comprise the amino acid sequence of SEQ ID NO:6.

The antibody, or antigen-binding fragment thereof, may comprise a VH comprising an amino acid sequence at least 90% identical to the amino acid sequence of SEQ ID NO:10. The VH may comprise an amino acid sequence at least 91%, 92%, 93%, 94%, 95%, 96%, 97%, 98%, or 99%, identical to the amino acid sequence of SEQ ID NO:10. The VH may comprise the amino acid sequence of SEQ ID NO:10.

The antibody, or antigen-binding fragment thereof, may comprise a VH comprising an amino acid sequence at least 90% identical to the amino acid sequence of SEQ ID NO:12. The VH may comprise an amino acid sequence at least 91%, 92%, 93%, 94%, 95%, 96%, 97%, 98%, or 99%, identical to the amino acid sequence of SEQ ID NO:12. The VH may comprise the amino acid sequence of SEQ ID NO:12.

The antibody or antigen-binding fragment may comprise a VL comprising an amino acid sequence at least 90% identical to the amino acid sequence of SEQ ID NO:1. The VL may comprise an amino acid sequence at least 91%, 92%, 93%, 94%, 95%, 96%, 97%, 98%, or 99%, identical to the amino acid sequence SEQ ID NO:1. The VL may comprise the amino acid sequence of SEQ ID NO:1.

The antibody or antigen-binding fragment may comprise a VL comprising an amino acid sequence at least 90% identical to the amino acid sequence of SEQ ID NO:5. The VL may comprise an amino acid sequence at least 91%, 92%, 93%, 94%, 95%, 96%, 97%, 98%, or 99%, identical to the amino acid sequene of SEQ ID NO:5. The VL may comprise the amino acid sequence of SEQ ID NO:5.

The antibody, or antigen-binding fragment thereof, may comprise a VH comprising an amino acid sequence at least 90% identical to the amino acid sequence SEQ ID NO:17. The VH may comprise an amino acid sequence at least 91%, 92%, 93%, 94%, 95%, 96%, 97%, 98%, or 99%, identical to the amino acid sequence of SEQ ID NO:17. The VH may comprise the amino acid sequence of SEQ ID NO:17.

The antibody, or antigen-binding fragment thereof, may comprise a VH comprising an amino acid sequence at least 90% identical to the amino acid sequence of SEQ ID NO:18. The VH may comprise an amino acid sequence at least 91%, 92%, 93%, 94%, 95%, 96%, 97%, 98%, or 99%, identical to the amino acid sequence of SEQ ID NO:18. The VH may comprise the amino acid sequence of SEQ ID NO:18.

The antibody or antigen-binding fragment may comprise a VL comprising an amino acid sequence at least 90% identical to the amino acid sequence of SEQ ID NO:13. The VL may comprise an amino acid sequence at least 91%, 92%, 93%, 94%, 95%, 96%, 97%, 98%, or 99%, identical to the amino acid sequence of SEQ ID NO:13. The VL may comprise the amino acid sequence of SEQ ID NO:13.

The antibody or antigen-binding fragment may comprise a VL comprising an amino acid sequence at least 90% identical to the amino acid sequence of SEQ ID NO:58. The VL may comprise an amino acid sequence at least 91%, 92%, 93%, 94%, 95%, 96%, 97%, 98%, or 99%, identical to the amino acid sequence of SEQ ID NO:58. The VL may comprise the amino acid sequence of SEQ ID NO:58.

In one aspect, the afucosylated antibody or antigen-binding fragment thereof may comprise a heavy chain comprising a VH selected from a VH comprising the amino acid sequence of SEQ ID NO:10, SEQ ID NO:12, SEQ ID NO:36, SEQ ID NO:52, SEQ ID NO:53, SEQ ID NO:54, SEQ ID NO:55, SEQ ID NO:56, or SEQ ID NO:57, and further comprising the IgG1 constant domain (SEQ ID NO:31). In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length heavy chain. In a further aspect, said variant shares at least 65%, at least 75%, at least 85%, at least 90%, at least 95%, at least 96%, at least 97%, at least 98%, or at least 99% sequence identity with the full length heavy chain, and wherein said antibody or antigen-binding fragment specifically binds CXCR5.

An afucosylated antibody of the disclosure may comprise a light chain comprising a VL comprising the amino acid sequence of SEQ ID NO:1, SEQ ID NO:5, SEQ ID NO:35, SEQ ID NO:47, SEQ ID NO:48, SEQ ID NO:49, SEQ ID NO:50, or SEQ ID NO:51, wherein the antibody further comprises a light chain constant domain. As more fully set forth elsewhere herein, the afucosylated antibody light chain constant domain can be selected from a CK or CA constant region, for example the CK constant region of SEQ ID NO:30. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length light chain. In a further aspect, said variant shares at least 65%, at least 75%, at least 85%, at least 90%, at least 95%, at least 96%, at least 97%, at least 98%, or at least 99% sequence identity with the full length light chain, and wherein said antibody or antigen-binding fragment specifically binds CXCR5.

The antibody or antigen-binding fragment may comprise a HC comprising an amino acid sequence at least 90%, 91%, 92%, 93%, 94%, 95%, 96%, 97%, 98%, or 99%, identical to the amino acid sequence of SEQ ID NO:29. The HC may comprise the amino acid sequence of SEQ ID NO:29. Preferably, the antibody is afucosylated.

The antibody or antigen-binding fragment may comprise a LC comprising an amino acid sequence at least 90%, 91%, 92%, 93%, 94%, 95%, 96%, 97%, 98%, or 99%, identical to SEQ ID NO:28. The LC may comprise the amino acid sequence of SEQ ID NO:28. Preferably, the antibody is afucosylated.

Preferably, the antibody, or antigen-binding fragment thereof, of the invention is afucosylated. Even more preferably, the antibody, or antigen-binding fragment thereof, is afucosylated and exhibits increased ADCC effector function compared to an otherwise identical antibody that is fucosylated.

Germline Substitutions

In certain embodiments, The antibody, or antigen-binding fragment thereof, comprises the following heavy chain CDR sequences: (i) CDR-H1 comprising SEQ ID NO:7, CDR-H2 comprising SEQ ID NO:8, and CDR-H3 comprising SEQ ID NO:9 or 11; and/or (ii) the following light chain CDR sequences: CDR-L1 comprising SEQ ID NO:2, CDR-L2 comprising SEQ ID NO:3, and CDR-L3 comprising SEQ ID NO:4. These are mouse CDRs and, preferably, are grafted or otherwise added in the context of a human VH and VL domain. A wide variety of acceptor human germline sequences are available and the process for "humanizing" a non-human species antibody to use in humans will well-known in the art and also discussed elsewhere herein. Therefore, the skilled artisan would appreciate that the above mouse CDR sequences can be placed in the context of human V domain amino acid sequences. In doing so, changes to the acceptor human germline sequences are generally made to preserve antibody binding and other desirable characteristics of the original parent (i.e., donor) antibody. Both the CDRs and framework regions (FW) may be engineered as follows.

In certain embodiments, no more than 11, or no more than 10, no more than 9, no more than 8, no more than 7, no more than 6, no more than 5, no more than 4, no more than 3, no more than 2, or no more than 1 substitution is made in CDR-L1, relative to the amino acid sequence of SEQ ID NO:2. In certain embodiments, no more than 6, no more than 5, no more than 4, no more than 3, no more than 3, no more than 2, or no more than one substitution is made in CDR-L2, relative to the amino acid sequence of SEQ ID NO:3. In certain embodiments, no more than 8, no more than 7, no more than 6, no more than 5, no more than 4, no more than 3, no more than 3, no more than 2, or no more than one substitution is made in CDR-L3, relative to the amino acid sequence of SEQ ID NO:4. In some embodiments, no more than 10, no more than 9, no more than 8, no more than 7, no more than 6, no more than 5, no more than 4, no more than 3, no more than 2, or no more than 1 substitution is made in CDR-H1, relative to the amino acid sequence of SEQ ID NO:7. In some embodiments, no more than no more than 17, no more than 16, no more than 15, no more than 14, no more than 13, no more than 12, no more than 11, or no more than one 10, no more than 9, no more than 8, no more than 7, no more than 6, no more than 5, no more than 4, no more than 3, no more than 2, or no more than 1 substitution is made in CDR-H2, relative to relative to the amino acid sequence of SEQ ID NO:8. In some embodiments, no more than 12, no more than 11, or no more than 10, no more than 9, no more than 8, no more than 7, no more than 6, no more than 5, no more than 4, no more than 3, no more than 2, or no more than 1 substitution is made in CDR-H3, relative to the amino acid sequence of SEQ ID NO:9 or relative to the amino acid sequence of SEQ ID NO:11. In certain embodiments, the substitution(s) do not change binding affinity ($K_D$) value by more than 1000-fold, more than 100-fold, or 10-fold. In certain embodiments, the substitution is a conservative substation according to Table 1.

In certain embodiments, the substitution is human germ line substitution in which a (donor) CDR residue is replaced with the corresponding human germline (acceptor) residue, to increase the human amino acid content and potentially reduce immunogenicity of the antibody as described in, e.g., US Patent Application Publication No. 2017/0073395 and Townsend et al., 2015, Proc. Nat. Acad. Sci. USA 112(50): 15354-15359). For example, if human germline DPK9 framework is used and the exemplary antibody mouse or humanized (XC154) 11G2 VL is compared, then the alignment of the CDR-L1 of 11G2 VL (mouse and humanized XC154) antibody (SEQ ID NO:2) and human germline DPK9 is as follows:

|  | Position | | | | | | | | |
| --- | --- | --- | --- | --- | --- | --- | --- | --- | --- |
|  | 27 | 28 | 29 | 30 | 31 | 32 | 33 | 34 | 35 |
| Human Germline DPK9 | Q | *S* | I | S | S | Y | L | N | W |
| 11G2 VL (SEQ ID NO: 2) | E | *S* | V | E | Y | H | G | T | S |

For amino acid position number 28 (italics), the human germline residue (acceptor) and the corresponding 11G2 VL (XC154) residues (donor) are the same, and a germline substitution is not possible. For positions 27, 29, 30, 31, 32, 33, 34 and 35 (bold and underlined), the human germline (acceptor) residue and the corresponding 11G2 VL (XC154) (donor) residue are different. Residues of 11G2 VL (XC154) at these positions may be replaced with the corresponding human germline DPK9 residue to further increase the human residue content. The same process can be followed for each heavy and light chain CDR to increase the content of human amino acid residues while conserving the binding characteristics, e.g., epitope binding, affinity, and the like, while minimizing the content of mouse residues thereby decreasing any potential immunogenicity, e.g., human anti mouse antibody (HAMA) immune response, to the antibody in a human.

Methods and libraries for introducing human germline residues in antibody CDRs are described in detail in US US Patent Application Publication No. 2017/0073395, and Townsend et al., 2015, Proc. Natl. Acad. Sci. USA. 112(50): 15354-15359, and both are herein incorporated by reference in their entirety.

The antibody, or antigen-binding fragment thereof, may comprise a VH framework comprising a human germline VH framework sequence. The VH framework sequence can be from a human VH3 germline, a VH1 germline, a VH5 germline, or a VH4 germline. Preferred human germline heavy chain frameworks are frameworks derived from VH1, VH3, or VH5 germlines. For example, VH frameworks from the following germlines may be used: IGHV3-23, IGHV3-7, or IGHV1-69 (germline names are based on IMGT germline definition). Preferred human germline light chain frameworks are frameworks derived from VK or Vλ germlines. For example, VL frameworks from the following germlines may be used: IGKV1-39 or IGKV3-20 (germline names are based on IMGT germline definition). Alternatively or in addition, the framework sequence may be a human germline consensus framework sequence, such as the framework of human Vλ1 consensus sequence, VK1 consensus sequence, VK2 consensus sequence, VK32 consensus sequence, VH3 germline consensus sequence, VH1 germline consensus sequence, VH5 germline consensus sequence, or VH4 germline consensus sequence. Sequences of human germline frameworks are available from various public databases, such as V-base, IMGT, NCBI, or Abysis.

The antibody, or antigen-binding fragment thereof, may comprise a VL framework comprising a human germline VL framework sequence. The VL framework may comprise one or more amino acid subsitutions, additions, or deletions, while still retaining functional and structural similarity with the germline from which it was derived. In some aspects, the VL framework is at least 90%, at least 91%, at least 92%, at least 93%, at least 94%, at least 95%, at least 96%, at least 97%, at least 98%, at least 99%, or 100% identical to a human germline VL framework sequence. In some aspects, the antibody, or antigen-binding fragment thereof, comprises a VL framework comprising 1, 2, 3, 4, 5, 6, 7, 8, 9, 10 amino acid substitutions, additions or deletions relative to the human germline VL framework sequence. In some aspects, the 1, 2, 3, 4, 5, 6, 7, 8, 9, or 10 amino acid substitutions, additions or deletions are only in the framework regions. In some aspects, the % identity is based on similarity with VL excluding those fragments herein defined as CDRs.

The human germline VL framework may be the framework of DPK9 (IMGT name: IGKV1-39). The human germline VL framework may be the framework of DPK12 (IMGT name: IGKV2D-29). The human germline VL framework may be the framework of DPK18 (IMGT name: IGKV2-30). The human germline VL framework may be the framework of DPK24 (IMGT name: IGKV4-1). The human germline VL framework may be the framework of HK102_V1 (IMGT name: IGKV1-5). The human germline VL framework may be the framework of DPK1 (IMGT name: IGKV1-33). The human germline VL framework may be the framework of DPK8 (IMGT name: IGKV1-9). The human germline VL framework may be the framework of DPK3 (IMGT name: IGKV1-6). The human germline VL framework may be the framework of DPK21 (IMGT name: IGKV3-15). The human germline VL framework may be the framework of Vg_38K (IMGT name: IGKV3-11). The human germline VL framework may be the framework of DPK22 (IMGT name: IGKV3-20). The human germline VL framework may be the framework of DPK15 (IMGT name: IGKV2-28). The human germline VL framework may be the framework of DPL16 (IMGT name: IGLV3-19). The human germline VL framework may be the framework of DPL8 (IMGT name: IGLV1-40). The human germline VL framework may be the framework of V1-22 (IMGT name: IGLV6-57). The human germline VL framework may be the framework of human Vλ consensus sequence. The human germline VL framework may be the framework of human Vλ1 consensus sequence. The human germline VL framework may be the framework of human Vλ3 consensus sequence. The human germline VL framework may be the framework of human VK consensus sequence. The human germline VL framework may be the framework of human VK1 consensus sequence. The human germline VL framework may be the framework of human VK2 consensus sequence. The human germline VL framework may be the framework of human VK3 consensus sequence.

In some aspects, the VL framework is DPK9. Other similar framework regions are also predicted to deliver advantageous antibodies of the invention comprising CDRs of SEQ ID NOs:2, 3, 4, 7, 8, 9, 11, 14, 15, 16; and CDRs specified by the following VL amino acid sequences: 1, 5, 13, 28, 35, 37, 39, 47, 48, 48, 50, 51, 58, 59, 60, 61, 62, 97, 98, including DPK5, DPK4, DPK1, IGKV1-5*01, DPK24, DPK21, DPK15, IGKV1-13*02, IGKV1-17*01, DPK8, IGKV3-11*01, and DPK22 which comprise 99, 97, 97, 96, 80, 76, 66, 97, 97, 96, 76, and 74% identity respectively to the FW region of DPK-9 and one or fewer amino acid differences in common structural features (Kabat Numbering) (A) residues directly underneath CDR (Vernier Zone), L2, L4, L35, L36, L46, L47, L48, L49, L64, L66, L68, L69, L71, (B) VH/VL Chain packing Residues: L36, L38, L44, L46, L87 and (C) canonical CDR Structural support residues L2, L48, L64, L71 (see Lo, "Antibody Humanization by CDR Grafting", (2004) Antibody Engineering, Vol. 248, Methods in Molecular Biology pp 135-159 and O'Brien and Jones, "Humanization of Monoclonal Antibodies by CDR Grafting", (2003) Recombinant Antibodies for Cancer Therapy, Vol. 207, Methods in Molecular Biology pp 81-100). Particularly preferred are framework regions of DPK5, DPK4, DPK1, IGKV1-5*01, DPK24, DPK21, and DPK15 sharing 99, 97, 97, 96, 80, 76, 66% identity to DPK9 respectively and have no amino acid differences in these common structural features. In some aspects, the % identity is based on similarity with VL excluding those fragments herein defined as CDRs.

The antibody, or antigen-binding fragment thereof, may comprise a VH framework comprising a human germline VH framework sequence. The VH framework may comprise one or more amino acid substitutions, additions, or deletions, while still retaining functional and structural similarity with the germline from which it was derived. In some aspects, the VH framework is at least 90%, at least 91%, at least 92%, at least 93%, at least 94%, at least 95%, at least 96%, at least 97%, at least 98%, at least 99%, or 100% identical to a human germline VH framework sequence. In some aspects, the antibody, or antigen-binding fragment thereof, comprises a VH framework comprising 1, 2, 3, 4, 5, 6, 7, 8, 9, 10 amino acid substitutions, additions or deletions relative to the human germline VH framework sequence. In some aspects, the 1, 2, 3, 4, 5, 6, 7, 8, 9, or 10 amino acid substitutions, additions or deletions are only in the framework regions. In some aspects, the % identity is based on similarity with VH excluding those fragments herein defined as CDRs.

The human germline VH framework may be the framework of DP54 or IGHV3-7. The human germline VH framework may be the framework of DP47 or IGHV3-23. The human germline VH framework may be the framework of DP71 or IGHV4-59. The human germline VH framework may be the framework of DP75 or IGHV1-2_02. The human germline VH framework may be the framework of DP10 or IGHV1-69. The human germline VH framework may be the framework of DP7 or IGHV1-46. The human germline VH framework may be the framework of DP49 or IGHV3-30. The human germline VH framework may be the framework of DP51 or IGHV3-48. The human germline VH framework may be the framework of DP38 or IGHV3-15. The human germline VH framework may be the framework of DP79 or IGHV4-39. The human germline VH framework may be the framework of DP78 or IGHV4-30-4. The human germline VH framework may be the framework of DP73 or IGHV5-51. The human germline VH framework may be the framework of DP50 or IGHV3-33. The human germline VH framework may be the framework of DP46 or IGHV3-30-3. The human germline VH framework may be the framework of DP31 or IGHV3-9. The human germline VH framework may be the framework of human VH germline consensus sequence. The human germline VH framework may be the framework of human VH3 germline consensus sequence. The human germline VH framework may be the framework of human VH5 germline consensus sequence. The human germline VH framework may be the framework of human VH1 germline consensus sequence. The human germline VH framework may be the framework of human VH4 germline consensus sequence.

In some aspects, the VH framework is DP-54. Other similar framework regions are also predicted to deliver advantageous antibodies of the invention comprising CDRs of SEQ ID NOs:7, 8, 9, 11,19, 20, 21, and CDRs specified by the following VH amino acid sequences: 6, 10, 12, 17, 18, 36, 38, 40, 52, 53, 54, 55, 56, 57, 63, 96, including DP-50, IGHV3-30*09, IGHV3-30*15, IGHV3-48*01, DP-77, DP-51, IGHV3-66*01, DP-53, DP-48, IGHV3-53*01, IGHV3-30*02, and DP-49 which comprise 93, 92, 92, 99, 97, 97, 96, 96, 94, 94, 93, 92% identity respectively to the FW region of DP-54 and one or fewer amino acid differences in common structural features (Kabat Numbering) (A) residues directly underneath CDR (Vernier Zone), H2, H47, H48, and H49, H67, H69, H71, H73, H93, H94, (B) VHNL Chain packing Residues: H37, H39, H45, H47, H91, H93 and (C) canonical CDR Structural support residues H24, H71, H94 (see Lo 2004, and O'Brien and Jones 2003). Particularly preferred are framework regions of DP-50, IGHV3-30*09, IGHV3-30*15 sharing 93, 92 and 92% identity to DP-54 respectively and have no amino acid differences in these common structural features. In some aspects, the % identity is based on similarity with VH excluding those fragments herein defined as CDRs.

In certain embodiments, the antibody, or antigen-binding fragment thereof, described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:8, and/or (ii) a VL comprising an amino acid sequence that is at least 50%, at least 60%, at least 66%, at least 70%, at least 75%, at least 76%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:1. Any combination of these VL and VH sequences is also encompassed by the invention.

In certain embodiments, the antibody, or antigen-binding fragment thereof, described herein comprises (i) a HC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:29; and/or (ii) a LC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:28. Any combination of these HC and LC sequences is also encompassed by the invention.

In certain embodiments, the antibody, or antigen-binding fragment thereof, described herein comprises an Fc domain. The Fc domain can be derived from IgA (e.g., IgA$_1$ or IgA$_2$), IgG, IgE, or IgG (e.g., IgG$_1$, IgG$_2$, IgG$_3$, or IgG$_4$).

Also provided by the invention is an antibody, or antigen-binding fragment thereof, that competes for binding to human CXCR5 with any of the antibody, or antigen-binding fragment thereof, described herein, such as any one of the antibodies provided herein (or antigen-binding fragment thereof). For example, if the binding of an antibody, or an antigen-binding fragment thereof, to human CXCR5 hinders the subsequent binding to human CXCR5 by CXCL13 the antibody or an antigen-binding fragment thereof competes with CXCL13 for human CXCR5 binding.

The antibodies and antigen-binding fragments provided by the invention include monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion, domain antibodies (dAbs), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies and antigen-binding fragments may be murine, rat, human, or any other origin (including chimeric or humanized antibodies). In some embodiments, the antibody is a monoclonal antibody. In some embodiments, the antibody is a chimeric, humanized or human antibody. In certain embodiments, the antibody is a human antibody. In certain embodiments, the antibody is a humanized antibody.

Epitope Mapping

Also provided by the invention is an antibody, or antigen-binding fragment thereof, that binds to the same human CXCR5 epitope as an antibody, or antigen-binding fragment thereof, described herein. For example, antibody competition assays (and overlapping epitope analysis) can be assessed by SPR, flow cytometry, and any other assay known in the art.

In one aspect, the invention encompasses an antibody, or antigen-binding fragment thereof, that binds human CXCR5, and cynomolgus CXCR5, but does not bind mouse CXCR5.

The invention also includes an antibody, or antigen-binding fragment thereof, that binds the N-terminus region ("N") of human CXCR5. The N-terminus of CXCR5 comprises amino acid residue numbers 1-51 based on the numbering of the amino acid sequence of SEQ ID NO:31.

The invention includes an antibody, or antigen-binding fragment thereof, that specifically binds CXCR5 at an epitope comprising leucine (L) at amino acid residue position number 11 according to the numbering of the amino acid sequence of SEQ ID NO:32.

In one aspect, the invention includes an antibody, or antigen-binding fragment thereof, that specifically binds CXCR5 at an epitope comprising aspartate (D) at amino acid residue position number 22 according to the numbering of the amino acid sequence of SEQ ID NO:32.

In one aspect, the invention includes an antibody, or antigen-binding fragment thereof, that specifically binds CXCR5 at an epitope comprising leucine at amino acid residue position number 11 and aspartate at amino acid residue position number 22 according to the numbering of the amino acid sequence of SEQ ID NO:32.

The invention includes an antibody, or antigen-binding fragment thereof, that specifically binds CXCR5 where the amino acid residue at position number 11 is leucine according to the numbering of the amino acid sequence of SEQ ID NO:32.

The invention includes an antibody, or antigen-binding fragment thereof, that specifically binds CXCR5 where the amino acid residue at position number 11 is leucine, but does not bind CXCR5 wherein the amino acid residue at position number 11 is threonine, according to the numbering of the amino acid sequence of SEQ ID NO:32.

In one aspect, the invention includes an antibody, or antigen-binding fragment thereof, that specifically binds wild type human CXCR5 but does not bind where amino acid residue position number 11, according to the numbering of the amino acid sequence of SEQ ID NO:32, is not leucine.

The invention includes an antibody, or antigen-binding fragment thereof, that specifically binds CXCR5 where the amino acid residue at position number 22 is aspartate according to the numbering of the amino acid sequence of SEQ ID NO:32.

In one aspect, the invention includes an antibody, or antigen-binding fragment thereof, that specifically binds wild type human CXCR5 but does not bind where the amino acid residue at position number 22 is not aspartate according to the numbering of the amino acid sequence of SEQ ID NO:32.

In one aspect, the invention includes an antibody, or antigen-binding fragment thereof, that specifically binds wild type human CXCR5 but does not bind where amino acid residue position number 22 is alanine, according to the numbering of the amino acid sequence of SEQ ID NO:32.

The invention includes an antibody, or antigen-binding fragment thereof, that specifically binds CXCR5 where the amino acid residue at position number 11 is leucine and the amino acid residue at position number 22 is aspartate, according to the numbering of the amino acid sequence of SEQ ID NO:32.

In one aspect, the invention includes an antibody, or antigen-binding fragment thereof, that specifically binds human CXCR5 but does not bind CXCR5 where the amino acid residue at position number 11 is not leucine and the amino acid residue at position number 22 is not aspartate, according to the numbering of the amino acid sequence of SEQ ID NO:32.

In one aspect, the invention includes an antibody, or antigen-binding fragment thereof, that specifically binds human CXCR5 but does not bind where the amino acid residue at position number 11 is threonine and the amino acid residue at position number 22 is alanine, according to the numbering of the amino acid sequence of SEQ ID NO:32.

The skilled artisan would appreciate, armed with the teachings of the present invention, that the amino acid residue at position number 11 and/or at position number 22, according to the numbering of the amino acid sequence of SEQ ID NO:32, are critical for the binding of an antibody of the invention. More specifically, these amino acid residues are crucial for binding to CXCR5 by antibody 11G2, or antigen-binding fragment thereof. Thus, the skilled artisan would understand that the invention includes an antibody, or antigen-binding fragment thereof, that specifically binds CXCR5 wherein the amino acid residue at position 11 is leucine and the amino acid residue at position 22 is aspartate. Substitution or deletion of these amino acid residues can result in loss of binding to CXCR5. Certain substitutions of the amino acid residue at position 11 may preserve binding, but not substitution of that (leucine) amino acid residue with threonine. Similarly, certain substitutions or deletion of the amino acid residue at position 22 may preserve binding, but not substitution of aspartate at that amino acid residue number with alanine. Therefore, a feature of the 11G2 antibody, or antigen-binding fragment thereof, or an antibody that competes for binding therewith, is that the antibody binds human CXCR5 wherein leucine 11 and aspartate 22 are present according to the numbering of the amino acid sequence of SEQ ID NO:32, but the antibody does not bind where leucine 11 is replaced with threonine, or another amino acid residue, and where the antibody does not bind where aspartate 22 is replaced with alanine, or another amino acid residue. Testing for loss of binding after amino acid substitution at amino acid residue position number 11 and/or number 22 can be performed using a wide variety of methods well-known in the art, including binding analysis using point mutation polypeptides as per the methods exemplified herein.

Based upon the teachings provided herein, one skilled in the art would appreciate that an antibody of the invention can compete with, e.g., 11G2, and yet not comprise an epitope comprising leucine at amino acid residue number 11 and/or aspartate at amino acid residue number 22 according to the numbering of the amino acid sequence of SEQ ID NO:32. That is, an antibody can compete with an antibody of invention for binding to CXCR5, but the competing antibody binding is not affected where the leucine at amino acid residue number 11 or the aspartate at amino acid residue number 22 are substituted with a different amino acid (e.g., threonine for leucine and/or alanine for aspartate), e.g., 2C9, 11A7 and 16D7. Thus, the antibody of the invention competes for binding to CXCR5 and also does not bind CXCR5 where amino acid residue number 11 is not leucine, and more specifically, it is threonine, and/or where amino acid residue number 22 is not aspartate, and more specifically, it is alanine. As stated previously elsewhere herein, production of mutant CXCR5 proteins and assays for assessing antibody competition binding are well-known in the art, including those methods described herein. Thus, based upon the teachings provided herein, the skilled artisan would be readily capable of identifying antibodies that bind CXCR5, compete for binding with an antibody of the invention, and lose the ability to bind CXCR5 muteins where certain amino acids have been substituted, e.g., leucine 11, aspartate 22, or both, all according to the numbering of the amino acid sequence of SEQ ID NO:32.

In another aspect, the invention includes an antibody, or antigen-binding fragment thereof, that competes for binding with antibody 11G2, or antigen-binding fragment thereof, where the antibody does not bind CXCR5 where amino acid residue number 11 is not leucine, according to the numbering of the amino acid sequence of SEQ ID NO:32.

In another aspect, the invention includes an antibody, or antigen-binding fragment thereof, that competes for binding with antibody 11G2, or antigen-binding fragment thereof, where the antibody does not bind CXCR5 where amino acid residue number 22 is not aspartate, according to the numbering of the amino acid sequence of SEQ ID NO:32.

In another aspect, the invention includes an antibody, or antigen-binding fragment thereof, that competes for binding with antibody 11G2, or antigen-binding fragment thereof, where the antibody does not bind CXCR5 where amino acid residue number 11 is not leucine and amino acid residue number 22 is not aspartate, according to the numbering of the amino acid sequence of SEQ ID NO:32.

In another aspect, the invention includes an antibody, or antigen-binding fragment thereof, that competes for binding with antibody 11G2, or antigen-binding fragment thereof, where the antibody does not bind CXCR5 where amino acid residue number 11 is threonine, according to the numbering of the amino acid sequence of SEQ ID NO:32.

In another aspect, the invention includes an antibody, or antigen-binding fragment thereof, that competes for binding with antibody 11G2, or antigen-binding fragment thereof, where the antibody does not bind CXCR5 where amino acid residue number 22 is alanine, according to the numbering of the amino acid sequence of SEQ ID NO:32.

In another aspect, the invention includes an antibody, or antigen-binding fragment thereof, that competes for binding with antibody 11G2, or antigen-binding fragment thereof, where the antibody does not bind CXCR5 where amino acid residue number 11 is threonine and where amino acid residue number 22 is alanine, according to the numbering of the amino acid sequence of SEQ ID NO:32.

Biological Activity of Anti-CXCR5 Antibodies

In addition to binding an epitope on CXCR5, the antibody, or antigen-binding fragment thereof, of the invention can mediate a biological activity. That is, the invention includes an isolated antibody, or antigen-binding fragment thereof, that specifically binds CXCR5 and mediates at least one detectable activity selected from the following: (a) binds CXCR5+ cells with high apparent affinity, but does not bind cells expressing CXCR5 mouse, rat or rabbit orthologs; (b) antagonizes CXCL13 inhibition of cAMP release triggered by forskolin; (c) triggers ADCC of CXCR5-expressing cells in human donor and cynomolgus PBMCs and human donor TMCs; (d) binds human CXCR5 but does not bind human chemokine receptors CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR6, CXCR7, or XCR1; (e) depletes B cells in the peripheral blood and/or secondary lymphoid organs (i.e., lymph nodes, spleen, Peyer's patches, and mucosa-associated lymphoid tissue); (f) depletes Tfh-like cells in the peripheral blood; (g) depletes bona fide Tfh cells in the secondary lymphoid organs; and (h) impairs a humoral immune memory response.

In one aspect, the invention includes an antibody, or binds CXCR5+ cells with high apparent affinity, but does not bind cells expressing CXCR5 mouse, rat or rabbit orthologs. Apparent affinity binding can be assessed using flow cytometry to detect antibody binding to cells expressing the target protein (e.g., CXCR5). The cells can be transiently or stably transfected with a nucleic acid encoding CXCR5. Alternatively, the cells can be cells that naturally express CXCR5 on their surface. Regardless of the sources of CXCR5+ cells, the binding of the antibody to the cells can be readily assessed using a variety of art-recognized methods. The antibody, or antigen-binding fragment thereof, bind human CXCR5, or cyno CXCR5, but do not detectably bind, or bind to a much lesser extent, mouse, rat or rabbit CXCR5.

The invention includes an antibody, or antigen-binding fragment thereof, that specifically binds CXCR5 and antagonizes an activity mediated by CXCL13 binding to CXCR5. There are many assays known in the art to determine the inhibition of an activity mediated by CXCR5-CXCL13 signaling. One such assay is a cAMP reporter assay. In such an assay, forskolin induces cAMP production which is inhibited by CXCR5-CXCL13 signaling in a cell stably expressing CXCR5. The ability of the anti-CXCR5 antibody to bind CXCR5 and antagonize the effect of CXCR5-CXCL13 signaling is therefore assessed by measuring the level of cAMP produced in the presence or absence of the antibody. Preferably, the antibody can mediate a dose-dependent increase in cAMP levels with an EC50 of about 50 pM, about 100 pM, about 200, pM, about 400 pM, about 600 pM, about 700 pM, about 750 pM, about 790 pM, about 800 pM, about 850 pM, about 900 pM, about 950 pM, about 960 pM, about 970 pM, about 980 pM, about 990 pm, or about 1000 pM. More preferably, the antibody, or antigen-binding fragment thereof, inhibits CXCL13 inhibition of cAMP triggered by forskolin with an EC50 of about 961 pM.

The invention includes an antibody, or antigen-binding fragment thereof, that specifically binds CXCR5 and that triggers ADCC of CXCR5-expressing cells in human donor and cynomolgus PBMCs and human donor tonsillar mononuclear cells (TMCs). Many ADCC assays can be used to assess the ADCC activity of an antibody. Once such exemplary assay is described herein in Examples 6 and 7, but the present invention is not limited to this specific ADCC assay. The invention includes an antibody, or antigen-binding fragment thereof, that exhibits an ADCC activity on human B cells, human Tfh-like cells, human Tfh cells and cynomolgus monkey B cells with an EC50 of about 0.11 pM, 0.2 pM, 0.5 pM, 1 pM. 1.5 pM, 2.0 pM, 2.5 pM, 3.0 pM, 4.5 pM, 4.8 pM, 5.0 pM, 6.0 pM, 7.0 pM, 8.0 pM, 9.0 pM, 10 pM, 11 pM, 12 pM, 15 pM, 20, pM, 25 pM, 30 pM, 35 pM, or 40 pM. More preferably, the antibody, or antigen-binding fragment thereof, exhibits ADCC activity with an EC50 of about 2.01±2.28 pM against human B cells, about 4.82±2.88 pM against human Tfh-like cells, about 0.11 pM against human Thf cells, and about 15.3±11.7 pM against cyno B cells. Even more preferably, the antibody, or antigen-binding fragment thereof, is afucosylated.

The invention encompasses an antibody, or antigen-binding fragment thereof, that binds human CXCR5 but does not detectably bind human proteins CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR6, CXCR7, or XCR1.

The invention encompasses an antibody, or antigen-binding fragment thereof, that specifically binds CXCR5 and exhibits dose-dependent depletion of B cells in the peripheral blood. The depletion can be permanent, or more preferably, the depletion is transient and/or reversible. In one aspect, the antibody dose sufficient to mediate B cell depletion can range from 0.001 to about 0.2 mg, wherein 0.0001 mg/kg can mediate a depletion of B cells and Tf h-like cells in the peripheral blood of cynomolgus monkeys of about 50% compared with the percentage of B cells or Tfh-like cells in the peripheral blood where the antibody is not administered. In addition, the antibody can mediate maximal depletion of B cells and Tfh-like cells in the peripheral blood of a cynomolgus monkey administered at a dose of less than 5 mg/kg administered intravenously (IV). Preferably, partial to full recovery of B cells, Tfh-like and Tfh cells occurs following administration of the antibody.

The invention includes an antibody, or antigen-binding fragment thereof, that specifically binds CXCR5 and impairs humoral immune memory response. In one aspect the humoral memory response is assessed using a vaccine recall assay. That is the antibody is administered to a subject that has been vaccinated previously with an antigen, e.g., tetanus toxoid (TT). The subject is given a second administration of the antigen and the immune response, e.g., IgM and IgG titers, is compared with the immune response in an otherwise identical subject to which the antibody is not administered. The skilled artisan would appreciated once provided the teachings disclosed herein, that many assays to determine a humoral memory response can be used to assess the ability of the antibody, or antigen-binding fragment thereof, to impair a humoral memory response. Further, the skilled artisan would appreciate that the ability to impair a humoral memory response is a desirable characteristic for an antibody, or antigen-binding fragment thereof, to be used as a therapeutic to treat or prevent an immune disease in a subject in need thereof.

The invention encompasses an antibody, or antigen-binding fragment thereof, that exhibits at least one, preferably, two, even more preferably, three, even more preferably, four, yet more preferably, five, even more preferably, six, more preferably, seven, and even more preferably, all of the above discussed biological activities.

III. Afucosylated Anti-CXCR5 Antibodies

In one embodiment, antibodies are provided having a carbohydrate structure that lacks fucose attached (directly or indirectly) to an Fc region (i.e., afucosylated antibodies). For example, the amount of fucose in a composition comprising a plurality of such antibodies may be from 0 percent to about 30 percent, from 0 percent to about 20 percent, from 0 percent to about 15 percent, from 0 percent to about 10 percent, and more preferably, from 0 percent to about 5 percent. In some embodiments, a composition comprising a plurality of such antibodies comprises at least 80 percent, more preferably, at least 85 percent, yet more preferably, at least 90 percent, even more preferably, at least 95 percent afucosylated antibodies, yet more preferably, at least 99 percent, and most preferably, at least 99.5 percent afucosylated antibodies. In some embodiments, the antibodies are 100 percent afucosylated; that is, fucose is not detected at Asn297 using an art-recognized method for detecting fucose in an antibody. The amount of fucose is determined by calculating the average amount of fucose within the sugar chain at Asn297, relative to the sum of all glycostructures attached to Asn 297 (e.g., complex, hybrid and high mannose structures).

In some embodiments, the level of fucosylation is no more than 0.5%, which is based on the limit of quantification (LOQ) for the test method. Thus, in some embodiments, the level of afucosylation is greater than or equal to 99.5%. The N-linked oligosaccharide profile method can be used to determine the level of fucosylation, sialylation, mannosylation, and terminal glactosylation in a sample. The N-linked Oligosaccharide method can be used to evaluate N-linked glycans. Briefly, N-linked glycans are enzymatically released from the protein with peptide-N-glycosidase F. The glycans are then derivatized by a fluorescent agent and analyzed using hydrophilic interaction liquid chromatography and fluorescence detection. The chromatographic profile is then compared to that of the reference material. This method and many other methods are known in the art for assessing fucosylation of an antibody, and can be used to determine the level of fucosylation present in the antibody of the present invention.

Non-limiting exemplary methods of detecting fucose in an antibody include MALDI-TOF mass spectrometry (see, e.g., WO 2008/077546), HPLC measurement of released fluorescently labeled oligosaccharides (see, e.g., Schneider et al, "N-Glycan analysis of monoclonal antibodies and other glycoproteins using UHPLC with fluorescence detection," Agilent Technologies, Inc. (2012); Lines, J. Pharm. Biomed. Analysis, 14: 601-608 (1996); Takahasi, J. Chrom., 720: 217-225 (1996)), capillary electrophoresis measurement of released fluorescently labeled oligosaccharides (see, e.g., Ma et al., Anal. Chem., 71: 5185-5192 (1999)), and HPLC with pulsed amperometric detection to measure monosaccharide composition (see, e.g., Hardy, et al, Analytical Biochem., 170: 54-62 (1988)). Asn297 refers to the asparagine residue located at about position 297 in the Fc region (EU numbering of Fc region residues); however, Asn297 may also be located about plus or minus 3 amino acids upstream or downstream of position 297, i.e., between positions 294 and 300, due to minor sequence variations in antibodies. In a CXCR5 antibody described herein, Asn297 is found in the sequence QYNST, and is in bold and underlined in Table 16 (e.g., SEQ ID NO:31 of wild type human IgG1 Fc domain).

Fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "afucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336: 1239-1249 (2004); Yamane-Ohnuki et al. Biotech. Bioeng. 87: 614 (2004). Examples of cell lines capable of producing afucosylated antibodies include Lec 13 CHO cells deficient in protein fucosylation (Ripka et al. Arch. Biochem. Biophys. 249:533-545 (1986); US Patent Application No. US 2003/0157108 A1, Presta, L; and WO 2004/056312, Adams et al., especially at Example 11), and knockout cell lines, such as cell lines lacking a functional alpha-1,6-fucosyltransferase gene, FUT8, e.g., knockout CHO cells (see, e.g., Yamane-Ohnuki et al. Biotech. Bioeng. 87: 614 (2004); Kanda, Y. et al., Biotechnol. Bioeng, 94(4):680-688 (2006); and WO2003/085107).

Antibodies are further provided with bisected oligosaccharides, e.g., in which a biantennary oligosaccharide attached to the Fc region of the antibody is bisected by GlcNAc. Such antibodies may have reduced fucosylation and/or improved ADCC function. Examples of such antibodies are described, e.g., in WO 2003/011878 (Jean-Mairet et al.); U.S. Pat. No. 6,602,684 (Umana et al.); and US 2005/0123546 (Umana et al.). Antibodies with at least one galactose residue in the oligosaccharide attached to the Fc region are also provided. Such antibodies may have improved CDC function. Such antibodies are described, e.g., in WO 1997/30087 (Patel et al.); WO 1998/58964 (Raju, S.); and WO 1999/22764 (Raju, S.).

In some embodiments of the invention, an afucosylated antibody mediates ADCC in the presence of human effector cells more effectively than a parent antibody that comprises fucose. Generally, ADCC activity may be determined using the in vitro ADCC assay as herein disclosed, but other assays or methods for determining ADCC activity, e.g. in an animal model etc., are contemplated.

In some embodiments, afucosylated anti-CXCR5 antibodies have enhanced ADCC activity in vitro and/or in vivo. In some embodiments, afucosylated anti-CXCR5 antibodies have enhanced ADCC activity in vitro. In some embodiments, ADCC activity in vitro is determined by a method described herein. Briefly, serial dilutions of anti-CXCR5 antibodies or an isotype control are incubated with peripheral blood mononuclear cells (PBMCs) from healthy human donors or cynomolgus monkeys. In this assay, the PBMCs are the source of the natural killer (NK) effector cells and the target CXCR5+ B and Tfh-like cells. Flow cytometry is used to quantify the number of B and Tfh-like cells remaining after approximately 20 hr. The cytotoxicity titration curves were generated by plotting the percentage of cytotoxicity of the antigen binding population against the log of PF-06835375 antibody concentration. $EC_{50}$ values were determined using GraphPad Prism® (version 6.0, GraphPad Software, Inc, San Diego, Calif.) nonlinear-regression curve fits and a sigmoidal log of agonist dose-response model, according to the following equation:

Log (agonist) vs. response–variable slope (four parameters)

$$Y=\text{Bottom}+(\text{Top}-\text{Bottom}/(1+10^{((\text{Log}EC_{50}-X)*\text{Hill-Slope})})$$

Where Y is the percentage of cytotoxicity, X is antibody concentration, Top is the maximum Y-value corresponding to the upper plateau of the sigmoidal curve, Bottom is the minimum Y-value corresponding to the lower plateau of the sigmoidal curve (constrained to 0), and LogEC$_{50}$ is the log of the concentration of antibody at the inflection point of the curve.

The EC$_{50}$ values were summarized across experiments using average and standard deviations (STDEV). In some embodiments, the ability of the humanized mAbs to induce ADCC of bona fide Tfh cells from human tonsil was assessed similarly using CD4+ T cells isolated from tonsillar mononuclear cells with the addition of NK cells isolated from PBMCs. In some embodiments, Ba/F3 cells that express CXCR5 are used as target cells. In some embodiments, cytotoxicity is determined by quantifying LDH release using CytoTox Non-Radioactive Cytotoxicity Assay (Promega, Madison, Wis.).

In some embodiments, maximal lysis is determined using 5 percent Triton X-100 and spontaneous release is determined in the absence of antibody. In some embodiments, the percentage of specific lysis may be determined using the formula: (experimental−spontaneous release)/(maximal−spontaneous release)×100=percent specific lysis. In some embodiments, an afucosylated anti-CXCR5 antibody having enhanced ADCC activity results in specific lysis that is at least 10, at least 15, at least 20, at least 25, at least 30, at least 35, at least 40, at least 45, at least 50, at least 60, at least 65, at least 70, or at least 75 percentage points greater than specific lysis with the same amount of a fucosylated antibody, at at least one concentration of antibody tested. In some embodiments, an afucosylated anti-CXCR5 antibody having enhanced ADCC activity results in specific lysis that is at least 10, at least 15, at least 20, at least 25, at least 30, at least 35, at least 40, at least 45, at least 50, at least 60, at least 65, at least 70, or at least 75 percentage points greater than specific lysis with a fucosylated antibody, where each antibody is at a concentration of between 0.01 and 1 microg/ml and the target cells are Ba/F3 cells expressing CXCR5. In some embodiments, the antibodies are tested at concentrations ranging from 0.000005 microg/ml to 5 microg/ml In some embodiments, afucosylated anti-CXCR5 antibodies have enhanced affinity for Fc gamma RIIIA. In some embodiments, afucosylated anti-CXCR5 antibodies have enhanced affinity for Fc gamma RIIIA(V158). In some embodiments, afucosylated anti-CXCR5 antibodies have enhanced affinity for Fc gamma RIIIA(F158). In some embodiments, antibody affinity for Fc gamma RIIIA is determined using surface plasmon resonance and/or as follows, which is described with reference to Fc gamma RIIIA(V158), but which is also suitable for determining affinity for Fc gamma RIIIA(F158). Briefly, in some embodiments, fucosylated or afucosylated anti-CXCR5 antibody is captured on a protein A-coated dextran chip. Fc gamma RIIIA (V158) (available from, e.g., R and D Systems) is injected at various concentrations. The association constant, dissociation constant, and affinity of Fc gamma RIIIA (V158) for fucosylated and afucosylated anti-CXCR5 antibody may be determined, e.g., using software provided with the surface plasmon resonance system (for example, Biacore T200 Evaluation Software 1:1 binding model). In some embodiments, an afucosylated anti-CXCR5 antibody can have enhanced affinity for Fc gamma RIIIA (such as Fc gamma RIIIA(V158) or Fc gamma RIIIA(F158)) and can bind to Fc gamma RIIIA with at least 2-fold, at least 3-fold, at least 4-fold, at least 5-fold, at least 7-fold, at least 10-fold, at least 12-fold, at least 15-fold, at least 17-fold, 20-fold, 30-fold, 50-fold, 100-fold, 500-fold, or at least 1000-fold greater affinity than a fucosylated anti-CXCR5 antibody.

IV. Anti-CXCR5 Antibody Expression and Production

Nucleic Acids Encoding Anti-CXCR5 Antibodies

The invention also provides polynucleotides encoding any of the antibodies, including antibody fragments and modified antibodies described herein. The invention also provides a method of making any of the polynucleotides described herein. Polynucleotides can be made and expressed by procedures known in the art.

The sequence of a desired antibody, defined antibody fragment, or antigen-binding fragment thereof, and nucleic acid encoding such antibody, or fragment thereof, can be determined using standard sequencing techniques. A nucleic acid sequence encoding a desired antibody, defined antibody fragment, or antigen-binding fragment thereof, may be inserted into various vectors (such as cloning and expression vectors) for recombinant production and characterization. A nucleic acid encoding the heavy chain, defined antibody fragment, or an antigen-binding fragment of the heavy chain, and a nucleic acid encoding the light chain, defined antibody fragment, or an antigen-binding fragment of the light chain, can be cloned into the same vector, or different vectors.

In one aspect, the invention provides polynucleotides encoding the amino acid sequences of any of the following CXCR5 antibodies and antigen-binding fragments thereof: mouse 11G2 VH, mouse 11G2 VL, chimeric 11G2 VH, chimeric 11G2 VL, h11G2 VH (XC152), h11G2 VH (XC155), h11G2 VH (XC156), h11G2 VH (XC157), h11G2 VH (XC350), h11G2 VH (XC351), h11G2 VH (XC352), h11G2 VH (XC353), h11G2 VH (XC354), h11G2 VL (XC151), h11G2 VL (XC153), h11G2 VL (XC154), h11G2 VL (XC346), h11G2 VL (XC347), h11G2 VL (XC348), h11G2 VL (XC349), mouse 41A10 VH, mouse 41A10 VL, chimeric 41A10 VH, chimeric 41A10 VL, humanized 41A10 VH (XC147), h41A10 VH (XC148), h41A10 VH (XC150), h41A10 VL (XC142), h41A10 VL (XC143), h41A10 VL (XC144), h41A10 VL (XC145), h41A10 VL (XC146), h41A10 VL (XC149), mouse 5H7 VH, mouse 5H7 VL, chimeric 5H7 VH, and chimeric 5H7 VL. The polynucleotide encoding the amino acid sequences above, encodes an amino acid sequence at least 91%, 92%, 93%, 94%, 95%, 96%, 97%, 98%, or 99%, and more preferably identical to, the amino acid sequence of the antibodies, or antigen-binding fragment thereof, of the present invention as disclosed herein.

The invention provides polynucleotides encoding the amino acid sequences an antibody, or antigen-binding fragment thereof, that binds substantial the same epitope as an antibody selected from the group consisting of: Chimeric 41A10, Humanized 41A10 (142/147), Humanized 41A10 (142/148), Chimeric 11G2, Afucosyl Chimeric 11G2, Humanized 11G2 (151/152), Humanized 11G2 (153/155), Humanized 11G2 (153/156), Humanized 11G2 (154/155), Humanized 11G2 (154/157) and Afucosylated humanized 11G2 (154/155).

The invention provides polynucleotides encoding the amino acid sequences of an antibody, or antigen-binding fragment thereof, that competes for binding to CXCR5 with an antibody selected from the group consisting of: Chimeric 41A10, Humanized 41A10 (142/147), Humanized 41A10 (142/148), Chimeric 11G2, Afucosyl Chimeric 11G2, Humanized 11G2 (151/152), Humanized 11G2 (153/155), Humanized 11G2 (153/156), Humanized 11G2 (154/155), Humanized 11G2 (154/157) and Afucosyl humanized 11G2 (154/155).

The invention provides polynucleotides encoding one or more proteins comprising the amino acid sequence selected from the group consisting of: SEQ ID NOs:1-29, SEQ ID NOs:35-40, and SEQ ID NOs:47-63.

The invention provides polynucleotides comprising the nucleic acid sequence as set forth as one or more of SEQ ID NOs: 106, 107, 108 and 109. The invention provides a polynucleotide comprising the nucleic acid sequence as set forth as SEQ ID NO:95. The invention provides a polynucleotide comprising the nucleic acid sequence as set forth as SEQ ID NO:96. The invention provides a polynucleotide comprising the nucleic acid sequence as set forth as SEQ ID NO:97. The invention provides a polynucleotide comprising the nucleic acid sequence as set forth as SEQ ID NO:98.

The invention provides a polynucleotide comprising one or both of the nucleic acid sequence of the DNA insert of the plasmid deposited with the ATCC and having Accession No. PTA-124323, and Accession No. PTA-124324.

The invention provides a polynucleotide comprising the nucleic acid sequence of the insert in the plasmid deposited with the ATCC and having Accession No. PTA-124323.

The invention provides a polynucleotide comprising the nucleic acid sequence of the insert in the plasmid deposited with the ATCC and having Accession No. PTA-124324.

The invention provides a polynucleotide comprising the nucleic acid sequence of the insert of the plasmid deposited with the ATCC and having Accession No. PTA-124323, and Accession No. PTA-124324.

The invention provides a polynucleotide comprising the nucleic acid sequence of the insert of the plasmid deposited with the ATCC and having Accession No. PTA-124323.

The invention provides a polynucleotide comprising the nucleic acid sequence of the insert of the plasmid deposited with the ATCC and having Accession No. PTA-124324.

The invention provides cells comprising one or more nucleic acid molecules as set forth in one or more of SEQ ID NOs: 106, 107, 108, and 109. The invention provides cells comprising one or more nucleic acid molecules as set forth in SEQ ID NOs:106 and 107. The invention provides cells comprising one or more nucleic acid molecules as set forth in SEQ ID NOs:108 and 109.

In another aspect, the invention provides polynucleotides and variants thereof encoding an anti-CXCR5 antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid sequences disclosed herein. These amounts are not meant to be limiting, and increments between the recited percentages are specifically envisioned as part of the disclosure.

The invention provides polypeptides encoded by the nucleic acid molecules described herein.

In one embodiment, the VH and VL domains, or antigen-binding fragment thereof, or full length HC or LC, are encoded by separate polynucleotides. Alternatively, both VH and VL, or antigen-binding fragment thereof, or HC and LC, are encoded by a single polynucleotide.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. In some embodiments, variants exhibit at least about 70% identity, in some embodiments, at least about 80% identity, in some embodiments, at least about 90% identity, and in some embodiments, at least about 95% identity to a polynucleotide sequence that encodes a native antibody or a portion thereof. These amounts are not meant to be limiting, and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

Vectors

In some embodiments, a vector is selected that is optimized for expression of polypeptides in CHO or CHO-derived cells, or in NSO cells. Exemplary such vectors are described, e.g., in Running Deer et al, Biotechnol. Prog. 20:880-889 (2004).

Suitable cloning and expression vectors can include a variety of components, such as promoter, enhancer, and other transcriptional regulatory sequences. The vector may also be constructed to allow for subsequent cloning of an antibody variable domain into different vectors. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen. Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Host Cells

The antibody, or antigen-binding fragment thereof, may be made recombinantly using a suitable host cell. A nucleic acid encoding the antibody or antigen-binding fragment thereof can be cloned into an expression vector, which can then be introduced into a host cell, such as E. coli cell, a yeast cell, an insect cell, a simian COS cell, a Chinese hamster ovary (CHO) cell, or a myeloma cell where the cell does not otherwise produce an immunoglobulin protein, to obtain the synthesis of an antibody in the recombinant host cell. Preferred host cells include a CHO cell, a Human embryonic kidney HEK-293 cell, or an Sp2.0 cell, among many cells well-known in the art. An antibody fragment can be produced by proteolytic or other degradation of a full-length antibody, by recombinant methods, or by chemical synthesis. A polypeptide fragment of an antibody, especially shorter polypeptides up to about 50 amino acids, can be conveniently made by chemical synthesis. Methods of chemical synthesis for proteins and peptides are known in the art and are commercially available.

In various embodiments, anti-CXCR5 heavy chains and/or anti-CXCR5 light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lecl3 CHO cells, and FUT8 CHO cells; PER.C6® cells (Crucell); and NSO cells. In some embodiments, anti-CXCR5 heavy chains and/or anti-CXCR5 light chains may be expressed in yeast. See, e.g., U.S. Publication No. US 2006/0270045 Al. In some embodiments, a particular eukaryotic host cell is selected based on its ability to make desired post-translational modifications to the anti-CXCR5 heavy chains and/or anti-CXCR5 light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

In some embodiments afucosylated anti-CXCR5 antibodies are produced in cells capable of producing afucosylated antibodies, such as Lec3 CHO cells deficient in protein fucosylation (Ripka et al. Arch. Biochem. Biophys. 249: 533-545 (1986); US Patent Application No. US 2003/0157108; and WO 2004/056312, especially at Example 11), and knockout cell lines, such as cell lines lacking a functional alpha-1,6-fucosyltransferase gene, FUT8, e.g., knockout CHO cells (see, e.g., Yamane-Ohnuki et al. Biotech. Bioeng. 87: 614 (2004); Kanda et al, Biotechnol. Bioeng, 94(4):680-688 (2006); and WO2003/085107). In some embodiments, afucosylated anti-CXCR5 antibodies are produced in CHO cells lacking a functional FUT8 gene. In some embodiments, afucosylated anti-CXCR5 antibodies are produced in Potelligent® CHOK1SV cells (BioWa/Lonza, Allendale, N.J.).

Anti-CXCR5 antibodies may be purified by any suitable method. Such methods include, but are not limited to, the use of affinity matrices or hydrophobic interaction chromatography. Suitable affinity ligands include the CXCR5 ECD and ligands that bind antibody constant regions. For example, a Protein A, Protein G, Protein A/G, or an antibody affinity column may be used to bind the constant region and to purify an anti-CXCR5 antibody. Hydrophobic interactive chromatography, for example, a butyl or phenyl column, may also suitable for purifying some polypeptides. Many methods of purifying polypeptides are known in the art.

In some embodiments, an anti-CXCR5 antibody is produced in a cell-free system. Non-limiting exemplary cell-free systems are described, e.g., in Sitaraman et al., Methods Mol. Biol. 498: 229-44 (2009); Spirin, Trends Biotechnol. 22: 538-45 (2004); Endo et al, Biotechnol. Adv. 21: 695-713 (2003).

V. Uses and Medical Therapies

In some aspects, the present disclosure provides for therapeutic methods for removing, inhibiting or reducing CXCR5 activity or signaling using an anti-CXCR5 antibody or antigen-binding fragment thereof, wherein the therapeutic methods comprise administering a therapeutically effective amount of a pharmaceutical composition comprising an anti-CXCR5 antibody or antigen-binding fragment thereof. A disorder treated is any disease or condition which is improved, ameliorated, inhibited or prevented by removal, inhibition or reduction of CXCR5 activity or signaling.

In some aspects, the present disclosure provides an anti-CXCR5 antibody, or antigen-binding fragment thereof, for use in removing, inhibiting or reducing CXCR5 activity or signaling. In some embodiments, the use may comprise administering a therapeutically effective amount of a pharmaceutical composition comprising an anti-CXCR5 antibody, or antigen-binding fragment thereof. In some embodiments, inhibition or reduction of CXCR5 activity or signaling may treat any disease or condition which is improved, ameliorated, inhibited or prevented by removal, inhibition or reduction of CXCR5 activity or signaling.

Such diseases, disorders or conditions include, but are not limited to, inflammatory responses such as systemic lupus erythematosus (SLE); chronic inflammatory responses; atherosclerosis; leukocyte adhesion deficiency; rheumatoid arthritis; diabetes mellitus (e. g. Type I diabetes mellitus or insulin dependent diabetes mellitis); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-person syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; idiopathic myxedema; graft versus host disease; muscular dystrophy (Duchenne, Becker, Myotonic, Limb-girdle, Facioscapulohumeral, Congenital, Oculopharyngeal, Distal, Emery-Dreifuss), and controlling the proliferation of cancer cells expressing CXCR5 such as cancers of the pancreas, colon, bladder, T-cell leukemia, and B-cell leukemia as would be appreciated by one skilled in the art provided with the teachings disclosed herein.

The anti-CXCR5 antibodies, or antigen-binding fragments thereof, of the present invention may also be used to detect and/or measure CXCR5, or CXCR5-expressing cells in a sample, e.g., for diagnostic purposes. For example, an anti-CXCR5 antibody, or fragment thereof, may be used to diagnose a condition or disease characterized by aberrant expression (e.g., over-expression, under-expression, lack of expression, etc.) of CXCR5. Exemplary diagnostic assays for CXCR5 may comprise, e.g., contacting a sample, obtained from a patient, with an anti-CXCR5 antibody of the invention, wherein the anti-CXCR5 antibody is labeled with a detectable label or reporter molecule.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy, 20th Ed., Mack Publishing, 2000).

VI. Compositions

The disclosure also provides pharmaceutical compositions comprising an effective amount of an CXCR5 antibody, or antigen-binding fragment thereof, described herein. Examples of such compositions, as well as how to formulate, are also described herein. In some embodiments, the composition comprises one or more CXCR5 antibodies. In other embodiments, the CXCR5 antibody recognizes CXCR5. In other embodiments, the CXCR5 antibody is a human antibody. In other embodiments, the CXCR5 antibody is a humanized antibody. In some embodiments, the CXCR5 antibody comprises a constant region that is capable of triggering a desired immune response, such as antibody-mediated lysis or ADCC. In other embodiments, the CXCR5 antibody comprises a constant region that is afucosylated and provides enhanced ADCC compared with an otherwise identical antibody that is fucosylated. In other embodiments, the CXCR5 antibody comprises one or more CDR(s) of the antibody (such as one, two, three, four, five, or, in some embodiments, all six CDRs).

It is understood that the compositions can comprise more than one CXCR5 antibody, or antigen-binding fragment thereof (e.g., a mixture of CXCR5 antibodies that recognize different epitopes of CXCR5). Other exemplary compositions comprise more than one CXCR5 antibody that recognize the same epitope(s), or different species of CXCR5 antibodies that bind to different epitopes of CXCR5. In some embodiments, the compositions comprise a mixture of CXCR5 antibodies that recognize different variants of CXCR5.

The composition used in the present disclosure can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

The CXCR5 antibody, antigen-binding fragment thereof, and compositions thereof can also be used in conjunction with other agents that serve to enhance and/or complement the effectiveness of the agents.

In certain embodiments, the CXCR5 antibody, or antigen-binding fragment thereof, is complexed with CXCR5 before administration. In certain embodiments, the CXCR5 antibody is not complexed with CXCR5 before administration.

The disclosure also provides compositions, including pharmaceutical compositions, comprising any of the polynucleotides of the disclosure. In some embodiments, the composition comprises an expression vector comprising a polynucleotide encoding the antibody as described herein. In other embodiments, the composition comprises an expression vector comprising a polynucleotide encoding any of the antibodies described herein. In still other embodiments, the composition comprises either or both of the polynucleotides encoding the sequence shown in SEQ ID NO: 1 and SEQ ID NO: 6, either or both of the polynucleotides encoding the sequence shown in SEQ ID NO: 1 and SEQ ID NO: 10, either or both of the polynucleotides encoding the sequence shown in SEQ ID NO:1 and SEQ ID NO:12, either or both of the polynucleotides encoding the sequence shown in SEQ ID NO:5 and SEQ ID NO:6, either or both of the polynucleotides encoding the sequence shown in SEQ ID NO:5 and SEQ ID NO:10, either or both of the polynucleotides encoding the sequence shown in SEQ ID NO:5 and SEQ ID NO:12, either or both of the polynucleotides encoding the sequence shown in SEQ ID NO:13 and SEQ ID NO:17, either or both of the polynucleotides encoding the sequence shown in SEQ ID NO:13 and SEQ ID NO:18, either or both of the polynucleotides encoding the sequence shown in SEQ ID NO:13 and SEQ ID NO:63, either or both of the polynucleotides encoding the sequence shown in SEQ ID NO:1 and SEQ ID NO:52, either or both of the polynucleotides encoding the sequence shown in SEQ ID NO:1 and SEQ ID NO:53, either or both of the polynucleotides encoding the sequence shown in SEQ ID NO:1 and SEQ ID NO:54, either or both of the polynucleotides encoding the sequence shown in SEQ ID NO:1 and SEQ ID NO:55, either or both of the polynucleotides encoding the sequence shown in SEQ ID NO:1 and SEQ ID NO:56, either or both of the polynucleotides encoding the sequence shown in SEQ ID NO:1 and SEQ ID NO:57, either or both of the polynucleotides encoding the sequence shown in SEQ ID NO:6 and SEQ ID NO:48, either or both of the polynucleotides encoding the sequence shown in SEQ ID NO:6 and SEQ ID NO:49, either or both of the polynucleotides encoding the sequence shown in SEQ ID NO:6 and SEQ ID NO: 50, either or both of the polynucleotides encoding the sequence shown in SEQ ID NO:6 and SEQ ID NO:51, either or both of the polynucleotides encoding the sequence shown in SEQ ID NO:17 and SEQ ID NO:58, either or both of the polynucleotides encoding the sequence shown in SEQ ID NO:17 and SEQ ID NO:59, either or both of the polynucleotides encoding the sequence shown in SEQ ID NO:17 and SEQ ID NO:60, either or both of the polynucleotides comprising the sequence shown in SEQ ID NO:17 and SEQ ID NO: 61, either or both of the polynucleotides encoding the sequence shown in SEQ ID NO:17 and SEQ ID NO:62, either or both of the polynucleotides encoding the sequence shown in SEQ ID NO: 52 and SEQ ID NO:1, either or both of the polynucleotides encoding the sequence shown in SEQ ID NO:52 and SEQ ID NO:5, either or both of the polynucleotides encoding the sequence shown in SEQ ID NO:52 and SEQ ID NO:47, either or both of the polynucleotides encoding the sequence shown in SEQ ID NO:52 and SEQ ID NO:48, either or both of the polynucleotides encoding the sequence shown in SEQ ID NO:52 and SEQ ID NO:49, either or both of the polynucleotides encoding the sequence shown in SEQ ID NO:52 and SEQ ID NO:50, either or both of the polynucleotides encoding the sequence shown in SEQ ID NO:52 and SEQ ID NO:51, or either or both of the polynucleotides encoding the sequence shown in SEQ ID NO:35 and SEQ ID NO:36.

In another aspect, the polynucleotide can encode the VH, VL and/or both VH and VL of the antibody of the disclosure. That is, the composition comprises a single polynucleotide or more than one polynucleotide encoding the antibody, or antigen-binding fragment thereof, or the disclosure.

Pharmaceutical compositions of the disclosure also can be administered in combination therapy, such as, combined with other agents. For example, the combination therapy can include CXCR5 antibody, or antigen-binding fragment thereof, of the present disclosure combined with at least one other therapy wherein the therapy may be surgery, immunotherapy, or drug therapy.

The pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition.

Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the present disclosure may be prepared, packaged, or sold in a formulation suitable for ophthalmic administration. Such formulations may, for example, be in the form of eye drops including, for example, a 0.1%-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences, Genaro, ed., Mack Publishing Co., Easton, Pa. (1985), which is incorporated herein by reference.

In one embodiment, the CXCR5 antibody, or antigen-binding fragment thereof, is administered in an intravenous formulation as a sterile aqueous solution containing 5 mg/mL, or in some embodiments, about 10 mg/mL, or in some embodiments, about 15 mg/mL, or in some embodiments, about 20 mg/mL of antibody, or in some embodiments, about 25 mg/mL, or in some embodiments, about 50 mg/mL, with sodium acetate, polysorbate 80, and sodium chloride at a pH ranging from about 5 to 6. In some embodiments, the intravenous formulation is a sterile aqueous solution containing 5 or 10 mg/mL of antibody, with 20 mM sodium acetate, 0.2 mg/mL polysorbate 80, and 140 mM sodium chloride at pH 5.5. Further, a solution comprising an antibody, or antigen-binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 50 mg/mL CXCR5 antibody or antigen-binding fragment of the present disclosure, 20 mM histidine, 8.5% sucrose, and 0.02% polysorbate 80, 0.005% EDTA at pH 5.8; in another embodiment a pharmaceutical composition of the present invention comprises the following components: 100 mg/mL CXCR5 antibody or antigen-binding fragment of the present disclosure, 10 mM histidine, 5% sucrose, and 0.01% polysorbate 80 at pH 5.8. This composition may be provided as a liquid formulation or as a lyophilized powder. When the powder is reconstituted at full volume, the composition retains the same formulation. Alternatively, the powder may be reconstituted at half volume, in which case the composition comprises 100 mg CXCR5 antibody or antigen-binding fragment thereof of the present disclosure, 20 mM histidine, 10% sucrose, and 0.02% polysorbate 80 at pH 5.8.

In one embodiment, part of the dose is administered by an intravenous bolus and the rest by infusion of the antibody formulation. For example, a 0.01 mg/kg intravenous injection of the CXCR5 antibody, or antigen-binding fragment thereof, may be given as a bolus, and the rest of the antibody dose may be administered by intravenous injection. A predetermined dose of the CXCR5 antibody, or antigen-binding fragment thereof, may be administered, for example, over a period of an hour and a half to two hours to five hours.

With regard to a therapeutic agent, where the agent is, e.g., a small molecule, it can be present in a pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment the compositions of the disclosure are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

In one embodiment, the disclosure comprises administering a composition wherein said administration is oral, parenteral, intramuscular, intranasal, vaginal, rectal, lingual, sublingual, buccal, intrabuccal, intravenous, cutaneous, subcutaneous or transdermal.

In another embodiment the disclosure further comprises administering a composition in combination with other therapies, such as surgery, chemotherapy, hormonal therapy, biological therapy, immunotherapy or radiation therapy.

VII. Dosing/Administration

To prepare pharmaceutical or sterile compositions including an CXCR5 antibody, or antigen-binding fragment thereof of the disclosure, the antibody is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N.Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32; Lipsky, et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Compositions comprising CXCR5 antibodies or antigen-binding fragments thereof, of the disclosure can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 15 mg/kg, at least 20 mg/kg, at least 25 mg/kg, or at least 50 mg/kg (see, e.g., Yang, et al., 2003, New Engl. J. Med. 349:427-434; Herold, et al., 2002, New Engl. J. Med. 346:1692-1698; Liu, et al., 1999, J. Neurol. Neurosurg. Psych. 67:451-456; Portielji, et al., 2003, Cancer. Immunol. Immunother. 52: 133-144). The dose may be at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For CXCR5 antibodies or antigen-binding fragments thereof of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the CXCR5 antibody or antigen-binding fragment thereof may be calculated using the patient's weight in kilograms (kg) multiplied by the dose to be administered in mg/kg. The dosage of the antibodies of the disclosure may be 150 pg/kg or less, 125 pg/kg or less, 100 pg/kg or less, 95 pg/kg or less, 90 pg/kg or less, 85 pg/kg or less, 80 pg/kg or less, 75 pg/kg or less, 70 pg/kg or less, 65 pg/kg or less, 60 pg/kg or less, 55 pg/kg or less, 50 pg/kg or less, 45 pg/kg or less, 40 pg/kg or less, 35 pg/kg or less, 30 pg/kg or less, 25 pg/kg or less, 20 pg/kg or less, 15 pg/kg or less, 10 pg/kg or less, 5 pg/kg or less, 2.5 pg/kg or less, 2 pg/kg or less, 1.5 µg/kg or less, 1 µg/kg or less, 0.5 µg/kg or less, or 0.1 µg/kg or less of a patient's body weight.

Unit dose of the CXCR5 antibodies or antigen-binding fragments thereof of the disclosure may be 0.1 mg to 200 mg, 0.1 mg to 175 mg, 0.1 mg to 150 mg, 0.1 mg to 125 mg, 0.1 mg to 100 mg, 0.1 mg to 75 mg, 0.1 mg to 50 mg, 0.1 mg to 30 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the CXCR5 antibodies or antigen-binding fragments thereof of the disclosure may achieve a serum titer of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL in a subject. Alternatively, the dosage of the antibodies of the disclosure may achieve a serum titer of at least 0.1 µg/mL, at least 0.5 µg/mL, at least 1 µg/mL, at least, 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL in the subject.

Doses of CXCR5 antibodies, or antigen-binding fragments thereof of the disclosure may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard, et al., 1996, A Handbook of SOPs for Good Clinical Practice, Interpharm Press, Boca Raton, Fla.; Dent, 2001, Good Laboratory and Good Clinical Practice, Urch Publ, London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., 1983, Biopolymers 22:547-556; Langer, et al., 1981, J. Biomed. Mater. Res. 15: 167-277; Langer, 1982, Chem. Tech. 12:98-105; Epstein, et al., 1985, Proc. Natl. Acad. Sci. USA 82:3688-3692; Hwang, et al., 1980, Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, the CXCR5 antibody, or antigen-binding fragment thereof, or a composition of the disclosure is administered using Alkermes AIR™ pulmonary drug delivery technology (Alkermes, Inc., Cambridge, Mass.).

A composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

If the CXCR5 antibodies, or antigen-binding fragments thereof, of the disclosure are administered in a controlled release or sustained release system, a pump may be used to achieve controlled or sustained release (see, Langer, supra; Sefton, 1987, CRC Crit. Ref. Biomed. Eng. 14:20; Buchwald et al., 1980, Surgery 88:501; Saudek et al., 1989, N. Engl. J. Med. 321:514).

Polymeric materials can be used to achieve controlled or sustained release of the therapies of the disclosure (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, J., Macromol. ScL Rev. Macromol. Chem. 23:61; see also Levy et al, 1985, Science 11 225:190; During et al., 19Z9, Ann. Neurol. 25:351; Howard et al, 1989, J. Neurosurg. 71: 105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), polyvinyl alcohol), polyacrylamide, polyethylene glycol), polylactides (PLA), polyoeactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, 1990, Science 249:1527-1533. Any technique known to one of skill in the art can be used to produce sustained release formulations comprising one or more antibodies of the disclosure or conjugates thereof. See, e.g., U.S. Pat. No. 4,526,938, International Patent Publication Nos. WO 91/05548, WO 96/20698, Ning et al., 1996, "Intratumoral Radioimmunotherapy of a Human Colon Cancer Xenograft Using a Sustained-Release Gel," Radiotherapy and Oncology 59:179-189, Song et al., 1995, "Antibody Mediated Lung Targeting of Long-Circulating Emulsions," PDA Journal of Pharmaceutical Science and Technology 50:372-397, Cleek et ah, 1997, "Biodegradable Polymeric Carriers for a bFGF Antibody for Cardiovascular Application," Pro. Ml. Symp. Control. Rel. Bioact. Mater. 24:853-854, and Lam et al., 1997, "Microencapsulation of Recombinant Humanized Monoclonal Antibody for Local Delivery," Proc. Ml. Symp. Control Rel. Bioact. Mater. 24:759-160, each of which is incorporated herein by reference in their entirety.

If the CXCR5 antibody, or antigen-binding fragment thereof, of the disclosure is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising CXCR5 antibodies, or antigen-binding fragments thereof, are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams and Wilkins, Phila., Pa.; Chabner and Longo (eds.) (2001) Cancer Chemotherapy and Biotherapy, Lippincott, Williams and Wilkins, Phila., Pa.). An effective amount of therapeutic may decrease the symptoms by at least 10 percent; by at least 20 percent; at least about 30 percent; at least 40 percent, or at least 50 percent.

Additional therapies (e.g., prophylactic or therapeutic agents), which can be administered in combination with the CXCR5 antibodies, or antigen-binding fragments of the disclosure, may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies of the disclosure. The two or more therapies may be administered within one same patient visit.

The CXCR5 antibodies, or antigen-binding fragments thereof, of the disclosure and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In one embodiment, the CXCR5 antibodies of the disclosure can be co-administered with compositions for treating autoimmune diseases and disorders, including, but not limited to, adriamycin, azathiopurine, busulfan, cyclophosphamide, cyclosporine A, Cytoxan, fludarabine, 5-fluorouracil, methotrexate, mycophenolate mofetil, 6-mercaptopurine, a corticosteroid, a nonsteroidal anti-inflammatory, sirolimus (rapamycin), and tacrolimus (FK-506). In alternative embodiments, the immunomodulatory or immunosuppressive agent is an antibody selected from the group consisting of muromonab-CD3, alemtuzumab (Campath®), basiliximab, daclizumab, muromonab (OKT3®), rituximab, antithymocyte globulin and IVIg, and others, which are known to persons skilled in the art.

In one embodiment, the CXCR5 antibodies of the disclosure can be co-administered with compositions for treating diabetes, including, but not limited to, biguanides (e.g., buformin, metformin, and phenform), hormones and analogs thereof (amylin, insulin, insulin aspart, insulin detemir, insulin glargine, insulin glulisine, insulin lispro, liraglutide, and pramlintide), sulfonylurea derivatives (acetohexamide, carbutamide, chlorpropamide, glibornuride, gliclazide, glimepiride, glipizide, gliquidone, glisoxepid, glyburide, glybuthiazole, glybuzole, glyhexamide, glymidine, tolazamide, tolbutamide, and tolcyclamide), thiazolidinediones (pioglitazone, rosiglitazone, and troglitazone), acarbose, exenatide, miglitol, mitiglinide, muraglitazar, nateglinide, repaglinide, sitagliptin, tesaglitazar, vildagliptin, and voglibose.

In certain embodiments, the CXCR5 antibodies, or antigen-binding fragments thereof of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989, J. Clin.

Pharmacol. 29:685). Exemplary targeting moieties include folate or biotin (see, e.g., U.S. Pat. No. 5,416,016); mannosides (Umezawa et al., Biochem. Biophys. Res. Commun. 153: 1038); antibodies (P. G. Bloeman et al., 1995, FEBS Lett. 357: 140; M. Owais et al., 1995, Antimicrob. Agents Chemother. 39: 180); surfactant protein A receptor (Briscoe et al. (1995) Am. J. Physiol. 1233: 134); p120 (Schreier et al. (1994) J. Biol. Chem. 269:9090); see also K. Keinanen; M. L. Laukkanen, 1994, FEBS Lett. 346:123; Killion; Fidler, 1994; Immunomethods 4:273.

The disclosure provides protocols for the administration of pharmaceutical composition comprising CXCR5 antibodies, or antigen-binding fragments thereof, of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising CXCR5 antibodies, or antigen-binding fragments thereof, of the disclosure are administered to a subject in a sequence and within a time interval such that the antibodies of the disclosure or conjugates thereof can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

VIII. Kits

The disclosure also provides kits comprising any or all of the antibodies described herein. Kits of the disclosure include one or more containers comprising an CXCR5 antibody described herein and instructions for use in accordance with any of the methods of the disclosure described herein. Generally, these instructions comprise a description of administration of the antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing an applicator, e.g., single and multi-chambered pre-filled syringes (e.g., liquid syringes and lyosyringes), are included.

The instructions relating to the use of a CXCR5 antibody generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a CXCR5 antibody of the disclosure. The container may further comprise a second pharmaceutically active agent.

Kits may optionally provide additional components such as buffers and interpretive information. Normally, the kit comprises a container and a label or package insert(s) on or associated with the container.

The disclosure also provides diagnostic kits comprising any or all of the antibodies described herein. The diagnostic kits are useful for, for example, detecting the presence of CXCR5 in a sample. In some embodiments, a diagnostic kit can be used to identify an individual with a latent disease, disorder or condition that may put them at risk of developing CXCR5-mediated disease, disorder or condition or a CXCR5 deficiency disease, disorder or condition. In some embodiments, a diagnostic kit can be used to detect the presence and/or level of CXCR5 in an individual suspected of having a CXCR5 mediated disease or a CXCR5 deficiency disease, disorder or condition.

Diagnostic kits of the disclosure include one or more containers comprising an CXCR5 antibody described herein and instructions for use in accordance with any of the methods of the disclosure described herein. Generally, these instructions comprise a description of use of the CXCR5 antibody to detect the presence of CXCR5 in individuals at risk for, or suspected of having, a CXCR5 mediated disease or a CXCR5 deficiency disease, disorder or condition. In some embodiments, an exemplary diagnostic kit can be configured to contain reagents such as, for example, a CXCR5 antibody, a negative control sample, a positive control sample, and directions for using the kit.

IX. Equivalents

The foregoing description and following Examples detail certain specific embodiments of the disclosure and describes the best mode contemplated by the inventors. It will be appreciated, however, that no matter how detailed the foregoing may appear in text, the disclosure may be practiced in many ways and the disclosure should be construed in accordance with the appended claims and any equivalents thereof.

Although the disclosed teachings have been described with reference to various applications, methods, kits, and compositions, it will be appreciated that various changes and modifications can be made without departing from the teachings herein and the claimed disclosure below. The following examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

X. General Techniques

It is to be understood that this invention is not limited to specific synthetic methods of making that may of course vary. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, N.Y. (2001); Ausubel et al., Current Protocols in Molecular Biology, John Wiley & Sons, NY (2002); Harlow and Lane Using Antibodies: A Laboratory Manual, Cold Spring Harbor Laboratory Press, Cold Spring Harbor, N.Y. (1998); Coligan et al., Short Protocols in Protein Science, John Wiley & Sons, NY (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

XI. Biological Deposit

Representative materials of the present invention were deposited in the American Type Culture Collection, 10801 University Boulevard, Manassas, Va. 20110-2209, USA, on Jul. 26, 2017. Vector h11G2-VH (XC155), having ATCC Accession No. PTA-124323, comprises a DNA insert encoding the heavy chain variable region of antibody h11G2 (XC155), and vector h11G2-VL (XC154), having ATCC Accession No. PTA-124324, comprises a DNA insert encoding the light chain variable region of antibody h11G2 (XC154). The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The owner of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Example 1: Hybridomas that Bind to Human CXCR5 and Cyno CXCR5

Figure 3:
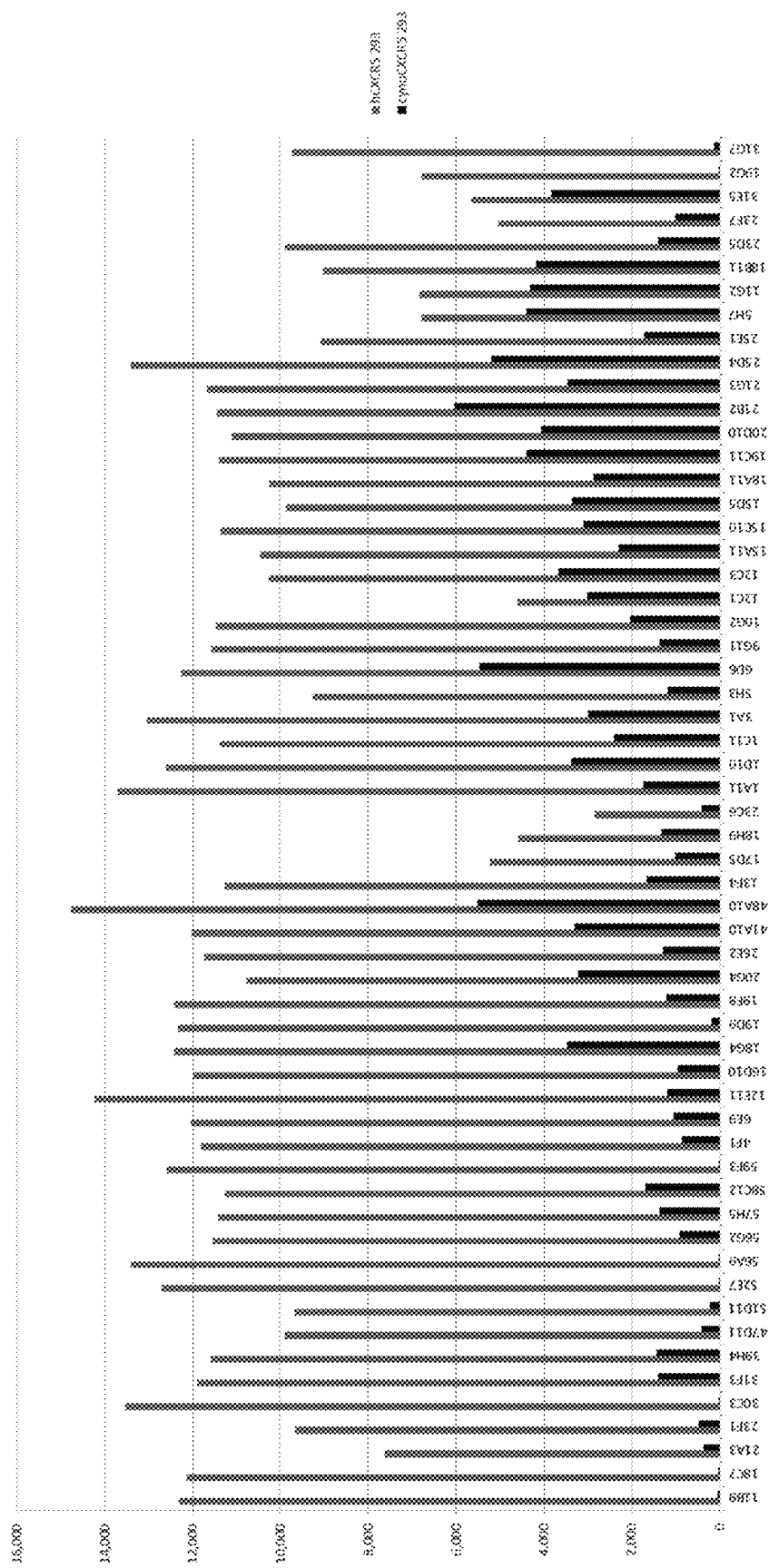
FIG. 3 depicts a bar graph showing the binding of various monoclonal antibodies (indicated on the x-axis) to HEK 293 cells expressing human CXCR5 (hCXCR5 293) (lighter bars) and/or HEK 293 cells expressing cynomolgus CXCR5 (cynoCXCR5 293) (darker bars). The monoclonal antibodies shown in FIG. 3 are, from left to right, 1169, 18C7, 21A3, 23F1, 30C3, 31F3, 39H4, 47D11, 51 D11, 52E7, 56A9, 56G2, 57H5, 58C12, 59F3, 4F1, 6E9, 12E11, 16D10, 18G4, 19D9, 19F8, 20G4, 26E2, 41A10, 48A10, 13F4, 17D5, 18H9, 23C6, 1A11, 1D10, 1C11, 3A1, 5H3, 6D6, 9G11, 10G2, 12C1, 12C3, 15A11, 15C10, 15D5, 18A11, 19C11, 20D10, 2162, 21G3, 25D4, 25E1, 5H7, 11G2, 18611, 23D5, 23F7, 31 E5, 19G2, and 31G7.
Figure 4A:
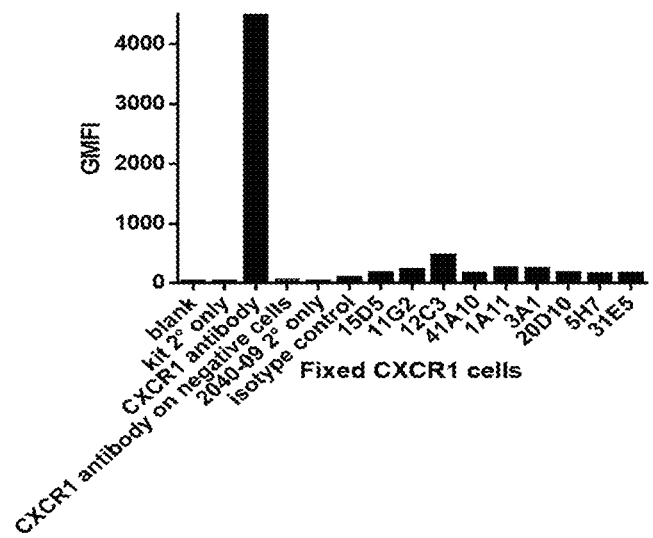
FIG. 4A depicts a diagram showing the lack of detectable binding of various anti-CXCR5 antibodies to cells expressing CXCR1.
Figure 4B:
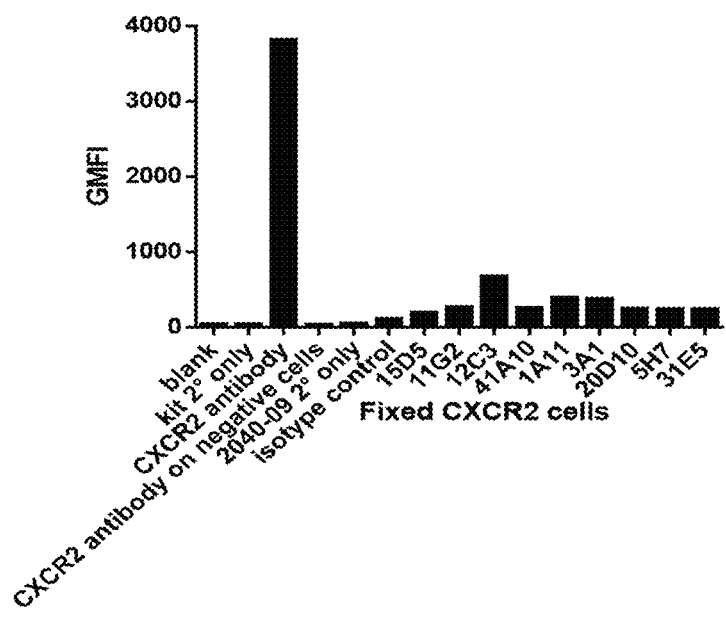
FIG. 4B depicts a diagram showing the lack of binding of various anti-CXCR5 antibodies to cells expressing CXCR2.
Figure 4C:
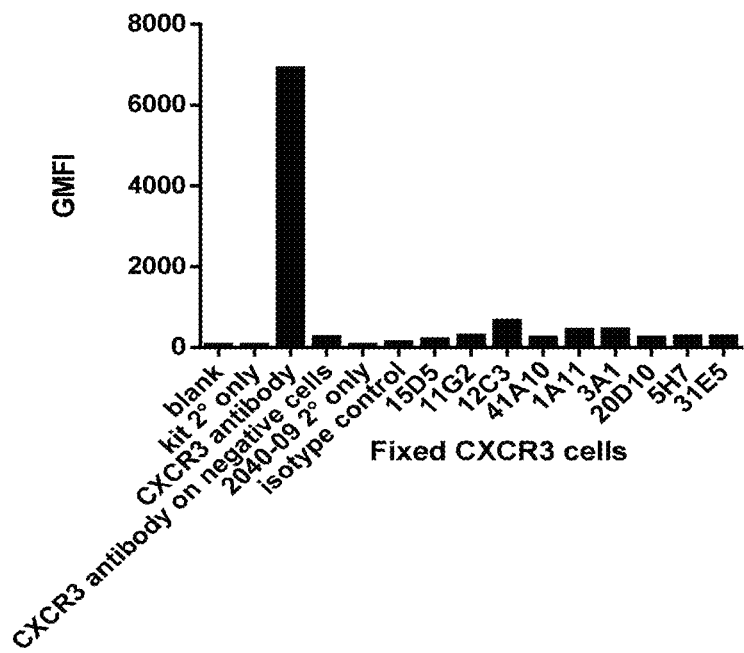
FIG. 4C depicts a diagram showing the lack of binding of various anti-CXCR5 antibodies to cells expressing CXCR3.
Figure 4D:
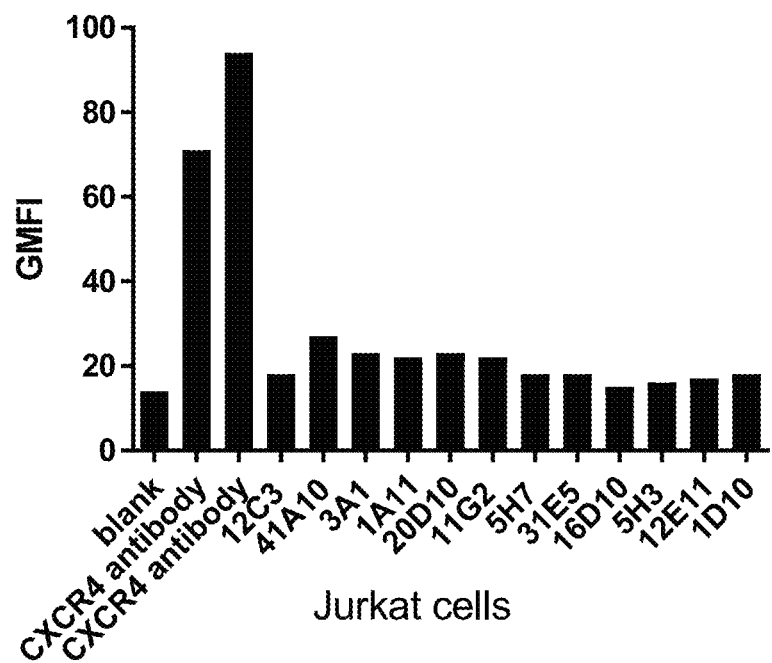
FIG. 4D depicts a diagram showing the binding of various anti-CXCR5 antibodies to Jurkat cells which naturally express CXCR4.

Female BALB/c mice were immunized three times with a mixture containing 1×10$^6$ BaF3 cells overexpressing human CXCR5 (SEQ ID NO:32) or 300.19 cells expressing human CXCR5 (SEQ ID NO:32) with 5 µg CPG (ODN1826) (Invivogen) adjuvant in series of three weeks apart. In the final boost, mice were immunized with 20 µg of virus-like particles (VLP) made from HEK-293 cells overexpressing human CXCR5 (SEQ ID NO:32) using MembranePro™ Functional Protein Expression System (Thermo Fisher). Five rounds of fusion were carried out and yielded eighty-eight clones that bound HEK-293 cells expressing human CXCR5 (hCXCR5-293). Those monoclonal antibodies were purified by protein A and tested for binding to hCXCR5 HEK-293 and HEK-293 cells expressing cynomolgus monkey CXCR5 (SEQ ID NO:33), i.e., cynoCXCR5-293. The hCXCR5-293 or cynoCXCR5-293 cells were stained with monoclonal antibodies at 10 µg/ml prior to staining with anti-mouse IgG PE (Southern Biotech). The cells were analyzed by flow cytometry using a FACSVerse Analyzer (BD Biosciences). Screening for binding to hCXCR5 HEK-293 and cynoCXCR5 HEK-293 cells identified thirty-four antibodies that bound both human and cynomolgus monkey CXCR5 (FIG. 3).

Example 2: Anti-CXCR5 Antibodies Binding to Raji Cells and Antagonist Activity in Calcium Flux Assay Antibodies that bound both hCXCR5-293 and cynoCXCR5-293 cells were further analyzed for cell binding to Raji cells by flow cytometry using a FACSVerse Analyzer (BD Biosciences, Franklin Lakes, N.J.). The apparent affinity of antibody binding to Raji cells was calculated as the $EC_{50}$ of equilibrium binding titration curves in which the geometric mean fluorescence intensity (gMFI) of the antigen binding population was quantified by flow cytometry and the results are shown in Table 2.

The data demonstrate that certain antibodies bound to Raji cells to a greater/lesser extent than other antibodies. These data demonstrate that the antibodies recognize endogenous CXCR5 on the Raji cells, which are derived from a Burkitt's lymphoma patient, suggesting antibodies can bind B cells in vivo. Further, the affinity for CXCR5 on Raji cells of antibody 11G2 is higher than reference anti-CXCR5 antibody 16D7 (WO 2009/032661) suggesting that 11G2 could be more potent than 16D7.

The antibodies that bound both hCXCR5-293 and cynoCXCR5-293 were also tested in a calcium flux assay for antagonistic activity. In addition, reference anti-CXCR5 antibodies 16D7 (WO 2009/032661) was included as a control. Briefly, hCXCR5 HEK-293 cells were plated in a 96 well plate in DMEM high glucose media. After overnight incubation, the media was removed and 100 µl of 1× Fluo-4 NW (Thermo Fisher Scientific, Waltham, Mass.) was added to the cells. The cells then were incubated at 37° C. for one hour. Serial dilutions of monoclonal antibodies were added to cells and incubated at room temperature for one hour. Calcium flux was measured on a Flexstation (Molecular Devices, Sunnyvale, Calif.) at excitation 485 nM and emission 525 nM by adding 111 nM of the recombinant hCXCL13 (BPS Bioscience, San Diego, Calif.). The data were collected at 1.52 seconds intervals. The instrument determined calcium flux by subtracting the lowest reading from the highest reading. The IC50 values for inhibition of ligand-induced calcium flux were determined using Graph-Pad Prism® (version 6.0, GraphPad Software, Inc, San Diego, Calif.) nonlinear-regression curve fits and a sigmoidal log of agonist dose-response model (Table 2). Inhibition of calcium flux is a demonstration of functional antagonism. Thus, 11G2 antibody is not only a potent depleter, via ADCC, but is also an antagonist providing a second mechanism of action. The antagonism of antibody 11G2 is on par with the comparator antibodies, e.g., 2C9 (reference antibody, see, e.g., WO 2012/010582) and 16D7 (reference antibody, see, e.g., WO 2009/032661). The cAMP reporter assay data also demonstrate functional antagonism (see below).

TABLE 2

| Antibody (hybridoma) | Raji cell binding EC50 (nM) | Ca2+ flux IC50 (nM) |
| --- | --- | --- |
| 5H3 | 4.767 | 13.60 |
| 5H7 | 1.014 | 5.555 |
| 11G2 | 0.9679 | 5.929 |
| 31E5 | 0.7292 | 5.050 |
| 18G4 | 0.7454 | 13.86 |
| 19D9 | 0.9022 | 9.395 |
| 20G4 | 0.5178 | 9.853 |
| 21A3 | 1.226 | 9.043 |
| 23F1 | 0.4062 | 6.982 |
| 39H4 | 0.3154 | Not tested |
| 47D11 | 0.8493 | 9.448 |
| 56G2 | 0.3871 | 14.36 |
| 4F1 | 0.4202 | 9.739 |
| 15D5 | 0.7949 | 11.21 |
| 20D10 | 0.3259 | 11.03 |
| 6E9 | 0.5879 | 14.28 |
| 12E11 | 0.6493 | 13.40 |
| 16D10 | 0.7862 | 14.47 |
| 26E2 | 1.424 | 18.40 |
| 1A11 | 0.4936 | 35.06 |
| 1D10 | 0.2164 | 33.66 |
| 10G2 | 0.4571 | 14.74 |
| 9G11 | 0.4976 | 38.61 |
| 12C3 | 0.4868 | 35.01 |
| 25E1 | 0.7682 | 14.13 |
| 18G11 | 0.3161 | 5.034 |
| 23D5 | 0.1483 | 5.886 |
| 31G7 | 0.2848 | 9.084 |

TABLE 2-continued

| Antibody (hybridoma) | Raji cell binding EC50 (nM) | Ca2+ flux IC50 (nM) |
| --- | --- | --- |
| 31F3 | 0.2705 | 18.23 |
| 51D11 | 0.2525 | 7.429 |
| 41A10 | 0.8046 | 14.67 |
| 48A10 | 0.7083 | 21.07 |
| 13F4 | 0.6225 | Not tested |
| 3A1 | 0.2572 | 20.22 |
| 19F8 | 2.378 | 30.03 |
| 2C9 | 0.21 | 3.486 |
| 16D7 | 0.65 | 11.43 |

Example 3: Cloning of Anti-CXCR5 Antibody Heavy and Light Chain Variable Regions The hybridomas producing the antibodies assayed in Example 2 were lysed using RNeasy mini kit (Qiagen, Hilden, Germany) and then the first strand of cDNA was synthesized using the superscript III first strand synthesis system (Thermo Fisher Scientific, Waltham, Mass.). The light and heavy chain variable regions (VL and VH) were amplified by PCR using mouse light and heavy chain degenerate primers comprising the nucleic acid sequences of SEQ ID NOs:64-88 shown in Table 16. After PCR, the VL and VH were cloned into the Zero blunt TA vectors (Thermo Fisher Scientific, Waltham, Mass.) and then they were sequenced. Amino acid sequences for the mouse VL and VH of the 11G2, 5H7 and 41A10 antibodies are shown in Table 16 at SEQ ID NOs:35-40. The CDRs are underlined.

Example 4: Generation of Afucosylated and Fucosylated Chimeric Antibodies

To assess the effect of afucosylation and fucosylation on antibody activity, fucosylated and afucosylated versions of the antibodies from Example 3 were produced in mammalian cells The VL and VH of antibodies of interest were further cloned into vectors containing the human kappa constant and human IgG1 constant regions, respectively. The variable heavy regions were cloned into the pSMED2 mammalian expression vector containing the human IgG1 constant region (SEQ ID NO: 89) producing chimeric mouse-human full length heavy chains. Variable light regions were cloned into the pSMEN3 mammalian expression vector containing the human kappa constant region (CK) (SEQ ID NO: 90) to produce chimeric mouse-human full length light chains.

The vectors containing chimeric antibody genes were transiently transfected into HEK-293F cells (Thermo Fisher Scientific, Waltham, Mass.) to produce fucosylated chimeric antibody. The fucosylated chimeric antibodies were then purified using protein A columns. The apparent affinity (cell binding EC50s) of chimeric antibody binding to Raji cells was determined by flow cytometry using a FACSVerse Analyzer (BD Bioscience, Franklin Lakes, N.J.) and are shown in Table 3.

TABLE 3

| Antibody (chimeric) | Raji cell binding EC50 (nM) (fucosylated) | CynoCXCR5-300.19 cells EC50 (nM) (fucosylated) |
| --- | --- | --- |
| 5H7 | 0.04215 | 0.06027 |
| 11G2 | 0.01746 | 0.02419 |
| 31E5 | Not tested | 0.05151 |
| 23F1 | 0.1687 | 66.03 |
| 47D11 | 0.4292 | 13.85 |
| 56G2 | 0.07613 | 6.376 |
| 4F1 | 0.3209 | 14.08 |
| 15D5 | 0.2695 | 1.387 |
| 20D10 | 0.1624 | 0.1478 |
| 6E9 | Not tested | 18.26 |
| 12E11 | 0.2883 | Not tested |
| 16D10 | 0.2909 | Not tested |
| 1A11 | 0.08464 | 0.2575 |
| 1D10 | 0.1530 | Not tested |
| 10G2 | 1.008 | Not tested |
| 12C3 | 0.1035 | 0.1767 |
| 25E1 | 0.4487 | 11.73 |
| 23D5 | 0.03410 | 4.168 |
| 31G7 | Not tested | 12.83 |
| 31F3 | 0.07858 | 4.072 |
| 51D11 | 0.08732 | 49.63 |
| 41A10 | 0.3899 | 0.8308 |
| 13F4 | 0.5557 | 4.381 |
| 3A1 | 0.09156 | 0.3059 |
| 2C9 | 0.09989 | 0.1305 |

Afucosylated chimeric antibodies were generated using the Potelligent® CHOK1SV cell line (BioWa/Lonza, Allendale, N.J.), which lacks both alleles of the gene responsible for fucose addition (α-1,6-fucosyltransferase, FUT8). The chimeric light chain containing a human kappa constant region was cloned into the Lonza pEE12.4 GS vector (Lonza Biologics, Basel, Switzerland) and the chimeric heavy chain containing a human IgG1 constant region was cloned into the Lonza pEE6.4 GS vector (Lonza Biologics, Basel, Switzerland). The heavy chain expression cassette from pEE6.4 was purified by digestion of Notl and Pvul and then cloned into Notl and Pvul sites in the pEE12.4 containing chimeric light chain. The final vector DGV containing both heavy and light chain expression cassettes was linearized with Pvul and then electroporated into Potelligent® CHOK1SV cells. After 24 hours post-transfection, the Potelligent® cells were plated into 96 well plates at 3-5K cells/well in CDCHO media (Thermo Fisher Scientific, Waltham, Mass.) supplemented with 1XHT (Thermo Fisher Scientific, Waltham, Mass.), 1 mM uridine (Sigma, St. Louis, Mo.) and 50 μM MSX (EMD Millipore, Billerica, Mass.). After three to four weeks of incubation, the supernatants from the clones were assayed for antibody titer on Octet (Pall Fortebio, Fremont, Calif.). The high expression clones were further scaled up for antibody production. The afucosylated chimeric antibodies were then purified on protein A columns.

To determine the specificity of the antibodies for CXCR5, the binding of the antibodies to cells expressing other cytokines was assessed. Briefly, FlowCellect chemokine receptor cell lines expressing CXCR1, CXCR2, or CXCR3 (EMD Millipore, Billerica, Mass.), and Jurkats (ATCC, Manassas, Va.), which express CXCR4, were stained with 5 μg/ml or 10 pg/ml of each anti-CXCR5 chimeric antibody. The cells were then incubated with goat anti-human conjugated with PE (Southern Biotech, Birmingham, Ala.) prior to analysis by flow cytometry using a FACSVerse Analyzer (BD Biosciences, Franklin Lakes, N.J.). As shown in FIGS. 4A-4D, all chimeric antibodies showed very low binding to cells expressing CXCR1 (FIG. 4A), CXCR2 (FIG. 4B), CXCR3 (FIG. 4C) or CXCR4/Jurkat cells (FIG. 4D) compared to the positive controls.

Example 5: Humanization of Mouse Monoclonal Antibodies

To avoid any potential HAMA (human anti mouse antibody) immunogenicity, 41A10 (C-41A10) and 11G2 (C-11G2) chimeric antibodies were humanized by using human germline frameworks sequences from IGKV1-39 (DPK9 light chain variable domain, GenBank Acc. No. X93627.1, SEQ ID NO:93) and human germline framework sequence from IGHV3 (DP54 heavy chain variable, GenBank Acc. No. AB019440, SEQ ID NO:91).

Humanized versions of the chimeric antibodies 11G2 (C-11G2) and chimeric 41A10 (C-41A10) were generated by complementarity determining region (CDR) grafting (referred to hereafter as "CDR-grafted"). That is, heavy chain CDRs were grafted onto a human DP-54 framework region (VH3 sub-group; SEQ ID NO:91) with a JH4 segment (SEQ ID NO:92), while light chain CDRs were grafted onto a human DPK9 framework (VKI sub-group; SEQ ID NO:93) with a JK4 segment (SEQ ID NO:94).

The humanized VH regions were joined to the human IgG1 constant region (SEQ ID NO:89) and then sub-cloned into a proprietary expression vector to generate the CDR-grafted heavy chains, including, but not limited to, SEQ ID NO:96 (11G2 CDR graft VH). The humanized VL regions were fused to the human kappa constant region (SEQ ID NO:90) and then sub-cloned into a proprietary expression vector to create the CDR-grafted light chains, including, but not limited to, SEQ ID NO:97 (11G2 CDR graft VL).

Example 6: Binding Affinity of Afucosylated or Fucosylated Anti-CXCR5 Antibodies The apparent affinity for cell surface CXCR5 of chimeric and humanized CXCR5 fucosylated and afucosylated antibodies was assessed. More specifically, to determine the apparent affinity of chimeric and humanized CXCR5 antibodies to CXCR5-expressing cells, cell binding experiments were performed on human and cynomolgus monkey peripheral blood mononuclear cells (PBMCs) and human tonsillar mononuclear cells (TMCs). The apparent affinity of CXCR5 mab binding to CXCR5+ cells (B cells, bona fide Tfh cells, and circulating Tfh-like cells) was calculated as the EC50 of equilibrium binding titration curves in which the geometric mean fluorescence intensity (gMFI) of the antigen binding population was quantified by flow cytometry.

Trima® residuals from healthy human donors, from Trima® apheresis collection and enriched for PBMCs, were obtained from Blood Centers of the Pacific (San Francisco, Calif.). PBMCs were isolated by density gradient centrifugation using SepMate™ tubes and Lymphoprep™ according to the manufacturer's instructions (STEMCELL Technologies, Vancouver, BC, Canada).

Tonsillar mononuclear cells (TMCs) were isolated from human tonsil obtained from BioOptions (Brea, Calif.). Briefly, the tonsil was dissected into small fragments (3-4 mm) in cold RPMI 1640 medium using a sterile scalpel. The tonsil tissue was then digested for 30 minutes at 37° C. in Digestion Medium (3 mL 10× Collagenase, 300 μL 100× Deoxyribonuclease (DNase), 6.7 mL RPMI 1640). RPMI 1640 supplemented with 10% Fetal Bovine Serum (FBS) was added to neutralize enzymatic activity and then the tissue was filtered sequentially through nylon filter cell strainers (70 μm and 40 μm mesh size nylon). Following centrifugation, red blood cell lysis was performed on the pellet using an ammonium chloride lysis buffer. Platelets were removed using a low speed centrifugation (200×g) for 10 minutes in Phosphate-Buffered Saline (PBS)/2% FBS/2 mM Ethylenediaminetetraacetic acid (EDTA). CD4+ T cells were purified out of the TMC mixture using an EasySep™ Human CD4+ T Cell Enrichment Kit, according to the manufacturer's instructions (STEMCELL Technologies, Vancouver, BC, Canada).

Following isolation, PBMCs were plated at a density of $1.0 \times 10^5$ cells per well and CD4+ TMCs were plated at a density of $2.0 \times 10^5$ cells per well in isolation buffer (PBS containing 1% FBS and 1 mM EDTA) in 96 well U-bottom plates. The plates were then centrifuged at 1500 rpm for 5 minutes at room temperature. PBMCs and CD4+ TMCs were resuspended in Fluorescence-activated cell sorting (FACS) buffer (PBS containing 1% FBS) containing human crystallized fragment Fc block (2 μL per well; Biolegend) and 4-fold serial dilutions of the antibodies (11-point dilution series, beginning at 5000 ng/mL for PBMCs and 312.5 ng/mL for CD4+ TMCs) and incubated on ice for 2 hours. PBMCs and CD4+ TMCs were then washed with FACS buffer 3 times and resuspended in 50-100 μL of FACs buffer containing fluorescent-conjugated antibodies for staining lymphocyte subsets and a fluorescent-conjugated secondary antibody against human Ig to detect CXCR5 monoclonal antibodies (mAbs). After incubation for 30 minutes at 4° C., PBMCs and CD4+ TMCs were washed with FACS buffer 2 times and resuspended in 125 μL of 0.5% paraformaldehyde (PFA) in PBS. Plates were stored at 4° C. until analysis by flow cytometry (BD LSRFortessa™ Cell Analyzer, BD Biosciences, Franklin Lakes, N.J.).

The cell binding titration curves were generated by plotting the gMFI of the antigen binding population against the log of CXCR5 antibody concentration. $EC_{50}$ values were determined using GraphPad Prism® (version 6.0, GraphPad Software, Inc, San Diego, Calif.) nonlinear-regression curve fits and a sigmoidal log of agonist dose-response model, according to the following equation Log (agonist) vs. response–variable slope (four parameters)

$$Y = \text{Bottom} + (\text{Top} - \text{Bottom}) / (1 + 10^{((\text{Log}EC_{50} - X) * \text{Hill-Slope})})$$

Where Y is the gMFI, X is antibody concentration, Top is the maximum Y-value corresponding to the upper plateau of the sigmoidal curve, Bottom is the minimum Y-value corresponding to the lower plateau of the sigmoidal curve, and $\text{Log}EC_{50}$ is the log of the concentration of antibody at the inflection point of the curve.

The $EC_{50}$ values were summarized across experiments using average and standard deviations (STDEV) where multiple replicates were performed. The results (i.e., the average apparent affinity of chimeric and humanized CXCR5 mAbs, which are fucosylated or afucosylated, for CXCR5-expressing cells) are shown in Table 4. The results also include affinity binding data obtained using anti-CXCR5 control antibodies 2C9 (WO 2012/010582), 16D7 (WO 2009/032661), and 11A7 (WO 2016/028573) which were included for comparison. Note that the fucosylated and afucosylated chimeric and humanized 11G2 antibodies having a variety of VL and VH combinations (i.e., h11G2 XC51/XC152, h11G2 XC153/XC155, h11Gh11G2 XC153/XC156, h11G2 XC154/XC155, and h11G2 XC154/XC157) have an apparent affinity for human B cells that is approximately equal. That is, the data show that afucosylation does not appear to affect the affinity of the antibody for CXCR5-expressing cells. Further, the data show that h11G2 XC154/XC155 antibodies (fucosylated and afucosylated) demonstrated approximately 10-fold higher affinity than control anti-CXCR5 antibody 2C9 and about 100-fold higher affinity than 11A7. Control anti-CXC5 antibody 16D7 did not show saturable binding. These data demonstrate that afucosylation did not affect the affinity of the 11G2 antibodies for binding to CXCR5-expressing cells. Since affinity is a measure of the strength of interaction between an epitope and the antibody antigen binding site (i.e., paratope), these data indicate that even if the antibodies bind a similar epitope, they do not bind the epitope with the same strength as 11G2.

TABLE 4

| CXCR5 mAb | Apparent Affinity Average EC50 ± STDEV (pM) | | | | |
|---|---|---|---|---|---|
| | Human B Cells | Human Tfh-like Cells | Human Tfh Cells | NHP B Cells | NHP Tfh-like Cells |
| Chimeric 41A10 | 161.28 ± 33.41 | ND | ND | 548.55 | ND |
| Humanized 41A10 142/147 | 153.38 ± 57.21 | ND | ND | 2049.50 | ND |
| Humanized 41A10 142/148 | 152.29 ± 75.51 | ND | ND | 1961.00 | ND |
| Chimeric 11G2 | 17.94 ± 8.48 | ND | 8.46 | 6.95 | ND |
| Afucosyl Chimeric 11G2 | 8.09 ± 2.93 | ND | 45.59 | ND | ND |
| Humanized 11G2 151/152 | 13.05 ± 10.9 | ND | 3.33 | 10.06 | ND |
| Humanized 11G2 153/155 | 7.79 ± 6.89 | ND | 4.82 | 7.03 | ND |
| Humanized 11G2 153/156 | 8.88 ± 6.39 | ND | 3.23 | 7.06 | ND |
| Humanized 11G2 154/155 | 7.08 ± 4.48 | 5.92 ± 1.55 | 8.25 | 4.13 | 5.65 |
| Humanized 11G2 154/157 | 19.12 ± 16.83 | ND | 7.24 | 8.65 | ND |
| Afucosyl humanized 11G2 154/155 | 6.60 ± 2.33 | 5.89 ± 1.40 | 10.59 | 1.32 | 10.47 |
| 2C9 (reference antibody) | 65.59 ± 37.95 | ND | ND | ND | ND |
| 16D7 (reference antibody) | Not saturable | ND | ND | ND | ND |
| 11A7 (reference antibody) | 563.63 ± 249.39 | ND | ND | ND | ND |

Example 7: Concentration-Dependent Binding of Afucosylated or Fucosylated Humanized 11G2 Antibodies Compared with Fucosylated Reference Antibodies Concentration-dependent binding to B cells from human PBMCs of fucosylated humanized 11G2 (h11G2 VL XC154/VH XC155 also referred to as h11G2 154/155 or h11G2 XC154/XC155) and afucosyl humanized 11G2 CXCR5 (afucosyl h11G2 154/155) was compared to the binding of comparator mAbs 2C9, 16D7, and 11A7. The cell binding titration curves were generated by plotting the gMFI of the antigen binding population against the log of CXCR5 antibody concentration and are shown in FIG. 5.

The data demonstrate that fucosylated and afucosylated h11G2 154/155 have an identical curve indicating that the presence or absence of fucose on the N-linked glycoform present at Asn297 on at least one, but preferably, both of the antibody constant chains does not affect the affinity of the antibodies for CXCR5 present on cells.

In addition, the data further demonstrate that the EC50 of the fucosylated (solid circles, $9.630\times10^{-12}$M) and the afucosylated (open circles, $1.188\times10^{-11}$ M) h11G2 154/155 antibodies was much lower that then EC50 of the comparator antibodies: 2C9 (solid triangles, $6.24\times10^{-11}$), 11A7 (solid diamonds, $9.265\div10^{-10}$) and 16D7 (solid squares, approximately 0.004945 and it was not saturable). These data show that the h11G2 154/155 antibodies have different binding characteristics than the comparator antibodies. These data therefore indicate that the 11G2 antibodies and 2C9, 11A7 and 16D7 do not bind the same epitope on CXCR5.

Example 8: ADCC Activity of Chimeric and Humanized CXCR5 Antibodies

To determine the potency and efficacy by which a cohort of chimeric and humanized CXCR5 antibodies stimulated activity-dependent cellular cytotoxicity (ADCC), serial dilutions of the CXCR5 antibodies or an isotype control were incubated with peripheral blood mononuclear cells (PBMCs) from healthy human donors or cynomolgus monkeys. In this assay, the PBMCs are the source of the natural killer (NK) effector cells and the target B and Tfh-like cells.

Flow cytometry was used to quantify the number of B and Tfh-like cells remaining after approximately 20 hr. Similarly, the ability of the humanized antibodies to induce ADCC of bona fide Tfh cells from human tonsil was assessed using CD4+ T cells isolated from tonsillar mononuclear cells with the addition of NK cells isolated from PBMCs.

As described in Example 6, Trima® residuals from healthy human donors, from Trima® apheresis collection and enriched for PBMCs, were obtained from Blood Centers of the Pacific (San Francisco, Calif.). PBMCs were isolated by density gradient centrifugation using SepMate™ tubes and Lymphoprep™ according to the manufacturer's instructions (STEMCELL Technologies, Vancouver, BC, Canada). Following isolation, PBMCs were plated in complete RPMI medium at a density of $2.0\times10^5$ cells per well in U-bottom, 96-well plates.

In this assay, the PBMCs are the source of the natural killer (NK) effector cells and the target B and Tfh-like cells. Serial dilutions of CXCR5 mAbs or isotype controls were added to the wells and the cells were incubated at 37° C., 5% CO2 for approximately 20 hours. The plates were then centrifuged at 1800 rpm for 5 minutes at room temperature (RT). PBMCs were then washed with ice-cold FACS and resuspended in 50 µl of ice-cold FACs buffer containing fluorescent-conjugated antibodies for staining lymphocyte subsets. After incubation for 15-30 minutes at 4° C., PBMCs were washed with ice-cold FACS buffer 2 times and resuspended in 100 µL of 0.5% paraformaldehyde (PFA) in PBS. CountBright™ Absolute Counting Beads (Thermo Fisher Scientific) were added to each well (15 µl per well). Plates were stored at 4° C. until analysis by flow cytometry (BD LSRFortessa™ Cell Analyzer).

Tonsillar mononuclear cells (TMCs) were also isolated as described previously in Example 6.

The cytotoxicity titration curves were made in accordance with the methods described for Example 6. The $EC_{50}$ values were summarized across experiments using average and standard deviations (STDEV) where multiple replicates were performed. The results are shown in Table 5. Data obtained using anti-CXCR5 reference antibodies 2C9, 16D7, and 11A7, were included for comparison.

TABLE 5

Average Cytotoxicity of Chimeric and Humanized CXCR5 mAbs for CXCR5-Expressing Cells

| | ADCC Activity Average EC50 ± STDEV (pM) | | | |
|---|---|---|---|---|
| CXCR5 mAb | Human B Cells | Human Tfh-like Cells | Human Tfh Cells | NHP B Cells |
| Chimeric 41A10 | 11732.28 ± 24781.14 | ND | ND | ND |
| Afucosyl Chimeric 41A10 | 54.47 ± 89.71 | ND | ND | ND |
| Humanized 41A10 142/147 | 1245 ± 881.03 | ND | ND | ND |
| Humanized 41A10 142/148 | 1109.25 ± 1081.15 | ND | ND | ND |
| Chimeric 11G2 | 564.01 ± 1643.77 | ND | 1.55 | 115.26 |
| Afucosyl Chimeric 11G2 | 4.39 ± 3.08 | ND | 0.07 | ND |
| Humanized 11G2 151/152 | 376.74 ± 606.13 | ND | ND | 43.61 |
| Humanized 11G2 153/155 | 463.17 ± 670.85 | ND | ND | 20.72 |
| Humanized 11G2 153/156 | 567.68 ± 847.34 | ND | ND | 28.06 |
| Humanized 11G2 154/155 | 253.72 ± 672.14 | 7.978 | 0.77 | 39.14 |
| Humanized 11G2 154/157 | 517.33 ± 1062.82 | ND | ND | 54.02 |
| Afucosyl humanized 11G2 154/155 | 2.01 ± 2.28 | 4.82 ± 2.88 | 0.11 | 15.26 ± 11.65 |
| 2C9 | 380.31 ± 757.04 | ND | ND | ND |
| 16D7 | 2590.61 ± 6343.88 | ND | ND | ND |
| 11A7 | 4.35 ± 4.03 | ND | ND | ND |

The data disclosed herein demonstrate that even fucosylated, the h11G2 154/155 antibody has greater ADCC activity (253.72±672.14) than comparator antibodies 2C9 (380.31±757.04) and 16D7 (2590.61±6343.88). Fucosylated antibody 11A7 demonstrated greater ADCC activity than any fucosylated antibody tested. However, the data show that afucosylated h11G2 154/155 had higher ADCC activity than any antibody tested including fucosylated 11A7. The characterization studies presented herein demonstrated that the chimeric CXCR5 mAbs 41A10 and 11G2 triggered ADCC of human B cells with an EC50 of 11.73 nM and 0.56 nM, respectively. Afucosyl versions of the chimeric CXCR5 mAbs 41A10 and 11G2 increased the potency of ADCC activity at least about 100-fold. The humanized variants triggered ADCC of human B cells with potencies comparable or superior to their corresponding chimeric counterparts. Just as with the chimeric CXCR5 mAbs, the afucosyl humanized variant increased the potency of ADCC compared to its normally fucosylated counterpart by at least about 100-fold. Afucosyl h11G2 was more potent at ADCC than fucosylated versions of 2C9 and 16D7, and afucosyl h11G2 was at least on par with fucosylated 11A7.

Example 9: 11G2 Antibodies Antagonize CXCL13 Signaling

To determine whether CXCR5 antibodies functionally antagonize CXCL13 signaling, a cyclic adenosine monophosphate (cAMP) reporter assay was utilized in an engineered cell line stably expressing human CXCR5. In these cells, CXCL13 inhibits cAMP production triggered by forskolin in a concentration-dependent manner.

To determine whether CXCR5 antibodies functionally antagonize CXCL13 signaling, a Hit Hunter® cAMP assay (DiscoveRx Corporation, Fremont, Calif.) was performed in CHO-K1 cells stably expressing human CXCR5. In this assay, active β-galactosidase (β-gal) is formed by Enzyme Fragment Complementation when cAMP is generated. β-gal can then convert a chemiluminescent substrate, generating an output signal detectable on a standard microplate reader. CXCR5's ligand, CXCL13, inhibits cAMP production triggered by forskolin (20 µM) in a concentration-dependent manner. To test the potency and efficacy of CXCR5 antibodies in inhibiting CXCL13-mediated forskolin-induced cAMP production, serial dilutions of each CXCR5 antibody were added to CXCR5-expressing CHO-K1 cells in the presence of forskolin (20 µM) and CXCL13 (used at its $IC_{50}$ of 600 µM).

The functional antagonism titration curves were made in accordance with that described for Example 6 including the $EC_{50}$ value determination. The results are shown in Table 6.

TABLE 6

In vitro stimulation of CXCL13-inhibited cAMP production in CXCR5+ CHO-K1 cells

| CXCR5 mAb | $EC_{50}$ (pM) | % Inhibition CXCL13 |
|---|---|---|
| Humanized 11G2 154/155 | 752.9 | 120.6 |
| 2C9 | 793.1 | 113.5 |
| 16D7 | 1104 | 102.4 |
| 11A7 | 1401 | 105.9 |

In a separate study, afucosyl humanized 11G2 154/155 was tested for functional antagonism and behaved similarly to humanized fucosylated 11G2 154/155 (i.e., $EC_{50}$=961.4 pM).

The data demonstrate that h11G2 154/155 inhibited CXCL13 signaling at least as well as reference antibodies 2C9, 16D7, 11A7. Indeed, h11G2 inhibited CXCL13 signaling (120.6%) to a significantly greater extent than 16D7 (102.4%) and 11A7 (105.9%). These data suggest that 11G2 antibodies can be a useful novel therapeutic to treat a disease, disorder or condition mediated by or associated with CXCR5-mediated CXCL13 signaling.

Example 10: Mapping the Binding Site on hCXCR5 of 11G2 Antibody

The afucosyl humanized 11G2 154/155 binding site on CXCR5 was identified by grafting amino acids from the extracellular N-terminus of mouse CXCR5 onto the human CXCR5.

More specifically, the mapping strategy took advantage of the fact that 11G2 binds human CXCR5 (SEQ ID NO:32), but does not bind mouse CXCR5 (SEQ ID NO:34). The alignment of the amino acid sequences of human CXCR5 (hCXCR5) and mouse CXCR5 (mCXCR5) is shown in FIG. 6. The amino acid residues of the extracellular domains of CXCR5 are indicated by underlining. The extracellular domains (ECD) of both mouse and human CXCR5 proteins are indicated in bold and labeled "N", "L1", "L2" and "L3" under the sequence of each region on FIG. 6. These ECDs were swapped between mouse and human proteins to identify the region(s) responsible for the specificity of 11G2 for human CXCR5 and for the lack of binding to mCXCR5. Each of those regions from mouse CXCR5 was exchanged with the same region in human CXCR5 to produce the chimeric proteins designated XC251, XC252, XC253, XC254, XC255 and XC256 wherein a human CXCR5 protein contains the specified corresponding mouse CXCR5 domain. Table 7 provides a key showing which mouse (m) regions were swapped into human CXCR5.

TABLE 7

| (ECD-swapped mouse/human chimeric CXCR5 proteins) | |
|---|---|
| XC251 | hCXCR5-mL3 |
| XC252 | hCXCR5-mL2 |
| XC253 | hCXCR5-mN |
| XC254 | hCXCR5-mL2-mL3 |
| XC255 | hCXCR5-mN-mL3 |
| XC256 | hCXCR5-mN-mL2 |

More specifically, mouse L3 domain was swapped for the corresponding human L3 domain to produce chimeric protein XC251 comprising the mouse L3 domain in the context of the human CXCR5 protein (hCXCR5-mL3). Similarly, mouse L2 was swapped for the corresponding human domain to produce chimeric protein XC252 (hCXCR5-mL2); mouse N domain was swapped for the corresponding human N domain to produce chimeric protein XC253 (hCXCR5-mN); mouse L2 and L3 domains were swapped for the corresponding human domains to produce chimeric protein XC254 (hCXCR5-mL2-mL3); mouse mN and L3 domains were swapped for the corresponding human domains to produce chimeric protein XC255 (hCXCR5-mN-mL3); and mouse mN and L2 domains were swapped for the corresponding human domains to produce chimeric protein XC255 (hCXCR5-mN-mL2).

The binding of 11G2 to mouse CXCR5, human CXCR5, and the various ECD-swapped mouse-human chimeric CXCR5 proteins (XC251-XC256) was assessed and compared to the binding of various antibodies, i.e., rat anti-mouse CXCR5 (rat) (catalog MAB6198, R&D systems, Minneapolis, Minn.), rabbit anti-human CXCR5 (Rb) (catalog, ab46218, Abcam, Cambridge, Mass.), 2C9, 16D7. The results are shown in Table 8. Numbers in bold indicate antibody binding to the protein.

TABLE 8

(FACS analysis of Antibody binding to ECD-swapped mouse-human CXCR5 chimeric proteins)

| | | Rb (hCXCR5) (GMFI) | rat (mCXCR5) (GMFI) | 2C9 (GMFI) | 16D7 (GMFI) | 11G2 (GMFI) |
|---|---|---|---|---|---|---|
| | hCXCR5 | 18575 | 2457 | 117099 | 149936 | 138584 |
| XC251 | hCXCR5-mL3 | 6594 | 3932 | 13287 | 19927 | 14559 |
| XC252 | hCXCR5-mL2 | 12496 | 3842 | 22383 | 26963 | 21650 |
| XC254 | hCXCR5-mL2-mL3 | 4681 | 3826 | 11446 | 16877 | 11471 |
| | mCXCR5 | 1037 | 12537 | 1183 | 958 | 901 |
| XC253 | hCXCR5-mN | 1549 | 37152 | 1779 | 1264 | 1215 |
| XC255 | hCXCR5-mN-mL3 | 1607 | 39099 | 1954 | 1341 | 1318 |
| XC256 | hCXCR5-mN-mL2 | 1525 | 31061 | 1966 | 1376 | 1262 |

The data show that where the antibody was specific for mouse CXCR5, it bound the ECD-swapped mouse-human chimeric CXCR5 as long as the chimera comprised the mouse N domain. Similarly, for antibodies that bound human CXCR5 (11G2, 2C9, 16D7, and Rb), the antibodies bound the chimeric CXCR5 if the human N domain was present in the chimera. Therefore, species specificity of the antibodies appears to be driven by binding located in the N domain. More importantly, these data demonstrate that the N domain of human CXCR5 was required for the binding of antibodies 11G2, 2C9 and 16D7,

Example 11: Identification of Amino Acid Residues Unique to 11G2 Antibody Binding to hCXCR5

To more precisely determine the specific amino acid residues crucial for antibody binding to hCXCR5 and to further differentiate between the anti-human CXCR5 antibodies, more detailed studies of the N domain of CXCR5 were undertaken. More specifically, point mutations were made in the N domain fragment of human CXCR5 (amino acids 1-58 according to the numbering of SEQ ID NO:32) to produce point mutant proteins each comprising a corresponding mouse amino acid residue of CXCR5. Stable transfectants were generated expressing each mutein and the cells were examined for antibody binding using flow cytometry. That is, nineteen (19) human CXCR5 N domain mutant proteins, referred to as XC276-XC294, were produced each containing a single amino acid substitution where a human residue of CXCR5 was replaced with the corresponding mouse residue as illustrated in Table 9. The human CXCR5 muteins further comprised a FLAG epitope (DYKDDDDK) shown using lower case letters in Table 9 at the N-terminus to allow for normalization based on expression level; the FLAG tag did not affect antibody binding to the muteins. Substitutions were typically not made where the human to mouse amino acid residue substitution would have been a conservative substitution, and these residues are indicated in italics.

Table 9 shows the amino acid sequence of the N region of hCXCR5 (the first 58 amino acids are shown), compared with the amino acid sequence of the N region of mouse CXCR5. The amino acids that differ between the two sequences are underlined. The figure also shows the various constructs (XC276-XC294) produced where the mouse amino acid residue was substituted for the corresponding human amino acid in hCXC5. For example, XC276 is human CXCR5 with a single amino acid substitution changing D (human) to G (mouse). The rest of the hCXCR5 amino acid sequence (SEQ ID NO:32) is not shown since it was not changed. The muteins were produced to determine which amino acid residue(s) were crucial for antibody binding to hCXCR5 since the antibodies tested did not bind mouse CXCR5.

humanized 11G2 154/155; 2C9; S16D7 or 11A7, followed by anti-human IgG PE (Southern Biotech, Birmingham, Ala.). The cells were analyzed by flow cytometry using an Accuri (BD Biosciences Franklin Lakes, N.J.). The geometric mean fluorescence intensity (gMFI) was determined and the ratio for the gMFI of each CXCR5 antibody and anti-flag was calculated.

Figure 7:
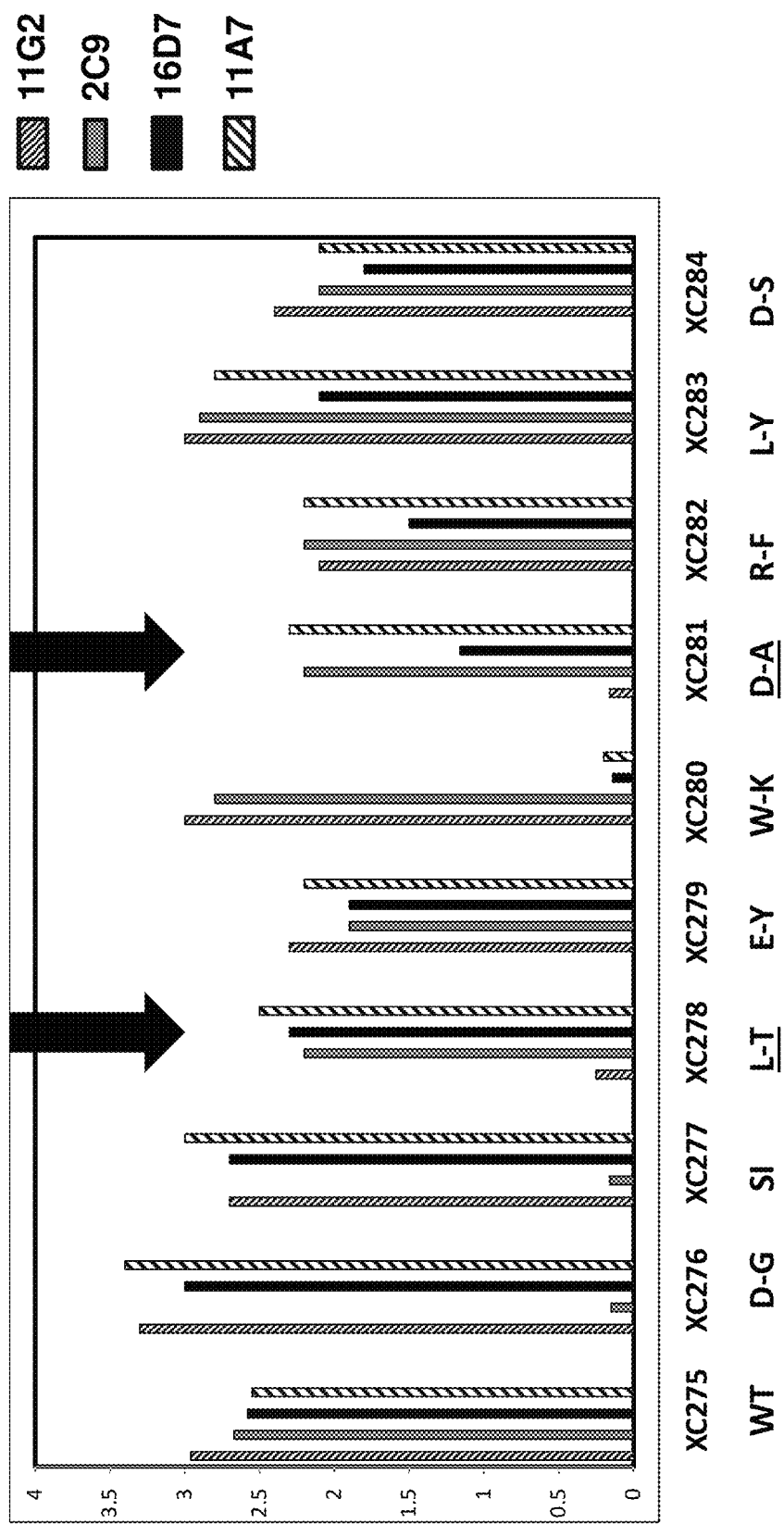
FIG. 7 depicts a bar graph showing that certain amino acid residues were crucial for antibody binding to hCXCR5. That is, changing D10G or inserting SI into the human sequenced, abolished binding by antibody 2C9 but did not affect binding by the other three antibodies. More importantly, substituting L11T or D22A abolished binding by 11G2 but did not affect binding of 2C9, 16D7 or 11A7. Changing W to K at amino acid residue number 19 (W19K) abolished binding by antibodies 16D7 and 11A7 but did not affecting binding by 11G2 and 2C9. These data demonstrate that these four antibodies do not share the same epitope on hCXCR5.
Figure 8A:
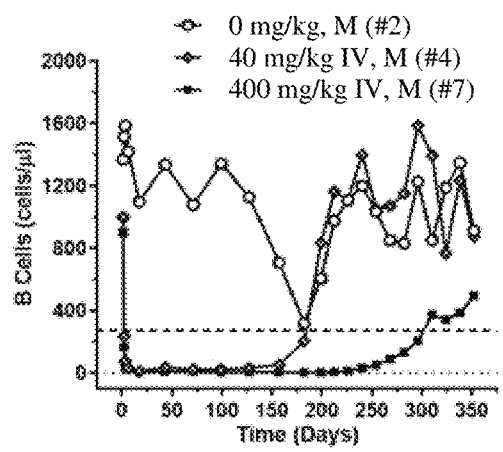
FIG. 8A depicts a graph showing the depletion and reconstitution of peripheral blood B cells in male cynomolgus monkeys. Peripheral blood B cell numbers per µl of blood in males are shown through Day 352 of the exploratory toxicity study. B cells were defined as CD3-CD20+. Individual animal data are shown. Historical range of B cells in male monkeys (272-2503 cells per µL) are denoted by dashed lines.
Figure 8B:
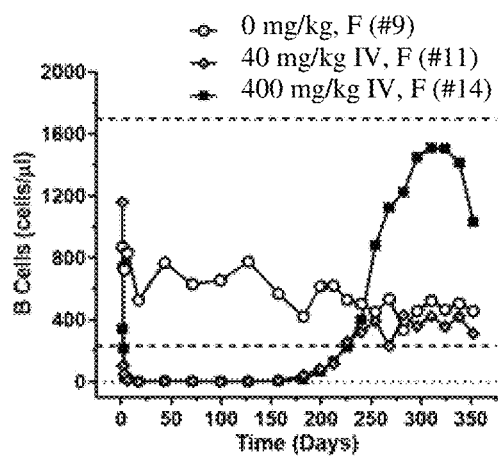
FIG. 8B depicts a graph showing the depletion and reconstitution of peripheral blood B cells in female cynomolgus monkeys. Peripheral blood B cell numbers per µl of blood in females are shown through Day 352 of the exploratory toxicity study. B cells were defined as CD3-CD20+. Individual animal data are shown. Historical ranges of B cells in female monkeys (233-1700 cells per µL) are denoted by dashed lines.
Figure 8C:
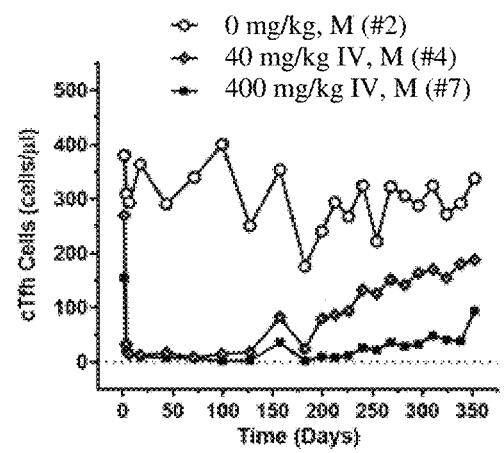
FIG. 8C depicts a graph showing the depletion and reconstitution of Tfh-like (also referred to as "cTfh" or "circulating Tfh" cells) cells in male cynomolgus monkeys. Peripheral blood Tfh-like cell numbers per µl of blood in males are shown through Day 352 of the exploratory toxicity study. Tfh-like cells were defined as the sum of CD3+CD4+CD95+ CXCR5+ cells and CD3+CD4+CD95+hIgG+ cells, because the test article interferes with the CXCR5 antibody used for immunophenotyping. Individual animal data are shown.
Figure 8D:
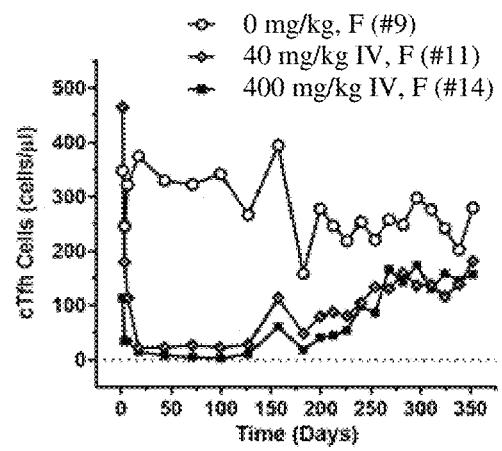
FIG. 8D depicts a graph showing the depletion and reconstitution of Tfh-like (also referred to as "cTfh" or "circulating Tfh" cells) cells in female cynomolgus monkeys. Peripheral blood Tfh-like cell numbers per µl of blood in females are shown through Day 352 of the exploratory toxicity study. Tfh-like cells were defined as the sum of CD3+CD4+CD95+ CXCR5+ cells and CD3+CD4+CD95+ hIgG+ cells, because the test article interferes with the CXCR5 antibody used for immunophenotyping. Individual animal data are shown.
Figure 9A:
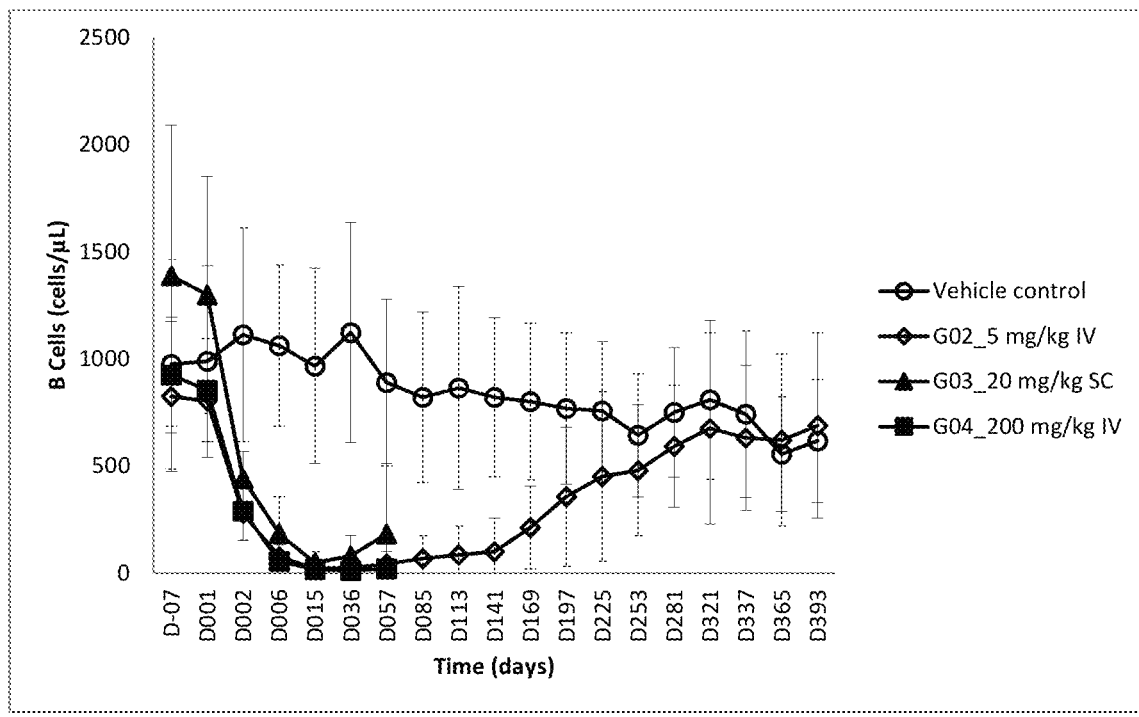
FIG. 9A depicts a graph showing depletion and reconstitution of peripheral blood B cells in cynomolgus monkeys. Peripheral blood B cell numbers per µl of blood in monkeys are shown through Day 393 of the pivotal GLP toxicity study. B cells were defined as CD3−CD20+HLA−DR+ cells. Group mean data (males and females combined) +/− standard deviation are shown.
Figure 9B:
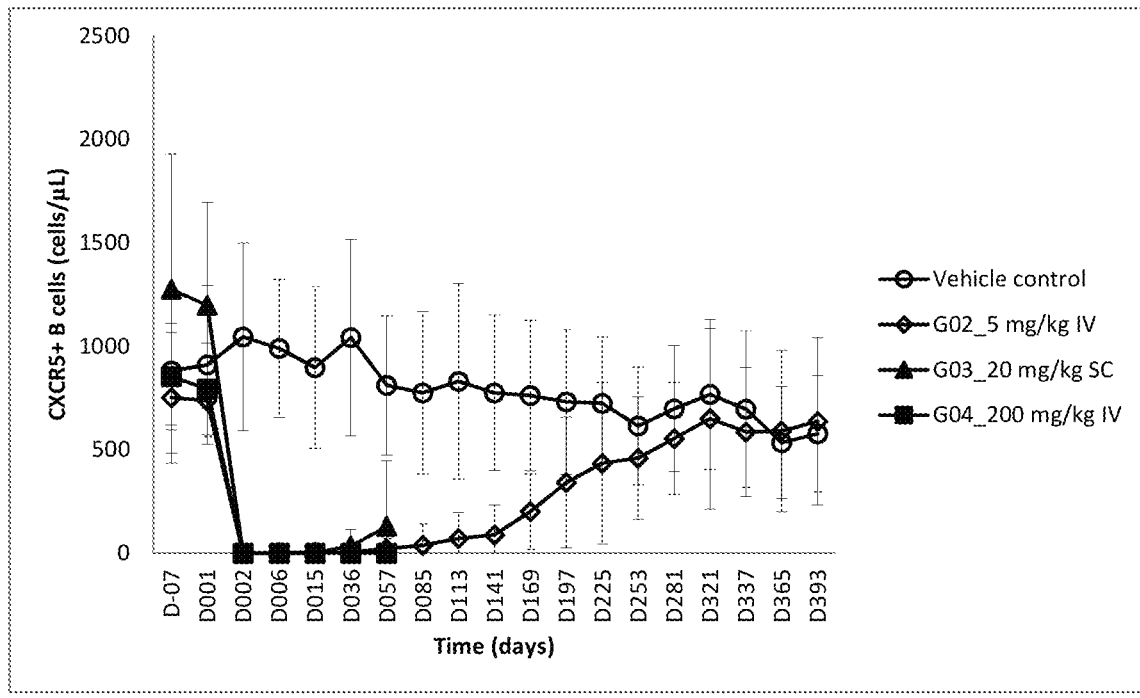
FIG. 9B depicts a graph showing depletion and reconstitution of peripheral blood CXCR5+ B cells in cynomolgus monkeys. Peripheral blood CXCR5+ B cell numbers per µl of blood in monkeys are shown through Day 393 of the pivotal GLP toxicity study. B cells were defined as CD3−CD20+HLA−DR+ cells. Group mean data (males and females combined) +/− standard deviation are shown.
Figure 9C:
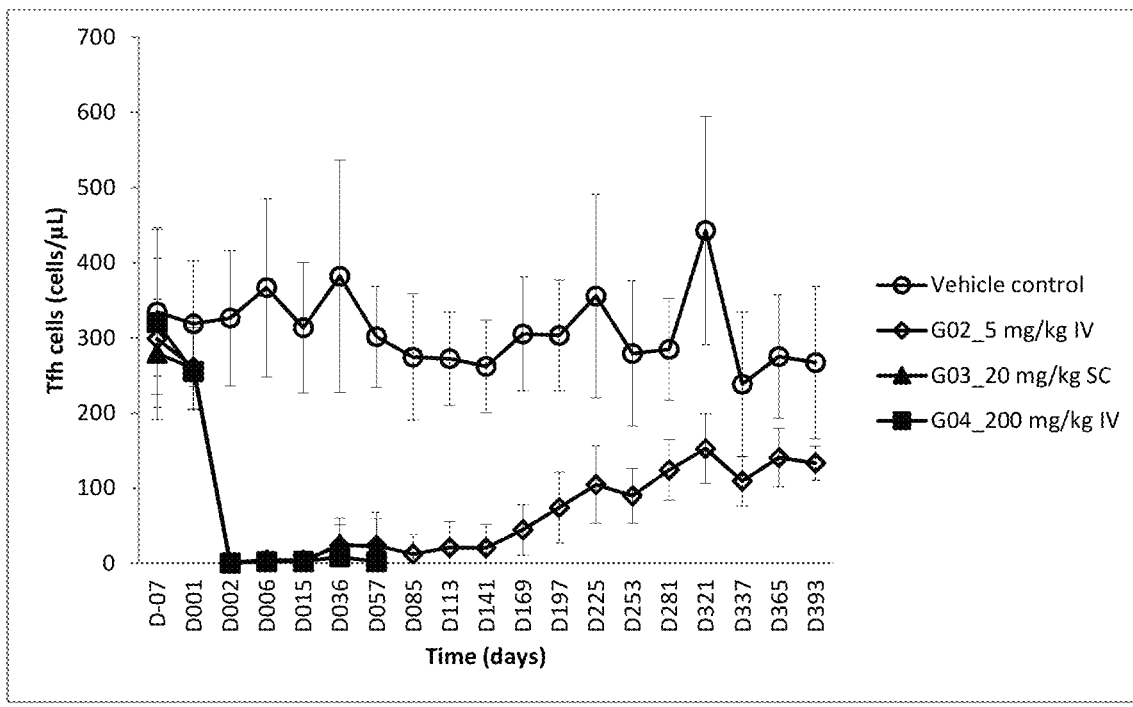
FIG. 9C depicts a graph showing depletion and reconstitution of peripheral blood circulating follicular T helper cells (cTfh; also referred to elsewhere herein as "Tfh-like cells") in cynomolgus monkeys. Peripheral blood cTfh cell numbers per µl of blood in monkeys are shown through Day 393 of the pivotal GLP toxicity study. cTfh cells were defined as CD3+CD4+CD95+ cells. Group mean data (males and females combined) +/− standard deviation are shown.
Figure 9D:
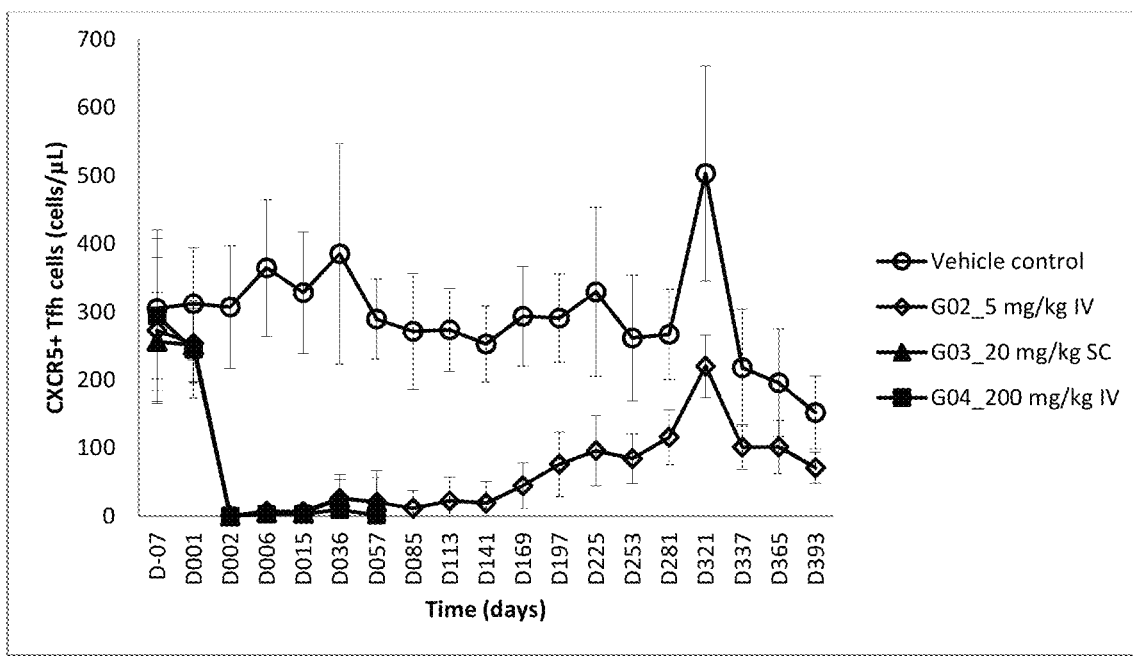
FIG. 9D depicts a graph showing depletion and reconstitution of peripheral blood CXCR5+cTfh cells (also referred to elsewhere herein as "Tfh-like cells") with detectable surface CXCR5 in cynomolgus monkeys. Peripheral blood CXCR5+ cTfh cell numbers per µl of blood in monkeys are shown through Day 393 of the pivotal GLP toxicity study. cTfh cells were defined as CD3+CD4+CD95+ cells. Group mean data (males and females combined) +/− standard deviation are shown.

As shown in FIG. 7, all four antibodies bound to wild type human CXCR5 (XC275; WT). The antibodies then give different patterns of binding the various point mutant peptides. That is, 2C9 did not bind XC276 (comprising the mutation D10G0) or XC277 (comprising an insertion of amino acid residues S and I into the human CXCR5 N domain), while 11G2, 16D7, and 11A7 bound those proteins. These data suggest that insertion of these two amino acids into the hCXCR5 sequence abrogated 2C9 binding but did not affect binding of the three other antibodies suggesting the epitope for 2C9 differs from that of 11G2, 16D7 and 11A7. More importantly, mutation of leucine (L) to threonine (T) at amino acid residue position 11 (based on the numbering of the sequence of SEQ ID NO:32) completely

TABLE 9

| Protein | Mutation per SEQ ID NO: 32 | Protein sequence showing change relative to human CXCR5 |
|---|---|---|
| hCXCR5 | WT | MdykddddkNYPLTLEMD--LENLEDLFWELDRLDNYNDTSLVENHLCPATEGPLMASFKAVFVPVAY |
| mCXCR5 |  | M-------NYPLTLDMGSITYNMDDLYKELAFYSNSTEIPLQDSNFCSTVEGPLLTSFKAVFMPVAY |
| XC276 | D10G | G |
| XC277 | SI (insertion) | SI |
| XC278 | L11T | T |
| XC279 | E12Y | Y |
| XC280 | W19K | K |
| XC281 | D22A | A |
| XC282 | R23F | F |
| XC283 | L24Y | Y |
| XC284 | D25S | S |
| XC285 | Y27S | S |
| XC286 | N28T | T |
| XC287 | T30I | I |
| XC288 | S31P | P |
| XC289 | V33Q | Q |
| XC290 | N35S | S |
| XC291 | H36N | N |
| XC292 | L37F | F |
| XC293 | P39S | S |
| XC294 | A40T | T |

Nucleic acids encoding each mutant peptide were transiently transfected into HEK-293T cells. 2 days post-transfection, the cells were harvested and stained with 1 µg/ml anti-FLAG PE (Biolegend) or 1 µg/ml or 3 µg/ml afucosyl abolished binding of only 11G2 to XC278 but did not affect the binding of antibodies 2C9, 16D7 or 11A7 to this protein. Thus, the Leucine residue present at position number 11 (relative to the amino acid sequence set forth in SEQ ID NO:32) appears crucial for binding of 11G2 to human CXCR5 but is not important for binding of 2C9, 16D7 or 11A7 to hCXCR5. These data demonstrate that the epitope of 11G2 is not the same as the epitope for those antibodies. In addition, FIG. 7 shows that all four antibodies bound XC279 such that the substitution of E to Y at amino acid residue number 12 (relative to the sequence of SEQ ID NO:32) was not crucial for binding of any of these antibodies to hCXCR5.

The biding of these four antibodies to XC280, which comprises a substitution W to lysine (K) at amino acid residue number 19 (according to the numbering of the sequence of SEQ ID NO:32) resulted in loss of binding to XC280 by antibodies 16D7 and 11A7, but did not affect the binding of antibodies 11G2 and 2C9 to the mutein (FIG. 7). These results further demonstrate that these four antibodies do not bind the same epitope on hCXCR5.

FIG. 7 also shows that changing D at position 22 (according to the numbering of the sequence of SEQ ID NO:32) to alanine (A) completely abrogates binding of 11G2 to the XC281 mutein but does not affect binding of antibodies 2C9, 16D7, and 11A7. This further emphasizes that the epitope for 11G2 is not the same as the epitope(s) of antibodies 2C9, 16D7, and 11A7.

All four antibodies bound to XC285-294 equally and their binding was not affected by any of the amino acid substitutions in these muteins. These data suggest that the amino acid residues at these positions (27, 28, 30, 31, 33, 35, 36, 37, 39 and 40; see Table 9) do not participate in antibody binding to CXCR5 for antibodies 11G2, 2C9, 11A7 and 16D7.

Thus, these data demonstrate that the leucine (L) residue at amino acid position number 11 and the aspartate (D) residue at amino acid position number 22 (both relative to the numbering of the amino acid sequence of SEQ ID NO:32) are critical for binding of 11G2 antibody to hCXCR5 since substituting either of these residues (or both of them) with the corresponding mouse amino acid residue at those positions abrogated binding of the antibody to hCXCR5. These data also show that antibody 11G2 does not have the same epitope as antibody 2C9, 16D7 or 11A7 since the change of L11 and/or W22 does not affect the binding of these antibodies to hCXCR5.

FIG. 7 also shows that all four antibodies bound mutant CXCR5 proteins XC282 through XC284. All four antibodies also bound proteins XC285 through XC294. These data suggest that the epitope for antibodies 11G2, 2C9, 16D7 and 11A7 is not in the region of the N domain of hCXCR5 indicated by muteins XC282 through XC294.

Example 12: 11G2 is Selective for CXCR5 and Does Not Bind Other Members of the Chemokine GPCR Family The selectivity of afucosyl humanized 11G2 154/155 was assessed against twenty (20) members of the Chemokine GPCR family using a β-Arrestin coupling assay (DiscoveRx). This assay uses whole cells stably transfected with each receptor, and directly measures GPCR activity by detecting the interaction of β-Arrestin with the activated GPCR. Because Arrestin recruitment is independent of G-protein signaling, these assays offer a universal screening and profiling platform that can be used for virtually any Gi, Gs, or Gq-coupled receptor, offering a standardized and efficient comparison across receptors or receptor families (regardless of G-protein coupling). The assay was performed in agonist (without ligand present) and antagonist mode (in presence of ligand at EC90). The following chemokine receptors were included in the selectivity panel: CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR5, CXCR6, CXCR7, XCR1.

No significant activity of afucosyl humanized 11G2 154/155 (tested at 200 nM) was observed on any other chemokine receptor when tested in an agonist mode and it was only significantly active as antagonist of CXCR5 (92% inhibition of ligand-induced β-arrestin coupling), when compared in antagonist mode to all other chemokine receptors evaluated, i.e., no significant inhibition was observed for any other chemokine receptor tested.

Example 13: h11G2 Does Not Demonstrate Polyreactivity Against DNA, Insulin or LPS The polyreactivity assay is used to determine if antibodies can potentially react to a variety of unrelated antigens in vivo. Lack of polyreactivity suggests that 11G2 is a CXCR5 specific antibody and that it does not bind to off targets in vivo.

Black DELFIA plates (Thermoscientific) were coated with 10 µg/ml of double-stranded DNA (dsDNA; Millipore), 5 µg/ml lipopolysaccharide (LPS; Sigma), 10 µg/m Insulin (Sigma, St. Louis, Mo.), or phosphate-buffered saline (PBS) and incubated at 4° C. overnight. The plates were then washed with water using a Biotek ELx405 microplate washer (Biotek, Winooski, Vt.) and the plate was then blocked with 200 µl of assay buffer containing 1×PBS, 0.05% Tween 20 and 1 mM EDTA at room temperature for one hour. Following an additional wash step, the plates were incubated at room temperature for one hour with serial dilutions of anti-CXCR5 antibodies (all antibodies were fucosylated). For detection, 100 µl of DELFIA-Eu-N1-anti-human IgG (50 µg/ml; Perkin Elmer, Waltham, Mass.) was added to the plates and incubated at room temperature for one hour. Finally, 100 µl of DELFIA enhancement solution was added to each well and the plates were shaken at room temperature for 15 minutes prior to being read on a VictorX4 Multilabel Plate Reader (PerkinElmer, Waltham, Mass.) under europium fluorescence. Data are shown in Table 10.

TABLE 10

Fluorescence (counts) for CXCR5 mAbs Polyreactivity

| CXCR5 mAb | Dose (nM) | Fluorescence (counts) | | | |
|---|---|---|---|---|---|
| | | Insulin Coat | DNA Coat | LPS Coat | PBS Coat |
| Humanized 11G2 154/155 | 1.2 | 161 | 1099 | 190 | 1788 |
| | 11 | 305 | 1780 | 829 | 1145 |
| | 100 | 6090 | 2696 | 4988 | 2314 |
| 2C9 | 1.2 | 267 | 919 | 328 | 523 |
| | 11 | 1690 | 1483 | 4144 | 1408 |
| | 100 | 21100 | 13970 | 21447 | 7758 |
| 16D7 | 1.2 | 175 | 701 | 222 | 1874 |
| | 11 | 1752 | 1974 | 1889 | 1733 |
| | 100 | 4899 | 14356 | 3850 | 2286 |
| 11A7 | 1.2 | 614 | 29862 | 334 | 1669 |
| | 11 | 3252 | 75133 | 1521 | 1608 |
| | 100 | 31720 | 108952 | 6510 | 10188 |

In a separate study, afucosylated humanized 11G2 154/155 was tested for polyreactivity and did not show binding to insulin, DNA, LPS, or PBS, consistent with the results for fucosylated humanized 11G2 154/155 shown in Table 10 above.

These data demonstrate that 11G2 is not reactive with insulin, DNA or LPS, and is less reactive than comparator antibodies 2C9, 16D7, and 11A7. These data suggest that 11G2 is a potential useful novel therapeutic. Polyreactive antibodies, by definition, bind in a non-specific manner to a range of biological molecules. That 11G2 does not react in a generic polyreactivity assay further supports that 11G2 is specific for CXCR5. PK, TK, and tox data also support that 11G2 has specificity for CXCR5.

Example 14: Summary of Differences Between 11G2 and Comparator Antibodies

Table 11 below summarizes the characteristics of 11 G2 and various comparator antibodies described previously elsewhere herein. ND means not determined.

These data demonstrate that antibody 11G2, both fucosylated and afucosylated, is quite different from comparator antibodies 2C9, 16D7 and 11A7. That is, 11G2 binding is abrogated by substitution of the mouse amino acid residue at positions 11 and 22 while the binding of the comparator antibodies is not affected by substitution of these residues (numbered according to the amino acid sequence of SEQ ID NO:32). Further, the binding of 2C9 requires the presence of amino acid residues W19, D22 and R23 for binding to hCXCR5, but none of the antibodies require all three, even though 11A7 biding to hCXCR5 is abrogated by substitution of alanine for W at position 19 (according to the numbering of the amino acid sequence of SEQ ID NO:32). Unlike all of the other antibodies, binding of 16D7 to hCXCR5 is abrogated by insertion of the two mouse residues between D10 and L11 of human CXCR5 (according to the numbering of the amino acid sequence of SEQ ID NO:32) (see FIG. 7). Thus, the data provided herein suggest that 11 G2 does not have the same epitope as antibodies 2C9, 16D7 and 11A7, and that these antibodies have different epitopes among themselves as well.

In addition, the data provided herein demonstrate that 11G2 has an affinity (expressed as EC50) which is at least 10-fold greater for hCXCR5, (7.08 pM) than 2C9 (65.59 pM) and at least 100-fold greater than 11A7 (563.63 pM), and very different from 16D7, which could not be compared because it was not saturable.

TABLE 11

| CXCR5 mAb | Epitope (critical residues for binding) | Polyreactivity | Apparent Affinity (EC$_{50}$, pM) | ADCC (EC$_{50}$, pM) | Functional Antagonism (EC$_{50}$, pM) |
|---|---|---|---|---|---|
| Humanized 11G2 154/155 | L11, D22 | No | 7.08 | 253.72 | 752.9 |
| Afucosyl humanized 11G2 154/155 | ND | No | 6.60 | 2.38 | 961.4 |
| 2C9 | W19, D22, R23 | No | 65.59 | 380.31 | 793.1 |
| 16D7 | D10, SI insertion | No | No saturable binding | 2590.61 | 1104 |
| 11A7 | W19 | Reactivity to DNA | 563.63 | 4.35 | 1401 |

These data all suggest that 11G2 is substantially different from comparator antibodies 2C9, 16D7 and 11A7, and is a potential novel useful therapeutic for the treatment or prevention of a disease, disorder or condition mediated by or associated with a biological activity of CXCR5, including but not limited to, CXCR5-mediated CXCL13 signaling. This is especially the case for the afucosylated version of 11G2 which demonstrated greatly enhanced ADCC activity, thereby increasing its potential usefulness as a therapeutic to treat, e.g., immune diseases mediated by or associated with cell expression of CXCR5.

Example 15: In Vivo Pharmacodynamics of Afucosylated h11G2 XC154/XC155

In vivo, doses ranging from 0.001 to 400 mg/kg/dose IV or SC have been explored in multiple cynomolgus monkey studies for afucosyl humanized 11G2 154/155. As used throughout this experiment, IV and SC formulations comprised the following components 50 mg/mL CXCR5 antibody or antigen-binding fragment of the present disclosure, 20 mM histidine, 8.5% sucrose, and 0.02% polysorbate 80, 0.005% EDTA at pH 5.8. Table 12 below sets forth the in vivo study design of studies of afucosylated 11G2 XC154/XC155 in cynomolgus monkeys.

TABLE 12

| Study Description | Dose (Route of Administration) | Dosing Regimen |
| --- | --- | --- |
| Single-Dose Pharmacodynamic (PD) Study in Cynomolgus Monkeys | 0.001, 0.002, 0.005, 0.1, and 0.2 mg/kg (IV) | Single dose |
| Repeat-Dose Exploratory Toxicity Study in Cynomolgus Monkeys (with 48-Week Recovery Phase) | 40 and 400 mg/kg/dose (IV), 260 (SC) | Three once-weekly doses on Days 1, 8, and 15 |
| Repeat-Dose GLP Toxicity Study in Cynomolgus Monkeys (with 11 month Recovery Phase) | 5 and 200 mg/kg/dose (IV), 20 (SC) | Five biweekly doses on Days 1, 15, 29, 43, and 57 |
| A PK, PD, Immunocompetency (Vaccine Recall Response) Study of afucosylated h11G2 VL XC154/VH XC155 in Cynomolgus Monkeys | 2 and 10 mg/kg/dose (IV) | Two once-weekly doses on Days 1 and 8 |

Dose-dependent depletion of B cells and Tfh-like cells in the peripheral blood was observed in cynomolgus monkeys at single doses of afucosylated h11G2 VL XC154/VH XC155 (afucosyl h11G2 XC154/XC155) ranging from 0.001 to 0.2 mg/kg; the lowest dose tested (0.001 mg/kg) resulted in approximately 50% depletion of B cells and Tfh-like (i.e., cTfh) cells in the peripheral blood.

In the exploratory and pivotal GLP toxicity studies in cynomolgus monkeys, doses of afucosyl h11G2 XC154/XC155≥5 mg/kg IV led to marked depletion of B cells and Tfh-like cells in the peripheral blood and decreased cellularity of lymphoid follicles in the spleen and other lymphoid tissues (axillary and mesenteric lymph nodes and gut associated lymphoid tissue); these effects correlated with pharmacologically-mediated reduced cellularity of B cell areas observed immunohistochemically. In the exploratory and pivotal studies, partial to full recovery of B cells, Tfh-like cells, and Tfh cells was observed. The kinetics of depletion and subsequent repletion were related to the exposure levels of afucosyl h11G2 XC154/XC155.

To determine whether afucosyl h11G2 XC154/XC155 impairs humoral memory responses, a vaccine recall response study was conducted in cynomolgus monkeys. Briefly, afucosyl h11G2 XC154/XC155 was given by IV bolus injection on Days 1 and 8 at levels of 2 and 10 mg/kg/dose to cynomolgus monkeys (N=6 per group) that had been vaccinated against TT (tetanus toxoid) prior to the study. Administration of afucosyl h11G2 XC154/XC155 was well tolerated and led to the expected pharmacology (i.e., a decrease in circulating B cells and Tfh-like cells). Increased immunoglobulin M (IgM) and IgG memory responses, as compared to Day 15, were observed in all animals in all dose groups on Day 22, 7 days post-secondary TT immunization. These responses were attenuated in animals administered afucosyl H11G2 XC154/XC155 (10 mg/kg/dose) with a peak anti-TT IgG mean titer of 42,667 as compared to 72,000 for the control group and a peak anti-TT IgM mean titer of 1583 as compared to 3500 for the control group. Rituxan® (rituximab), a B cell depleting antibody used as a comparator, did not affect anti-TT IgG memory responses. In conclusion, these data demonstrate that afucosyl h11G2 XC154/XC155 impairs humoral memory responses in vivo.

Safety Pharmacology

Electrocardiography and heart rate measurements were incorporated into the design of the pivotal toxicity study. There were no abnormal electrocardiographic findings attributable to the administration of afucosyl h11G2 XC154/XC155. All the electrocardiograms were qualitatively and quantitatively within normal limits and no arrhythmias were present.

Example 16: In Vivo Pharmacokinetics and Metabolism of Afucosylated h11G2 XC154/XC155

An electrochemiluminescent (ECL) assay was validated to detect the presence of ADA in cynomolgus monkey serum on the Meso Scale Discovery® (MSD) assay platform). A positive control, anti-CXCR5 anti-idiotypic antibody, spiked into cynomolgus monkey serum, and a negative control consisting of pooled normal cynomolgus monkey serum, were included on each plate to monitor assay performance. Biotin-labeled afucosyl h11G2 XC154/XC155 and ruthenium-labeled afucosyl h11G2 XC154/XC155 were co-incubated with study samples, the positive control, and the negative control. Antibodies to afucosyl h11G2 XC154/XC155 present in the samples must bind to both the biotin- and ruthenium-labeled versions of afucosyl h11G2 XC154/XC155 to be detected in this assay. Complexes were captured via the biotinylated afucosyl h11G2 XC154/XC155 to streptavidin coated MSD multi-array plates, which were read on the MSD Sector Imager instrument. Final detection was conducted by using the ruthenium-labeled afucosyl h11G2 XC154/XC155 and tripropylamine to produce an ECL signal (RLUs) within the MSD Sector Imager instrument.

Study samples were tested for ADA using a tiered strategy. Samples were initially tested in a screening assay at a dilution factor of 75. Samples that generated a RLU below the assay cutpoint were reported as negative (<1.88). Samples that generated a RLU at or above the assay cutpoint were reanalyzed in a full dilution series to determine the antibody titer. The antibody titer was defined as the reciprocal dilution of the sample that would generate an RLU equal to the cutpoint RLU. The log (base 10) of that titer was reported.

Conclusions regarding the induction of ADA were made based on the comparison of samples collected prior to dosing on Study Day 1 and postdose sample results. If the predose sample tested negative for ADA and the corresponding postdose sample tested positive, the animal was considered to be positive for the induction of ADA. If both the predose and postdose samples tested positive for ADA, the animal was considered to be positive for the induction of ADA only if the postdose sample titer was at least 0.48 (log 3, the serial dilution factor) or higher than the titer of the predose sample.

Single-Dose Pharmacokinetics

Afucosyl h11G2 XC154/XC155 PK were characterized after single IV dosing at 0.001, 0.002, 0.005, 0.1 or 0.2 mg/kg of afucosyl h11G2 XC154/XC155 as part of a study to assess the depletion and repletion of peripheral blood B cells and follicular T helper (Tfh)-like (Tfh-like) cells in male and female cynomolgus monkeys (n=1/sex/dose group). As used throughout this experiment, IV and SC formulations comprised the following components 50 mg/mL CXCR5 antibody or antigen-binding fragment of the present disclosure, 20 mM histidine, 8.5% sucrose, and 0.02% polysorbate 80, 0.005% EDTA at pH 5.8.

After single IV dosing, systemic exposures increased with increasing dose, and afucosyl h11G2 XC154/XC155 PK were characterized by low CL and low $V_{ss}$, with mean values ranging across dose levels from approximately 0.2 to 2.6 mL/h/kg and 0.03 to 0.1 L/kg, respectively. The mean $t^{1/2}$ values across dose levels ranged from approximately 1 to 4 days. At low doses (0.001-0.005 mg/kg), there was evidence of higher CL, possibly due to antibody-dependent cell cytotoxicity (ADCC)-mediated cell depletion that may also result in clearance of afucosyl h11G2 XC154/XC155/CXCR5 complex (Kryzanski et al., 2016, J. Pharmacokinet. Pharmacodyn. 43(5):513-527; Wang et al., 2010, AAPS J. 12(4):729-740). A similar clearance mechanism/non linearity may be seen in humans at low doses. As described previously elsewhere herein, dose-dependent depletion of B cells and Tfh-like cells in peripheral blood was observed, and the depletion of circulating B cells was more robust than depletion of Tfh-like cells.

Repeat-Dose Toxicokinetics (TK) in Cynomolgus Monkeys

TK and ADA evaluations were conducted after bi-weekly (every 2 weeks) IV or SC dosing of afucosyl h11G2 XC154/XC155 at 5 (IV), 20 (SC), or 200(IV) mg/kg (for a total of 5 doses) to male and female cynomolgus monkeys (n=3 or 4/sex/dose group) as part of a GLP repeat-dose toxicity study.

There were no quantifiable concentrations of afucosyl h11G2 XC154/XC155 in samples collected and analysed from the vehicle control group. There were no apparent sex-related differences in systemic exposures across dose groups; therefore group mean TK parameters are presented using combined data from both male and female cynomolgus monkeys (Table 13).

Following bi-weekly dosing at 5 (IV), 20 (SC) or 200 (IV) mg/kg, systemic exposure was higher after repeat dosing, with accumulation ratios (Study Day 43/Study Day 1) ranging from approximately 1.4 to 1.7. Further, systemic exposures increased in a dose-proportional manner following IV dosing. The last quantifiable concentrations of afucosyl h11G2 XC154/XC155 in the recovery animals from the 5 mg/kg (IV) dose group was observed from Study Day 148 to 281 of the 11-month recovery period. Following SC dosing, bioavailability of afucosyl h11G2 XC154/XC155 was estimated to be at least about 50%.

The incidence of ADA to afucosyl h11G2 XC154/XC155 was 19% (3/16 animals), 17% (1/6 animals) and 0% (0/6 animals) after dosing of afucosyl h11G2 XC154/XC155 at 5 (IV), 20 (SC) or 200 (IV) mg/kg, respectively, and serum concentrations on Study Day 43 were generally lower in ADA-positive animals compared to ADA-negative animals. It should be noted that circulating concentrations of afucosyl h11G2 XC154/XC155 may have interfered with the detection of ADA.

TABLE 13

| Dose (mg/kg/week)/Route | Study Day | $C_{max}$ (µg/mL) | $T_{max}$ (hours) | $AUC_{168}$ (µg · h/mL) |
|---|---|---|---|---|
| 5 (IV) | 1 | 112 | 0.61 | 8340 |
|  | 43 | 142 | 5.5 | 11300 |
| 20 (SC) | 1 | 131 | 100 | 18800 |
|  | 43 | 219 | 40 | 31600 |
| 200 (IV) | 1 | 4610 | 0.25 | 316000 |
|  | 43 | 5220 | 1.2 | 438000 |

$AUC_{168}$ = Area under the drug concentration-time curve from zero to 168 hours postdose; $C_{max}$ = Maximum observed concentration; IV = Intravenous; NA = Not applicable; SC = Subcutaneous; $T_{max}$ = Time to first occurrence of $C_{max}$.

Distribution

Protein binding and tissue distribution studies were not conducted for afucosyl h11G2 XC154/XC155 in nonclinical species. The VSs of afucosyl h11G2 XC154/XC155 in cynomolgus monkeys ranged from approximately 0.03 to 0.1 L/kg after single IV dosing, consistent with the limited distribution expected for an IgG (Lin et al., 1999, J. Pharmacol. Exp. Ther. 288(1):371-378; Mascelli et al., 2007, J. Clin. Pharmacol. 47(5):553-565).

Metabolism

Metabolism studies were not conducted with afucosyl h11G2 XC154/XC155. Similar to other therapeutic proteins with molecular weights above the glomerular filtration cut-off, afucosyl h11G2 XC154/XC155 is expected to be metabolized primarily by catabolic degradation (Lobo et al., 2004, J. Pharm. Sci. 93(11):2645-2668; Mascelli et al., 2007, supra; Vugmeyster et al., 2012, World J. Biol. Chem. 3(4):73-95). Pharmacokinetic Drug Interactions In vitro or in vivo pharmacokinetic drug interaction studies were not conducted. afucosyl h11G2 XC154/XC155 is a humanized monoclonal antibody (mAb) directed against CXCR5 and has been shown to modulate cytokine release in vitro, but not in vivo. Cytokines have been shown to modulate expression of cytochrome P450 (CYP) enzymes and transporters (Lee et al., 2010, Clin. Pharmacokinet. 49(5):295-310; Mahmood & Green, 2007, J. Clin. Pharmacol. 47(12):1540-1554). Therefore, treatment with afucosyl h11G2 XC154/XC155 can potentially affect CYP enzyme and transporter levels and consequently modulate the clearance of concomitant medications that are substrates for these enzymes or transporters. However, cytokine-mediated drug interactions observed in the clinic for other drugs have been modest, resulting in less than 2-fold changes in the exposure of a co-administered small molecule drugs (Huang et al., 2010, Clin. Pharmacol. Ther. 87(4):497-503; Evers et al., 2013, Drug Metab. Dispos. 41(9):1598-1609). Thus, without wishing to be bound by any particular theory, if concomitant medication alters target expression, it can potentially impact the PK of afucosyl h11G2 XC154/XC155.

Prediction of Human Pharmacokinetics

The PK profiles of afucosyl h11G2 XC154/XC155 in cynomolgus monkey were typical for a human IgG1 mAb in monkey. Therefore, the predicted 2-compartment PK parameter values in human are expected to be the same as those of a typical therapeutic IgG1 mAb and are assumed to be linear across the dose range to be tested. The PK parameter values used were similar to those reported earlier (Singh et al., 2015, In: Developability of Biotherapeutics: Computational Approaches, S. Kumar, Singh S. Kumar, Eds., CRC Press). These parameters are as follows: 3.2 L for central volume ($V_c$), 2.2 L for peripheral volume ($V_p$), 0.25 L/day for central clearance ($CL_c$), 0.45 L/day for distributive clearance (Q), 0.26 1/day for SC absorption rate constant ($k_a$) and 60% for SC bioavailability. Based on the data disclosed herein, the predicted human serum half-life of afucosylated h11G2 XC154/XC155 is about 17 days.

Prediction of Human Efficacious Dose

A model-based approach was adopted to characterize the relationship between dose, afucosyl h11G2 XC154/XC155 concentrations, and modulation of B and Tfh-like cells in the serum of cynomolgus monkeys. Subsequently, published monkey and human pharmacokinetics/pharmacodynamics (PK/PD) data for SBI-087, a humanized small modular immunopharmaceutical (SMIP) that, like RITUXIMAB, binds CD-20 on and depletes B cells, was used to translate B cell depletion parameters for afucosyl h11G2 XC154/XC155 from monkey to human (Cohen et al., 2016, Clin. Ther. 38(6):1417-1434; Dunussi-Joannopoulos et al., 2008, Ann. Rheum. Dis. 64(Suppl II):190 (Abstr THU0171). Unlike B cells, no human data were available for Tfh-like depletion; therefore, translation of Tfh-like cell depletion was assumed to be similar to that of B cells. Using baseline B and Tfh-like cell counts in SLE patients (Belouski et al., 2010, Cytometry B Clin. Cytom. 78(1):49-58) and predicted human cell depletion parameters, B and Tfh-like cell depletion kinetics following afucosyl h11G2 XC154/XC155 administration in humans were simulated.

The predicted human efficacious dose of afucosyl h11G2 XC154/XC155 is approximately 10 to 30 mg (IV), and is based on the assumption B cells in blood need to be depleted to ≤1 cell/µL for approximately 8 weeks for clinical efficacy. afucosyl h11G2 XC154/XC155 serum concentrations following the second dose of 10 to 30 mg IV (dose on Day 1 and Day 29) were estimated as noted above, and the predicted $C_{max}$ was approximately 5 to 15 µg/mL, the predicted area under the concentration time curve over dosing interval tau ($AUC_{tau}$) was approximately 38 to 114 µg/day/mL, and the predicted average concentration ($C_{av}$; calculated as $AUC_{tau}/28$) was 1.36 to 4.06 µg/mL.

Example 17: Toxicology Studies of Afucosylated h11G2 XC154/XC155

Afucosylated h11G2 XC154/XC155 was assessed in a series of nonclinical toxicity studies in the overview of the toxicity testing studies as summarized in Table 14. The intravenous (IV) or subcutaneous (SC) routes of administration were selected because they are the intended routes of clinical administration. As used throughout this experiment, IV and SC formulations comprised the following components 50 mg/mL CXCR5 antibody or antigen-binding fragment of the present disclosure, 20 mM histidine, 8.5% sucrose, and 0.02% polysorbate 80, 0.005% EDTA at pH 5.8. As discussed previously elsewhere herein, studies using human or cynomolgus monkey peripheral blood mononuclear cells demonstrated that afucosyl h11G2 XC154/XC155 binds CXCR5 expressing cells with comparable affinity and triggers antibody-dependent cellular cytotoxicity (ADCC) similarly between human and monkey cells. Also as previously demonstrated elsewhere herein, afucosyl h11G2 XC154/XC155 does not bind mouse, rat, or rabbit CXCR5 orthologs. Therefore, nonclinical toxicity studies were only conducted in cynomolgus monkeys.

TABLE 14

| Study[b] | Concentration or Dose | GLP Status |
|---|---|---|
| Repeat-Dose Toxicity Exploratory Study | | |
| 17-Day Intravenous and Subcutaneous Exploratory Toxicity Study of afucosyl h11G2 XC154/XC155 in Cynomolgus Monkeys With Recovery | 0 (IV, SC), 40 (IV), 260 (SC), 400 IV (once weekly) | No |
| Pivotal Study | | |
| 2-Month Intravenous and Subcutaneous Toxicity Study of afucosyl h11G2 XC154/XC155 in Cynomolgus Monkeys With a Recovery Period | 0 (IV, SC), 5 (IV), 20 (SC), 200 (IV) (every 2 weeks) | Yes |
| Other Toxicity Studies | | |
| A Preliminary Study to Establish the Immunohistochemical Staining Method For afucosyl h11G2 XC154/XC155 | 0.5-25 µg/mL | No |
| A Tissue Cross-Reactivity Study of Biotinylated afucosyl h11G2 XC154/XC155 in Normal Human and Cynomolgus Monkey Tissues | 1, 5 µg/mL | Yes |
| Afucosyl h11G2 XC154/XC155 In Vitro Human Cytokine Release Assay | 1-1000 µg/mL or 1-100 µg/well[d] | No |

The abbreviations in Table 14 are as follows: GLP = Good Laboratory Practice; IV = Intravenous; OECD = Organization for Economic Co-operation and Development; PBMC = Peripheral blood mononuclear cells; SC = Subcutaneous.

All GLP studies were conducted in an OECD mutual acceptance of data compliant member state. All in vivo studies were conducted with male and female animals. Unless specified otherwise, all doses are expressed as mg protein per kg of body weight per dose. Human whole blood was assayed at 1, 10, 100, or 1000 µg/mL (soluble phase) or human PBMC were assayed at 1, 10, or 100 µg/well (solid phase).

Afucosyl h11G2 XC154/XC155 was administered to monkeys in IV and SC studies with weekly dosing up to 400 mg/kg/dose (IV) for 17 days (3 total doses) or every 2 weeks up to 200 mg/kg/dose (IV) for 2 months (5 total doses). The 17-day exploratory monkey study included a recovery phase through Day 352. The pivotal (GLP) 2-month monkey study had an 11-month recovery phase (Day 401). Afucosyl h11G2 XC154/XC155 induced cytokine release in an in vitro assay. The target organ identified in these studies was the hematolymphopoietic system. The no observed adverse effect level (NOAEL) in the 2-month monkey study was the highest dose tested of 200 mg/kg/dose (IV) with a $C_{max}$ of 5220 µg/mL and $AUC_{168}$ of 438,000 µg·h/mL on Day 43.

Repeat-Dose Toxicity

Exploratory and pivotal repeat-dose toxicity studies were conducted with afucosyl h11G2 XC154/XC155 in cynomolgus monkeys.

Exploratory Toxicity Study afucosyl h11G2 XC154/XC155 was administered in an exploratory non-GLP study by IV or SC injection to monkeys (1-2 sex/dose) once weekly at 0 (IV, SC vehicle), 40 (IV), 260 (SC), or 400 (IV) mg/kg/dose (3 total doses) followed by a recovery phase in the vehicle, 40(IV) and 400 (IV) groups (1/sex/group) through Day 352. All animals survived until their scheduled necropsy on either Day 17 or Day 352. There were no test-article related clinical signs and no effects on body weight, food consumption, or serum cytokines.

During the dosing phase, there were decreases in total B cells, CXCR5+ B cells, and circulating Tfh-like cells in the peripheral blood relative to baseline (0.00×-0.02×, 0.00×-0.02×, and 0.03×-0.09×, respectively) beginning on Days 2 or 3, with the greatest decreases from baseline observed on Day 17. The magnitude of depletion was similar at all doses. In the spleen, markedly lower numbers of B cells, CXCR5+ B cells, and bona fide Tfh cell numbers were observed (0.018×-0.144×, 0.003×-0.033×, and 0.037×-0.245×, respectively) at all doses compared with controls. In peripheral blood, decreases (0.33×-0.67× baseline) in absolute lymphocytes in all but one animal at 40 mg/kg/dose by Day 2 and increases (1.11×-1.81× baseline) in immunoglobulin (Ig) G in animals at ≥40 mg/kg/dose on Day 17 were observed. There were transient decreases in natural killer (NK) cell counts on Day 2 (0.05×-0.14× baseline) with partial to complete recovery by Day 6 in most animals. There was moderate to marked decreased cellularity of splenic lymphoid follicles; minimal decreased cellularity of lymphoid follicles in the submandibular, axillary and inguinal lymph nodes, and in the tonsil at ≥40 mg/kg/dose and at 260 mg/kg/dose (SC) there was microscopic mixed cellular infiltration of injection sites. Immunohistochemistry demonstrated non-dose dependent decreased CD20-positive cells and CXCR5-positive cells in the spleen, and decreased CD20-positive cells in the submandibular and inguinal lymph nodes. The effects on lymphoid tissues correlated with the decreases in B cells and Tfh-like cells as well as total lymphocytes in the peripheral blood, and are consistent with the pharmacology of afucosyl h11G2 XC154/XC155, which is a depleting antibody that targets CXCR5-expressing cells.

During the recovery phase, decreases in B cell, CXCR5+ B cell, and Tfh-like cell peripheral blood counts increased (slowly) by Day 199, and at the end of the recovery phase on Day 352, all animals had partial or complete recovery for these cell types. NK cells and IgG returned to baseline range during the recovery phase (FIGS. 8A-8D). There were no test article-related microscopic findings (including CD20 and CXCR5 immunohistochemistry evaluation of spleen and submandibular and inguinal lymph nodes) and in the spleen, B cells, CXCR5+ B cells, and bona fide Tfh cell numbers were similar to or higher than values for the vehicle control animals, suggesting full recovery.

There were no effects observed on serum cytokines or on T cells, T helper cells, or T cytotoxic cells in the peripheral blood or spleen at any dose. There was no apparent anti-drug antibody (ADA) detected in this study.

FIGS. 8A-8D are graphs showing the depletion and reconstitution of peripheral blood B cells and Tfh-like cells in cynomolgus monkeys. Peripheral blood B cell (FIG. 8A and FIG. 8B) and Tfh-like cell (FIG. 8C and FIG. 8D) levels per µl of blood in males (FIG. 8A and FIG. 8C) and females (FIG. 8B and FIG. 8D) are shown through Day 352 of the exploratory toxicity study. B cells were defined as CD3-CD20+. Tfh-like cells were defined as the sum of CD3+CD4+CD95+ CXCR5+ cells and CD3+CD4+CD95+hIgG+ cells, because the test article interferes with the CXCR5 antibody used for immunophenotyping. Historical ranges of B cells in male monkeys (FIG. 8A, 272-2503 cells per µL) and female monkeys (FIG. 8B, 233-1700 cells per µL) are denoted by dashed lines.

Pivotal (GLP) Toxicity Study

Afucosyl h11G2 XC154/XC155 was administered in a pivotal study by IV or SC injection to monkeys (3-8/sex/group) every 2 weeks at 0 (IV, SC), 5 (IV), 20 (SC), or 200 (IV) mg/kg/dose (5 total doses) followed by an 11-month recovery phase (Day 401). Monkeys were injected on Day 22 (dosing phase) and on Day 253 (recovery phase) with keyhole limpet hemocyanin (KLH) and tetanus toxoid (TT) to assess the primary and secondary T cell dependent antibody response (TDAR), respectively. Animals were immunized with TT but were KLH-naïve prior to study start. Blood samples were collected prior to the start of the study (for baseline) on Days 22, 25, 29, 36, 43, 58, 253 (prior to recovery phase immunization), 256, 260, 267, 274, and 281 and evaluated for the production of anti-KLH-IgM, anti-KLH-IgG, anti-TT-IgM, and anti-TT-IgG.

All dosing phase animals survived until their scheduled necropsy on Day 58. There were no test-article related clinical signs and no effects on body weight, food consumption, plasma cytokines, coagulation, clinical chemistry, TDAR-KLH parameters, or electrocardiogram parameters. All afucosyl h11G2 XC154/XC155-related findings in this study included non-adverse and reversible changes in hematologic, immunophenotyping parameters in peripheral blood, dose-independent decreases in TDAR-TT IgG values, and microscopic findings and immunophenotyping changes in spleen and/or lymph nodes for males and females at 5 and 200 mg/kg/dose IV and 20 mg/kg/dose SC. During the recovery phase, one control female was euthanized on Day 330 due to a blood collection complication. All remaining recovery animals survived to necropsy on Day 401.

Afucosyl h11G2 XC154/XC155-related hematology changes included generally dose-independent, mild to moderate decreases in lymphocytes (0.34×-0.60× baseline) at all doses, with the highest incidence on Day 2 and lower incidence at subsequent time points, which contributed to decreases in total white blood cell counts (0.25×-0.59× baseline) for individual animals at all doses. Lymphocytes approximated baseline and/or control values within the first 1 to 2 months of the recovery phase. There were also mildly decreased basophils (0.17×-0.50×) at 200 mg/kg/dose IV on Day 2 and for individual animals at 5 mg/kg/dose IV and 20 mg/kg/dose SC at subsequent time points with subsequent recovery within the first 1 to 3 months of the recovery phase, and transient minimally decreased (0.79×-0.82×) red blood cell mass (hemoglobin, red blood cell count, and hematocrit) for females at 200 mg/kg/dose IV on Day 6.

There were marked afucosyl h11G2 XC154/XC155-related decreases in total B cells, CXCR5+ B cells, and Tfh-like cells (0.00×-0.56×) in the peripheral blood relative to baseline in all animals and dose groups as early as Day 2, and persisted through the end of the dosing phase (Day 58), with return to baseline or had absolute values for each subset that were within the range of values observed in vehicle control animals in 5 mg/kg/dose IV dosed animals during the recovery phase by Day 393 (FIGS. 9A-9D). There were also marked decreases in NK cell numbers in the peripheral blood on Day 2 in all animals relative to baseline (0.04×-0.46×); however, partial to complete recovery was observed by Day 6 for most animals, although NK cells remained below baseline levels at one or more later time points for some animals with return to baseline by the end of the recovery phase. There were also transient decreases in some animals in total T cells, T helper cells, and T cytotoxic cells on Day 2 (0.45×-0.66×); however, these cell populations returned to baseline levels by Day 6 in the majority of animals and by Day 36 in all animals. There were no afucosyl h11G2 XC154/XC155-related changes in interleukin (IL)-2, IL-6, IL-10, IL-13, interferon (IFN)-γ, and tumor necrosis factor (TNF)-α at any dose.

Afucosyl h11G2 XC154/XC155-related dose-independent decreased cellularity of splenic lymphoid follicles, and of lymphoid follicles in the axillary and mesenteric lymph nodes, and gut associated lymphoid tissue (GALT) was observed at mg/kg/dose IV and at 20 mg/kg/dose SC. This was associated with decreased lymphoid follicular cellularity of CD20+ and CXCR5+ cells in the spleen assessed by immunohistochemistry, except for 1 male at 20 mg/kg/dose SC; however, afucosyl h11G2 XC154/XC155 exposure in this animal may have been impacted due to prevalence of ADA from Day 15 onwards. In addition, there were lower numbers of B cells, CXCR5+ B cells, and Tfh cells in the spleen at necropsy on Day 58 compared with vehicle controls. Some animals had lower NK cell numbers in the spleen compared with controls. At the end of the recovery on Day 401, absolute values for each subset examined in all animals administered afucosyl h11G2 XC154/XC155 were within the range of values for animals in the vehicle control group, indicating recovery from the afucosyl h11G2 XC154/XC155-related lower numbers observed during the dosing phase of the study.

Decreased lymphoid cellularity in spleen and lymphoid follicles in the lymph nodes along with lower numbers of B cells, CXCR5+ B cells, and Tfh cells in the spleen correlated with decreases in total lymphocytes and B cells, CXCR5+ B cells, and Tfh-like cells in peripheral blood at mg/kg/dose IV and at 20 mg/kg/dose SC. At the end of recovery phase (Day 401), there were no afucosyl h11G2 XC154/XC155-related microscopic findings in the 5 mg/kg IV dose group, indicating complete recovery. These findings are consistent with the pharmacology of afucosyl h11G2 XC154/XC155, which is expected to deplete CXCR5-expressing cells. The lower numbers of NK cells in the peripheral blood and/or spleen may be due to NK effector cell death, which has been described in NK cells following antibody-dependent cell cytotoxicity (Warren et al., 2011, J. Immunol. Meth. 370: 86-92) and/or tissue redistribution; however, other mechanisms cannot be excluded.

There was no afucosyl h11G2 XC154/XC155-related effects on the primary T cell-dependent antibody response (TDAR) to keyhole limpet hemocyanin (KLH). Anti-KLH-immunoglobulin (Ig)M and IgG responses were observed in all groups. All monkeys had been vaccinated against tetanus toxoid (TT) prior to being on-study. Increased IgM and IgG memory responses were observed in all animals in all dose groups. Afucosyl h11G2 XC154/XC155-related, dose-independent decreases in the secondary TDAR to TT (IgG center point titer values) were observed in both male and female animals in the 5 IV, 20 SC, and/or 200 IV mg/kg/dose groups at 7, 14, 21, and 36 days post-immunization. Statistically significant decreases in group mean anti-TT IgG antibodies were observed for the 5 and 200 mg/kg/dose IV groups at 7 days post-immunization.

Following the recovery phase immunization, there were anti-KLH IgM and IgG memory responses in all animals in the 5 mg/kg afucosyl h11G2 XC154/XC155 dose group at 1 or more time points that were within the vehicle-control group range. During the recovery time points, there was an afucosyl h11G2 XC154/XC155-related statistically significant decrease in the group anti-TT-IgG center point titer (CPT) values observed in the 5 mg/kg dose group animals at 7 days post-immunization in the recovery phase. All the recovery phase animals' CPT values were within the control group range with the exception of 2 of 8 animals in the 5 mg/kg dose group that had CPT values lower than the control range at all recovery time points up to 28-days post TT immunization in the recovery phase. There were no changes in anti-TT IgM values that were attributed to afucosyl h11G2 XC154/XC155 administration during the dosing or recovery phases.

There were anti-KLH IgM and IgG primary responses in all groups; some animals in the 5 and 200 mg/kg/dose groups had CPTs above the range of control at 1 or more time points following the primary immunization. There were no statistically significant differences in group mean anti-KLH IgM or IgG antibodies in any of the groups at any time points. As the individual animal changes were sporadic, lacked dose-dependence, and the group CPT values were in the range of the control animals, they were not considered afucosyl h11G2 XC154/XC155 related. During the recovery time points, all animals were within the range of control with the exception of 1 of 8 animals in the 5 mg/kg dose group that had CPT values slightly below the range of control on 14, 21, and 28-days post KLH immunization. These data (dose or recovery phase) demonstrate that all afucosyl h11G2 XC154/XC155 dosed animals (both male and female) were capable of generating primary IgM and IgG responses to KLH immunization similar to control animals.

Despite marked decreases in total B cells, CXCR5+B cells, Tfh-like cells, and NK cells in peripheral blood and marked lower numbers of B cells, CXCR5+ B cells, and Tfh cells in the spleen as detected by immunophenotyping, the decreases in lymphocyte count and decreased lymphoid cellularity in spleen, lymph nodes, and GALT, all findings were nonadverse due to the lack of associated clinical signs and lack of an effect on the primary TDAR. Other hematological findings including decreases in total white blood cell, basophils and red blood cell parameters were not adverse due to the limited severity and lack of microscopic correlates. No afucosyl h11G2 XC154/XC155-related microscopic and immunohistochemistry findings were noted on Day 401, indicating complete recovery.

The NOAEL for afucosyl h11G2 XC154/XC155 in monkeys following SC or IV administration every other week for 2 months was 200 mg/kg/dose. Systemic exposures ($C_{max}$ and $AUC168$) at the NOAEL were 5220 μg/mL and 438,000 μg·h/mL, respectively. Anti-afucosyl h11G2 XC154/XC155 antibodies were detected in this study and the data are summarized elsewhere herein. A risk assessment of the target organ toxicities noted in the repeat-dose toxicity program is provided elsewhere herein. Threshold concentrations of afucosyl h11G2 XC154/XC155 associated with key responses in monkeys can be found elsewhere herein.

Reproductive and Developmental Toxicity

There were no test article-related effects in male or female reproductive tissues evaluated in the repeat-dose toxicity study in cynomolgus monkeys.

Local Tolerance

Stand-alone local tolerance studies with afucosyl h11G2 XC154/XC155 have not been conducted although injection sites were examined macroscopically and microscopically in the in vivo toxicity studies.

In the exploratory monkey study, in the SC injection site at 260 mg/kg/dose there was moderate perivascular mixed leukocytic cellular infiltration (mononuclear leukocytes, neutrophils, and fewer eosinophils) compared with minimal to mild infiltrates in the SC injection sites of control animals. In the 260 mg/kg/dose SC male, the infiltrate multifocally extended into the tunica muscularis of the small vessels. In the 260 mg/kg/dose SC female, several multinucleated giant cells infiltrated subcutaneous collagen, and there were intracytoplasmic basophilic or eosinophilic bits of fibrillar material in these cells. In the pivotal 2-month monkey study, microscopic findings in the IV and SC administration sites were not considered test article related.

Antigenicity

Immunogenicity was assessed by measuring ADA levels in the repeat-dose toxicity studies in cynomolgus monkeys; these data are described previously herein.

Immunotoxicity

In vitro and in vivo studies characterized the effect of afucosyl h11G2 XC154/XC155 on the immune system. The potential for afucosyl h11G2 XC154/XC155 to induce release of cytokines (TNF-α, IL-6, and IFN-γ) was determined in human cytokine release assays using 2 different in vitro formats: a soluble phase assay using whole blood and a solid phase assay using immobilized afucosyl h11G2 XC154/XC155 and peripheral blood mononuclear cells (PBMCs). Samples from 8 healthy human donors were evaluated in each of these formats. In both cytokine release assay formats afucosyl h11G2 XC154/XC155-induced cytokine release (TNF-α, IL-6, and IFN-γ) was observed. In vivo, repeat-dose exploratory and pivotal toxicity studies in monkeys characterized the in vivo cytokine release profile, as well as the effects of afucosyl h11G2 XC154/XC155 on immune system cells and tissues. Afucosyl h11G2 XC154/XC155 did not induce cytokines in vivo. Depletion of lymphocytes, B cells, CXR5+ B cells, and Tfh/Tfh-like cells were observed in the peripheral blood and spleen of monkeys administered afucosyl h11G2 XC154/XC155 as described elsewhere herein, effects consistent with expected mechanism of action of a CXCR5 depleting antibody. Following the recovery phase in the exploratory and pivotal toxicity studies, lymphocyte parameters in the spleen and lymph nodes were comparable to vehicle controls.

Primary and secondary TDAR responses to KLH and TT, respectively, were evaluated in the pivotal 2-month toxicity study as discussed elsewhere herein. There were no afucosyl h11G2 XC154/XC155-related effects on the primary TDAR to KLH. All animals produced a secondary TDAR response to TT, but afucosyl h11G2 XC154/XC155-related decreases were observed in the center point titers for the 5 and 200 mg/kg/dose IV groups at 7 days post-immunization during the dosing and recovery phases of the study.

Tissue Cross Reactivity (TCR)

Extensive preliminary method development work, including multiple runs and methods, was conducted in the preliminary staining method study with afucosyl h11G2 XC154/XC155. None of these assay conditions consistently demonstrated membrane staining in the expected cells and tissues. In the GLP-compliant tissue cross-reactivity study binding of biotinylated afucosyl h11G2 XC154/XC155 (afucosyl h11G2 XC154/XC155-Bio; 1 and 5 µg/mL) to cryosections of cynomolgus monkey and human tissues was evaluated. Staining patterns overlapped between cynomolgus monkey and human tissues. Staining common to both human and monkey was observed in mononuclear cells, reticuloendothelial cells, various epithelia, glial cells and/or pituicytes, representing expected reactivity of afucosyl h11G2 XC154/XC155 (Breitfeld et al., 2000, J Exp Med 192(11):1545-1552; Carlsen et al., 2002, Gut 51(3):364-371; Flynn et al., 2003, J. Neuroimmunol. 136(1-2):84-93; Schaerli et al., 2000, J. Exp. Med. 192(11):1553-1562; Schmutz et al., 2005, Arthritis Res. Ther. 7(2):R217-R229), as well as the colloid of the thyroid. Positive afucosyl h11G2 XC154/XC155 staining was observed for other monkey or human tissues. For human tissues, staining was observed for nerve fibers in the optic nerve and neurons in the spinal nerve roots, smooth myocytes of the prostate, interstitial cells in the testis, and lens fibers in the eye.

Tissues that stained only in cynomolgus monkey were hematopoietic precursor cells in the bone marrow, mast cells of the skin and cervix, neuropil in the brain and spinal cord, cardiac myocytes, and spindle cells in the placenta and optic nerve sheath. While this may represent unexpected cross-reactivity of the test article, the staining was cytoplasmic in nature, had no microanatomic specificity, and lacked clear plasma membrane staining. Such cytoplasmic staining poorly differentiates CXCR5-expressing versus nonexpressing cells and tissues. The cytoplasmic staining would not be expected to be accessible to the test article in vivo, and generally is considered to be of little to no toxicologic significance (Hall et al., 2008, In: Preclinical Safety Evaluation of Biopharmaceuticals: A Science-Based Approach to Facilitating Clinical Trials, p. 208-240, Cavagnaro, J. A., ed., Wiley-Interscience; Leach et al., 2010, Toxicol. Pathol. 38(7):1138-1166). The lack of clear membranous staining suggests that a robust method was not obtainable to make a complete evaluation. The lack of adverse findings in the 2-month repeat-dose toxicity study supports that the staining observed in the ex vivo tissue cross-reactivity study does not translate into in vivo effects. While multiple attempts were made to obtain a robust TCR method, the binding observed yielded no safety concerns beyond what is expected based on intended pharmacology.

Relationship of Findings to Pharmacokinetics

The serum concentrations of afucosyl h11G2 XC154/XC155 were determined after SC or IV administration to male and female monkeys at doses of 5 (IV), 20 (SC), or 200 (IV) mg/kg/dose every 2 weeks for 2 months (total of 5 doses). There were no apparent sex-related differences in systemic exposures across dose groups; therefore, group mean TK parameters are presented using combined data from both male and female cynomolgus monkeys. Systemic exposure was higher after repeat dosing, with accumulation ratios (Study Day 43/Study Day 1) ranging from approximately 1.4 to 1.7. Further, systemic exposures increased in a dose-proportional manner following IV dosing. Following SC dosing, bioavailability of afucosyl h11G2 XC154/XC155 was estimated to be >50%.

The threshold serum concentrations of afucosyl h11G2 XC154/XC155 associated with key responses and exposure margins calculated against these key responses are provided in Table 15.

TABLE 15

| Key Responses | Dose (mg/kg/dose) | $C_{av}$ (µg/mL) | $C_{max}$ (µg · h/mL) | Exposure Margin |
|---|---|---|---|---|
| Repeat-Dose Toxicity Studies 17-day toxicity study in monkeys (1-2/sex/dose) - Once weekly dosing (all findings nonadverse) | | | | |
| Peripheral blood: ↓ total B cells, ↓ CXCR5+ B cells, ↓ Tfh-like cells, ↓ NK cells; spleen: ↓ total B cells, ↓ CXCR5+ total B cells, ↓ bona fide Tfh cells; ↓ lymphocytes; ↑ IgG; spleen: ↓ cellularity (follicular CD20-positive cells and CXCR5-positive cells); lymph nodes and tonsil: ↓ cellularity (in lymph nodes: follicular CD20 positive cells) | 40 (IV) | 844 | 1020 | 208 |
| Same as above plus, injection site: perivascular leukocytic cellular infiltration | 260 (SC) | 2810 | 3340 | 692 |
| Same as 40 mg/kg/dose | 400 (IV) | 7500 | 9610 | 1850 |
| 2-month toxicity study in monkeys (3-8/sex/dose) - Every 2 weeks dosing (all findings nonadverse) | | | | |
| Peripheral blood: ↓ total B cells, ↓ CXCR5+ B cells, ↓ Tfh-like cells, ↓ NK cells, ↓ T cells, ↓ T helper cells, ↓ T cytotoxic cells, ↓ WBC, ↓ lymphocytes, ↓ basophils, spleen: ↓ B cells, ↓ CXCR5+ total B cells, ↓ bona fide Tfh cells, ↓ NK cells; spleen: ↓ cellularity (follicular CD20+ cells and CXCR5+ cells); lymph nodes and GALT: ↓ lymphoid cellularity; TDAR: secondary (memory) anti TT IgG response | 5 (IV) | 67.3 | 142 | 17 |
| Same as above | 20 (SC) | 188 | 219 | 46 |
| Same as above plus, ↓ red blood cell mass | 200 (IV) NOAEL | 2610 | 5220 | 643 |

Abbreviations used in Table 15 are as follows: AUC = Area under the concentration-time curve; $C_{av}$ = Average concentration; $C_{max}$ = Maximum (mean) plasma concentration; Tfh-like cells (alternatively, cTfh); CXCR5 = Chemokine receptor type 5; GALT = Gut-associated lymphoid tissue; IgG = Immunoglobulin G; IV = Intravenous; NK = Natural killer; NOAEL = No observed adverse effect level; SC = Subcutaneous; TDAR = T cell dependent antibody response; Tfh = Follicular T helper cells; TT = Tetanus toxoid; WBC = White blood cell.

In repeat-dose studies, $C_{max}$ values indicate mean plasma concentrations. $C_{av}$ values are calculated by dividing the AUC by the sampling interval (48 or 168 hours). Reported values were obtained near the end of the dosing phase.

Exposure margins were calculated by dividing $C_{av}$ values in animal toxicity studies by the predicted human $C_{av}$ of 4.06 µg/mL at the predicted human efficacious dose of 30 mg, IV.

Target Organ Toxicity

Based on the nonclinical studies conducted, the hematolymphopoietic system (spleen, lymph nodes, GALT, tonsil, circulating lymphocytes, white blood cells, red blood cell parameters, in vitro cytokine release) was identified as potential target organs/tissues. In the nonpivotal 17-day monkey study conducted with afucosyl h11G2 XC154/XC155, test article-related changes in these tissues were consistent with those observed in the pivotal 2-month toxicity study. All afucosyl h11G2 XC154/XC155-related findings fully or partially returned to baseline or vehicle control group values during the recovery phase in the nonpivotal and pivotal toxicity studies. None of the test article-related effects were considered adverse, due to the absence of any clinical findings or opportunistic infections, and due to the minimal impact on immune function measured by the TDAR assay. Therefore, a NOAEL of 200 mg/kg/dose IV in monkeys for afucosyl h11G2 XC154/XC155-related effects was established.

Hematolymphopoietic System

In repeat-dose toxicity studies in cynomolgus monkeys, afucosyl h11G2 XC154/XC155-related decreases in peripheral blood lymphocytes were observed at doses mg/kg/dose (IV) and 20 mg/kg/dose (SC), beginning on Study Day 2. These decreases correlated with observed decreases in total B cells, CXCR5+ B cells, and Tfh-like cells, which persisted until Day 57. Decreases in these lymphocyte subsets demonstrated full or partial return to baseline values by the end of the recovery phase in the exploratory toxicity study. There were also afucosyl h11G2 XC154/XC155-related decreases in NK cells, total T cells, T helper cells, and T cytotoxic cells at mg/kg/dose beginning on Day 2, but partial to complete return to baseline values was achieved by the end of the dosing phase. In addition to decreases in lymphocyte populations in the peripheral blood, transient, minimal decreases in RBC mass were observed for female monkeys administered 200 mg/kg/dose on Day 6.

Decreased lymphocyte populations in the peripheral blood correlated with afucosyl h11G2 XC154/XC155-related lower lymphoid cellularity in the spleen and lymph nodes at mg/kg/dose. Lower lymphoid cellularity was reflected in lower numbers of total B cells, CXCR5+ B cells, bona fide Tfh cells, and NK cells, and lower follicular CD20+ and CXCR5+ cells in the spleen. Lower follicular lymphoid cellularity was observed in the lymph nodes and GALT at ≥5 mg/kg/dose and the tonsils at ≥40 mg/kg/dose.

Following the recovery phase in the exploratory and pivotal toxicity studies, lymphocyte parameters in the spleen and lymph nodes were comparable to vehicle controls.

Decreases in total B cells, CXCR5+ B cells, and Tfh/Tfh-like cells are consistent with the expected mechanism of action of afucosyl h11G2 XC154/XC155, which is expected to deplete CXCR5-expressing cells. Lower NK cell numbers in the peripheral blood and spleen is likely due to effector cell death, known to occur in NK cells following ADCC.

Although decreases in lymphocyte parameters were observed in the peripheral blood and spleen of monkeys administered afucosyl h11G2 XC154/XC155, there was no afucosyl h11G2 XC154/XC155-related effect on the primary TDAR to KLH. All animals produced a secondary TDAR to TT, but statistically significant decreases were observed at doses of mg/kg/dose.

All afucosyl h11G2 XC154/XC155-related findings were considered nonadverse due to the lack of associated clinical signs or opportunistic infections. The effects of afucosyl h11G2 XC154/XC155 on peripheral blood lymphocytes, total B cells, CXCR5+ B cells, Tfh-like cells, and NK cells, as well as primary and secondary TDAR responses can be monitored in humans in the clinic.

In both soluble and solid in vitro cytokine release assay formats afucosyl h11G2 XC154/XC155-induced cytokine release (TNF-α, IL-6, and IFN-γ) was observed. Afucosyl h11G2 XC154/XC155 induced cytokine release in vitro is anticipated due to the expected pharmacology of this molecule. Afucosyl h11G2 XC154/XC155 did not induce cytokine release in the exploratory or pivotal in vivo monkey studies. Serum cytokines and clinical indicators of systemic cytokine release are readily monitored in the clinic.

TABLE 16

(SEQUENCES)

| Name | Sequence Identifier No. | Sequence |
|---|---|---|
| humanized (h) 11G2 VL (XC154) | SEQ ID NO: 1 | DIQMTQSPSSLSASVGDRVTITCRAS<u>ESVEYHGTS</u>LMHWYQ QKPGKAPKLLIY<u>AASNVESG</u>VPSRFSGSGSGTDFTLTISSLQ PEDFATYYC<u>QQSRKVPWT</u>FGQGTKVEIK |
| h11G2 VL (X0154) CDR-L1 | SEQ ID NO: 2 | <u>ESVEYHGTS</u> |
| h11G2 VL (XC154) CDR-L2 | SEQ ID NO: 3 | <u>AASNVESG</u> |
| h11G2 VL (XC154) CDR-L3 | SEQ ID NO: 4 | <u>QQSRKVPWT</u> |
| h11G2 VL (XC153) | SEQ ID NO: 5 | DIQMTQSPSSLSASVGDRVTITCRAS<u>ESVEYHGTS</u>LMHWYQ QKPGKAPKLLIY<u>AASNVESG</u>VPSRFSGSGSGTDFTLTISSLQ PEDFATYFC<u>QQSRKVPWT</u>FGQGTKVEIK |
| h11G2 VH (XC155) | SEQ ID NO: 6 | EVQLVESGGGLVQPGGSLRLSCAAS<u>GFTFTDFY</u>MSWVRQA PGKGLEWVGF<u>IRNKANGYT</u>TEYSASVKGRFTISRDNAKNSL YLQMNSLRAEDTAVYYC<u>ARVYGSTLHY</u>WGQGTLVTVSS |
| h11G2 VH (XC155) CDR-H1 (also XC156) | SEQ ID NO: 7 | <u>GFTFTDFY</u> |
| h11G2 VH (XC155) CDR-H2 (also XC156) | SEQ ID NO: 8 | <u>IRNKANGYT</u> |
| h11G2 VH (XC155) CDR-H3 | SEQ ID NO: 9 | <u>ARVYGSTLHY</u> |
| h11G2 VH (XC156) | SEQ ID NO: 10 | EVQLVESGGGLVQPGGSLRLSCATS<u>GFTFTDFY</u>MSWVRQA PGKGLEWVGF<u>IRNKANGYT</u>TEYSASVKGRFTISRDNAKNSL YLQMNSLRAEDTAVYYC<u>VRVYGSTLHY</u>VVGQGTLVTVSS |
| h11G2 VH (XC156) CDR-H3 | SEQ ID NO: 11 | <u>VRVYGSTLHY</u> |
| h11G2 VH (XC157) | SEQ ID NO: 12 | EVQLVESGGGLVQPGGSLRLSCATS<u>GFTFTDFY</u>MSWVRQA PGKGLEWVGF<u>IRNKANGYT</u>TEYSASVKGRFTISRDNAKSSL YLQMNSLRAEDTAVYYC<u>VRVYGSTLHY</u>VVGQGTLVTVSS |
| h41A10 VL (XC142) | SEQ ID NO: 13 | DIQMTQSPSSLSASVGDRVTITCSAS<u>SSVNY</u>IHWYQQKPGK APKRLIY<u>ETSRLAS</u>GVPSRFSGSGSGTDYTLTISSLQPEDFA TYYC<u>QQWSSNPLT</u>FGQGTKVEIK |
| h41A10 VL (XC142) CDR-L1 | SEQ ID NO: 14 | <u>SSVNY</u> |

TABLE 16-continued (SEQUENCES)

| Name | Sequence Identifier No. | Sequence |
|---|---|---|
| h41A10 VL (XC142) CDR-L2 | SEQ ID NO: 15 | ETSRLASG |
| h41A10 VL (XC142) CDR-L3 | SEQ ID NO: 16 | QQWSSNPLT |
| h41A10 VH (XC148) | SEQ ID NO: 17 | EVQLVESGGGLVQPGGSLRLSCAAS<u>GFTFRSYGMS</u>WVRQA PGKGLEWVAT<u>ISSGGTY</u>TFYPDILKGRFTISRDNAKNSLYLQ MNSLRAEDTAVYYC<u>ARRGEDYRGALEH</u>WGQGTLVTVSSA |
| h41A10 VH (XC147) | SEQ ID NO: 18 | EVQLVESGGGLVQPGGSLRLSCAAS<u>GFTFRSYGMS</u>WVRQA PGKGLEWVAT<u>ISSGGTY</u>TFYPDILKGRITISRDNAKNSLYLQM NSLRAEDTAVYYC<u>ARRGEDYRGALEH</u>WGQGTLVTVSSA |
| h41A10 VH (X0147) CDR-H1 (same as XC148) | SEQ ID NO: 19 | <u>GFTFRSYG</u> |
| h41A10 (XC147) CDR-H2 (same as XC148) | SEQ ID NO: 20 | <u>ISSGGTY</u> |
| h41A10 (XC147 CDR-H3 (same as XC148) | SEQ ID NO: 21 | <u>ARRGEDYRGALEH</u> |
| c11G2 chimeric full length Light Chain (cLC) (mouse VL in uppercase and human kappa constant region in lowercase) *indicates stop codon | SEQ ID NO: 22 | DVVVTQSPDSLAVSLGQRATISCRAS<u>ESVEYHGTSLMH</u>WYQ QKPGQPPKLLIY<u>AASNVES</u>GVPARFSGSGSGTDFSLNIHPVE EGDIAMYFC<u>QQSRKVPWT</u>FGGGTKLEIKrtvaapsvfifppsdeqlk sgtasvvcllnnfypreakvqwkvdnalqsgnsqesvteqdskdstys lsstltlskadyekhkvyacevthqglsspvtksfnrgec* |
| c11G2 chimeric full length heavy chain (cHC) (mouse VH in uppercase and human IgG1 constant region in lowercase) *indicates stop codon | SEQ ID NO: 23 | EVKLVESGGGLVQPGGSLRLSCATS<u>GFTFTDFYMS</u>WVRQP PGRALEWLGF<u>IRNKANGYTT</u>EYSASVKGRFTISRDNSQSILY LQMNTLRAGDSATYYC<u>VRVYGSTLHY</u>WGQGTILTVSSastkg psvfplapssksstsggtaalgclvkdyfpepvtvswnsgaltsgvhtfpavlqssglysl ssvvtvpssslgtqtyicnvnhkpsntkvdkkvepkscdkthtcppcpapellggpsv flfppkpkdtlmisrtpevtcvwdvshedpevkfnwyvdgvevhnaktkpreeqyn styrvvsvltvlhqdwlngkeykckvsnkalpapiektiskakgqprepqvytlppsre emtknqvsltclvkgfypsdiavewesngqpennykttppvldsdgsfflyskltvdks rwqqgnvfscsvmhealhnhytqkslslspg* |
| c41A10 chimeric light chain *indicates stop codon | SEQ ID NO: 24 | QIVLTQSPAVMSASPGEKVTMTCSAS<u>SSVNY</u>IHWYQQKSGT SPKRWIY<u>ETSRLASG</u>VPVRFSGSGSGTSYSLTISTMEAEDAA TYYC<u>QQWSSNPLT</u>FGAGTKLELKrtvaapsvfifppsdeqlksgtasvv cllnnfypreakvqwkvdnalqsgnsqesvteqdskdstyslsstltlskadyekhkv yacevthqglsspvtksfnrgec* |
| c41A10 chimeric heavy chain (mouse VH in uppercase and human IgG1 constant region | SEQ ID NO: 25 | EVQLVESGGDLVKPGGSLKLSCAAS<u>GFTFRSYGMS</u>WVRQT PDKRLEWVAT<u>ISSGGTY</u>TFYPDILKGRITISRDNAKNTLYLQM SNLKSEDTAMYYC<u>ARRGEDYRGALEH</u>WGQGTSVTVSSastk gpsvfplapssksstsggtaalgclvkdyfpepvtvswnsgaltsgvhtfpavlqssgly slsswtvpssslgtqtyicnvnhkpsntkvdkkvepkscdkthtcppcpapellggp svflfppkpkdtlmisrtpevtcvwdvshedpevkfnwyvdgvevhnaktkpreeq ynstyrwsvltvlhqdwlngkeykckvsnkalpapiektiskakgqprepqvytlpps |

TABLE 16-continued (SEQUENCES)

| Name | Sequence Identifier No. | Sequence |
|---|---|---|
| in lowercase) *indicates stop codon | | reemtknqvsltclvkgfypsdiavewesngqpennykttppvldsdgsfflyskltvd ksrwqqgnvfscsvmhealhnhytqkslslspg* |
| c5H7 chimeric full length light chain (cLC) *indicates stop codon | SEQ ID NO: 26 | DVVVTQSPDSLAVSLGQRATISCRAS<u>ESVEYHGTS</u>LMHWYQ QKPGQPPKLLIY<u>AASNVES</u>GVPARFSGSGSGTDFSLNIHPVE EGDVSMFFC<u>QQSRKVPWT</u>FGGGTKLEIKrtvaapsvfifppsdeqlk sgtasvvcllnnfypreakvqwkvdnalqsgnsqesvteqdskdstyslsstltlskad yekhkvyacevthqglsspvtksfnrgec* |
| c5H7 chimeric full length heavy chain (cHC) (mouse VH in uppercase and human IgG1 constant region in lowercase) *indicates stop codon | SEQ ID NO: 27 | EVKLVESGGGLVQPGDSLRLSCATS<u>GFTFTDFY</u>MSWVRQP PGRALEWLGF<u>IRNKANGYTTEY</u>SASVKGRFTISRDNSQSILY LQMNTLRAGDSATYYCVR<u>VYGSTLHY</u>WGQGTILTVSSastkg psvfplapssksstsggtaalgclvkdyfpepvtvswnsgaltsgvhtfpavlqssglysl ssvvtvpssslgtqtyicnvnhkpsntkvdkkvepkscdkthtcppcpapellggpsv flfppkpkdtlmisrtpevtcvvvdvshedpevkfnwyvdgvevhnaktkpreeqyn styrvvsvltvlhqdwlngkeykckvsnkalpapiektiskakgqprepqvytlppsre emtknqvsltclvkgfypsdiavewesngqpennykttppvldsdgsfflyskltvdks rwqqgnvfscsvmhealhnhytqkslslspg* |
| h11G2 (XC154) Full Light Chain (VL indicated by allcaps and CK indicated by lowercase letters) | SEQ ID NO: 28 | DIQMTQSPSSLSASVGDRVTITCRAS<u>ESVEYHGTS</u>LMHWYQ QKPGKAPKLLIY<u>AASNVES</u>GVPSRFSGSGSGTDFTLTISSLQ PEDFATYYC<u>QQSRKVPWT</u>FGQGTKVEIKrtvaapsvfifppsdeqlk sgtasvvcllnnfypreakvqwkvdnalqsgnsqesvteqdskdstyslsstltlskad yekhkvyacevthqglsspvtksfnrgec |
| h11G2 (XC155) Full length HEAVY CHAIN (VL indicated by allcaps and IgG1 Fc indicated by lowercase letters) | SEQ ID NO: 29 | EVQLVESGGGLVQPGGSLRLSCAAS<u>GFTFTDFY</u>MSWVRQA PGKGLEWVGF<u>IRNKANGYTTEY</u>SASVKGRFTISRDNAKNSL YLQMNSLRAEDTAVYYCA<u>RVYGSTLHY</u>WGQGTLVTVSSast kgpsvfplapssksstsggtaalgclvkdyfpepvtvswnsgaltsgvhtfpavlqssgl yslssvvtvpssslgtqtyicnvnhkpsntkvdkkvepkscdkthtcppcpapellgg psvflfppkpkdtlmisrtpevtcvvvdvshedpevkfnwyvdgvevhnaktkpree qynstyrwsvltvlhqdwlngkeykckvsnkalpapiektiskakgqprepqvytlpp sreemtknovsltclvkgfypsdiavewesngopennykttppvldsdgsfflyskltv dksrwqqgnvfscsvmhealhnhytqkslslspg |
| human kappa Constant Light Chain domain (Cκ) | SEQ ID NO: 30 | rtvaapsvfifppsdeqlksgtasvvcllnnfypreakvqwkvdnalqsgnsqesvte odskdstyslsstltlskadyekhkvyacevthqglsspvtksfnrgec |
| human wild type IgG1 Fc (includes portion of $C_H1$ and hinge, $C_H2$ and $C_H3$) wild type LLGG effector function sequence is indicated in italics NST Asn297 N-linked glycosylation site | SEQ ID NO: 31 | astkgpsvfplapssksstsggtaalgclvkdyfpepvtvswnsgaltsgvhtfpavlqs sglyslssvvtvpssslgtqtyicnvnhkpsntkvdkkvepkscdkthtcppcpapel*l ggp*svflfppkpkdtlmisrtpevtcvvvdvshedpevkfnwyvdgvevhnaktkpr eeqy<u>NST</u>yrvvsvltvlhqdwlngkeykckvsnkalpapiektiskakgqprepqv ytlppsreemtknqvsltclvkgfypsdiavewesngqpennykttppvldsdgsffly skltvdksrwqqgnvfscsvmhealhnhytqkslslspg |
| human CXCR5 (h11G2 critical epitope binding amino acid residues L11 and D22 are indicated in _bold italics_) | SEQ ID NO: 32 | MNYPLTLEMDLENLEDLFWEL*D*RLDNYNDTSLVENHLCPAT EGPLMASFKAVFVPVAYSLIFLLGVIGNVLVLILERHRQTRS STETFLFHLAVADLLLVFILPFAVAEGSVGWVLGTFLCKTVIAL HKVNFYCSSLLLACIAVDRYLAIVHAVHRYRHRRLLSIHITCGT IWLVGFLLALPEILFAKVSQGHHNNSLPRCTFSQENQAETHA WFTSRFLYHVAGFLLPMLVMGWCYVGVVHRLRQAQRRPQ RQKAVRVAILVTSIFFLCWSPYHIVIFLDTLARLKAVDNTCKLN GSLPVAITMCEFLGLAHCCLNPMLYTFAGVKFRSDLSRLLTK LGCTGPASLCQLFPSWRRSSLSESENATSLTTF |

TABLE 16-continued (SEQUENCES)

| Name | Sequence Identifier No. | Sequence |
|---|---|---|
| Cynomolgous CXCR5 | SEQ ID NO: 33 | MNYPLMLEMDLENLEDLFLEFDKFDNYNDTSLVENHLCPAT EGPLMASFKAVFVPVAYSLIFLLGVIGNVLVLVILERHRQTRS STETFLFPHLAVADLLLVFILPFAVAEGSVGWVLGTFLCKTVIAL HKVNFYCSSLLLACIAVDRYLAIVHAVHAYRHRRLLSHITCGT IWLVGFLFALPEILFAKVSQAHPNNSLPRCTFSQENQAETHA WFTSRFLYHVAGFLLPMLVMGWCYVGVVHRLRQAQRRPQ RQKAVRVAILVTSIFFLCWSPYHIVIFLDTLVRLKAVDNTCELN GSLPVAITMCEFLGLAHCCLNPMLYTFAGVKFRSDLSRLLTK LGCTGPASLCQLFPSWRKSSLSESENATSLTTF |
| Mouse CXCR5 | SEQ ID NO: 34 | MNYPLTLDMGSITYNMDDLYKELAFYSNSTEIPLQDSNFCST VEGPLLTSFKAVFMPVAYSLIFLLGMMGNILVLVILERHRHTR SSTETFLFPHLAVADLLLVFILPFAVAEGSVGWVLGTFLCKTVI ALHKINFYCSSLLLACIAVDRYLAIVHAVHAYRRRRLLSIHITC TAIWLAGFLFALPELLFAKVGQPHNNSLPQCTFSQENEAET RAWFTSRFLYHIGGFLLPMLVMGWCYVGVVHRLLQAQRRP QRQKAVRVAILVTSIFFLCWSPYHIVIFLDTLERLKAVNSSCEL SGYLSVAITLCEFLGLAHCCLNPMLYTFAGVKFRSDLSRLLT KLGCAGPASLCQLFPNWRKSSLSESENATSLTTF |
| Mouse 11G2 VL | SEQ ID NO: 35 | DVVVTQSPDSLAVSLGQRATISCRAS<u>ESVEYHGTSLMH</u>WYQ QKPGQPPKLLIY<u>AASNVES</u>GVPARFSGSGSGTDFSLNIHPVE EGDIAMYFC<u>QQSRKVPWT</u>FGGGTKLEIK |
| Mouse 11G2 VH | SEQ ID NO: 36 | EVKLVESGGGLVQPGGSLRLSCATS<u>GFTFTDFYMS</u>WVRQP PGRALEWLGF<u>IRNKANGYTTEY</u>SASVKGRFTISRDNSQSILY LQMNTLRAGDSATYYC<u>VRVYGSTLHY</u>WGQGTILTVSSA |
| Mouse 41A10 VL | SEQ ID NO: 37 | QIVLTQSPAVMSASPGEKVTMTCSAS<u>SSVNY</u>IHWYQQKSGT SPKRWIY<u>ETSRLAS</u>GVPVRFSGSGSGTSYSLTISTMEAEDAA TYYC<u>QQWSSNPLT</u>FGAGTKLELK |
| Mouse 41A10 VH | SEQ ID NO: 38 | EVQLVESGGDLVKPGGSLKLSCAAS<u>GFTFRSYGMS</u>WVRQT PDKRLEWVAT<u>ISSGGTYT</u>FYPDILKGRITISRDNAKNTLYLQM SNLKSEDTAMYYC<u>ARRGEDYRGALEH</u>WGQGTSVTVSSA |
| Mouse 5H7 VL | SEQ ID NO: 39 | DVVVTQSPDSLAVSLGQRATISCRAS<u>ESVEYHGTSLMH</u>WYQ QKPGQPPKLLIY<u>AASNVES</u>GVPARFSGSGSGTDFSLNIHPVE EGDVSMFFC<u>QQSRKVPWT</u>FGGGTKLEIK |
| Mouse 5H7 VH | SEQ ID NO: 40 | EVKLVESGGGLVQPGDSLRLSCATS<u>GFTFTDFYMS</u>WVRQP PGRALEWLGF<u>IRNKANGYTTEY</u>SASVKGRFTISRDNSQSILY LQMNTLRAGDSATYYC<u>VRVYGSTLHY</u>WGQGTILTVSSA |
| 2C9 Light Chain (VL indicated by allcaps and CK domain indicated by lowercase letters) | SEQ ID NO: 41 | DIVMTQSPDSLAVSLGERATINCKSS<u>QSVLYSSNNKNYLA</u>W YQQKPGQPPKLLIY<u>WAS</u>TRDSGVPDRFSGSGSGTDFTLTIS SLQAEDVAVYYC<u>HQYLSSYT</u>FGGGTKVEIKrtvaapsvflfppsdeq lksgtasvvcllnnfypreakvqwkvdnalqsgnsqesvteqdskdstyslsstltlsk adyekhkvyacevthqglsspvtksfnrgec* |
| 2C9 heavy chain (VH indicated by allcaps and constant region indicated by lowercase letters) | SEQ ID NO: 42 | EVQLVESGGGLVKPGGSLRLSCAAS<u>GFTFSTNAMN</u>WVRQA PGKGLERVAR<u>IRSKSNNYAT</u>YYADSVKDRFTISRDDSKNTLY LQMNSLKTEDTAVYYC<u>VTMIPFAY</u>WGQTLVTVSSastkgpsvf plapssksstsggtaalgclvkdyfpepvtvswnsgaltsgvhtfpavlqssglyslssv vtvpssslgtqtyicnvnhkpsntkvdkkvepkscdkthtcppcpapellggpsvflfp pkpkdtlmisrtpevtcvvvdvshedpevkfnwyvdgvevhnaktkpreeqynsty rvvsvltvlhqdwlngkeykckvsnkalpapiektiskakgqprepqvytlppsreem tknqvsltclvkgfypsdiavewesngqpennykttppvldsdgsfflyskltvdksrw qqgnvfscsvmhealhnhytqkslslspg* |
| 16D7 light chain | SEQ ID NO: 43 | DIVMTQAAPSVAVTPGASVSISCRSS<u>KSLLHSSGKTYLY</u>WFL QRPGQSPQLLIY<u>RLS</u>SLASGVPDRFSGSGSGTAFTLRISRVE AEDVGVYYC<u>MQHLEYPYT</u>FGGGTKLEIKrtvaapsvfifppsdeqlks gtaswcllnnfypreakvqwkvdnalqsgnsqesvteqdskdstyslsstltlskady ekhkvyacevthqglsspvtksfnrgec* |
| 16D7 heavy chain (VH indicated by allcaps and constant region | SEQ ID NO: 44 | QVQLKESGPGLVAPSESLSITCTVS<u>GFSLIDYG</u>VNWIRQPPG KGLEWLGV<u>IWGDTTYYNPSLKSR</u>LSISKDNSKSQVFLKVTS LTTDDDTAMYYC<u>ARIVY</u>WGQGTLVTVSAastkgpsvfplapssksstsg gtaalgclvkdyfpepvtvswnsgaltsgvhtfpavlqssglyslssvvtvpssslgtqt yicnvnhkpsntkvdkkvepkscdkthtcppcpapellggpsvflfppkpkdtlmisrt |

TABLE 16-continued

(SEQUENCES)

| Name | Sequence Identifier No. | Sequence |
|---|---|---|
| indicated by lowercase letters) | | pevtcvvvdvshedpevkfnwyvdgvevhnaktkpreeqynstyrwsvltvlhqd wlngkeykckvsnkalpapiektiskakgqprepqvytlppsreemtknqvsltclvk gfypsdiavewesngqpennykttppvldsdgsfflyskltvdksrwqqgnvfscsv mhealhnhytqkslslspg* |
| 11A7 light chain | SEQ ID NO: 45 | QPVLIQPPSVSKDLRQTATLICTGN<u>SNNVGNQ</u>GATVVLQQH QGHPPKLLSY<u>KNNN</u>RPSGISERFSASRSGNTASLTITGLQPE DEADYYC<u>SAWDSSLSAWV</u>FGGGTQLTVLGQPKaapsvtlfppss eelqankatlyclisdfypgavtvawkadsspvkagvetttpskqsnnkyaassylslt peqwkshrsyscqvthegstvektvaptecs* |
| 11A7 heavy chain | SEQ ID NO: 46 | EVQLVESGGGLVQPGGSLRLSCAASG<u>FTVSSN</u>YMSWVRQA PGKGLEWVS<u>VIYSGGST</u>YYADSVKGRFTISRHNSKNTLYLQ MNSLRAEDTAVYYC<u>ARGYVV</u>WGQGTLVTVSSastkgpsvfplap sskstsggtaalgclvkdyfpepvtvswnsgaltsgvhtfpavlqssglysLssvvtvp ssslgtqtyicnvnhkpsntkvdkkvepkscdkthtcppcpapellggpsvflfppkp kdtlmisrtpevtcvvvdvshedpEvkfnwyvdgvevhnaktkpreeqynstyrvv svltvlhqdwlngkeykckvsnkalpapiektiskakgqprepqvytlppsreemtkn qvsltclvkgfypsdiavewesngqpennykttppvldsdgsfflyskltvdksrwqqg nvfscsvmhealhnhytqkslslspg |
| h11G2 VL (XC151) | SEQ ID NO: 47 | DIQMTQSPSSLSASVGDRVTITCRAS<u>ESVEYHGTS</u>LMHWYQ QKPGKAPKLLIY<u>AASNVESG</u>VPSRFSGSGSGTDFTLTISSLQ PEDFATYYC<u>QQSRKVPWT</u>FGQGTKVEIK |
| h11G2 VL (XC346) | SEQ ID NO: 48 | DVQMTQSPSSLSASVGDRVTITCRAS<u>ESVEYHGTS</u>LMHWY QQKPGKAPKLLIY<u>AASNVESG</u>VPSRFSGSGSGTDFTLTISSL QPEDFATYYC<u>QQSRKVPWT</u>FGQGTKVEIK |
| h11G2 VL (XC347) | SEQ ID NO: 49 | DVQVTQSPSSLSASVGDRVTITCRAS<u>ESVEYHGTS</u>LMHWY QQKPGKAPKLLIY<u>AASNVESG</u>VPSRFSGSGSGTDFTLTISSL QPEDFATYYC<u>QQSRKVPWT</u>FGQGTKVEIK |
| h11G2 VL (XC348) | SEQ ID NO: 50 | DVQVTQSPSSLSASVGDRVTITCRAS<u>ESVEYHGTS</u>LMHWY QQKPGKAPKLLIY<u>AASNVESG</u>VPSRFSGSGSGTDFTLTISSL QPEDFATYFC<u>QQSRKVPWT</u>FGQGTKVEIK |
| h11G2 VL (XC349) | SEQ ID NO: 51 | DIQVTQSPSSLSASVGDRVTITCRAS<u>ESVEYHGTS</u>LMHWYQ QKPGKAPKLLIY<u>AASNVESG</u>VPSRFSGSGSGTDFTLTISSLQ PEDFATYYC<u>QQSRKVPWT</u>FGQGTKVEIK |
| h11G2 VH (XC152) | SEQ ID NO: 52 | EVQLVESGGGLVKPGGSLRLSCAAS<u>GFTFTDFY</u>MSWVRQA PGKGLEWLGF<u>IRNKANGYTT</u>EYSAPVKGRFTISRDDSKNTLY LQMNSLKTEDTAVYYC<u>VRVYGSTLHY</u>VVQGQTLVTVSSAS |
| h11G2 VH (XC350) | SEQ ID NO: 53 | EVQLVESGGGLVQPGGSLRLSCAAS<u>GFTFTDFY</u>MSWVRQA PGKGLEWVAF<u>IRNKANGYTT</u>EYSASVKGRFTISRDNAKNSL YLQMNSLRAEDTAVYYC<u>A</u>RVYGSTLHYWGQGTLVTVSS |
| 11G2 VH (XC351) | SEQ ID NO: 54 | EVQLVESGGGLVQPGGSLRLSCATS<u>GFTFTDFY</u>MSWVRQA PGKGLEWLGF<u>IRNKANGYTT</u>EYSASVKGRFTISRDNAKNSL YLQMNSLRAEDTAVYYC<u>VRVYGSTLHY</u>VVQGQTLVTVSS |
| 11G2 VH (XC352) | SEQ ID NO: 55 | EVQLVESGGGLVQPGGSLRLSCATS<u>GFTFTDFY</u>MSWVRQA PGKGLEWVAF<u>IRNKANGYTT</u>EYSASVKGRFTISRDNAKNSL YLQMNSLRAEDTAVYYC<u>A</u>RVYGSTLHYWGQGTLVTVSS |
| h11G2 VH (XC353) | SEQ ID NO: 56 | EVQLVESGGGLVQPGGSLRLSCAAS<u>GFTFTDFY</u>MSWVRQA PGKGLEWVAF<u>IRNKANGYTT</u>EYSASVKGRFTISRDNAKNSL YLQMNSLRAEDTAVYYC<u>VRVYGSTLHY</u>VVQGQTLVTVSS |
| h11G2 VH (XC354) | SEQ ID NO: 57 | EVQLVESGGGLVQPGGSLRLSCAAS<u>GFTFTDFY</u>MSWVRQA PGKGLEWLGF<u>IRNKANGYTT</u>EYSASVKGRFTISRDNAKNSL YLQMNSLRAEDTAVYYC<u>A</u>RVYGSTLHYWGQGTLVTVSS |
| h41A10 VL (XC143) | SEQ ID NO: 58 | DIQMTQSPSSLSASVGDRVTITCSAS<u>SSVNY</u>IHWYQQKPGK APKRWIY<u>ETSRLAS</u>GVPSRFSGSGSGTDFTLTISSLQPEDFA TYYC<u>QQWSSNPLT</u>FGQGTKVEIK |
| h41A10 VL (XC144) | SEQ ID NO: 59 | DIQLTQSPSSLSASVGDRVTITCSAS<u>SSVNY</u>IHWYQQKPGKA PKRLIY<u>ETSRLAS</u>GVPSRFSGSGSGTDYTLTISSLQPEDFAT YYC<u>QQWSSNPLT</u>FGQGTKVEIK |
| h41A10 VL (XC145) | SEQ ID NO: 60 | diqltqspsslsasvgdrvtitcsas<u>ssvny</u>ihwyqqkpgkapkrwiy<u>etsrlas</u>qvps rfsgsgsgTdytltisslqpedfatyyc<u>qqwssnplt</u>fgqgtkveik |

TABLE 16-continued (SEQUENCES)

| Name | Sequence Identifier No. | Sequence |
|---|---|---|
| h41A10 VL (XC146) | SEQ ID NO: 61 | diqmtqspsslsasvgdrvtitcsas<u>ssvny</u>ihwyqqkpgkapkrliy<u>etsrlas</u>qvps rfsgsgsgtdftltisslqpedfatyyc<u>ddwssnplt</u>fgqgtkveik |
| h41A10 VL (XC149) | SEQ ID NO: 62 | diqmtqspsslsasvgdrvtitcsas<u>ssvny</u>ihwyqqkpgkapklliy<u>etsrlas</u>qvps rfsgsgsgtdftltisslqpedfatyyc<u>qqwssnplt</u>fgqgtkveik |
| h41A10 VH (XC150) | SEQ ID NO: 63 | evqlvesgggglvqpggslrlscaas<u>gftfrsyq</u>mswvrqapgkglewvat<u>issqqtytf</u> ypdsvkgrftisrdnaknslylqmnslraedtavyyc<u>arrcedyrqaleh</u>wgqgtlvtv ssas |
| Primer 5' VL1 | SEQ ID NO: 64 | ATCACGCGGCCGCCTCACCATGAAGTTGCCTGTTAGGCT GTTGGTGCTG |
| Primer 5' VL2 | SEQ ID NO: 65 | ATCACGCGGCCGCCTCACCATGGAG(A/T)CAGACACACTC CTG(C/T)TATGGGT |
| Primer 5' VL3 | SEQ ID NO: 66 | ATCACGCGGCCGCCTCACCATGAGTGTGCTCACTCAGGT CCIGG(C/G)GTTG |
| Primer 5' VL4 | SEQ ID NO: 67 | ATCACGCGGCCGCCTCACCATGAGG(A/G)CCCCTGCTCA G(A/T)TT(C/T)TTGG(A/C)(A/T)CTTG |
| Primer 5' VL5 | SEQ ID NO: 68 | ATCACGCGGCCGCCTCACCATGGATTT(A/T)CAGGTGCAG ATT(A/T)TCAGCTTC |
| Primer 5' VL6 | SEQ ID NO: 69 | ATCACGCGGCCGCCTCACCATGAGGT(G/T)C(C/T)(C/T)TG (C/T)T(G/C)AG(C/T)(C/T)CTG(G/A)GG |
| Primer 5' VL7 | SEQ ID NO: 70 | ATCACGCGGCCGCCTCACCATGGGC(AfT)TCAAGATGGAG TCACA(G/T)(A/T)(C/T)(C/T)C(A/T)GG |
| Primer 5' VL8 | SEQ ID NO: 71 | ATCACGCGGCCGCCTCACCATGIGGGGA(C/T)CT(G/T)TTT (C/T)C(A/C)(A/C)TTTTTCAATTG |
| Primer 5' VL9 | SEQ ID NO: 72 | ATCACGCGGCCGCCTCACCATGGT(A/G)TCC(A/T)CA(C/G) CTCAGTTCCTTG |
| Primer 5' VL10 | SEQ ID NO: 73 | ATCCACGCGGCCGCCTCACCATGTATATATGTTTGTTGTC TATTTCT |
| Primer 5' VL11 | SEQ ID NO: 74 | ATCACGCGGCCGCCTCACCATGGAAGCCCCAGCTCAGCT TCTCTTCC |
| Primer 3' VL | SEQ ID NO: 75 | CAGTTGGTGCAGCATCCGTACGTTTGATTTCCAG |
| Primer 5' VH1 | SEQ ID NO: 76 | ACTAGCGGCCGCATGAAATGCAGCTGGGTCAT(C/G)TTCT TC |
| Primer 5' VH2 | SEQ ID NO: 77 | ACTAGCGGCCGCATGGGATGGAGCT(A/G)TATCAT(C/G) (C/T)TCT |
| Primer 5' VH3 | SEQ ID NO: 78 | ACTAGCGGCCGCATGAAG(A/T)TGTGGTTAAACTGGGTTT TTT |
| Primer 5' VH4 | SEQ ID NO: 79 | ACTAGCGGCCGCATG(A/G)ACTTTGGG(C/T)TCAGCTTG (A/G)TTT |
| Primer 5' VH5 | SEQ ID NO: 80 | ACTAGCGGCCGCATGGACTCCAGGCTCAATTTAGTTTTCC TT |
| Primer 5' VH6 | SEQ ID NO: 81 | ACTAGCGGCCGCATGGCTGTC(C/T)T(G/A)G(C/G)GCT (G/A)CTCTTCTGC |
| Primer 5' VH7 | SEQ ID NO: 82 | ACTAGCGGCCGCATGG(A/G)ATGGAGC(G/T)GG(A/G)TCTT T(C/A)TCTT |
| Primer 5' VH8 | SEQ ID NO: 83 | ACTAGCGGCCGCATGAGAGTGCTGATTCTTTTGTG |
| Primer 5' VH9 | SEQ ID NO: 84 | ACTAGCGGCCGCATGG(A/C)TTGGGTGTGGA(A/C)CTTGC TATTCCTG |

TABLE 16-continued (SEQUENCES)

| Name | Sequence Identifier No. | Sequence |
|---|---|---|
| Primer 5' VH10 | SEQ ID NO: 85 | ACTAGCGGCCGCATGGATTTTGGGCTGATTTTTTTATTG |
| Primer 5' VH11 | SEQ ID NO: 86 | ACTAGCGGCCGCATGGGCAGACTTACATTCTCATTCCTG |
| Primer 5' VH12 | SEQ ID NO: 87 | ACTAGCGGCCGCATGATGGTGTTAAGTCTTCTGTACCTG |
| Primer 3' VH | SEQ ID NO: 88 | GGGGGTGTCGTCGACGCTG(A/C)(G/A)GAGAC(G/A)GTGA |
| Human IgG1 constant region | SEQ ID NO: 89 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDILMISRTPEVICVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFF LYSKLTVDKSRWQQGNVFSCSVMHEALHNHYTQKSLSLSP GK |
| Human kappa light chain constant region (Cκ) | SEQ ID NO: 90 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| human DP-54 VH germline showing framework region (VH3 sub-group) with a JH4 segment | SEQ ID NO: 91 | EVQLVESGGGLVQPGGSLRLSCAASGFTFSSYWMSWVRQ APGKGLEWVANIKQDGSEKYYVDSVKGRFTISRDNAKNSLY LQMNSLRAEDTAVYYCARYFDYWGQGTLVTVSS |
| JH4 | SEQ ID NO: 92 | WGQGTLVTVSS |
| human VL germline DPK9 framework (VKI sub-group) with a JK4 segment | SEQ ID NO: 93 | DIQMTQSPSSLSASVGDRVTITCRASQSISSYLNWYQQKPG KAPKLLIYAASSLQSGVPSRFSGSGSGTDFTLTISSLQPEDFA TYYCQQSYSTPLTFGGGTKVEIK |
| JK4 | SEQ ID NO: 94 | FGGGTKVEIK |
| Nucleic Acid Sequence encoding h11G2 VL (XC154) | SEQ ID NO: 95 | GACATCCAGATGACCCAGAGCCCTTCCAGCCTGAGCGCTT CCGTGGGAGATAGGGTGACCATCACCTGCAGGGCCAGC GAGTCCGTGGAGTACCACGGCACCAGCCTGATGCACTGG TACCAGCAGAAGCCCGGCAAGGCCCCCAAGCTGCTGATC TACGCCGCCAGCAACGTGGAGAGCGGCGTGCCTAGCAG ATTCAGCGGCAGCGGAAGCGGCACCGACTTCACCCTGAC CATTAGCAGCCTGCAGCCCGAGGACTTCGCCACCTACTA CTGTCAGCAGAGCAGGAAGGTGCCCTGGACCTTCGGCCA GGGCACCAAGGTCGAGATCAAG |
| Nucleic Acid Sequence encoding h11G2 VH (XC155) | SEQ ID NO: 96 | GAGGTGCAGCTGGTGGAGAGCGGAGGAGGACTGGTGCA GCCTGGCGGAAGCCTGAGACTGAGCTGCGCCGCCAGCG GCTTCACCTTTACCGACTTCTACATGAGCTGGGTGAGGCA GGCTCCCGGCAAAGGACTGGAGTGGGTGGGTTTCATCAG GAACAAGGCCAACGGCTACACCACCGAGTATAGCGCCTC CGTGAAGGGCAGGTTCACCATCAGCAGGGACAACGCCAA GAACAGCCTGTACCTGCAGATGAACAGCCTGAGGGCCGA GGACACCGCCGTGTACTACTGCGCCAGAGTGTACGGCAG CACACTGCACTACTGGGGCCAGGGCACCCTGGTGACCGT GAGCAGCGCG |
| Nucleic Acid Sequence encoding h11G2 | SEQ ID NO: 97 | GACATCCAGATGACCCAGAGCCCTTCCAGCCTGAGCGCT TCCGTGGGAGATAGGGTGACCATCACCTGCAGGGCCAGC GAGTCCGTGGAGTACCACGGCACCAGCCTGATGCACTGG TACCAGCAGAAGCCCGGCAAGGCCCCCAAGCTGCTGATC |

TABLE 16-continued (SEQUENCES)

| Name | Sequence Identifier No. | Sequence |
|---|---|---|
| (XC154) Full length Light Chain (LC) constant domain is indicated by lower case letters | | TACGCCGCCAGCAACGTGGAGAGCGGCGTGCCTAGCAG<br>ATTCAGCGGCAGCGGAAGCGGCACCGACTTCACCCTGAC<br>CATTAGCAGCCTGCAGCCCGAGGACTTCGCCACCTACTA<br>CTGTCAGCAGAGCAGGAAGGTGCCCTGGACCTTCGGCCA<br>GGGCACCAAGGTCGAGATCAAGcgtacggtggctgcaccatctgtcttcatctt<br>cccgccatctgatgagcagttgaaatctggaactgcctctgttgtgtgcctgctg<br>aataacttctatcccagagaggccaaagtacagtggaaggtggataacgccctca<br>atcgggtaactcccaggagagtgtcacagagcaggacagcaaggacagcaccta<br>cagcctcagcagcaccctgacgctgagcaaagcagactacgagaaacacaaagt<br>ctacgcctgcgaagtcacccatcagggcctgagctcgcccgtcacaaagagcttca<br>acaggggagagtgttag |
| Nucleic Acid Sequence encoding h11G2 (XC155) full length heavy chain (HC) constant domain is indicated by lower case letters | SEQ ID NO: 98 | GAGGTGCAGCTGGTGGAGAGCGGAGGAGGACTGGTGCA<br>GCCTGGCGGAAGCCTGAGACTGAGCTGCGCCGCCAGCG<br>GCTTCACCTTTACCGACTTCTACATGAGCTGGGTGAGGCA<br>GGCTCCCGGCAAAGGACTGGAGTGGGTGGGTTTCATCAG<br>GAACAAGGCCAACGGCTACACCACCGAGTATAGCGCCTC<br>CGTGAAGGGCAGGTTCACCATCAGCAGGGACAACGCCAA<br>GAACAGCCTGTACCTGCAGATGAACAGCCTGAGGGCCGA<br>GGACACCGCCGTGTACTACTGCGCCAGAGTGTACGGCAG<br>CACACTGCACTACTGGGGCCAGGGCACCCTGGTGACCGT<br>GAGCAGCgcgtcgaccaagggcccatcggtcttccccctggcaccctcctccaa<br>gagcacctctgggggcacagcggccctgggctgcctggtcaaggactacttccccg<br>aaccggtgacggtgtcgtggaactcaggcgccctgaccagcggcgtgcacaccttc<br>ccggctgtcctacagtcctcaggactctactccctcagcagcgtggtgaccgtgccctc<br>cagcagcttgggcacccagacctacatctgcaacgtgaatcacaagcccagcaac<br>accaaggtggacaagaaagttgagcccaaatcttgtgacaaaactcacacatgccc<br>accgtgcccagcacctgaactcctgggggaccgtcagtcttcctcttccccccaaaa<br>cccaaggacaccctcatgatctcccggacccctgaggtcacatgcgtggtggtggac<br>gtgagccacgaagaccctgaggtcaagttcaactggtacgtggacggcgtggaggt<br>gcataatgccaagacaaagccgcgggaggagcagtacaacagcacgtaccgtgt<br>ggtcagcgtcctcaccgtcctgcaccaggactggctgaatggcaaggagtacaagt<br>gcaaggtctccaacaaagccctcccagcccccatcgagaaaaccatctccaaagc<br>caaagggcagccccgagaaccacaggtgtacaccctgcccccatcccgggagga<br>gatgaccaagaaccaggtcagcctgacctgcctggtcaaaggcttctatcccagcg<br>acatcgccgtggagtgggagagcaatgggcagccggagaacaactacaagacc<br>acgcctcccgtgctggactccgacggctccttcttcctctatagcaagctcaccgtgga<br>caagagcaggtggcagcaggggaacgtcttctcatgctccgtgatgcatgaggctct<br>gcacaaccactacacgcagaagagcctctccctgtccccgggttga |
| nucleic acid sequence encoding human wild type IgG1 Fc | SEQ ID NO: 99 | gcgtcgaccaagggcccatcggtcttccccctggcaccctcctccaagagcacctct<br>gggggcacagcggccctgggctgcctggtcaaggactacttccccgaaccggtgac<br>ggtgtcgtggaactcaggcgccctgaccagcggcgtgcacaccttcccggctgtcct<br>acagtcctcaggactctactccctcagcagcgtgactgtgccctccagcagcttg<br>ggcacccagacctacatctgcaacgtgaatcacaagcccagcaacaccaaggtgg<br>acaagaaagttgagcccaaatcttgtgacaaaactcacacatgcccaccgtgccca<br>gcacctgaactcctgggggaccgtcagtcttcctcttccccccaaaacccaaggac<br>accctcatgatctcccggacccctgaggtcacatgcgtggtggtggacgtgagccac<br>gaagaccctgaggtcaagttcaactggtacgtggacggcgtggaggtgcataatgc<br>caagacaaagccgcgggaggagcagtacaacagcacgtaccgtgtggtcagcgt<br>cctcaccgtcctgcaccaggactggctgaatggcaaggagtacaagtgcaaggtct<br>ccaacaaagccctcccagcccccatcgagaaaaccatctccaaagccaaagggc<br>agccccgagaaccacaggtgtacaccctgcccccatcccgggaggagatgacca<br>agaaccaggtcagcctgacctgcctggtcaaaggcttctatcccagcgacatcgccg<br>tggagtgggagagcaatgggcagccggagaacaactacaagaccacgcctcccg<br>tgctggactccgacggctccttcttcctctatagcaagctcaccgtggacaagagcag<br>gtggcagcaggggaacgtcttctcatgctccgtgatgcatgaggctctgcacaacca<br>ctacacgcagaagagcctctccctgtccccgggttga |
| nucleic acid sequence encoding human wild type Kappa constant domain (Cκ) | SEQ ID NO: 100 | cgtacggtggctgcaccatctgtcttcatcttcccgccatctgatgagcagttgaaatct<br>ggaactgcctctgttgtgtgcctgctgaataacttctatcccagagaggccaaagtaca<br>gtggaaggtggataacgccctccaatcgggtaactcccaggagagtgtcacagagc<br>aggacagcaaggacagcacctacagcctcagcagcaccctgacgctgagcaaa<br>gcagactacgagaaacacaaagtctacgcctgcgaagtcacccatcagggcctga<br>gctcgcccgtcacaaagagcttcaacaggggagagtgttag |

(CDR amino acid residues are underlined)

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety for all purposes. In the event that one or more of the incorporated literature and similar materials differs from or contradicts this application, including but not limited to defined terms, term usage, described techniques, or the like, this application controls.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated antibody, or antigen-binding fragment thereof, that specifically binds C-X-C-chemokine receptor 5 (CXCR5), wherein the antibody, or antigen-binding fragment thereof, is at least one antibody, or antigen-binding fragment thereof, selected from the group consisting of:
   a) an antibody, or antigen-binding fragment thereof, comprising a CDR-L1 comprising the amino acid sequence of SEQ ID NO:2; a CDR-L2 comprising the amino acid sequence of SEQ ID NO:3; a CDR-L3 comprising the amino acid sequence of SEQ ID NO:4; a CDR-H1 comprising the amino acid sequence of SEQ ID NO:7; a CDR-H2 comprising the amino acid sequence of SEQ ID NO:8; and a CDR-H3 comprising the amino acid sequence of SEQ ID NO:9;
   b) an antibody, or antigen-binding fragment thereof, comprising a CDR-L1 comprising the amino acid sequence of SEQ ID NO:2; a CDR-L2 comprising the amino acid sequence of SEQ ID NO:3; a CDR-L3 comprising the amino acid sequence of SEQ ID NO:4; a CDR-H1 comprising the amino acid sequence of SEQ ID NO:7; a CDR-H2 comprising the amino acid sequence of SEQ ID NO:8; and a CDR-H3 comprising the amino acid sequence of SEQ ID NO:11;
   c) an antibody, or antigen-binding fragment thereof, comprising a CDR-L1 comprising the amino acid sequence of SEQ ID NO:14; a CDR-L2 comprising the amino acid sequence of SEQ ID NO:15; a CDR-L3 comprising the amino acid sequence of SEQ ID NO:16; a CDR-H1 comprising the amino acid sequence of SEQ ID NO:19; a CDR-H2 comprising the amino acid sequence of SEQ ID NO:20; and a CDR-H3 comprising the amino acid sequence of SEQ ID NO:21;
   d) an antibody, or antigen-binding fragment thereof, comprising a VL comprising an amino acid sequence encoded by the insert of the plasmid deposited with the ATCC and having Accession Number PTA-124324 and a VH comprising an amino acid sequence encoded by the insert of the plasmid deposited with the ATCC having Accession Number PTA-124323;
   e) an antibody, or antigen-binding fragment thereof, comprising a VL comprising the amino acid sequence of SEQ ID NO:1, and a VH comprising the amino acid sequence of SEQ ID NO:6;
   f) an antibody, or antigen-binding fragment thereof, comprising a VL comprising the amino acid sequence of SEQ ID NO:13, and a VH comprising the amino acid sequence of SEQ ID NO:18;
   g) an antibody, or antigen-binding fragment thereof, comprising a VL comprising the amino acid sequence of SEQ ID NO:47, and a VH comprising the amino acid sequence of SEQ ID NO:52;
   h) an antibody, or antigen-binding fragment thereof, comprising a VL comprising the amino acid sequence of SEQ ID NO:5, and a VH comprising the amino acid sequence of SEQ ID NO:6;
   i) an antibody, or antigen-binding fragment thereof, comprising a VL comprising the amino acid sequence of SEQ ID NO:5, and a VH comprising the amino acid sequence of SEQ ID NO:10;
   j) an antibody, or antigen-binding fragment thereof, comprising a VL comprising the amino acid sequence of SEQ ID NO:13, and a VH comprising the amino acid sequence of SEQ ID NO:17;
   k) an antibody, or antigen-binding fragment thereof, comprising a VL comprising the amino acid sequence of SEQ ID NO:1, and a VH comprising the amino acid sequence of SEQ ID NO:12;
   l) an antibody, or antigen-binding fragment thereof, comprising a LC comprising the amino acid sequence of SEQ ID NO:22, and a HC comprising the amino acid sequence of SEQ ID NO:23;
   m) an antibody, or antigen-binding fragment thereof, comprising a LC comprising the amino acid sequence of SEQ ID NO:24, and a HC comprising the amino acid sequence of SEQ ID NO:25;
   n) an antibody, or antigen-binding fragment thereof, comprising a LC comprising the amino acid sequence of SEQ ID NO:26, and a HC comprising the amino acid sequence of SEQ ID NO:27;
   o) an antibody, or antigen-binding fragment thereof, comprising a LC comprising the amino acid sequence of SEQ ID NO:28, and a HC comprising the amino acid sequence of SEQ ID NO:29.

2. The antibody, or antigen-binding fragment thereof, of claim 1, wherein said antibody, or antigen-binding fragment thereof, exhibits at least one of the following biological activities:
   a) binds CXCR5+ human B cells with an apparent affinity of an EC50 of less than about 26 pM, but does not bind cells expressing CXCR5 mouse, rat or rabbit orthologs;
   b) antagonizes CXCL13 inhibition of cAMP release triggered by forskolin;
   c) triggers ADCC of CXCR5-expressing cells in human donor and cynomolgus PBMCs and human donor TMCs;
   d) binds human CXCR5 but does not bind human chemokine receptors CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR6, CXCR7, or XCR1;
   e) depletes B cells in the peripheral blood;
   f) depletes Tfh-like cells in the peripheral blood;
   g) depletes bona fide Tfh cells in the spleen; and
   h) impairs a humoral immune memory response.

3. The antibody, or antigen-binding fragment thereof, of claim 1, wherein said antibody, or antigen-binding fragment thereof, is afucosylated.

4. An isolated nucleic acid encoding the antibody, or antigen-binding fragment thereof, of claim 1.

5. A pharmaceutical composition comprising the antibody, or antigen-binding fragment thereof, of claim 1, and a pharmaceutically acceptable carrier or excipient.

6. The antibody, or antigen-binding fragment thereof, of claim 1, comprising a VL comprising the amino acid sequence of SEQ ID NO:1, and a VH comprising the amino acid sequence of SEQ ID NO:6.

7. The antibody, or antigen-binding fragment thereof, of claim 1, comprising a LC comprising the amino acid sequence of SEQ ID NO:28, and a HC comprising the amino acid sequence of SEQ ID NO:29.

8. An isolated antibody that specifically binds CXCR5 comprising a LC consisting of the amino acid sequence of SEQ ID NO:28, and a HC consisting of the amino acid sequence of SEQ ID NO:29.

9. The antibody of claim 8, wherein the antibody is afucosylated.

10. An isolated antibody that specifically binds CXCR5 comprising:
   an antibody VL region comprising the first, second and third CDRs from the VL region comprising the amino acid sequence of SEQ ID NO:1; and an antibody VH region comprising the first, second and third CDRs from the VH region comprising the amino acid sequence of SEQ ID NO:6.

11. The antibody of claim 10, wherein the antibody is afucosylated.

12. An isolated antibody that specifically binds CXCR5 comprising:
   a) an antibody VL region comprising the first, second and third CDRs from the VL region comprising the amino acid sequence of SEQ ID NO:1;
   an antibody VH region comprising the first, second and third CDRs from the VH region comprising the amino acid sequence of SEQ ID NO:6;
   an antibody constant light (CL) region comprising the amino acid sequence of SEQ ID NO:30; and
   an antibody constant heavy (CH) region comprising the amino acid sequence of SEQ ID NO:31; or
   b) an antibody VL region at least 95% identical to the amino acid sequence of SEQ ID NO: 1 and comprising a CDR-L1 consisting of the amino acid sequence of SEQ ID NO:2; a CDR-L2 consisting of the amino acid sequence of SEQ ID NO:3; a CDR-L3 consisting of the amino acid sequence of SEQ ID NO:4; and an antibody VH region at least 95% identical to the amino acid sequence of SEQ ID NO:6 and a CDR-H1 consisting of the amino acid sequence of SEQ ID NO:7; a CDR-H2 consisting of the amino acid sequence of SEQ ID NO:8; and a CDR-H3 consisting of the amino acid sequence of SEQ ID NO:9.

13. The antibody of claim 12, wherein the antibody is afucosylated.

14. An isolated antibody, or antigen-binding fragment thereof, that specifically binds C-X-C-chemokine receptor 5 (CXCR5), wherein the antibody, or antigen-binding fragment thereof, comprises a CDR-L1 comprising the amino acid sequence of SEQ ID NO:2; a CDR-L2 comprising the amino acid sequence of SEQ ID NO:3; a CDR-L3 comprising the amino acid sequence of SEQ ID NO:4; a CDR-H1 comprising the amino acid sequence of SEQ ID NO:7; a CDR-H2 comprising the amino acid sequence of SEQ ID NO:8; and a CDR-H3 comprising the amino acid sequence of SEQ ID NO:9.

15. The antibody, or antigen-binding fragment thereof of claim 14, wherein said antibody, or antigen-binding fragment thereof, exhibits at least one of the following biological activities:
   a) binds hCXCR5 expressed on human B cells with an apparent affinity of an EC50 of about 6.60 pM with a standard deviation of about plus or minus 2.33 pM;
   b) binds hCXCR5 expressed on human circulating follicular T helper-like cells with an apparent affinity of an EC50 of about 5.89 pM with a standard deviation of about plus or minus 1.40 pM;
   c) binds hCXCR5 expressed on human follicular T helper (Tfh) cells with an apparent affinity of an EC50 of about 10.6 pM;
   d) binds cynoCXCR5 expressed on cynomolgus monkey B cells with an apparent affinity of an EC50 of about 1.32 pM;
   e) binds cynoCXCR5 expressed on cynomolgus monkey Tfh-like cells with an apparent affinity of an EC50 of about 10.5 pM;
   f) antagonizes CXCR5-CXCL13 signaling in a cAMP reporter assay with an EC50 of about 961 pM;
   g) exhibits ADCC activity against human B cells expressing hCXCR5 with an EC50 of about 2.01 pM with a standard deviation of about plus or minus 2.28 pM;
   h) exhibits ADCC activity against human Tfh-like cells expressing hCXCR5 with an EC50 of about 4.28 pM with a standard deviation of about plus or minus 2.88 pM;
   i) exhibits ADCC activity against human Tfh cells expressing hCXCR5 with an EC50 of about 0.11 pM;
   j) exhibits ADCC activity against cynomolgus monkey B cells expressing cynoCXCR5 with an EC50 of about 15.3 pM with a standard deviation of about plus or minus 11.7 pM;
   k) binds hCXCR5 but does not detectably bind human chemokine receptors CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR6, CXCR7, and XCR1;
   l) inhibits binding of CXCR5 to CXCL13;
   m) binds CXCR5+ human B cells with an apparent affinity of an EC50 of less than about 26 pM, but does not bind cells expressing CXCR5 mouse, rat or rabbit orthologs;
   n) antagonizes CXCL13 inhibition of cAMP release triggered by forskolin;
   o) triggers ADCC of CXCR5-expressing cells in human donor and cynomolgus PBMCs and human donor TMCs;
   p) binds human CXCR5 but does not bind human chemokine receptors CCR1, CCR2, CCR3, CCR4, CCR5, CCR6, CCR7, CCR8, CCR9, CCR10, CMKLR1, CXCR3R1, CXCR1, CXCR2, CXCR3, CXCR4, CXCR6, CXCR7, or XCR1;
   q) depletes B cells in the peripheral blood;
   r) depletes Tfh-like cells in the peripheral blood;
   s) depletes bona fide Tfh cells in the spleen; and
   t) impairs humoral immune memory response.

* * * * *